US008362008B2

(12) United States Patent
Webster et al.

(10) Patent No.: US 8,362,008 B2
(45) Date of Patent: Jan. 29, 2013

(54) AMIDO-THIOPHENE COMPOUNDS AND THEIR USE AS 11-BETA-HSD1 INHIBITORS

(75) Inventors: Scott Peter Webster, Lothian (GB); Jonathan Robert Seckl, Lothian (GB); Brian Robert Walker, Lothian (GB); Peter Ward, Middlesex (GB); Thomas David Pallin, Harlow (GB); Hazel Joan Dyke, Harlow (GB); Trevor Robert Perrior, Bury St Edmunds (GB)

(73) Assignee: The University Of Edinburgh, Edinburgh (GB)

( * ) Notice: Subject to any disclaimer, the term of this patent is extended or adjusted under 35 U.S.C. 154(b) by 295 days.

(21) Appl. No.: 12/747,110

(22) PCT Filed: Dec. 11, 2008

(86) PCT No.: PCT/GB2008/004068
§ 371 (c)(1),
(2), (4) Date: Jun. 9, 2010

(87) PCT Pub. No.: WO2009/074789
PCT Pub. Date: Jun. 18, 2009

(65) Prior Publication Data
US 2010/0267696 A1 Oct. 21, 2010

Related U.S. Application Data

(60) Provisional application No. 61/013,042, filed on Dec. 12, 2007.

(30) Foreign Application Priority Data

Dec. 12, 2007 (GB) .................................. 0724251.4

(51) Int. Cl.
*A61P 3/10* (2006.01)
*A61K 31/381* (2006.01)
*C07D 333/38* (2006.01)
*C07D 409/06* (2006.01)
*C07D 409/14* (2006.01)
*C07D 413/14* (2006.01)
*C07D 453/02* (2006.01)
*C07D 471/04* (2006.01)

(52) U.S. Cl. ......... 514/214.03; 514/217.03; 514/217.04; 514/230.8; 514/235.5; 514/249; 514/253.06; 514/307; 514/314; 514/316; 514/323; 514/326; 514/339; 514/414; 540/581; 540/596; 540/597; 544/128; 544/129; 544/130; 544/349; 544/363; 546/125; 546/146; 546/164; 546/187; 546/200; 546/212; 546/276.7; 548/465

(58) Field of Classification Search ............. 514/214.03, 514/217.03, 217.04, 230.8, 235.5, 249, 253.06, 514/307, 314, 316, 323, 326, 339, 414; 540/581, 540/596, 597; 544/128, 129, 130, 349, 363; 546/125, 146, 164, 187, 200, 212, 276.7; 548/465
See application file for complete search history.

(56) References Cited

U.S. PATENT DOCUMENTS

| | | | |
|---|---|---|---|
| 5,087,631 | A | 2/1992 | Shaffer et al. |
| 6,340,678 | B1 | 1/2002 | Matsuhisa |
| 2006/0111366 | A1 | 5/2006 | Andersen et al. |
| 2007/0117800 | A1 | 5/2007 | Arnold et al. |
| 2010/0197662 | A1 | 8/2010 | Ogawa |
| 2011/0015178 | A1 | 1/2011 | Webster et al. |
| 2012/0095046 | A1 | 4/2012 | Webster |

FOREIGN PATENT DOCUMENTS

| | | |
|---|---|---|
| EP | 1894919 A1 | 3/2008 |
| WO | WO 98/39325 A1 | 9/1998 |
| WO | WO 00/51608 A1 | 9/2000 |
| WO | WO 03/044009 A1 | 5/2003 |
| WO | WO 2004/016617 A1 | 2/2004 |
| WO | WO 2005/046685 A1 | 5/2005 |
| WO | WO 2005/047250 A1 | 5/2005 |
| WO | WO 2005/121145 A2 | 12/2005 |
| WO | WO 2006/132197 A1 | 12/2006 |
| WO | WO 2007/053776 A1 | 5/2007 |
| WO | WO 2007/082808 A2 | 7/2007 |
| WO | WO 2008/011453 A2 | 1/2008 |
| WO | WO 2009/074789 A1 | 6/2009 |
| WO | WO 2009/090239 A1 | 7/2009 |
| WO | WO 2009/112845 A1 | 9/2009 |
| WO | WO 2010/023161 A1 | 3/2010 |
| WO | WO 2010/146338 A1 | 12/2010 |
| WO | WO 2011/033255 A1 | 3/2011 |
| WO | WO 2011/135276 A1 | 11/2011 |

OTHER PUBLICATIONS

Registry No. 727385-01-5, entered STN Aug. 16, 2004.*
Registry No. 717867-85-1 and 717867-57-7, entered STN Jul. 28, 2004.*
Andrews, R.C., et al., 2003, "Effects of the 11β-hydroxysteroid dehydrogenase inhibitor carbenoxolone on insulin sensitivity in men with type 2 diabetes," *J. Clin. Endocrinol. Metab.*, vol. 88, pp. 285-291.

(Continued)

*Primary Examiner* — Brenda Coleman
(74) *Attorney, Agent, or Firm* — Swanson & Bratschun, L.L.C.

(57) ABSTRACT

The present invention pertains generally to the field of therapeutic compounds. More specifically the present invention pertains to certain amido-thiophene compounds that, inter alia, inhibit 11β-hydroxysteroid dehydrogenase type 1 (11β-HSD1). The present invention also pertains to pharmaceutical compositions comprising such compounds, and the use of such compounds and compositions, both in vitro and in vivo, to inhibit 11β-hydroxysteroid dehydrogenase type 1; to treat disorders that are ameliorated by the inhibition of 11β-hydroxysteroid dehydrogenase type 1; to treat the metabolic syndrome, which includes disorders such as type 2 diabetes and obesity, and associated disorders including insulin resistance, hypertension, lipid disorders and cardiovascular disorders such as ischaemic (coronary) heart disease; to treat CNS disorders such as mild cognitive impairment and early dementia, including Alzheimer's disease; etc.

44 Claims, No Drawings

OTHER PUBLICATIONS

Christy, C., et al., 2003, "11β-hydroxysteroid dehydrogenase type 2 in mouse aorta; Localization and influence on response to glucocorticoids," *Hypertension*, vol. 42, pp. 580-587.

Cooper, M.S., et al., Sep. 2000, "Expression and functional consequences of 11β-hydroxysteroid dehydrogenase activity in human bone," *Bone*, vol. 27(3), pp. 375-381.

Gotthardt, H., 1971, "1.3-Dipolare Cycloadditionen Mit 1.3.2-Oxathiazolium-5-oxiden. Ein Neuer Weg in Die 5-Aryl-Isothiazol-Reihe", *Tetrahedron Letters*, No. 17, pp. 1281-1284.

Hadoke, P.W.F., et al., 2001, "Endothelial cell dysfunction in mice after transgenic knockout of type 2, but not type 1, 11β-hydroxysteroid dehydrogenase," *Circulation*, vol. 104, pp. 2832-2837.

Hwang et al., 2001, "4-Hydroxy-6-oxo-6,7-dihydro-thieno[2,3-b]pyrimidine derivatives: synthesis and their biological evaluation for the glycine site acting on the N-methyl-D-aspartate (NMDA) receptor", *Archives of Pharmacol. Research*, vol. 24, No. 4, pp. 270-275.

Kotelevtsev, Y.V., et al., Dec. 1997, "11β-Hydroxysteroid dehydrogenase type 1 knockout mice show attenuated glucocorticoid inducible responses and resist hyperglycaemia on obesity and stress," *Proc. Natl. Acad. Sci.*, vol. 94, pp. 14924-14929.

Masuzaki, H., et al., 2001, "A Transgenic Model of Visceral Obesity and the Metabolic Syndrome," *Science*, vol. 294, pp. 2166-2170.

Moisan, M. P., et al., 1990, "11β-hydroxysteroid dehydrogenase bioactivity and messenger RNA expression in rat forebrain: localization in hypothalamus, hippocampus, and cortex," *Endocrinology*, vol. 127(3), pp. 1450-1455.

Morton, N.M., et al., Nov. 2, 2001, "Improved lipid and lipoprotein profile, hepatic insulin sensitivity, and glucose tolerance in 11β-hydroxysteroid dehydrogenase type 1 null mice," *J. Biol. Chem.*, vol. 276(44), pp. 41293-41300.

Morton, N.M., et al., Apr. 2004, "Novel adipose tissue-mediated resistance to diet-induced visceral obesity in 11β-hydroxysteroid dehydrogenase type 1 deficient mice," *Diabetes*, vol. 53, pp. 931-938.

Patani, G.A., et al., 1996, "Bioisosterism: A rational approach in drug design", *American Chemical Society*, vol. 96, pp. 3147-3176.

Paterson, J.M., et al., May 4, 2004, "Metabolic syndrome without obesity: hepatic overexpression of 11β-hydroxysteroid dehydrogenase type 1 in transgenic mice," *Proc. Natl. Acad. Sci.*, vol. 101(18), pp. 7088-7093).

Rask, E., et al., 2001, "Tissue-specific dysregulation of cortisol metabolism in human obesity," *J. Clin. Endocrinol. Metab.*, vol. 86(3), pp. 1418-1421.

Rauz, S., et al., 2001, "Expression and putative role of 11β-hydroxysteroid dehydrogenase isozymes within the human eye," *Investigative Opthalmology & Visual Science*, vol. 42(9), pp. 2037-2042.

Sandeep, T.C., et al., Apr. 27, 2004, "11β-hydroxysteroid dehydrogenase inhibition improves cognitive function in healthy elderly men and type 2 diabetics," *Proc. Natl. Acad. Sci.*, vol. 101(17), pp. 6734-6739.

Seckl, J.R., Walker, B.R., 2001, "11β-Hydroxysteroid dehydrogenase type 1—a tissue-specific amplifier of glucocorticoid action," *Endocrinology*, vol. 142(4), pp. 1371-1376.

Small, G.R., et al., Aug. 23, 2005, "Preventing local regeneration of glucocorticoids by 11β-hydroxysteroid dehydrogenase type 1 enhances angiogenesis," *Proc. Natl. Acad. Sci.*, vol. 102(34), pp. 12165-12170.

Stimson, R.H., et al., 2010, "Extra-adrenal cortisol production in obese men with type two diabetes mellitus—how big is the therapeutic target for 11βHSD1 inhibitors?" $92^{nd}$ Annual Meeting of the Endocrine Society, San Diego, USA.

Walker, B.R., et al., 1991, "11β-Hydroxysteroid dehydrogenase in vascular smooth muscle and heart: implications for cardiovascular responses to glucocorticoids," *Endocrinology*, vol. 129(6), pp. 3305-3312.

Walker, B.R., et al., 1995, "Carbenoxolone increases hepatic insulin sensitivity in man: a novel role for 11-oxosteroid reductase in enhancing glucocorticoid receptor activation," *J. Clin. Endocrinol. Metab.*, vol. 80(11), pp. 3155-3139.

Yau, J.L.W., et al., Apr. 10, 2001, "Lack of tissue glucocorticoid reactivation in 11β-hydroxysteroid dehydrogenase type 1 knockout mice ameliorates age-related learning impairments," *Proc. Natl. Acad. Sci.*, vol. 98(8), pp. 4716-4721.

GB Search Report for UK Patent Appln No. 0724251.4, Mar. 27, 2003.
ISR and WOISA for PCT/GB2008/004068, Feb. 6, 2009.
IPRP for PCT/GB2008/004068, Jun. 15, 2010.
GB Search Report for UK Patent Appln No. 0804685.6, Jul. 10, 2008.
ISR and WOISA for PCT/GB2009/000686, Jun. 5, 2009.
IPRP for PCT/GB2009/000686, Sep. 14, 2010.
ISR and WOISA for PCT/GB2010/001155, Sep. 27, 2010.
IPRP for PCT/GB2010/001155, Dec. 16, 2011.
ISR and WOISA for PCT/GB2010/001732, Mar. 20, 2012.
IPRP for PCT/GB2010/001732, Mar. 20, 2012.

* cited by examiner

AMIDO-THIOPHENE COMPOUNDS AND THEIR USE AS 11-BETA-HSD1 INHIBITORS

RELATED APPLICATIONS

This application is a 35 U.S.C. §371 national phase application of PCT/GB2008/004068 (WO 2009/074789) filed 11 Dec. 2008, entitled "Amido-Thiophene Compounds and Their Use as 11β-HSD1 Inhibitors." PCT/GB2008/004068 is a non-provisional application of U.S. provisional patent application No. 61/013,042 filed 12 Dec. 2007 and United Kingdom patent application number 0724251.4 filed 12 Dec. 2007, the contents of both of which are incorporated herein by reference in their entirety.

TECHNICAL FIELD

The present invention pertains generally to the field of therapeutic compounds. More specifically the present invention pertains to certain amido-thiophene compounds that, inter alia, inhibit 11β-hydroxysteroid dehydrogenase type 1 (11β-HSD1). The present invention also pertains to pharmaceutical compositions comprising such compounds, and the use of such compounds and compositions, both in vitro and in vivo, to inhibit 11β-hydroxysteroid dehydrogenase type 1; to treat disorders that are ameliorated by the inhibition of 11β-hydroxysteroid dehydrogenase type 1; to treat the metabolic syndrome, which includes disorders such as type 2 diabetes and obesity, and associated disorders including insulin resistance, hypertension, lipid disorders and cardiovascular disorders such as ischaemic (coronary) heart disease; to treat CNS disorders such as mild cognitive impairment and early dementia, including Alzheimer's disease; etc.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Glucocorticoids (cortisol in man, corticosterone in rodents) are hormones that regulate a range of pathways involved in stress and metabolic signalling. They are antagonists of insulin action and impair insulin-dependent glucose uptake, increase lipolysis, and enhance hepatic gluconeogenesis. These effects are evident in Cushing's syndrome, which is caused by elevated circulating levels of glucocorticoids. The features of Cushing's syndrome are diverse and reflect the tissue distribution of glucocorticoid receptors in the body. They include a cluster of metabolic (central/visceral obesity, insulin resistance, hyperglycaemia, dyslipidaemia) and cardiovascular (hypertension) abnormalities which, when observed in patients without Cushing's syndrome, constitute the metabolic syndrome. These abnormalities confer a substantial risk of cardiovascular disease. In addition, Cushing's syndrome is associated with neuropsychiatric manifestations including depression and cognitive impairment. The features of Cushing's syndrome are reversible upon removal of the cause of glucocorticoid excess.

It is recognised that glucocorticoid activity is controlled at the tissue level by the intracellular conversion of active cortisol and inactive cortisone by 11β-hydroxysteroid dehydrogenases (see, e.g., Seckl et al., 2001). These enzymes exist in two distinct isoforms. 11β-HSD1, which catalyses the reaction that activates cortisone, is expressed in liver, adipose tissue, brain, skeletal muscle, vascular smooth muscle and other organs, while, 11β-HSD2, which inactivates cortisol, is predominantly expressed in the kidney. Pharmacological inhibition of 11β-HSD1 in rat and man with carbenoxolone (see, e.g., Walker et al., 1995), and transgenic knockout in mice (see, e.g., Kotelevtsev et al., 1997), results in enhanced hepatic insulin sensitivity and reduced gluconeogenesis and glycogenolysis, suggesting that 11β-HSD1 inhibition will be a useful treatment in type 2 diabetes and other insulin resistance syndromes. Furthermore, mice lacking 11β-HSD1 possess low triglycerides, increased HDL cholesterol, and increased apo-lipoprotein A-I levels (see, e.g., Morton et al., 2001), suggesting that inhibitors of 11β-HSD1 may be of utility in the treatment of atherosclerosis.

The link between 11β-HSD1 and the metabolic syndrome has been strengthened by studies in transgenic mice and man. 11β-HSD1 knockout mice on two different genetic backgrounds are protected from dietary obesity (see, e.g., Morton et al., 2004), while administration of carbenoxolone to patients with type 2 diabetes enhances insulin sensitivity (see, e.g., Andrews et al., 2003). However, it has become apparent that the key tissue in which 11β-HSD1 exerts the greatest influence upon metabolic disease is the adipose tissue rather than the liver. Mice with transgenic overexpression of 11β-HSD1 in adipose tissue (see, e.g. Masuzaki et al., 2001) have a more profound metabolic syndrome and obesity than mice with overexpression in liver (see, e.g., Paterson et al., 2004). In obese humans, 11β-HSD1 activity is increased in adipose tissue, but enzyme activity is decreased in the liver (see, e.g., Rask et al., 2001).

In the CNS, 11β-HSD1 is highly expressed in regions important for cognition such as hippocampus, frontal cortex, and cerebellum (see, e.g., Moison et al., 1990). Elevated cortisol is associated with cognitive dysfunction, and glucocorticoids have a range of neurotoxic effects. 11β-HSD1 knockout mice are protected against age-related cognitive dysfunction (see, e.g., Yau et al., 2001), while administration of the 11β-HSD inhibitor carbenoxolone has been shown to enhance cognitive function in elderly men and type 2 diabetics who have a selective impairment in verbal memory (see, e.g., Sandeep et al., 2004). Thus, 11β-HSD1 inhibitors are of potential therapeutic utility in the treatment of diseases such as Alzheimer's Disease, which are characterised by cognitive impairment.

The isozymes of 11β-HSD are also expressed in the blood vessel wall (see, e.g., Walker et al., 1991; Christy et al., 2003). 11β-HSD1 is expressed in vascular smooth muscle, while 11β-HSD2 is expressed in endothelial cells where it modulates endothelial-dependent vasodilation (see, e.g., Hadoke et al., 2001). 11β-HSD1 knockout mice have normal vascular function, but they exhibit enhanced angiogenesis in response to inflammation or ischaemia (see, e.g., Small et al., 2005). This offers therapeutic potential in the treatment of myocardial infarction, since inhibition of 11β-HSD1 may enhance revascularisation of ischaemic tissues.

Studies have shown that 11β-HSD1 affects intraocular pressure in man (see, e.g., Rauz et al., 2001). Inhibition of 11β-HSD1 may be useful in reducing intraocular pressure in the treatment of glaucoma.

Glucocorticoids are involved in the regulation of bone formation and skeletal development. Treatment of healthy volunteers with carbenoxolone led to a decrease in bone resorption markers suggesting that 11β-HSD1 plays a role in bone resorption (see, e.g., Cooper et al., 2000). 11β-HSD1 inhibitors could be used as protective agents in the treatment of osteoporosis.

The inventors have discovered compounds that inhibit 11β-hydroxysteroid dehydrogenase type 1 (11β-HSD1) that are useful in the treatment, control, and/or prevention of disorders (e.g., diseases) that are responsive to the inhibiton of 11β-HSD1.

SUMMARY OF THE INVENTION

One aspect of the invention pertains to certain amido-thiophenes (referred to herein as AMTP compounds), as described herein.

Another aspect of the invention pertains to a composition (e.g., a pharmaceutical composition) comprising an AMTP compound, as described herein, and a pharmaceutically acceptable carrier or diluent.

Another aspect of the invention pertains to a method of preparing a composition (e.g., a pharmaceutical composition) comprising the step of admixing an AMTP compound, as described herein, and a pharmaceutically acceptable carrier or diluent.

Another aspect of the present invention pertains to a method of inhibiting 11β-hydroxysteroid dehydrogenase type 1 (11β-HSD1) function (e.g., in a cell), in vitro or in vivo, comprising contacting the cell with an effective amount of an AMTP compound, as described herein.

Another aspect of the present invention pertains to a method of treatment comprising administering to a subject in need of treatment a therapeutically-effective amount of an AMTP compound, as described herein, preferably in the form of a pharmaceutical composition.

Another aspect of the present invention pertains to an AMTP compound as described herein for use in a method of treatment of the human or animal body by therapy.

Another aspect of the present invention pertains to use of an AMTP compound, as described herein, in the manufacture of a medicament for use in treatment.

In one embodiment, the treatment is treatment or prevention of a disorder (e.g., a disease) that is ameliorated by the inhibition of 11β-hydroxysteroid dehydrogenase type 1 (11β-HSD1).

In one embodiment, the treatment is treatment or prevention of metabolic syndrome, which includes conditions such as type 2 diabetes and obesity, and associated disorders including insulin resistance, hypertension, lipid disorders and cardiovascular disorders such as ischaemic (coronary) heart disease.

In one embodiment, the treatment is treatment or prevention of a CNS disorder (e.g., a CNS disease) such as mild cognitive impairment and early dementia, including Alzheimer's disease.

Another aspect of the present invention pertains to a kit comprising (a) an AMTP compound, as described herein, preferably provided as a pharmaceutical composition and in a suitable container and/or with suitable packaging; and (b) instructions for use, for example, written instructions on how to administer the compound.

Another aspect of the present invention pertains to an AMTP compound obtainable by a method of synthesis as described herein, or a method comprising a method of synthesis as described herein.

Another aspect of the present invention pertains to an AMTP compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain amido-thiophenes (for convenience, collectively referred to herein as "amido-thiophene compounds" or "AMTP compounds").

In one embodiment, the compounds are selected from compounds of the following formula, and pharmaceutically acceptable salts, hydrates, and solvates thereof:

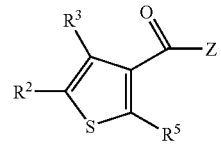

wherein:
—$R^2$ is independently —$R^{2A}$, —$R^{2B}$, —$R^{2C}$, or —$R^{2D}$;
—$R^3$ is independently —H, —$R^{3A}$, —$R^{3B}$, or —$R^{3C}$;
—$R^5$ is independently —H, —$R^{5A}$, —$R^{5B}$, or —$R^{5C}$; and
—Z is independently -$J^1$, -$J^2$, -$J^3$, or -$J^4$;
with the proviso that:
if: —$R^2$ is —$R^{2A}$, then: —$R^3$ is not —$R^{3A}$; and
with the proviso that:
if: —$R^2$ is —$R^{2A}$, and —$R^5$ is —H or —$R^{5A}$, then: —Z is independently -$J^2$ or -$J^3$;
wherein:
—$R^{2A}$ is independently —$R^{2A1}$, —$R^{2A2}$, or —$R^{2A3}$;
—$R^{2A1}$ is independently saturated aliphatic $C_{1-6}$alkyl;

—$R^{2A2}$ is independently saturated aliphatic $C_{1-6}$alkyl substituted with one or more fluorine atoms;
—$R^{2A3}$ is independently saturated aliphatic $C_{1-6}$alkyl substituted with —CN;
—$R^{2B}$ is independently —$R^{2BL}$-M-$R^{2BR}$;
—$R^{2BL}$— is independently saturated aliphatic $C_{1-4}$alkylene;
-M- is independently —O—, —S—, —S(=O)—, or —S(=O)$_2$—;
—$R^{2BR}$ is independently —$R^{2B1}$, —$R^{2B2}$, or —$R^{2B3}$;
—$R^{2B1}$ is independently saturated aliphatic $C_{1-6}$alkyl, and is optionally substituted;
—$R^{2B2}$ is independently $C_{6-10}$carboaryl, and is optionally substituted;
—$R^{2B3}$ is independently $C_{5-10}$heteroaryl, and is optionally substituted;
—$R^{2C}$ is independently non-aromatic $C_{4-7}$heterocyclyl, and is optionally substituted;
—$R^{2D}$ is independently saturated $C_{3-7}$cycloalkyl, and is optionally substituted;
—$R^{3A}$ is independently saturated aliphatic $C_{1-4}$alkyl;
—$R^{3B}$ is independently —F, —Cl or —Br;
—$R^{3D}$ is independently —CN;
—$R^{5A}$ is independently saturated aliphatic $C_{1-4}$alkyl;
—$R^{5B}$ is independently —F, —Cl or —Br; and
—$R^{5D}$ is independently —CN;
-$J^1$ is independently a monocyclic non-aromatic heterocyclyl group having from 4 to 8 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said non-aromatic heterocyclyl group is optionally substituted;
-$J^2$ is independently a fused bicyclic non-aromatic heterocyclyl group having from 9 to 12 ring atoms, wherein: exactly 1 of said ring atoms is a ring heteroatom, and is N; or exactly 2 of said ring atoms are ring heteroatoms, and are both N; or exactly 2 of said ring atoms are ring heteroatoms, and are N and O; or exactly 2 of said ring atoms are ring heteroatoms, and are N and S; or exactly 3 of said ring atoms are ring heteroatoms, wherein one ring heteroatom is N, and the other two ring heteroatoms are selected from N, O, and S; and wherein said fused bicyclic non-aromatic heterocyclyl group is optionally substituted;
-$J^3$ is independently a bridged non-aromatic heterocyclyl group having from 7 to 11 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said bridged non-aromatic heterocyclyl group is optionally substituted; and
-$J^4$ is independently a Spiro non-aromatic heterocyclyl group having from 8 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, or exactly 3 of said ring atoms are ring heteroatoms, one of which is N, and each of the other two is independently N, O, or S, and wherein said Spiro non-aromatic heterocyclyl group is optionally substituted.

For the avoidance of doubt, it is not intended that —$R^2$, —$R^3$, and —$R^5$ are attached to one another other than as shown in the above formula. For example, it is not intended that —$R^2$ and —$R^3$ together form a ring fused to the central thiophene ring. Similarly, it is not intended that —$R^2$ and —$R^5$ together form a ring fused to the central thiophene ring. Similarly, it is not intended that —$R^3$ and —$R^5$ together form a ring fused to the central thiophene ring.

Also for the avoidance of doubt, it is not intended that —$R^2$, —$R^3$, and —$R^5$ are attached to —Z other than as shown in the above formula. For example, it is not intended that —$R^2$ and —Z together form a ring fused to the central thiophene ring. Similarly, it is not intended that —$R^3$ and —Z together form a ring fused to the central thiophene ring. Similarly, it is not intended that —$R^5$ and —Z together form a ring fused to the central thiophene ring.

The Group —$R^2$

In one embodiment, —$R^2$ is independently —$R^{2A}$, —$R^{2B}$, —$R^{2C}$, or —$R^{2D}$.

In one embodiment, —$R^2$ is independently —$R^{2B}$, —$R^{2C}$, or —$R^{2D}$.

In one embodiment, —$R^2$ is independently —$R^{2A}$ or —$R^{2B}$.

In one embodiment, —$R^2$ is independently —$R^{2C}$ or —$R^{2D}$.

In one embodiment, —$R^2$ is independently —$R^{2A}$.
In one embodiment, —$R^2$ is independently —$R^{2B}$.
In one embodiment, —$R^2$ is independently —$R^{2C}$.
In one embodiment, —$R^2$ is independently —$R^{2D}$.

The Group —Z

In one embodiment, —Z is independently -$J^1$, -$J^2$, -$J^3$, or -$J^4$.

In one embodiment, —Z is independently -$J^2$, -$J^3$, or -$J^4$.
In one embodiment, —Z is independently -$J^1$.
In one embodiment, —Z is independently -$J^2$.
In one embodiment, —Z is independently -$J^3$.
In one embodiment, —Z is independently -$J^4$.

The Group —$R^3$

In one embodiment, —$R^3$ is independently —H, —$R^{3A}$, —$R^{3B}$, or —$R^{3C}$.

In one embodiment, —$R^3$ is independently —H.
In one embodiment, —$R^3$ is independently —$R^{3A}$, —$R^{3B}$, or —$R^{3C}$.

In one embodiment, —$R^3$ is independently —$R^{3B}$ or —$R^{3C}$.

In one embodiment, —$R^3$ is independently —$R^{3A}$.
In one embodiment, —$R^3$ is independently —$R^{3B}$.
In one embodiment, —$R^3$ is independently —$R^{3C}$.

The Group —$R^5$

In one embodiment, —$R^5$ is independently —H, —$R^{5A}$, —$R^{5B}$, or —$R^{5C}$.

In one embodiment, —$R^5$ is independently —$R^{5A}$, —$R^{5B}$, or —$R^{5C}$.

In one embodiment, —$R^5$ is independently —H, —$R^{5B}$, or —$R^{5C}$.

In one embodiment, —$R^5$ is independently —$R^{5B}$ or —$R^{5C}$.

In one embodiment, —$R^5$ is independently —H.
In one embodiment, —$R^5$ is independently —$R^{5A}$.
In one embodiment, —$R^5$ is independently —$R^{5B}$.
In one embodiment, —$R^5$ is independently —$R^{5C}$.

The Group —$R^{2A}$

In one embodiment, —$R^{2A}$ is independently —$R^{2A1}$, —$R^{2A2}$, or —$R^{2A3}$.

In one embodiment, —$R^{2A}$ is independently —$R^{2A1}$ or —$R^{2A2}$.

In one embodiment, —$R^{2A}$ is independently —$R^{2A1}$.

In one embodiment, —$R^{2A}$ is independently —$R^{2A2}$.
In one embodiment, —$R^{2A}$ is independently —$R^{2A3}$.

The Group —$R^{2A1}$

In one embodiment, —$R^{2A1}$ is independently saturated aliphatic $C_{1-6}$alkyl.

In one embodiment, —$R^{2A1}$ is independently -Me, -Et, -nPr, -iPr, -nBu, -sBu, -tBu, or -nPentyl.

In one embodiment, —$R^{2A1}$ is independently -Me, -Et, -nPr, or -iPr.

In one embodiment, —$R^{2A1}$ is independently -Me or -Et.

In one embodiment, —$R^{2A1}$ is independently -Me.

In one embodiment, —$R^{2A1}$ is independently -Et.

In one embodiment, —$R^{2A1}$ is independently -iPr.

In one embodiment, —$R^{2A1}$ is independently -nPr.

In one embodiment, —$R^{2A1}$ is independently -tBu.

In one embodiment, —$R^{2A1}$ is independently -nPentyl.

The Group —$R^{2A2}$

In one embodiment, —$R^{2A2}$ is independently saturated aliphatic $C_{1-6}$alkyl substituted with one or more (e.g., 1, 2, 3, etc.) fluorine atoms.

In one embodiment, —$R^{2A2}$ is independently —$CF_3$ or —$CH_2CF_3$.

In one embodiment, —$R^{2A2}$ is independently —$CH_2CF_3$.

The Group —$R^{2A3}$

In one embodiment, —$R^{2A3}$ is independently saturated aliphatic $C_{1-4}$alkyl substituted with —CN.

In one embodiment, —$R^{2A3}$ is independently —$CH_2$—CN.

The Group —$R^{2B}$

In one embodiment, —$R^{2B}$ is independently —$R^{2BL}$-M-$R^{2BR}$.

In one embodiment, —$R^{2BL}$— is independently saturated aliphatic $C_{1-4}$alkylene.

In one embodiment, —$R^{2BL}$— is independently —$CH_2$—.

In one embodiment, -M- is independently —O—, —S—, —S(=O)—, or —S(=O)$_2$—.

In one embodiment, -M- is independently —O— or —S—.

In one embodiment, -M- is independently —O—.

In one embodiment, —$R^{2BR}$ is independently —$R^{2B1}$, —$R^{2B2}$, or —$R^{2B3}$.

In one embodiment, —$R^{2BR}$ is independently —$R^{2B1}$.

In one embodiment, —$R^{2BR}$ is independently —$R^{2B2}$ or —$R^{2B3}$.

In one embodiment, —$R^{2BR}$ is independently —$R^{2B2}$.

In one embodiment, —$R^{2BR}$ is independently —$R^{2B3}$.

The Group —$R^{2B1}$

In one embodiment, —$R^{2B1}$ is independently saturated aliphatic $C_{1-6}$alkyl, and is optionally substituted.

In one embodiment, —$R^{2B1}$ is independently saturated aliphatic $C_{1-4}$alkyl, and is optionally substituted.

In one embodiment, —$R^{2B1}$ is independently saturated aliphatic $C_{1-2}$alkyl, and is optionally substituted.

In one embodiment, —$R^{2B1}$ is independently -Me.

The Group —$R^{2B2}$

In one embodiment, —$R^{2B2}$ is independently $C_{6-10}$carboaryl, and is optionally substituted.

In one embodiment, —$R^{2B2}$ is independently phenyl, and is optionally substituted.

The Group —$R^{2B3}$

In one embodiment, —$R^{2B3}$ is independently $C_{5-10}$heteroaryl, and is optionally substituted.

In one embodiment, —$R^{2B3}$ is independently furanyl, thienyl, pyrrolyl, imidazolyl, pyrazolyl, triazolyl, oxazolyl, isoxazolyl, thiazolyl, isothiazolyl, pyridyl, pyrimidinyl, pyridazinyl, indolyl, isoindolyl, benzofuranyl, isobenzofuranyl, benzothienyl, isobenzothienyl, indazolyl, benzimidazolyl, benzothiazolyl, benzoxazolyl, quinolinyl, isoquinolinyl, cinnolinyl, or quinazolinyl, and is optionally substituted.

In one embodiment, —$R^{2B3}$ is independently $C_{5-6}$heteroaryl, and is optionally substituted.

In one embodiment, —$R^{2B3}$ is independently furanyl, thienyl, pyrrolyl, imidazolyl, pyrazolyl, triazolyl, oxazolyl, isoxazolyl, thiazolyl, isothiazolyl, pyridyl, pyrimidinyl, pyridazinyl, and is optionally substituted.

In one embodiment, —$R^{2B3}$ is independently $C_{9-10}$heteroaryl, and is optionally substituted.

In one embodiment, —$R^{2B3}$ is independently indolyl, isoindolyl, benzofuranyl, isobenzofuranyl, benzothienyl, isobenzothienyl, indazolyl, benzimidazolyl, benzothiazolyl, benzoxazolyl, quinolinyl, isoquinolinyl, cinnolinyl, or quinazolinyl, and is optionally substituted.

The Group —$R^{2C}$

In one embodiment, —$R^{2C}$ is independently non-aromatic $C_{4-7}$heterocyclyl, and is optionally substituted.

In one embodiment, —$R^{2C}$ is independently azetidinyl, oxitanyl, pyrrolidinyl, tetrahydrofuranyl, piperidinyl, tetrahydropyridinyl, tetrahydropyranyl, piperazinyl, morpholinyl, thiomorpholinyl, tetrahydrothiopyranyl, tetrahydrothiopyran-1,1-dioxide, azepanyl, diazepanyl, or oxazepanyl, and is optionally substituted.

In one embodiment, —$R^{2C}$ is independently azetidinyl, oxitanyl, pyrrolidinyl, tetrahydrofuranyl, piperidinyl, tetrahydropyridinyl, tetrahydropyranyl, piperazinyl, morpholinyl, thiomorpholinyl, azepanyl, diazepanyl, or oxazepanyl, and is optionally substituted.

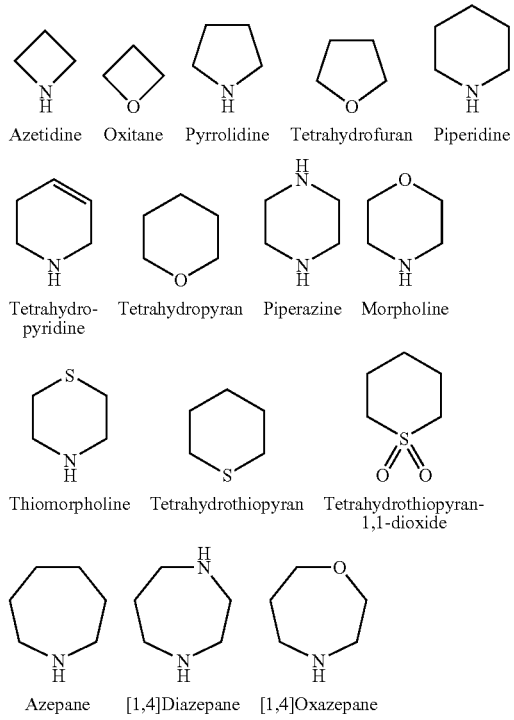

Azetidine  Oxitane  Pyrrolidine  Tetrahydrofuran  Piperidine

Tetrahydropyridine  Tetrahydropyran  Piperazine  Morpholine

Thiomorpholine  Tetrahydrothiopyran  Tetrahydrothiopyran-1,1-dioxide

Azepane  [1,4]Diazepane  [1,4]Oxazepane

In one embodiment, —$R^{2C}$ is independently tetrahydropyranyl, and is optionally substituted.

In one embodiment, —$R^{2C}$ is independently tetrahydropyran-4-yl, and is optionally substituted.

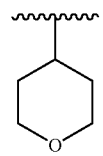

Tetrahydropyran-4-yl

In one embodiment, —$R^{2C}$ is independently piperidinyl, and is optionally substituted.

In one embodiment, —$R^{2C}$ is independently piperidin-1-yl, and is optionally substituted.

In one embodiment, —$R^{2C}$ is independently piperidin-3-yl, and is optionally substituted.

In one embodiment, —$R^{2C}$ is independently piperidin-2-yl, and is optionally substituted.

In one embodiment, —$R^{2C}$ is independently piperidin-4-yl, and is optionally substituted.

In one embodiment, —$R^{2C}$ is independently piperidin-2-one-4-yl, and is optionally substituted.

In one embodiment, —$R^{2C}$ is independently piperidin-2-one-5-yl, and is optionally substituted.

In one embodiment, —$R^{2C}$ is independently piperidin-2-one-6-yl, and is optionally substituted.

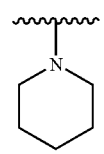 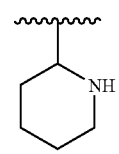 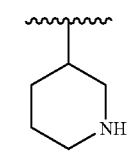

Piperidin-1-yl (also known as piperidino)   Piperidin-2-yl   Piperidin-3-yl

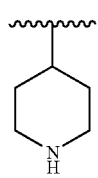 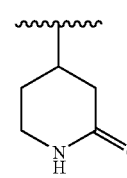 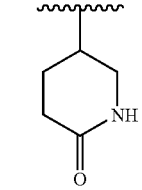

Piperidin-4-yl   Piperidin-2-one-4-yl   Piperidin-2-one-5-yl

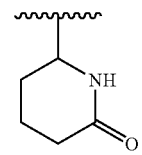

Piperidin-2-one-6-yl

For example, in one embodiment, —$R^{2C}$ is independently piperidin-4-yl, and is N-substituted, for example, with a substituent as defined herein (see "Optional Substituents on the Group —$R^{2C}$").

For example, in one embodiment, —$R^{2C}$ is independently selected from:

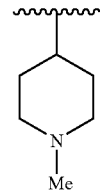 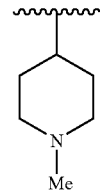 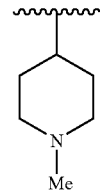 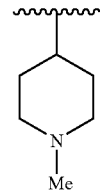

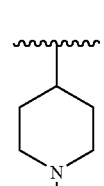 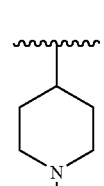 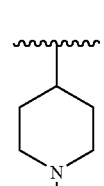

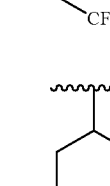 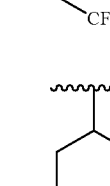 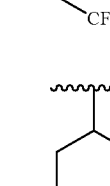

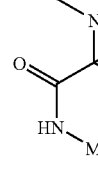 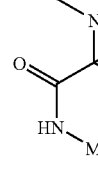 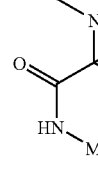

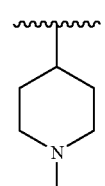 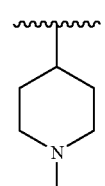 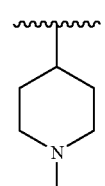

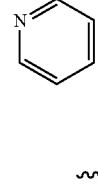 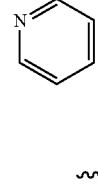 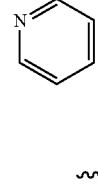

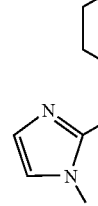 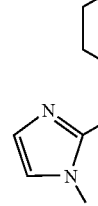 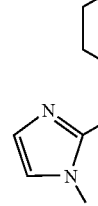

  

For example, in one embodiment, —$R^{2C}$ is independently selected from:
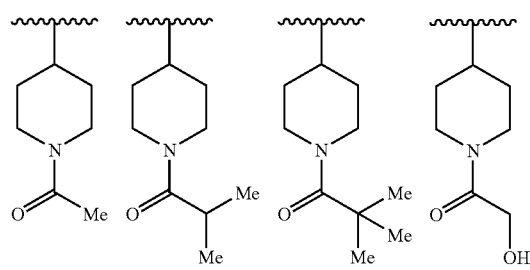
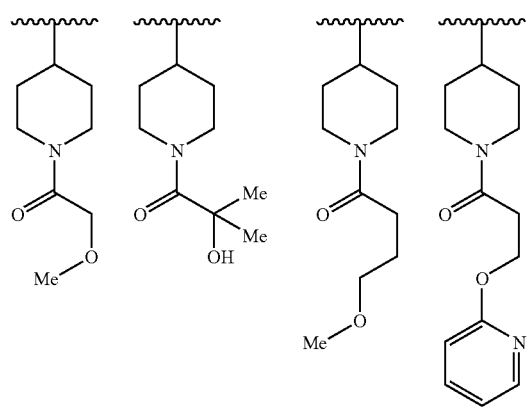
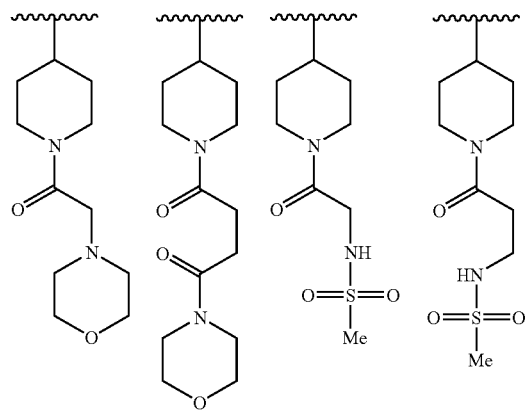
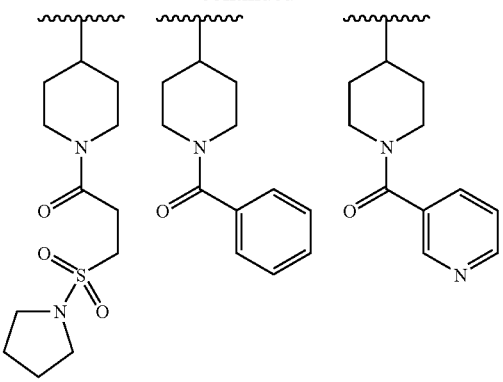
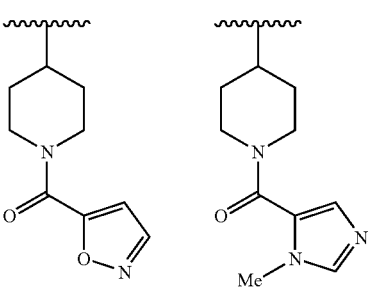
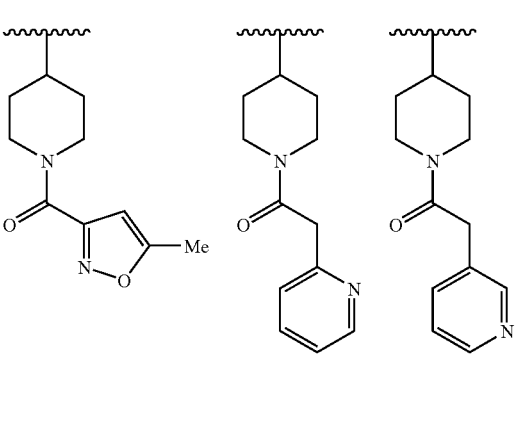
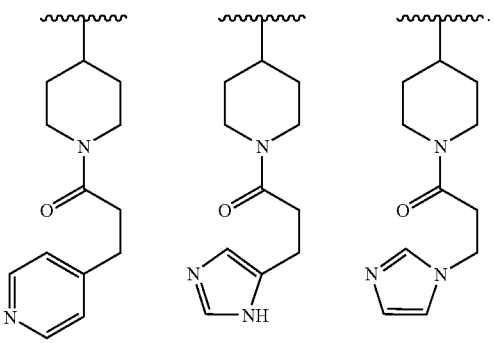

For example, in one embodiment, —R$^{2C}$ is independently selected from:

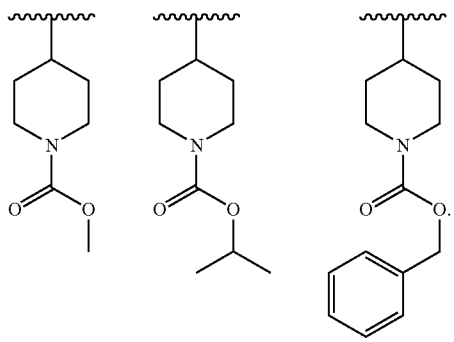

For example, in one embodiment, —R$^{2C}$ is independently selected from:

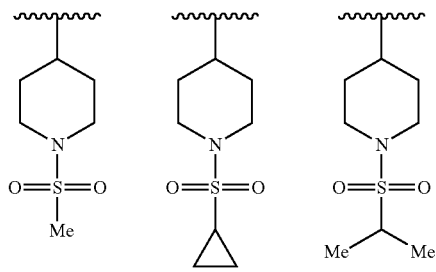

For example, in one embodiment, —R$^{2C}$ is independently selected from:

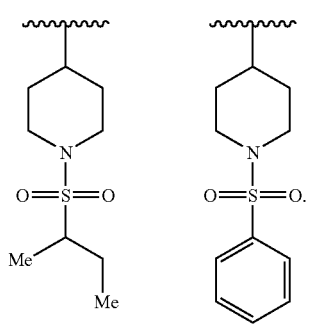

For example, in one embodiment, —R$^{2C}$ is independently selected from:

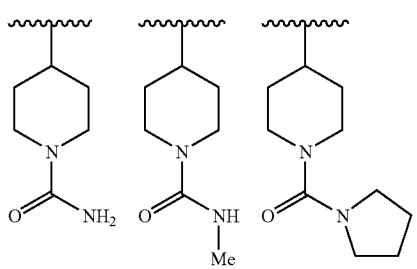

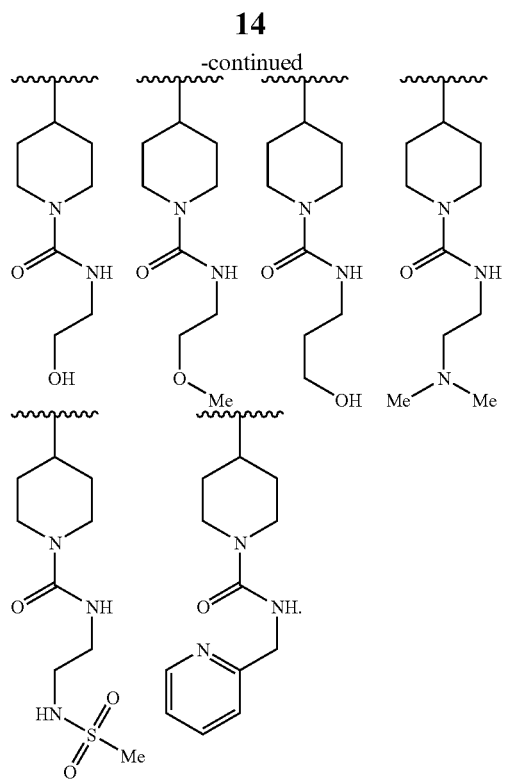

In one embodiment, —R$^{2C}$ is independently tetrahydropyridinyl, and is optionally substituted.

In one embodiment, —R$^{2C}$ is independently 1,2,3,6-tetrahydropyridin-4-yl, and is optionally substituted.

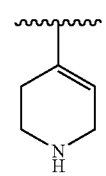

1,2,3,6-Tetrahydro-pyridin-4-yl

For example, in one embodiment, —R$^{2C}$ is independently 1,2,3,6-tetrahydropyridin-4-yl, and is N-substituted, for example, with a substituent as defined herein (see "Optional Substituents on the Group —R$^{2C}$").

For example, in one embodiment, —R$^{2C}$ is independently selected from:

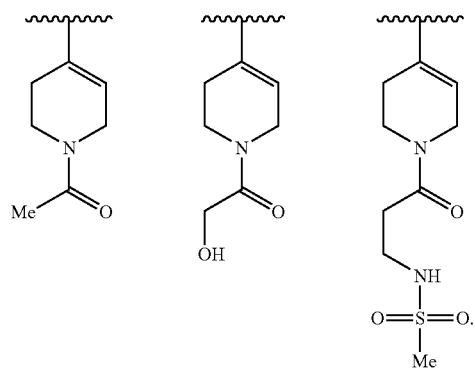 [SMILES: *C1=CCN(C(C)=O)CC1 ; *C1=CCN(C(=O)CO)CC1 ; *C1=CCN(C(=O)CCNS(C)(=O)=O)CC1]

In one embodiment, —R$^{2C}$ is independently piperazinyl, and is optionally substituted.

In one embodiment, —R$^{2C}$ is independently piperazin-1-yl, and is optionally substituted.

In one embodiment, —R$^{2C}$ is independently piperazin-2-one-1-yl, and is optionally substituted.

In one embodiment, —R$^{2C}$ is independently piperazin-3-one-1-yl, and is optionally substituted.

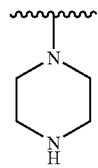 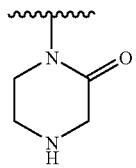 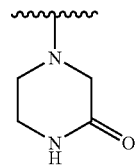

Piperazin-1-yl    Piperazin-2-one-1-yl    Piperazin-3-one-1-yl

In one embodiment, —R$^{2C}$ is independently pyrrolidinyl, and is optionally substituted.

In one embodiment, —R$^{2C}$ is independently pyrrolidin-1-yl, and is optionally substituted.

In one embodiment, —R$^{2C}$ is independently pyrrolidin-2-one-1-yl, and is optionally substituted.

In one embodiment, —R$^{2C}$ is independently pyrrolidin-3-yl, and is optionally substituted.

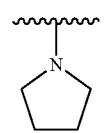 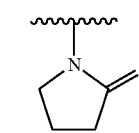 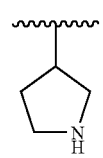

Pyrrolidin-1-yl    Pyrrolidin-2-one-1-yl    Pyrrolidin-3-yl

For example, in one embodiment, —R$^{2C}$ is independently pyrrolidin-3-yl, and is N-substituted, for example, with a substituent as defined herein (see "Optional Substituents on the Group —R$^{2C}$").

For example, in one embodiment, —R$^{2C}$ is independently:

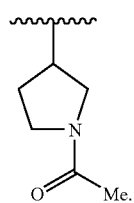 [SMILES: *C1CCN(C(C)=O)C1]

In one embodiment, —R$^{2C}$ is independently azetidinyl, and is optionally substituted.

In one embodiment, —R$^{2C}$ is independently azetidin-1-yl, and is optionally substituted.

In one embodiment, —R$^{2C}$ is independently azetidin-3-yl, and is optionally substituted.

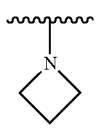

Azetidin-1-yl

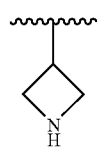

Azetidin-3-yl

In one embodiment, —R$^{2C}$ is independently morpholinyl, and is optionally substituted.

In one embodiment, —R$^{2C}$ is independently morpholin-4-yl, and is optionally substituted.

In one embodiment, —R$^{2C}$ is independently morpholin-3-one-4-yl, and is optionally substituted.

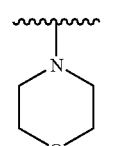

Morpholin-4-yl
(also known as morpholino)

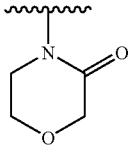

Morpholin-3-one-4-yl

In one embodiment, —R$^{2C}$ is independently thiomorpholinyl, and is optionally substituted.

In one embodiment, —R$^{2C}$ is independently thiomorpholin-4-yl, and is optionally substituted.

In one embodiment, —R$^{2C}$ is independently thiomorpholin-3-one-4-yl, and is optionally substituted.

In one embodiment, —R$^{2C}$ is independently thiomorpholin-1,1-dioxide-4-yl, and is optionally substituted.

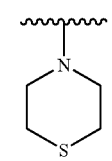

Thiomorpholin-4-yl
(also known as thiomorpholino)

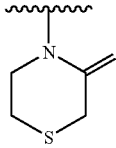

Thiomorpholin-3-one-4-yl

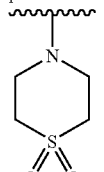

Thiomorpholin-1,1-dioxide-4-yl

The Group —$R^{2D}$

In one embodiment, —$R^{2D}$ is independently saturated $C_{3-7}$cycloalkyl, and is optionally substituted.

In one embodiment, —$R^{2D}$ is independently saturated $C_{5-6}$cycloalkyl, and is optionally substituted.

In one embodiment, —$R^{2D}$ is independently cyclohexyl, and is optionally substituted.

The Group —$R^{3A}$

In one embodiment, —$R^{3A}$ is independently saturated aliphatic $C_{1-4}$alkyl.

In one embodiment, —$R^{3A}$ is independently -Me, -Et, -nPr, or -iPr.

In one embodiment, —$R^{3A}$ is independently -Me.

The Group —$R^{3B}$

In one embodiment, —$R^{3B}$ is independently —F, —Cl, or —Br.

In one embodiment, —$R^{3B}$ is independently —Cl or —Br.

In one embodiment, —$R^{3B}$ is independently —Cl.

In one embodiment, —$R^{3B}$ is independently —Br.

The Group —$R^{3C}$

In one embodiment, —$R^{3C}$ is independently —CN.

The Group —$R^{5A}$

In one embodiment, —$R^{5A}$ is independently saturated aliphatic $C_{1-4}$alkyl.

In one embodiment, —$R^{5A}$ is independently -Me, -Et, -nPr, or -iPr.

In one embodiment, —$R^{5A}$ is independently -Me.

The Group —$R^{5B}$

In one embodiment, —$R^{5B}$ is independently —F, —Cl, or —Br.

In one embodiment, —$R^{5B}$ is independently —Cl or —Br.

In one embodiment, —$R^{5B}$ is independently —Cl.

In one embodiment, —$R^{5B}$ is independently —Br.

The Group —$R^{5C}$

In one embodiment, —$R^{5C}$ is independently —CN.

The Group -$J^1$

In one embodiment, -$J^1$ is independently a monocyclic non-aromatic heterocyclyl group having from 4 to 8 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said non-aromatic heterocyclyl group is optionally substituted.

In one embodiment, the monocyclic non-aromatic heterocyclyl group has from 4 to 7 ring atoms.

In one embodiment, the monocyclic non-aromatic heterocyclyl group has from 5 to 7 ring atoms.

In one embodiment, the monocyclic non-aromatic heterocyclyl group has 6 or 7 ring atoms.

In one embodiment, exactly 1 of said ring atoms is a ring heteroatom, and is N.

In one embodiment, exactly 2 of said ring atoms are ring heteroatoms, and are both N.

In one embodiment, exactly 2 of said ring atoms are ring heteroatoms, and are N and O.

In one embodiment, exactly 2 of said ring atoms are ring heteroatoms, and are N and S.

In one embodiment, -$J^1$ is independently selected from the following groups and corresponding groups having one or more substituents, for example, one or more substituents selected from saturated aliphatic $C_{1-3}$alkyl, phenyl, and pyridyl:

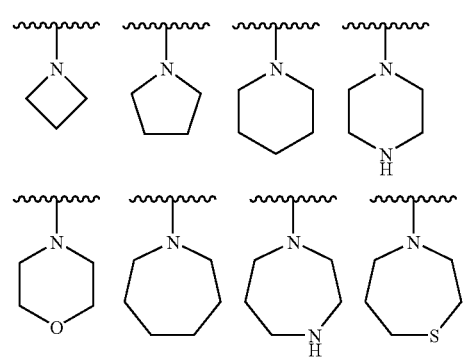

In one embodiment, -$J^1$ is independently selected from the following groups and corresponding groups having one or more substituents, for example, one or more substituents selected from saturated aliphatic $C_{1-3}$alkyl, phenyl, and pyridyl:

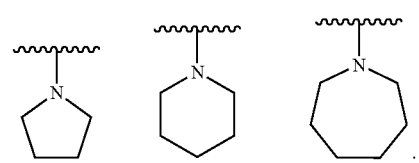 [SMILES: *N1CCCC1 ; *N1CCCCC1 ; *N1CCCCCC1]

Examples of such groups which additionally bear one or more substituents (e.g., —F, -Me, phenyl, pyridyl) include the following:

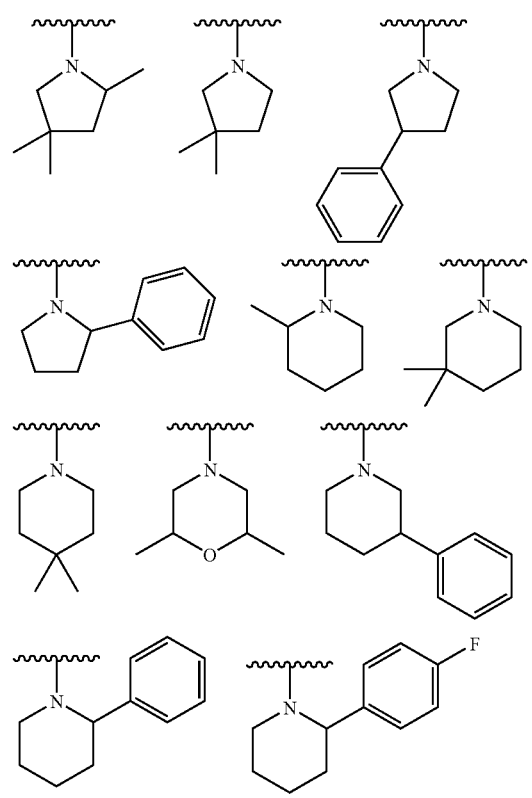

19

-continued

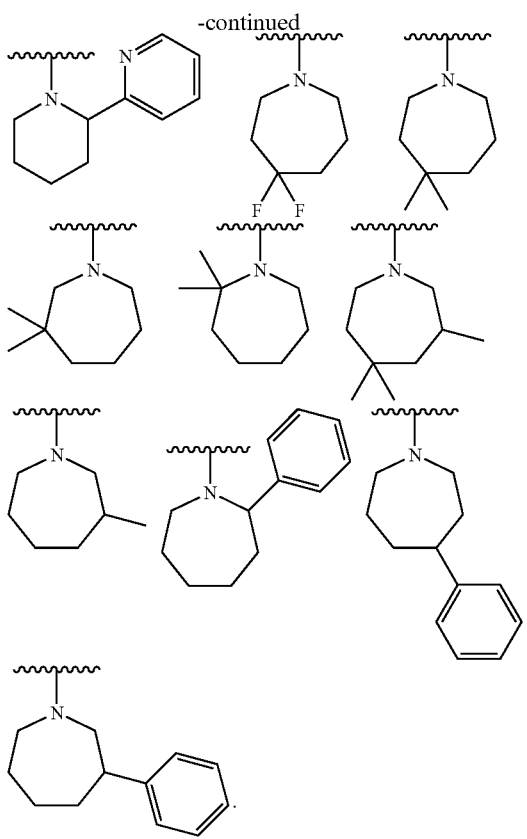

The Group -J²

In one embodiment, -J² is independently a fused bicyclic non-aromatic heterocyclyl group having from 9 to 12 ring atoms, wherein: exactly 1 of said ring atoms is a ring heteroatom, and is N; or exactly 2 of said ring atoms are ring heteroatoms, and are both N; or exactly 2 of said ring atoms are ring heteroatoms, and are N and O; or exactly 2 of said ring atoms are ring heteroatoms, and are N and S; or exactly 3 of said ring atoms are ring heteroatoms, wherein one ring heteroatom is N, and the other two ring heteroatoms are selected from N, O, and S; and wherein said fused bicyclic non-aromatic heterocyclyl group is optionally substituted.

In one embodiment, -J² is independently a fused bicyclic non-aromatic heterocyclyl group having from 9 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said fused bicyclic non-aromatic heterocyclyl group is optionally substituted.

In one embodiment, the fused bicyclic non-aromatic heterocyclyl group has 9 to 10 ring atoms.

In one embodiment, the fused bicyclic non-aromatic heterocyclyl group has 9 ring atoms.

In one embodiment, the fused bicyclic non-aromatic heterocyclyl group has 10 ring atoms.

In one embodiment, exactly 1 of said ring atoms is a ring heteroatom, and is N.

In one embodiment, exactly 2 of said ring atoms are ring heteroatoms, and are both N.

In one embodiment, exactly 2 of said ring atoms are ring heteroatoms, and are N and O.

20

In one embodiment, exactly 2 of said ring atoms are ring heteroatoms, and are N and S.

In one embodiment, exactly 3 of said ring atoms are ring heteroatoms, wherein one ring heteroatom is N, and the other two ring heteroatoms are selected from N, O, and S.

In one embodiment, -J² is independently selected from the following groups and corresponding groups having one or more substituents, for example, one or more substituents selected from saturated aliphatic $C_{1-3}$alkyl:

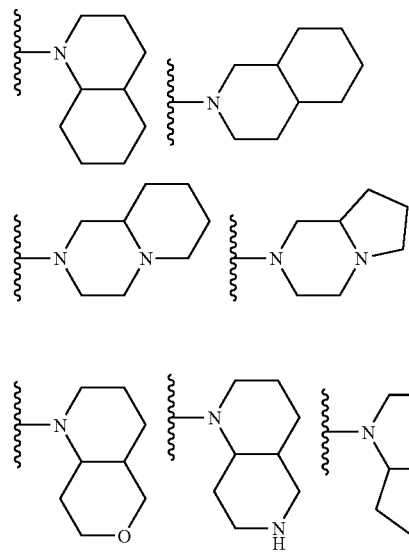

In one embodiment, -J² is independently selected from the following groups and corresponding groups having one or more substituents, for example, one or more substituents selected from saturated aliphatic $C_{1-3}$alkyl:

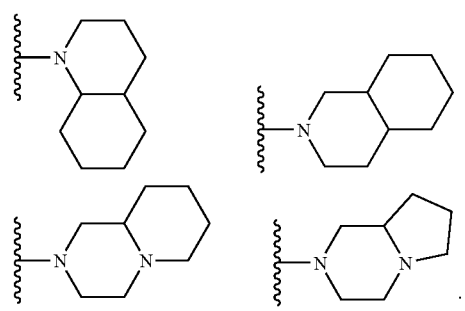

In one embodiment, -J² is independently selected from the following group and corresponding groups having one or more substituents, for example, one or more substituents selected from saturated aliphatic $C_{1-3}$alkyl:

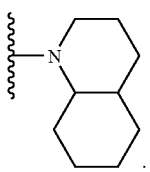 [SMILES: *N1CCCC2CCCCC21]

An example of such groups which additionally bear one or more substituents (e.g., —F, -Me, phenyl, pyridyl) include the following:

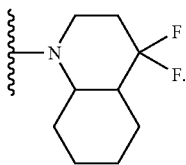 [SMILES: *N1CCC(F)(F)C2CCCCC21]

In one embodiment, -J² is independently:

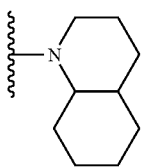

In one embodiment, -J² is independently selected from:

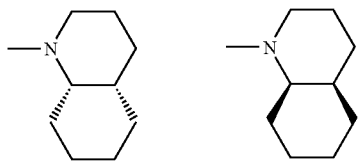

In one embodiment, -J² is independently selected from:

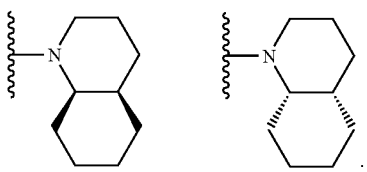 [SMILES: *N1CCC[C@H]2CCCC[C@H]21 ; *N1CCC[C@@H]2CCCC[C@@H]21]

The Group -J³

In one embodiment, -J³ is independently a bridged non-aromatic heterocyclyl group having from 7 to 11 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said bridged non-aromatic heterocyclyl group is optionally substituted.

In one embodiment, the bridged non-aromatic heterocyclyl group has 7 ring atoms.

In one embodiment, the bridged non-aromatic heterocyclyl group has 8 ring atoms.

In one embodiment, the bridged non-aromatic heterocyclyl group has 9 ring atoms.

In one embodiment, the bridged non-aromatic heterocyclyl group has 11 ring atoms.

In one embodiment, exactly 1 of said ring atoms is a ring heteroatom, and is N.

In one embodiment, exactly 2 of said ring atoms are ring heteroatoms, and are both N.

In one embodiment, exactly 2 of said ring atoms are ring heteroatoms, and are N and O.

In one embodiment, exactly 2 of said ring atoms are ring heteroatoms, and are N and S.

In one embodiment, -J³ is independently selected from the following groups and corresponding groups having one or more substituents, for example, one or more substituents selected from saturated aliphatic $C_{1-3}$alkyl:

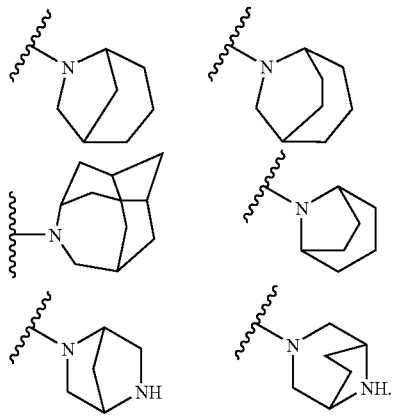

In one embodiment, -J³ is independently selected from the following groups and corresponding groups having one or more substituents, for example, one or more substituents selected from saturated aliphatic $C_{1-3}$alkyl:

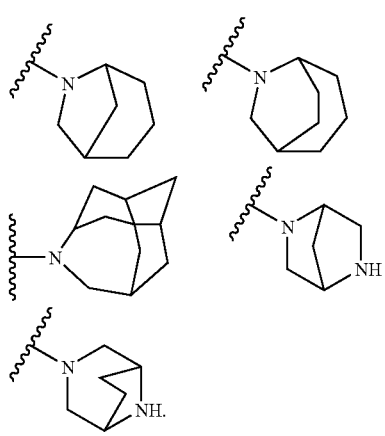

Examples of such groups which additionally bear one or more substituents (e.g., -Me) include the following:

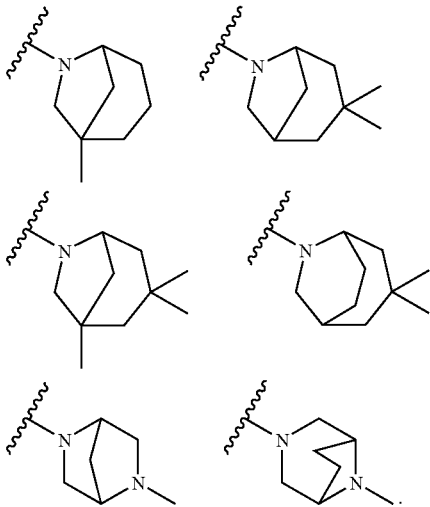

In one embodiment, -J³ is independently selected from the following groups and corresponding groups having one or more substituents, for example, one or more substituents selected from saturated aliphatic C₁₋₃alkyl:

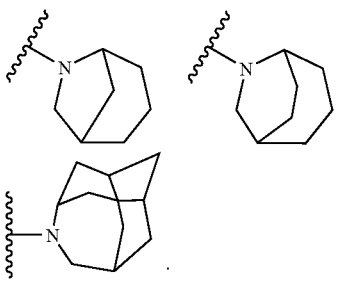

In one embodiment, -J³ is independently:

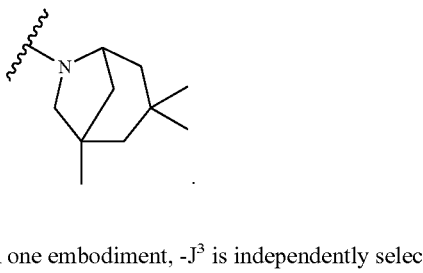

In one embodiment, -J³ is independently selected from:

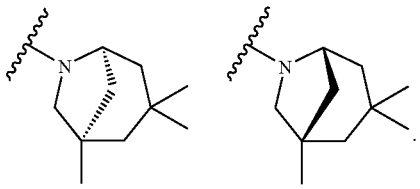 [SMILES: *N1C[C@@]2(C)C[C@@H]1CC(C)(C)C2 ; *N1C[C@]2(C)C[C@H]1CC(C)(C)C2]

The Group -J⁴

In one embodiment, -J⁴ is independently a Spiro non-aromatic heterocyclyl group having from 8 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, or exactly 3 of said ring atoms are ring heteroatoms, one of which is N, and each of the other two is independently N, O, or S, and wherein said spiro non-aromatic heterocyclyl group is optionally substituted.

In one embodiment, the Spiro non-aromatic heterocyclyl group has 8 ring atoms.

In one embodiment, the spiro non-aromatic heterocyclyl group has 10 ring atoms.

In one embodiment, the spiro non-aromatic heterocyclyl group has 11 ring atoms.

In one embodiment, the spiro non-aromatic heterocyclyl group has 12 ring atoms.

In one embodiment, exactly 1 of said ring atoms is a ring heteroatom, and is N.

In one embodiment, exactly 2 of said ring atoms are ring heteroatoms, and are both N.

In one embodiment, exactly 2 of said ring atoms are ring heteroatoms, and are N and O.

In one embodiment, exactly 2 of said ring atoms are ring heteroatoms, and are N and S.

In one embodiment, exactly 3 of said ring atoms are ring heteroatoms, and are N, N, and O.

In one embodiment, exactly 3 of said ring atoms are ring heteroatoms, and are N, O, and O.

In one embodiment, exactly 3 of said ring atoms are ring heteroatoms, and are N, N, and S.

In one embodiment, exactly 3 of said ring atoms are ring heteroatoms, and are N, O, and S.

In one embodiment, -J⁴ is independently selected from the following groups and corresponding groups having one or more substituents, for example, one or more substituents selected from saturated aliphatic C₁₋₃alkyl:

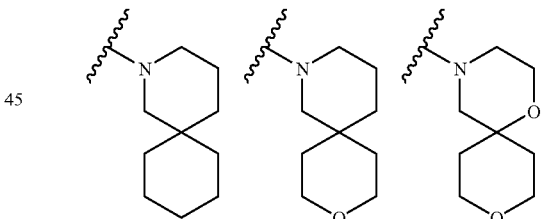

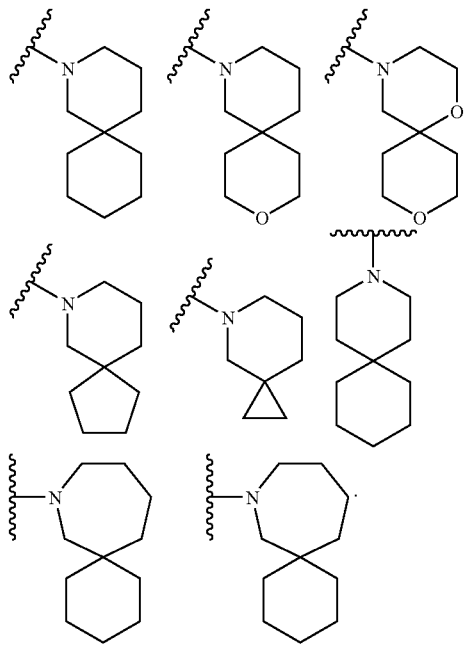

In one embodiment, -J⁴ is independently selected from the following groups and corresponding groups having one or more substituents, for example, one or more substituents selected from saturated aliphatic C₁₋₃alkyl:

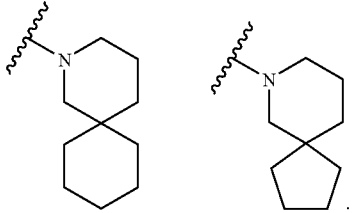 [SMILES: *N1CCCC2(CCCCC2)C1 ; *N1CCCC2(CCCC2)C1]

Optional Substituents on the Group —R^{2B1}

In one embodiment, —R^{2B1} is independently optionally substituted.

In one embodiment, —R^{2B1} is independently unsubstituted.

In one embodiment, optional substituents on —R^{2B1}, if present, are independently selected from:
—R^R,
—F, —Cl, —Br,
—CF₃, —OCF₃,
—OH, —R^L—OH, —O—R^L—OH
—OR^P, —R^L—OR^P, —O—R^L—OR^P,
—SR^P,
—S(=O)₂R^P,
—S(=O)₂NH₂, —S(=O)₂NHR^P, —S(=O)₂NR^P₂, —S(=O)₂R^M,
—NH₂, —NHR^P, —NR^P₂, —R^M,
—NHC(=O)R^P, —NR^PC(=O)R^P,
—NHS(=O)₂R^P, —NR^PS(=O)₂R^P
—C(=O)OH, —C(=O)OR^P,
—C(=O)NH₂, —C(=O)NHR^P, —C(=O)NR^P₂, —C(=O)R^M,
—C(=O)R^P, and
=O.

In one embodiment, optional substituents on —R^{2B1}, if present, are independently selected from:
—R^R,
—F,
—CF₃, —OCF₃,
—OH
—OR^P,
—SR^P,
—S(=O)₂R^P,
—S(=O)₂NH₂, —S(=O)₂NHR^P, —S(=O)₂NR^P₂, —S(=O)₂R^M,
—NHR^P, —NR^P₂, —R^M,
—NHC(=O)R^P, —NR^PC(=O)R^P,
—NHS(=O)₂R^P, —NR^PS(=O)₂R^P,
—C(=O)OH, —C(=O)OR^P,
—C(=O)NH₂, —C(=O)NHR^P, —C(=O)NR^P₂, and
—C(=O)R^M.

In one embodiment, optional substituents on —R^{2B1}, if present, are independently selected from:
—R^R,
—F,
—S(=O)₂R^P,
—S(=O)₂NH₂, —S(=O)₂NHR^P, —S(=O)₂NR^P₂, —S(=O)₂R^M,
—NHR^P, —NR^P₂, —R^M,
—NHC(=O)R^P, —NR^PC(=O)R^P,
—NHS(=O)₂R^P, —NR^PS(=O)₂R^P,
—C(=O)OH, —C(=O)OR^P,
—C(=O)NH₂, —C(=O)NHR^P, —C(=O)NR^P₂, and
—C(=O)R^M.

Optional Substituents on the —R^{2B2} and —R^{2B3}

In one embodiment, —R^{2B2} is independently optionally substituted.

In one embodiment, —R^{2B2} is independently unsubstituted.

In one embodiment, —R^{2B3} is independently optionally substituted.

In one embodiment, —R^{2B3} is independently unsubstituted.

In one embodiment, optional substituents on each of —R^{2B2} and —R^{2B3}, if present, are independently selected from:
—R^Q,
—R^R,
—F, —Cl, —Br,
—OH, —R^L—OH, —O—R^L—OH
—OR^P, —R^L—OR^P, —O—R^L—OR^P,
—SR^P,
—NH₂, —NHR^P, —NR^P₂, —R^M,
—NHC(=O)R^P, —NR^PC(=O)R^P,
—C(=O)OH, —C(=O)OR^P,
—C(=O)NH₂, —C(=O)NHR^P, —C(=O)NR^P₂, —C(=O)R^M,
—C(=O)R^P,
—S(=O)₂R^P,
—S(=O)₂NH₂, —S(=O)₂NHR^P, —S(=O)₂NR^P₂, —S(=O)₂R^M,
—NHS(=O)₂R^P, —NR^PS(=O)₂R^P, —NHS(=O)₂R^M, —NR^PS(=O)₂R^M,
—NO₂, and
—CN;
or two adjacent substituents, if present, together form —O—CH₂—O— or —O—CH₂CH₂—O—.

In one embodiment, optional substituents on each of —R^{2B2} and —R^{2B3}, if present, are independently selected from:
—R^Q,
—R^R,
—F, —Cl, —Br,
—R^L—OH,
—OR^P, —R^L—OR^P,
—NH₂, —NHR^P, —NR^P₂, —R^M,
—NHC(=O)R^P, —NR^PC(=O)R^P,
—C(=O)OH, —C(=O)OR^P,
—C(=O)NH₂, —C(=O)NHR^P, —C(=O)NR^P₂, —C(=O)R^M,
—S(=O)₂NH₂, —S(=O)₂NHR^P, —S(=O)₂NR^P₂, —S(=O)₂R^M,
—NHS(=O)₂R^P, —NR^PS(=O)₂R^P, —NHS(=O)₂R^M, —NR^PS(=O)₂R^M,
—NO₂, and
—CN;
or two adjacent substituents, if present, together form —O—CH₂—O— or —O—CH₂CH₂—O—.

In one embodiment, optional substituents on each of —R^{2B2} and —R^{2B3}, if present, are independently selected from:
—R^Q,
—R^R,
—F, —Cl, —Br,
—OR^P,
—NH₂, —NR^P₂, —R^M,
—NHC(=O)R^P, —NR^PC(=O)R^P,
—C(=O)OH, —C(=O)OR^P, —C(=O)NH$_2$,   —C(=O)NHR$^P$,   —C(=O)NR$^P_2$,
—C(=O)R$^M$,
—NO$_2$, and
—CN.

Optional Substituents on the Groups —R$^{2C}$ and —R$^{2D}$

In one embodiment, —R$^{2C}$ is independently optionally substituted.

In one embodiment, —R$^{2C}$ is independently unsubstituted.

In one embodiment, —R$^{2D}$ is independently optionally substituted.

In one embodiment, —R$^{2D}$ is independently unsubstituted.

In one embodiment, optional substituents on each of —R$^{2C}$ and —R$^{2D}$, if present, are independently selected from:

substituents on carbon, independently selected from:
—R$^Q$,
—R$^R$,
—R$^L$—R$^R$,
—F, —Cl, —Br,
=O,
—OH, —R$^L$—OH, —O—R$^L$—OH, —NH—R$^L$—OH, —NR$^P$—R$^L$—OH,
—OR$^P$, —R$^L$—OR$^P$, —O—R$^L$—OR$^P$, —NH—R$^L$—OR$^P$, —NR$^P$—R$^L$—OR$^P$,
—NH$_2$, —NHR$^P$, —NR$^P_2$, —R$^M$,
—R$^L$—NH$_2$, —R$^L$—NHR$^P$, —R$^L$—NR$^P_2$, —R$^L$—R$^M$,
—O—R$^L$—NH$_2$, —O—R$^L$—NHR$^P$, —O—R$^L$—NR$^P_2$, —O—R$^L$—R$^M$,
—NH—R$^L$—NH$_2$, —NH—R$^L$—NHR$^P$, —NH—R$^L$—NR$^P_2$, —NH—R$^L$—R$^M$,
—NR$^P$—R$^L$—NH$_2$, —NR$^P$—R$^L$—NHR$^P$, —NR$^P$—R$^L$—NR$^P_2$, —NR$^P$—R$^L$—R$^M$,
—S(=O)$_2$NH$_2$, —S(=O)$_2$NHR$^P$, —S(=O)$_2$NR$^P_2$, —S(=O)$_2$R$^M$,
—R$^L$—S(=O)$_2$NH$_2$, —R$^L$—S(=O)$_2$NHR$^P$, —R$^L$—S(=O)$_2$NR$^P_2$, —R$^L$—S(=O)$_2$R$^M$,
—O—R$^L$—S(=O)$_2$NH$_2$, —O—R$^L$—S(=O)$_2$NHR$^P$, —O—R$^L$—S(=O)$_2$NR$^P_2$, —O—R$^L$—S(=O)$_2$R$^M$,
—NHS(=O)$_2$R$^P$, —NR$^P$S(=O)$_2$R$^P$, —NHS(=O)$_2$R$^M$, —NR$^P$S(=O)$_2$R$^M$,
—R$^L$—NHS(=O)$_2$R$^P$, —R$^L$—NR$^P$S(=O)$_2$R$^P$, —R$^L$—NHS(=O)$_2$R$^M$, —R$^L$—NR$^P$S(=O)$_2$R$^M$,
—R$^L$—NHS(=O)$_2$R$^P$, —O—R$^L$—NR$^P$S(=O)$_2$R$^P$,
—S(=O)$_2$R$^P$,
—R$^L$—S(=O)$_2$R$^P$,
—O—R$^L$—S(=O)$_2$R$^P$,
—SR$^P$,
—C(=O)OH, —C(=O)OR$^P$,
—R$^L$—C(=O)OH, —R$^L$—C(=O)OR$^P$,
—C(=O)NH$_2$, —C(=O)NHR$^P$, —C(=O)NR$^P_2$, —C(=O)R$^M$,
—R$^L$—C(=O)NH$_2$, —R$^L$—C(=O)NHR$^P$, —R$^L$—C(=O)NR$^P_2$, —R$^L$—C(=O)R$^M$,
—C(=O)R$^P$,
—CN,
—NHC(=O)R$^P$, —NR$^P$C(=O)R$^P$,
—R$^L$—NHC(=O)R$^P$, —R$^L$—NR$^P$C(=O)R$^P$,
—NHC(=O)—OR$^P$, —NR$^P$C(=O)—OR$^P$,
—NHC(=O)—R$^L$—OH, —NHC(=O)—R$^L$—OR$^P$,
—NR$^P$C(=O)—R$^L$—OH, —NR$^P$C(=O)—R$^L$—OR$^P$,
—NHC(=O)—NH$_2$, —NHC(=O)—NHR$^P$, —NHC(=O)—NR$^P_2$, —NHC(=O)—R$^M$,
—NR$^P$C(=O)—NH$_2$, —NR$^P$C(=O)—NHR$^P$, —NR$^P$C(=O)—NR$^P_2$, —NR$^P$C(=O)—R$^M$,
—NHC(=O)—R$^L$—NH$_2$, —NHC(=O)—R$^L$—NHR$^P$, —NHC(=O)—R$^L$—NR$^P_2$, —NHC(=O)—R$^L$—R$^M$,
—NR$^P$C(=O)—R$^L$—NH$_2$, —NR$^P$C(=O)—R$^L$—NHR$^P$,
—NR$^P$C(=O)—R$^L$—NR$^P_2$, —NR$^P$C(=O)—R$^L$—R$^M$,
—NHC(=O)—R$^L$—NHS(=O)$_2$R$^P$, —NHC(=O)—R$^L$—NR$^P$S(=O)$_2$R$^P$,
—NR$^P$C(=O)—R$^L$—NHS(=O)$_2$R$^P$, —NR$^P$C(=O)—R$^L$—NR$^P$S(=O)$_2$R$^P$,
—NHC(=O)—R$^L$—NHS(=O)$_2$R$^M$, —NHC(=O)—R$^L$—NR$^P$S(=O)$_2$R$^M$,
—NR$^P$C(=O)—R$^L$—NHS(=O)$_2$R$^M$, —NR$^P$C(=O)—R$^L$—NR$^P$S(=O)$_2$R$^M$,
—NHC(=O)—R$^L$—S(=O)$_2$NH$_2$, —NR$^P$C(=O)—R$^L$—S(=O)$_2$NH$_2$,
—NHC(=O)—R$^L$—S(=O)$_2$NHR$^P$, —NR$^P$C(=O)—R$^L$—S(=O)$_2$NHR$^P$,
—NHC(=O)—R$^L$—S(=O)$_2$NR$^P_2$, —NR$^P$C(=O)—R$^L$—S(=O)$_2$NR$^P_2$,
—NHC(=O)—R$^L$—S(=O)$_2$R$^M$, —NR$^P$C(=O)—R$^L$—S(=O)$_2$R$^M$,
—NHS(=O)$_2$NH$_2$, —NHS(=O)$_2$NHR$^P$, —NHS(=O)$_2$NR$^P_2$, —NHS(=O)$_2$R$^M$,
—NR$^P$S(=O)$_2$NH$_2$, —NR$^P$S(=O)$_2$NHR$^P$, —NR$^P$S(=O)$_2$NR$^P_2$, —NR$^P$S(=O)$_2$R$^M$,
—NH—R$^L$—NHS(=O)$_2$R$^P$, —NH—R$^L$—NR$^P$S(=O)$_2$R$^P$,
—NR$^P$—R$^L$—NHS(=O)$_2$R$^P$, —NR$^P$—R$^L$—NR$^P$S(=O)$_2$R$^P$,
—NH—R$^L$—S(=O)$_2$NH$_2$, —NR$^P$—R$^L$—S(=O)$_2$NH$_2$,
—NH—R$^L$—S(=O)$_2$NHR$^P$, —NR$^P$—R$^L$—S(=O)$_2$NHR$^P$,
—NH—R$^L$—S(=O)$_2$NR$^P_2$, —NR$^P$—R$^L$—S(=O)$_2$NR$^P_2$,
—NH—R$^L$—S(=O)$_2$R$^M$, —NR$^P$—R$^L$—S(=O)$_2$R$^M$,
—NH—R$^L$—S(=O)$_2$R$^P$, and —NR$^P$—R$^L$—S(=O)$_2$R$^P$;

and additionally, for —R$^{2C}$, substituents on nitrogen, if present, independently selected from:
—R$^Q$,
—R$^R$,
—R$^L$—R$^R$,
—C(=O)R$^Q$, —C(=O)R$^R$, —C(=O)—R$^L$—R$^R$,
—C(=O)—R$^L$—OH, —C(=O)—R$^L$—OR$^P$,
—C(=O)—R$^L$—NH$_2$, —C(=O)—R$^L$—NHR$^P$, —C(=O)—R$^L$—NR$^P_2$, —C(=O)—R$^L$—R$^M$,
—C(=O)—R$^L$—C(=O)—NH$_2$, —C(=O)—R$^L$—C(=O)—NHR$^P$,
—C(=O)—R$^L$—C(=O)—NR$^P_2$, —C(=O)—R$^L$—C(=O)—R$^M$,
—C(=O)—R$^L$—NH—C(=O)R$^P$, —C(=O)—R$^L$—NR$^P$—C(=O)R$^P$,
—C(=O)—R$^L$—NHS(=O)$_2$R$^P$, —C(=O)—R$^L$—NR$^P$S(=O)$_2$R$^P$,
—C(=O)—R$^L$—NHS(=O)$_2$R$^M$, —C(=O)—R$^L$—NR$^P$S(=O)$_2$R$^M$,
—C(=O)—R$^L$—S(=O)$_2$NH$_2$, —C(=O)—R$^L$—S(=O)$_2$NHR$^P$,
—C(=O)—R$^L$—S(=O)$_2$NR$^P_2$, —C(=O)—R$^L$—S(=O)$_2$R$^M$,
—C(=O)OR$^Q$, —C(=O)OR$^R$, —C(=O)O—R$^L$—R$^R$,
—C(=O)NH$_2$, —C(=O)NHR$^P$, —C(=O)NR$^P_2$, —C(=O)R$^M$,
—C(=O)NH—R$^L$—R$^R$, —C(=O)NR$^P$—R$^L$—R$^R$,
—C(=O)NH—R$^L$—OH, —C(=O)NR$^P$—R$^L$—OH,
—C(=O)NH—R$^L$—OR$^P$, —C(=O)NR$^P$—R$^L$—OR$^P$,
—C(=O)NH—R$^L$—NH$_2$, —C(=O)NR$^P$—R$^L$—NH$_2$,
—C(=O)NH—R$^L$—NHR$^P$, —C(=O)NR$^P$—R$^L$—NHR$^P$,
—C(=O)NH—R$^L$—NR$^P_2$, —C(=O)NR$^P$—R$^L$—NR$^P_2$,
—C(=O)NH—R$^L$—R$^M$, —C(=O)NR$^P$—R$^L$—R$^M$, —C(=O)NH—R$^L$—NH—S(O)$_2$R$^P$, —C(=O)NR$^P$—R$^L$—NH—S(O)$_2$R$^P$,
—C(=O)NH—R$^L$—NR$^P$—S(O)$_2$R$^P$, —C(=O)NR$^P$—R$^L$—NR$^P$—S(O)$_2$R$^P$,
—S(=O)$_2$NH$_2$, —S(=O)$_2$NHR$^P$, —S(=O)$_2$NR$^P_2$, —S(=O)$_2$R$^M$,
—S(=O)$_2$R$^P$,
—R$^L$—OH, —R$^L$—OR$^P$,
—R$^L$—CH(OH)—R$^L$—OH, —R$^L$—CH(OH)—R$^L$—OR$^P$,
—R$^L$—CH(OR$^P$)—R$^L$—OH, —R$^L$—CH(OR$^P$)—R$^L$—OR$^P$,
—R$^L$—C(=O)NH$_2$, —R$^L$—C(=O)NHR$^P$, —R$^L$—C(=O)NR$^P_2$, —R$^L$—C(=O)R$^M$,
—R$^L$—NH$_2$, —R$^L$—NHR$^P$, —R$^L$—NR$^P_2$, —R$^L$—R$^M$,
—R$^L$—NH(C=O)R$^P$, —R$^L$—NR$^P$C(=O)R$^P$,
—R$^L$—NHS(=O)$_2$R$^P$, —R$^L$—NR$^P$S(=O)$_2$R$^P$,
—R$^L$—S(=O)$_2$NH$_2$, —R$^L$—S(=O)$_2$NHR$^P$, —R$^L$—S(=O)$_2$NR$^P_2$, R$^L$—S(=O)$_2$R$^M$, and
—R$^L$—S(=O)$_2$R$^P$.

For example, when —R$^{2C}$ is piperidin-4-yl, it may have a "substituent on nitrogen", specifically, at the 1-position (e.g., as in 1-methyl-piperidin-4-yl, shown below). Additionally, it may have a "substituent on carbon", for example, at one or more of the 2-, 3-, 4-, 5- or 6-positions (e.g., as in piperidin-2-one-4-yl, shown below). Of course, it may be both a "substituent on nitrogen" and "substituents on carbon" (e.g., as in 1-methyl-piperidin-2-one-4-yl, shown below).

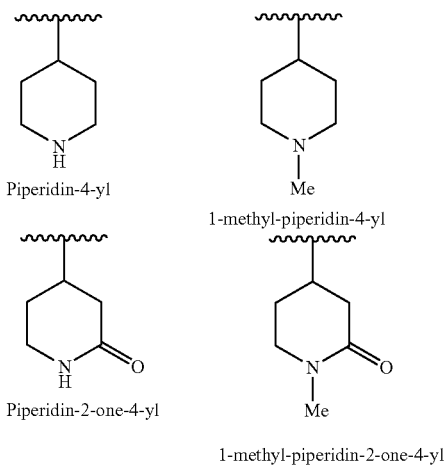

Piperidin-4-yl
1-methyl-piperidin-4-yl
Piperidin-2-one-4-yl
1-methyl-piperidin-2-one-4-yl In one embodiment, for the optional substituents on each of —R$^{2C}$ and —R$^{2D}$, if present, substituents on carbon, if present, are independently selected from:
—R$^Q$,
—R$^R$,
—R$^L$—R$^R$,
—F,
—OH, —R$^L$—OH,
—OR$^P$, —R$^L$—OR$^P$, —O—R$^L$—OR$^P$,
—C(=O)OH, —C(=O)OR$^P$,
—C(=O)NH$_2$, —C(=O)NHR$^P$, —C(=O)NR$^P_2$, —C(=O)R$^M$,
—R$^L$—C(=O)NH$_2$, —R$^L$—C(=O)NHR$^P$, —R$^L$—C(=O)NR$^P_2$, —R$^L$—C(=O)R$^M$,
—NHC(=O)R$^P$, —NR$^P$C(=O)R$^P$,
—R$^L$—NHC(=O)R$^P$, —R$^L$—NR$^P$C(=O)R$^P$,
—S(=O)$_2$NH$_2$, —S(=O)$_2$NHR$^P$, —S(=O)$_2$NR$^P_2$, —S(=O)$_2$R$^M$,
—R$^L$—S(=O)$_2$NH$_2$, —R$^L$—S(=O)$_2$NHR$^P$, —R$^L$—S(=O)$_2$NR$^P_2$, —R$^L$—S(=O)$_2$R$^M$,
—NHS(=O)$_2$R$^P$, —NR$^P$S(=O)$_2$R$^P$, —NHS(=O)$_2$R$^M$, —NR$^P$S(=O)$_2$R$^M$,
—R$^L$—NHS(=O)$_2$R$^P$, —R$^L$—NR$^P$S(=O)$_2$R$^P$, —R$^L$—NHS(=O)$_2$R$^M$, —R$^L$—NR$^P$S(=O)$_2$R$^M$,
—S(=O)$_2$R$^P$,
—CN, and
=O.

In one embodiment, for the optional substituents on each of —R$^{2C}$ and —R$^{2D}$, if present, substituents on carbon, if present, are independently selected from:
—R$^Q$,
—R$^R$,
—R$^L$—R$^R$
—F,
—OH, —R$^L$—OH,
—OR$^P$, —R$^L$—OR$^P$,
—C(=O)NHR$^P$, —C(=O)NR$^P_2$,
—NHC(=O)R$^P$, —NR$^P$C(=O)R$^P$,
—CN, and
=O.

In one embodiment, for the optional substituents on —R$^{2C}$, if present, substituents on nitrogen, if present, are independently selected from:
—C(=O)R$^Q$, —C(=O)R$^R$, —C(=O)—R$^L$—R$^R$,
—C(=O)—R$^L$—OH, —C(=O)—R$^L$—OR$^P$,
—C(=O)—R$^L$—NH$_2$, —C(=O)—R$^L$—NHR$^P$,
—C(=O)—R$^L$—NR$^P_2$, —C(=O)—R$^L$—R$^M$,
—C(=O)—R$^L$—C(=O)—NH$_2$, —C(=O)—R$^L$—C(=O)—NHR$^P$,
—C(=O)—R$^L$—C(=O)—NR$^P_2$, —C(=O)—R$^L$—C(=O)—R$^M$,
—C(=O)—R$^L$—NH—C(=O)R$^P$, —C(=O)—R$^L$—NR$^P$—C(=O)R$^P$,
—C(=O)—R$^L$—NHS(=O)$_2$R$^P$, —C(=O)—R$^L$—NR$^P$S(=O)$_2$R$^P$,
—C(=O)—R$^L$—NHS(=O)$_2$R$^M$, —C(=O)—R$^L$—NR$^P$S(=O)$_2$R$^M$,
—C(=O)—R$^L$—S(=O)$_2$NH$_2$, —C(=O)—R$^L$—S(=O)$_2$NHR$^P$,
—C(=O)—R$^L$—S(=O)$_2$NR$^P_2$, —C(=O)—R$^L$—S(=O)$_2$R$^M$,
—C(=O)OR$^Q$, —C(=O)OR$^R$, —C(=O)O—R$^L$—R$^R$,
—C(=O)NH$_2$, —C(=O)NHR$^P$, —C(=O)NR$^P_2$, —C(=O)R$^M$,
—C(=O)NH—R$^L$—R$^R$, —C(=O)NR$^P$—R$^L$—R$^R$,
—C(=O)NH—R$^L$—OH, —C(=O)NR$^P$—R$^L$—OH,
—C(=O)NH—R$^L$—OR$^P$, —C(=O)NR$^P$—R$^L$—OR$^P$,
—C(=O)NH—R$^L$—NH$_2$, —C(=O)NR$^P$—R$^L$—NH$_2$,
—C(=O)NH—R$^L$—NHR$^P$, —C(=O)NR$^P$—R$^L$—NHR$^P$,
—C(=O)NH—R$^L$—NR$^P_2$, —C(=O)NR$^P$—R$^L$—NR$^P_2$,
—C(=O)NH—R$^L$—R$^M$, —C(=O)NR$^P$—R$^L$—R$^M$,
—C(=O)NH—R$^L$—NH—S(O)$_2$R$^P$, —C(=O)NR$^P$—R$^L$—NH—S(O)$_2$R$^P$,
—C(=O)NH—R$^L$—NR$^P$—S(O)$_2$R$^P$, —C(=O)NR$^P$—R$^L$—NR$^P$—S(O)$_2$R$^P$,
—S(=O)$_2$NH$_2$, —S(=O)$_2$NHR$^P$, —S(=O)$_2$NR$^P_2$, —S(=O)$_2$R$^M$, and
—S(=O)$_2$R$^P$.

In one embodiment, for the optional substituents on —R$^{2C}$, if present, substituents on nitrogen, if present, are independently selected from:
—C(=O)NH$_2$, —C(=O)NHR$^P$, —C(=O)NR$^P_2$, —C(=O)R$^M$,
—C(=O)NH—R$^L$—R$^R$, —C(=O)NR$^P$—R$^L$—R$^R$, —C(=O)NH—R$^L$—OH, —C(=O)NR$^P$—R$^L$—OH,
—C(=O)NH—R$^L$—OR$^P$, —C(=O)NR$^P$—R$^L$—OR$^P$,
—C(=O)NH—R$^L$—NH$_2$, —C(=O)NR$^P$—R$^L$—NH$_2$,
—C(=O)NH—R$^L$—NHR$^P$, —C(=O)NR$^P$—R$^L$—NHR$^P$,
—C(=O)NH—R$^L$—NR$^P{}_2$, —C(=O)NR$^P$—R$^L$—NR$^P{}_2$,
—C(=O)NH—R$^L$—R$^M$, —C(=O)NR$^P$—R$^L$—R$^M$,
—C(=O)NH—R$^L$—NH—S(O)$_2$R$^P$, —C(=O)NR$^P$—R$^L$—NH—S(O)$_2$R$^P$,
—C(=O)NH—R$^L$—NR$^P$—S(O)$_2$R$^P$, and —C(=O)NR$^P$—R$^L$—NR$^P$—S(O)$_2$R$^P$.

In one embodiment, for the optional substituents on —R$^{2C}$, if present, substituents on nitrogen, if present, are independently selected from:
—C(=O)R$^Q$, —C(=O)R$^R$, —C(=O)—R$^L$—R$^R$,
—C(=O)—R$^L$—OH, —C(=O)—R$^L$—OR$^P$,
—C(=O)—R$^L$—NH$_2$, —C(=O)—R$^L$—NHR$^P$,
—C(=O)—R$^L$—NR$^P{}_2$, —C(=O)—R$^L$—R$^M$,
—C(=O)—R$^L$—NHS(=O)$_2$R$^P$, —C(=O)—R$^L$—NR$^P$S(=O)$_2$R$^P$,
—C(=O)—R$^L$—NHS(=O)$_2$R$^M$, —C(=O)—R$^L$—NR$^P$S(=O)$_2$R$^P$,
—C(=O)—R$^L$—S(=O)$_2$NH$_2$, —C(=O)—R$^L$—S(=O)$_2$NHR$^P$S(=O)$_2$R$^M$,
—C(=O)—R$^L$—S(=O)$_2$NR$^P{}_2$, —C(=O)—R$^L$—S(=O)$_2$R$^M$,
—C(=O)OR$^Q$, —C(=O)OR$^R$, —C(=O)O—R$^L$—R$^R$,
—C(=O)NH$_2$, —C(=O)NHR$^P$, —C(=O)NR$^P{}_2$,
—C(=O)R$^M$,
—S(=O)$_2$NH$_2$, —S(=O)$_2$NHR$^P$, —S(=O)$_2$NR$^P{}_2$,
—S(=O)$_2$R$^M$, and
—S(=O)$_2$R$^P$.

In one embodiment, for the optional substituents on —R$^{2C}$, if present, substituents on nitrogen, if present, are independently selected from:
—R$^R$,
—R$^L$—R$^R$,
—R$^L$—OH, —R$^L$—OR$^P$,
—R$^L$—CH(OH)—R$^L$—OH, —R$^L$—CH(OH)—R$^L$—OR$^P$,
—R$^L$—CH(OR$^P$)—R$^L$—OH, —R$^L$—CH(OR$^P$)—R$^L$—OR$^P$,
—R$^L$—C(=O)NH$_2$, —R$^L$—C(=O)NHR$^P$, —R$^L$—C(=O)NR$^P{}_2$, —R$^L$—C(=O)R$^M$,
—R$^L$—NH$_2$, —R$^L$—NHR$^P$, —R$^L$—NR$^P{}_2$, —R$^L$—R$^M$,
—R$^L$—NHC(=O)R$^P$, —R$^L$—NR$^P$C(=O)R$^P$,
—R$^L$—NHS(=O)$_2$R$^P$, —R$^L$—NR$^P$S(=O)$_2$R$^P$,
—R$^L$—S(=O)$_2$NH$_2$, —R$^L$—S(=O)$_2$NHR$^P$, —R$^L$—S(=O)$_2$NR$^P{}_2$, —R$^L$—S(=O)$_2$R$^M$, and
—R$^L$—S(=O)$_2$R$^P$.

In one embodiment, for the optional substituents on —R$^{2C}$, if present, substituents on nitrogen, if present, are independently selected from:
—R$^R$,
—R$^L$—R$^R$,
—R$^L$—OH, —R$^L$—OR$^P$,
—R$^L$—C(=O)NH$_2$, —R$^L$—C(=O)NHR$^P$, —R$^L$—C(=O)NR$^P{}_2$, —R$^L$—C(=O)R$^M$,
—R$^L$—NH$_2$, —R$^L$—NHR$^P$, —R$^L$—NR$^P{}_2$,
—R$^L$—NHC(=O)R$^P$, —R$^L$—NR$^P$C(=O)R$^P$,
—R$^L$—NHS(=O)$_2$R$^P$, —R$^L$—NR$^P$S(=O)$_2$R$^P$,
—R$^L$—S(=O)$_2$NH$_2$, —R$^L$—S(=O)$_2$NHR$^P$, —R$^L$—S(=O)$_2$NR$^P{}_2$, —R$^L$—S(=O)$_2$R$^M$, and
—R$^L$—S(=O)$_2$R$^P$.

In one embodiment, optional substituents on each of —R$^{2D}$ and —R$^{2D}$, if present, are independently selected from:
substituents on carbon, independently selected from:
—R$^Q$,
—R$^R$,
—R$^L$—R$^R$
—F,
—OH, —R$^L$—OH,
—OR$^P$, —R$^L$—OR$^P$,
—C(=O)NHR$^P$, —C(=O)NR$^P{}_2$,
—NHC(=O)R$^P$, —NR$^P$C(=O)R$^P$,
—CN, and
=O;

substituents on nitrogen, if present, independently selected from:
—C(=O)R$^R$, —C(=O)—R$^L$—R$^R$,
—C(=O)—R$^L$—OH, —C(=O)—R$^L$—OR$^P$,
—C(=O)—R$^L$—NH$_2$, —C(=O)—R$^L$—NHR$^P$,
—C(=O)—R$^L$—NR$^P{}_2$, —C(=O)—R$^L$—R$^M$,
—C(=O)—R$^L$—NHS(=O)$_2$R$^P$, —C(=O)—R$^L$—NR$^P$S(=O)$_2$R$^P$,
—C(=O)—R$^L$—NHS(=O)$_2$R$^M$, —C(=O)—R$^L$—NR$^P$S(=O)$_2$R$^M$,
—C(=O)—R$^L$—S(=O)$_2$NH$_2$, —C(=O)—R$^L$—S(=O)$_2$NHR$^P$,
—C(=O)—R$^L$—S(=O)$_2$NR$^P{}_2$, —C(=O)—R$^L$—S(=O)$_2$R$^M$,
—C(=O)OR$^Q$, —C(=O)OR$^R$, —C(=O)O—R$^L$—R$^R$,
—S(=O)$_2$NH$_2$, —S(=O)$_2$NHR$^P$, —S(=O)$_2$NR$^P{}_2$,
—S(=O)$_2$R$^M$, and
—S(=O)$_2$R$^P$.

In one embodiment, optional substituents on —R$^{2D}$, if present, are independently selected from:
—R$^Q$,
—R$^R$,
—R$^L$—R$^R$
—F,
—OH, —R$^L$—OH,
—OR$^P$, —R$^L$—OR$^P$,
—C(=O)NHR$^P$, —C(=O)NR$^P{}_2$,
—NHC(=O)R$^P$, —NR$^P$C(=O)R$^P$, and
—CN.

Optional Substituents on -J$^1$, -J$^2$, -J$^3$, and -J$^4$

In one embodiment, each of -J$^1$, -J$^2$, -J$^3$, and -J$^4$ is independently optionally substituted.
In one embodiment, each of -J$^1$, -J$^2$, -J$^3$, and -J$^4$ is independently unsubstituted.
In one embodiment, -J$^1$ is independently unsubstituted.
In one embodiment, -J$^2$ is independently unsubstituted.
In one embodiment, -J$^3$ is independently unsubstituted.
In one embodiment, -J$^4$ is independently unsubstituted.
In one embodiment, optional substituents on each of -J$^1$, -J$^2$, -J$^3$, and -J$^4$, if present, are independently selected from:
substituents on carbon, independently selected from:
—R$^Q$,
—R$^R$,
—F, —Cl, —Br,
—OH, —R$^L$—OH, —O—R$^L$—OH,
—OR$^P$, —R$^L$—OR$^P$, —O—R$^L$—OR$^P$,
—SR$^P$,
—NH$_2$, —NHR$^P$, —NR$^P{}_2$, —R$^M$,
—NHC(=O)R$^P$, —NR$^P$C(=O)R$^P$,
—C(=O)NH$_2$, —C(=O)NHR$^P$, —C(=O)NR$^P{}_2$,
—C(=O)R$^M$,
—C(=O)OH, —C(=O)OR$^P$,
—S(=O)$_2$NH$_2$, —S(=O)$_2$NHR$^P$, —S(=O)$_2$NR$_2{}^P$,
—S(=O)$_2$R$^M$,
—NHS(=O)$_2$R$^P$, —NR$^P$S(=O)$_2$R$^P$, —NHS(=O)$_2$R$^M$,
—NR$^P$S(=O)$_2$R$^M$, —CN,
—$R^L$—S(=O)$_2$NH$_2$, —$R^L$—S(=O)$_2$NHR$^P$, —$R^L$—S(=O)$_2$NR$^P{}_2$, —$R^L$—S(=O)$_2$R$^M$,
—$R^L$—NH$_2$, —$R^L$—NHR$^P$, —$R^L$—NR$^P{}_2$, —$R^L$—R$^M$,
—$R^L$—NHC(=O)R$^P$, —$R^L$—NR$^P$C(=O)R$^P$,
—$R^L$—NHS(=O)$_2$R$^P$, —$R^L$—NR$^P$S(=O)$_2$R$^P$, —$R^L$—NHS(=O)$_2$R$^M$, —$R^L$—NR$^P$S(=O)$_2$R$^M$,
—$R^L$—C(=O)OH, —$R^L$—C(=O)OR$^P$,
—$R^L$—C(=O)NH$_2$, —$R^L$—C(=O)NHR$^P$, —$R^L$—C(=O)NR$^P{}_2$, —$R^L$—C(=O)R$^M$, and
=O; and substituents on nitrogen, if present, independently selected from:
—$R^Q$,
—$R^R$,
—$R^L$—$R^R$,
—C(=O)OR$^Q$, —C(=O)OR$^R$, —C(=O)O—$R^L$—$R^R$,
—C(=O)R$^Q$, —C(=O)R$^R$, —C(=O)—$R^L$—$R^R$,
—C(=O)—$R^L$—OH, —C(=O)—$R^L$—OR$^P$,
—C(=O)NH$_2$, —C(=O)NHR$^P$, —C(=O)NR$^P{}_2$, —C(=O)R$^M$,
—C(=O)—$R^L$—NH$_2$, —C(=O)—$R^L$—NHR$^P$, —C(=O)—$R^L$—NR$^P{}_2$, —C(=O)—$R^L$—$R^M$,
—C(=O)—$R^L$—NHS(=O)$_2$R$^P$, —C(=O)—$R^L$—NR$^P$S(=O)$_2$R$^P$,
—C(=O)—$R^L$—NHS(=O)$_2$R$^M$, —C(=O)—$R^L$—NR$^P$S(=O)$_2$R$^M$,
—C(=O)—$R^L$—S(=O)$_2$NH$_2$, —C(=O)—$R^L$—S(=O)$_2$NHR$^P$,
—C(=O)—$R^L$—S(=O)$_2$NR$^P{}_2$, —C(=O)—$R^L$—S(=O)$_2$R$^M$,
—S(=O)$_2$NH$_2$, —S(=O)$_2$NHR$^P$, —S(=O)$_2$NR$^P{}_2$, —S(=O)$_2$R$^M$,
—S(=O)$_2$R$^P$,
—$R^L$—OH, —$R^L$—OR$^P$,
—$R^L$—NH$_2$, —$R^L$—NHR$^P$, —$R^L$—NR$^P{}_2$, —$R^L$—R$^M$,
—$R^L$—NHS(=O)$_2$R$^P$, —$R^L$—NR$^P$S(=O)$_2$R$^P$,
—$R^L$—S(=O)$_2$NH$_2$, —$R^L$—S(=O)$_2$NHR$^P$, —$R^L$—S(=O)$_2$NR$^P{}_2$, —$R^L$—S(=O)$_2$R$^M$, and
—$R^L$—S(=O)$_2$R$^P$; and substituents on sulfur, if present, independently selected from:
=O and (=O)$_2$.

In one embodiment, optional substituents on each of -$J^1$, -$J^2$, -$J^3$, and -$J^4$, if present, are independently selected from:
substituents on carbon, independently selected from:
—$R^Q$,
—$R^R$,
—F, —Cl, —Br,
—OH, —$R^L$—OH, —O—$R^L$—OH,
—OR$^P$, —$R^L$—OR$^P$, —O—$R^L$—OR$^P$,
—SR$^P$,
—NH$_2$, —NHR$^P$, —NR$^P{}_2$, —R$^M$,
—NHC(=O)R$^P$, —NR$^P$C(=O)R$^P$,
—C(=O)NH$_2$, —C(=O)NHR$^P$, —C(=O)NR$^P{}_2$, —C(=O)R$^M$,
—C(=O)OH, —C(=O)OR$^P$,
—S(=O)$_2$NH$_2$, —S(=O)$_2$NHR$^P$, —S(=O)$_2$NR$^P{}_2$, —S(=O)$_2$R$^M$,
—NHS(=O)$_2$R$^P$, —NR$^P$S(=O)$_2$R$^P$, —NHS(=O)$_2$R$^M$, —NR$^P$S(=O)$_2$R$^M$,
—CN,
—$R^L$—S(=O)$_2$NH$_2$, —$R^L$—S(=O)$_2$NHR$^P$, —$R^L$—S(=O)$_2$NR$^P{}_2$, —$R^L$—S(=O)$_2$R$^M$,
—$R^L$—NH$_2$, —$R^L$—NHR$^P$, —$R^L$—NR$^P{}_2$, —$R^L$—R$^M$,
—$R^L$—NHC(=O)R$^P$, —$R^L$—NR$^P$C(=O)R$^P$,
—$R^L$—NHS(=O)$_2$R$^P$, —$R^L$—NR$^P$S(=O)$_2$R$^P$, —$R^L$—NHS(=O)$_2$R$^M$, —$R^L$—NR$^P$S(=O)$_2$R$^M$,
—$R^L$—C(=O)OH, —$R^L$—C(=O)OR$^P$,
—$R^L$—C(=O)NH$_2$, —$R^L$—C(=O)NHR$^P$, —$R^L$—C(=O)NR$^P{}_2$, and —$R^L$—C(=O)R$^M$; and substituents on nitrogen, if present, independently selected from:
—$R^Q$,
—$R^R$,
—$R^L$—$R^R$,
—C(=O)OR$^Q$, —C(=O)OR$^R$, —C(=O)O—$R^L$—$R^R$,
—C(=O)R$^Q$, —C(=O)R$^R$, —C(=O)—$R^L$—$R^R$,
—C(=O)—$R^L$—OH, —C(=O)—$R^L$—OR$^P$,
—C(=O)NH$_2$, —C(=O)NHR$^P$, —C(=O)NR$^P{}_2$, —C(=O)R$^M$,
—C(=O)—$R^L$—NH$_2$, —C(=O)—$R^L$—NHR$^P$, —C(=O)—$R^L$—NR$^P{}_2$, —C(=O)—$R^L$—$R^M$,
—C(=O)—$R^L$—NHS(=O)$_2$R$^P$, —C(=O)—$R^L$—NR$^P$S(=O)$_2$R$^P$,
—C(=O)—$R^L$—NHS(=O)$_2$R$^M$, —C(=O)—$R^L$—NR$^P$S(=O)$_2$R$^M$,
—C(=O)—$R^L$—S(=O)$_2$NH$_2$, —C(=O)—$R^L$—S(=O)$_2$NHR$^P$,
—C(=O)—$R^L$—S(=O)$_2$NR$^P{}_2$, —C(=O)—$R^L$—S(=O)$_2$R$^M$,
—S(=O)$_2$NH$_2$, —S(=O)$_2$NHR$^P$, —S(=O)$_2$NR$^P{}_2$, —S(=O)$_2$R$^M$,
—S(=O)$_2$R$^P$,
—$R^L$—OH, —$R^L$—OR$^P$,
—$R^L$—NH$_2$, —$R^L$—NHR$^P$, —$R^L$—NR$^P{}_2$, —$R^L$—R$^M$,
—$R^L$—NHS(=O)$_2$R$^P$, —$R^L$—NR$^P$S(=O)$_2$R$^P$,
—$R^L$—S(=O)$_2$NH$_2$, —$R^L$—S(=O)$_2$NHR$^P$, —$R^L$—S(=O)$_2$NR$^P{}_2$, —$R^L$—S(=O)$_2$R$^M$, and
—$R^L$—S(=O)$_2$R$^P$.

In one embodiment, for the optional substituents on -$J^1$, if present, substituents on carbon, if present, are independently selected from:
—$R^R$,
—$R^Q$,
—F,
—OH, —$R^L$—OH,
—OR$^P$, —$R^L$—OR$^P$,
—NHC(=O)R$^P$, —NR$^P$C(=O)R$^P$,
—C(=O)NH$_2$, —C(=O)NHR$^P$, —C(=O)NR$^P{}_2$, —C(=O)R$^M$,
—CN,
—$R^L$—S(=O)$_2$NH$_2$, —$R^L$—S(=O)$_2$NHR$^P$, —$R^L$—S(=O)$_2$NR$^P{}_2$, —$R^L$—S(=O)$_2$R$^M$,
—$R^L$—NHC(=O)R$^P$, —$R^L$—NR$^P$C(=O)R$^P$,
—$R^L$—NHS(=O)$_2$R$^P$, —$R^L$—NR$^P$S(=O)$_2$R$^P$, —$R^L$—NHS(=O)$_2$R$^M$, —$R^L$—NR$^P$S(=O)$_2$R$^M$,
—$R^L$—C(=O)OH, —$R^L$—C(=O)OR$^P$,
—$R^L$—C(=O)NH$_2$, —$R^L$—C(=O)NHR$^P$, —$R^L$—C(=O)NR$^P{}_2$, and —$R^L$—C(=O)R$^M$.

In one embodiment, optional substituents on each of -$J^1$, -$J^2$, -$J^3$, and -$J^4$, if present, are independently selected from:
substituents on carbon, independently selected from:
—F, —OH, —OR$^X$, —R$^X$, —CF$_3$, —CN, phenyl, and pyridinyl, wherein phenyl and pyridinyl are optionally substituted with one or more groups selected from —F, —Cl, —Br, —OH, —OR$^X$, and —R$^X$; and substituents on nitrogen, if present, independently selected from:
—R$^X$, —S(=O)$_2$R$^X$ and —C(=O)R$^X$;
wherein each —R$^X$ is independently saturated aliphatic C$_{1-4}$alkyl.

In one embodiment, optional substituents on each of -$J^1$, -$J^2$, -$J^3$, and -$J^4$, if present, are independently selected from:
  substituents on carbon, independently selected from:
    —F, —OH, —OMe, -Me, —$CF_3$, —CN, phenyl, and pyridinyl; and
  substituents on nitrogen, if present, independently selected from:
    -Me, —S(=O)$_2$Me and —C(=O)Me.

In one embodiment, optional substituents on each of -$J^1$, -$J^2$, -$J^3$, and -$J^4$, if present, are independently selected from:
  substituents on carbon, independently selected from:
    —F and saturated aliphatic $C_{1-3}$alkyl; and
  substituents on nitrogen, if present, independently selected from:
    saturated aliphatic $C_{1-3}$alkyl.

In one embodiment, optional substituents on each of -$J^1$, -$J^2$, -$J^3$, and -$J^4$, if present, are independently selected from: saturated aliphatic $C_{1-3}$alkyl.

The Group —$R^P$

In one embodiment, each —$R^P$ is independently —$R^Q$ or —$R^R$.

In one embodiment, each —$R^P$ is independently —$R^Q$.

In one embodiment, each —$R^P$ is independently —$R^R$.

The Group —$R^Q$

In one embodiment, each —$R^Q$ is independently saturated aliphatic $C_{1-4}$alkyl or saturated $C_{3-6}$cycloalkyl, and is optionally substituted, for example, with one or more fluorine atoms.

In one embodiment, each —$R^Q$ is independently saturated aliphatic $C_{1-4}$alkyl, and is optionally substituted, for example, with one or more fluorine atoms.

The Group —$R^R$

In one embodiment, each —$R^R$ is independently phenyl or $C_{5-10}$heteroaryl (e.g., furanyl, thienyl, pyrrolyl, imidazolyl, pyrazolyl, triazolyl, oxazolyl, isoxazolyl, thiazolyl, isothiazolyl, pyridyl, pyrimidinyl, pyridazinyl, benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzopyridyl, benzopyrimidinyl, or benzopyridazinyl, and is optionally substituted, for example, with one or more substitutents independently selected from:
  —F, —Cl, —Br,
  —$R^{K1}$, —$CF_3$,
  —OH, —$OR^{K1}$, —$OCF_3$,
  —$NH_2$, —$NHR^{K1}$, —$NR^{K1}{}_2$,
  —NHC(=O)$R^{K1}$, —$NR^{K1}$C(=O)$R^{K1}$,
  —C(=O)OH, —C(=O)$OR^{K1}$,
  —C(=O)$NH_2$, —C(=O)$NHR^{K1}$, —C(=O)$NR^{K1}{}_2$,
  —$NO_2$, and
  —CN;
wherein each —$R^{K1}$ is independently saturated aliphatic $C_{1-4}$alkyl.

In one embodiment, each —$R^R$ is independently phenyl or $C_{5-6}$heteroaryl (e.g., furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl), and is optionally substituted, for example, with one or more substituents independently selected from:
  —F, —Cl, —Br,
  —$R^{K1}$, —$CF_3$,
  —OH, —$OR^{K1}$, —$OCF_3$,
  —$NH_2$, —$NHR^{K1}$, —$NR^{K1}{}_2$,
  —NHC(=O)$R^{K1}$, —$NR^{K1}$C(=O)$R^{K1}$,
  —C(=O)OH, —C(=O)$OR^{K1}$,
  —C(=O)$NH_2$, —C(=O)$NHR^{K1}$, —C(=O)$NR^{K1}{}_2$,
  —$NO_2$, and
  —CN;
wherein each —$R^{K1}$ is independently saturated aliphatic $C_{1-4}$alkyl.

The Group —$R^M$

In one embodiment, each —$R^M$ is independently azetidino, pyrrolidino, piperidino, piperazino, morpholino, azepino, or diazepino, and is optionally substituted, for example, on carbon, with one or more substitutents independently selected from:
  —F, —$R^{K2}$, —OH, —$OR^{K2}$, —$OCF_3$, —CN, and =O; and
on nitrogen, if present, with one or more substitutents independently selected from:
  —C(=O)$R^{K2}$, —$R^{K2}$, —C(=O)Ph, —S(=O)$_2R^{K2}$, —S(=O)$_2$Ph, —S(=O)$_2NH_2$,
  —S(=O)$_2NHR^{K2}$, —S(=O)$_2NR^{K2}{}_2$, and —S(=O)$_2$NHPh;
wherein each —$R^{K2}$ is independently saturated aliphatic $C_{1-4}$alkyl.

In one embodiment, each —$R^M$ is independently azetidino, pyrrolidino, piperidino, piperazino, morpholino, azepino, or diazepino, and is optionally substituted, for example, on carbon, with one or more substitutents independently selected from:
  —F, —$R^{K2}$, —OH, —$OR^{K2}$, —$OCF_3$, and —CN; and
on nitrogen, if present, with one or more substitutents independently selected from:
  —C(=O)$R^{K2}$, —$R^{K2}$, —C(=O)Ph, —S(=O)$_2R^{K2}$, —S(=O)$_2$Ph, —S(=O)$_2NH_2$,
  —S(=O)$_2NHR^{K2}$, —S(=O)$_2NR^{K2}{}_2$, and —S(=O)$_2$NHPh;
wherein each —$R^{K2}$ is independently saturated aliphatic $C_{1-4}$alkyl.

In one embodiment, each —$R^M$ is independently azetidino, pyrrolidino, piperidino, piperazino, morpholino, azepino, or diazepino, and is optionally substituted, for example, on carbon, with one or more substitutents independently selected from —$R^{K2}$, wherein each —$R^{K2}$ is independently saturated aliphatic $C_{1-4}$alkyl.

The Group —$R^L$—

In one embodiment, each —$R^L$— is independently saturated aliphatic $C_{1-4}$alkylene.

In one embodiment, each —$R^L$— is independently saturated aliphatic $C_{1-3}$alkylene.

In one embodiment, each —$R^L$— is independently —$CH_2$—, —CH($CH_3$)$_2$—, —$CH_2CH_2$—, —$CH_2CH_2CH_2$— or —$CH_2CH_2CH_2CH_2$—.

In one embodiment, each —$R^L$— is independently —$CH_2$—, —$CH_2CH_2$—, —$CH_2CH_2CH_2$— or —$CH_2CH_2CH_2CH_2$—.

In one embodiment, each —$R^L$— is independently —$CH_2$— or —$CH_2CH_2$—.

Molecular Weight

In one embodiment, the AMTP compound has a molecular weight of from 181 to 1200.

In one embodiment, the bottom of range is from 190, 200, 225, 250, 275, 300, or 350.

In one embodiment, the top of range is 1100, 1000, 900, 800, 700, or 600.

In one embodiment, the range is 200 to 600.

Combinations

Each and every compatible combination of the embodiments described above is explicitly disclosed herein, as if each and every combination was individually and explicitly recited.

Examples of Specific Embodiments

In one embodiment, the compounds are selected from compounds of the following formulae and pharmaceutically acceptable salts, hydrates, and solvates thereof:

| Code No. | Synthesis | Structure |
|---|---|---|
| AA-001 | 45 | 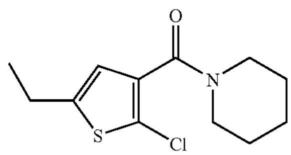 [SMILES: CCc1cc(C(=O)N2CCCCC2)c(Cl)s1] |
| AA-002 | 40 | 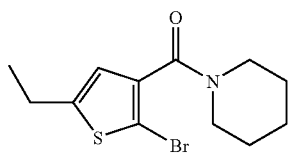 [SMILES: CCc1cc(C(=O)N2CCCCC2)c(Br)s1] |
| AA-003 | 41 | 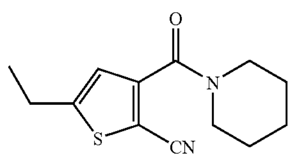 |
| AA-004 | 45 | 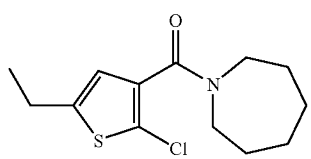 |
| AA-005 | 40 | 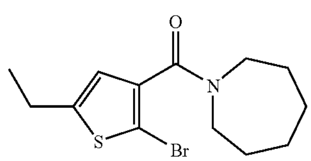 [SMILES: CCc1cc(C(=O)N2CCCCCC2)c(Br)s1] |
| AA-006 | 41 | 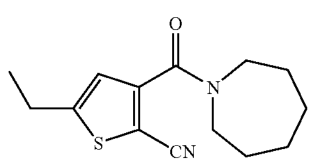 [SMILES: CCc1cc(C(=O)N2CCCCCC2)c(C#N)s1] |
| AA-008 | 45 | 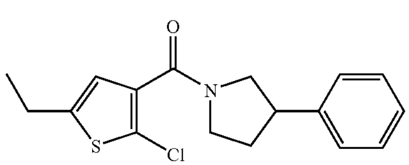 [SMILES: CCc1cc(C(=O)N2CCC(c3ccccc3)C2)c(Cl)s1] |
| AA-009 | 37 | 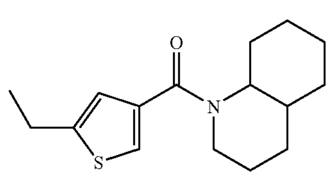 [SMILES: CCc1cc(C(=O)N2CCCC3CCCCC32)cs1] |
| AA-010 | 37 | |
| AA-011 | 9 | |
| AA-012 | 9 | CIS ISOMERS |
| AA-013 | 45 | |
| AA-014 | 37 | |
| AA-015 | 37 | |
| AA-016 | 37 | |
| AA-017 | 9 | |

-continued
| Code No. | Synthesis | Structure |
|---|---|---|
| AA-018 | 9 | 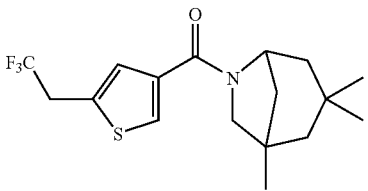 [SMILES: CC1(C)CC2CC(C)(CN2C(=O)c2csc(CC(F)(F)F)c2)C1] |
| AA-019 | 37 | 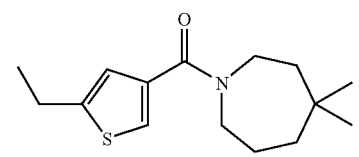 [SMILES: CCc1cc(C(=O)N2CCCC(C)(C)CC2)cs1] |
| AA-020 | 37 | 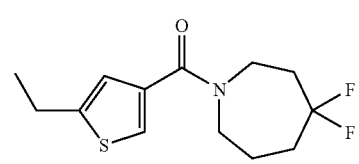 |
-continued
| Code No. | Synthesis | Structure |
|---|---|---|
| AA-021 | 37 | 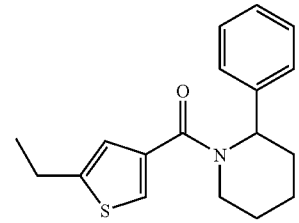 [SMILES: CCc1cc(C(=O)N2CCCCC2c2ccccc2)cs1] |
| AA-022 | 74 | 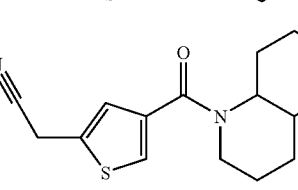<br>DHQ [CIS-M] |
In one embodiment, the compounds are selected from compounds of the following formulae and pharmaceutically acceptable salts, hydrates, and solvates thereof:
| Code No. | Synthesis | Structure |
|---|---|---|
| BB-001 | 50 | 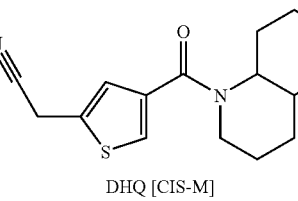 |
| BB-002 | 50 | 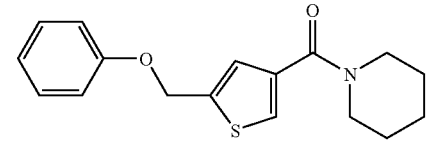 [SMILES: O=C(c1csc(COc2ccccc2)c1)N1CCCCC1] |
| BB-003 | 50 | 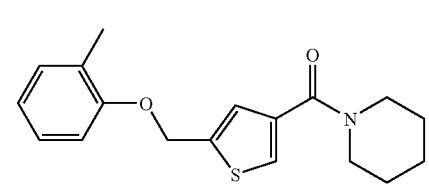 [SMILES: Cc1ccccc1OCc1cc(C(=O)N2CCCCC2)cs1] |
| BB-004 | 50 | 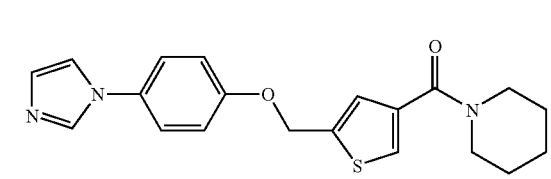 [SMILES: O=C(c1csc(COc2ccc(-n3ccnc3)cc2)c1)N1CCCCC1] |
| BB-005 | 9 | 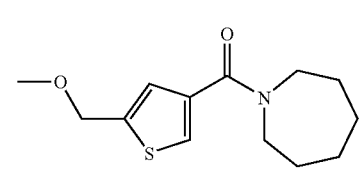 [SMILES: COCc1cc(C(=O)N2CCCCCC2)cs1] |

| Code No. | Synthesis | Structure |
|---|---|---|
| BB-006 | 9 | 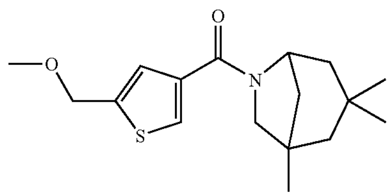 |
| BB-007 | 9 | 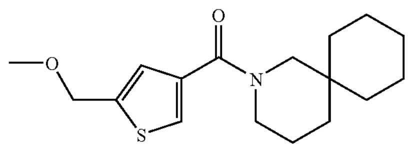 [SMILES: COCc1cc(C(=O)N2CCCC3(CCCCC3)C2)cs1] |

In one embodiment, the compounds are selected from compounds of the following formulae and pharmaceutically acceptable salts, hydrates, and solvates thereof:

| Code No. | Synthesis | Structure |
|---|---|---|
| CC-001 | 4 | 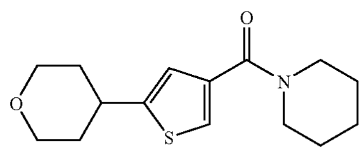 [SMILES: O=C(c1csc(C2CCOCC2)c1)N1CCCCC1] |
| CC-002 | 4 | 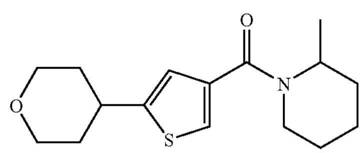 [SMILES: CC1CCCCN1C(=O)c1csc(C2CCOCC2)c1] |
| CC-003 | 4 | 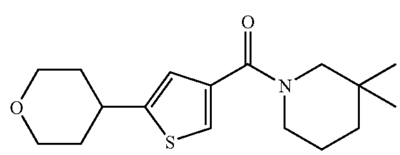 [SMILES: CC1(C)CCCN(C(=O)c2csc(C3CCOCC3)c2)C1] |
| CC-004 | 4 | 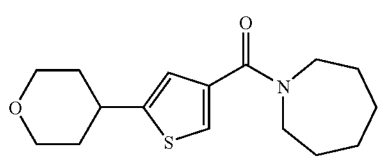 [SMILES: O=C(c1csc(C2CCOCC2)c1)N1CCCCCC1] |
| CC-005 | 5 | 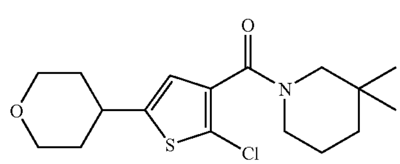 [SMILES: CC1(C)CCCN(C(=O)c2cc(C3CCOCC3)sc2Cl)C1] |
| CC-006 | 5 | 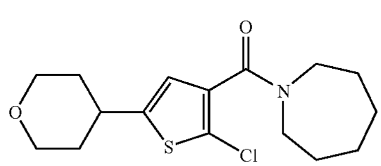 [SMILES: O=C(c1cc(C2CCOCC2)sc1Cl)N1CCCCCC1] |

-continued

| Code No. | Synthesis | Structure |
|---|---|---|
| CC-007 | 13 | 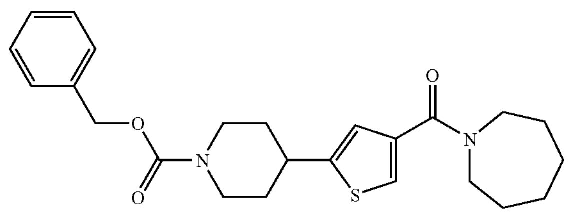 [SMILES: O=C(OCc1ccccc1)N1CCC(c2cc(C(=O)N3CCCCCC3)cs2)CC1] |
| CC-008 | 14 | 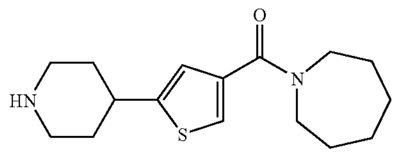 [SMILES: O=C(c1csc(C2CCNCC2)c1)N1CCCCCC1] |
| CC-009 | 34 | 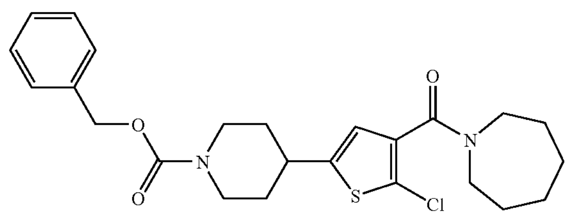 [SMILES: O=C(OCc1ccccc1)N1CCC(c2cc(C(=O)N3CCCCCC3)c(Cl)s2)CC1] |
| CC-010 | 68 | 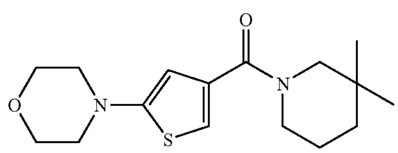 [SMILES: CC1(C)CCCN(C(=O)c2csc(N3CCOCC3)c2)C1] |
| CC-011 | 4 | 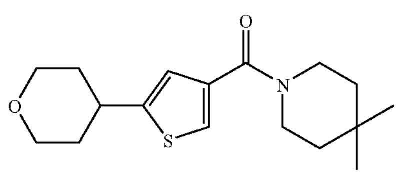 [SMILES: CC1(C)CCN(C(=O)c2csc(C3CCOCC3)c2)CC1] |
| CC-012 | 18 | 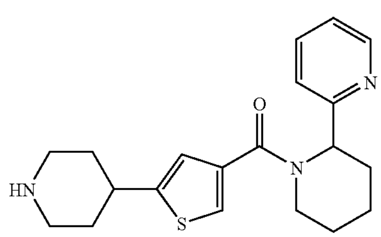 [SMILES: O=C(c1csc(C2CCNCC2)c1)N1CCCCC1c1ccccn1] |
| CC-013 | 18 | 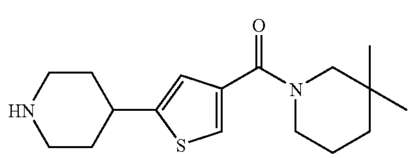 [SMILES: CC1(C)CCCN(C(=O)c2csc(C3CCNCC3)c2)C1] |
| CC-014 | 59 | 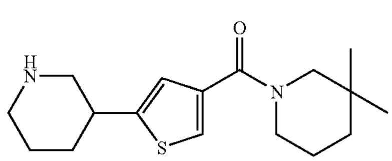 [SMILES: CC1(C)CCCN(C(=O)c2csc(C3CCCNC3)c2)C1] |

-continued

| Code No. | Synthesis | Structure |
|---|---|---|
| CC-015 | 59 | 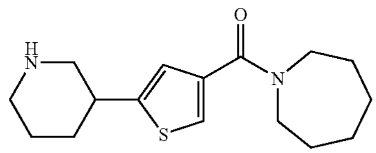 [SMILES: O=C(c1csc(C2CCCNC2)c1)N1CCCCCC1] |
| CC-016 | 66 | 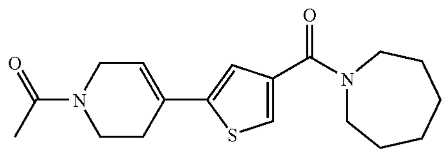 [SMILES: CC(=O)N1CC=C(c2cc(C(=O)N3CCCCCC3)cs2)CC1] |
| CC-017 | 18 | 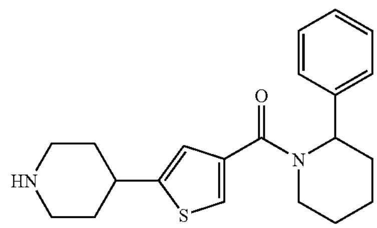 [SMILES: O=C(c1csc(C2CCNCC2)c1)N1CCCCC1c1ccccc1] |
| CC-018 | 18 | 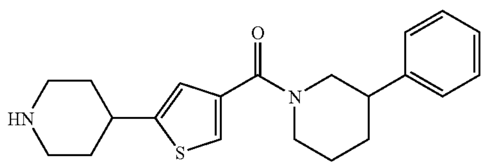 [SMILES: O=C(c1csc(C2CCNCC2)c1)N1CCCC(c2ccccc2)C1] |
| CC-019 | 18 | 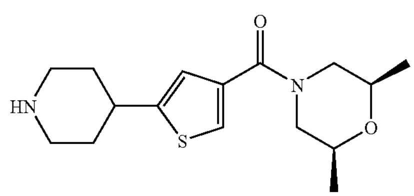 [SMILES: C[C@@H]1CN(C(=O)c2csc(C3CCNCC3)c2)C[C@H](C)O1] |
| CC-020 | 18 | 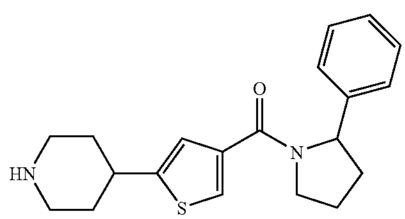 [SMILES: O=C(c1csc(C2CCNCC2)c1)N1CCCC1c1ccccc1] |
| CC-021 | 4 | 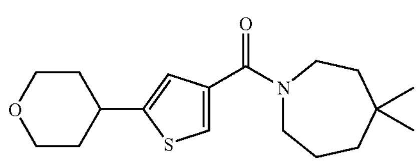 [SMILES: CC1(C)CCCN(C(=O)c2csc(C3CCOCC3)c2)CC1] |
| CC-022 | 4 | 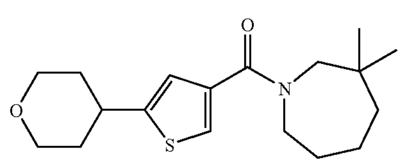 [SMILES: CC1(C)CCCCN(C(=O)c2csc(C3CCOCC3)c2)C1] |

-continued
| Code No. | Synthesis | Structure |
|---|---|---|
| CC-023 | 18 | 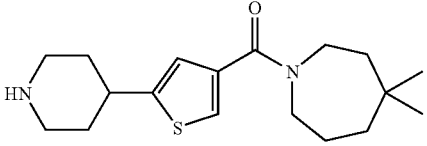 [SMILES: CC1(C)CCCN(C(=O)c2csc(C3CCNCC3)c2)CC1] |
| CC-024 | 18 | 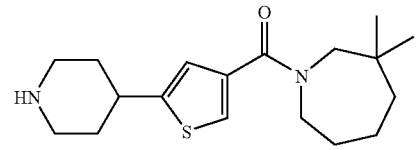 [SMILES: CC1(C)CCCCN(C(=O)c2csc(C3CCNCC3)c2)C1] |
| CC-025 | 19 | 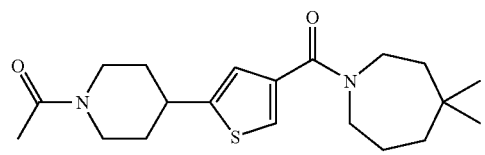 [SMILES: CC(=O)N1CCC(c2cc(C(=O)N3CCCC(C)(C)CC3)cs2)CC1] |
| CC-026 | 19 | 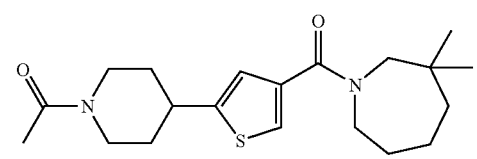 [SMILES: CC(=O)N1CCC(c2cc(C(=O)N3CCCCC(C)(C)C3)cs2)CC1] |
| CC-027 | 4 | 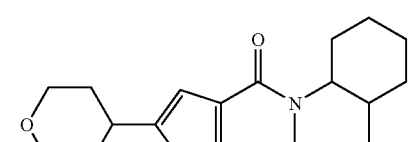<br>CIS ISOMERS |
| CC-028 | 4 | 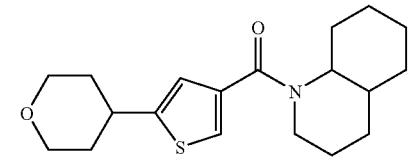<br>TRANS ISOMERS |
| CC-029 | 4 | 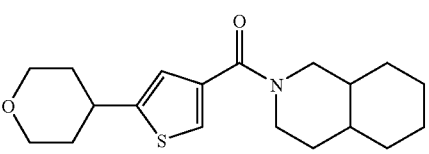 [SMILES: O=C(c1csc(C2CCOCC2)c1)N1CCC2CCCCC2C1] |
| CC-030 | 5 | 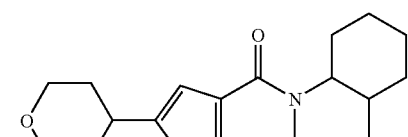 |
| CC-031 | 5 | 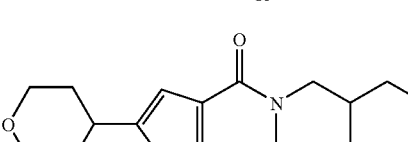 |

-continued
| Code No. | Synthesis | Structure |
|---|---|---|
| CC-032 | 13 | 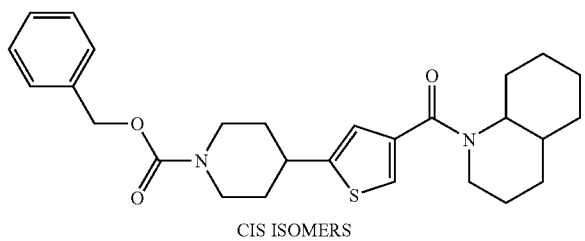 [SMILES: O=C(OCc1ccccc1)N1CCC(c2cc(C(=O)N3CCCC4CCCCC43)cs2)CC1]<br>CIS ISOMERS |
| CC-033 | 23A | 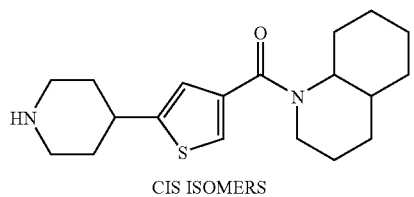<br>CIS ISOMERS |
| CC-034 | 21 | 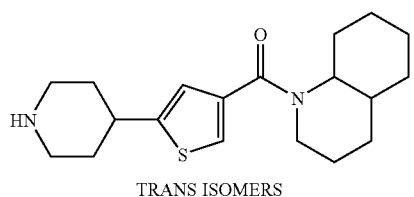<br>TRANS ISOMERS |
| CC-035 | 26 | 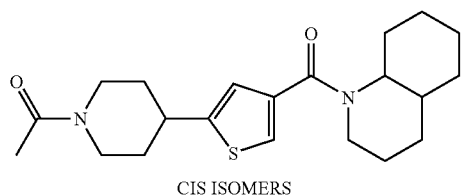 [SMILES: CC(=O)N1CCC(c2cc(C(=O)N3CCCC4CCCCC43)cs2)CC1]<br>CIS ISOMERS |
| CC-036 | 26 | 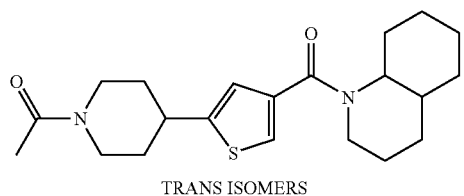 [SMILES: CC(=O)N1CCC(c2cc(C(=O)N3CCCC4CCCCC43)cs2)CC1]<br>TRANS ISOMERS |
| CC-037 | 19 | 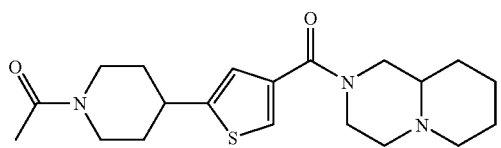 [SMILES: CC(=O)N1CCC(c2cc(C(=O)N3CCN4CCCCC4C3)cs2)CC1] |
| CC-038 | 31 | 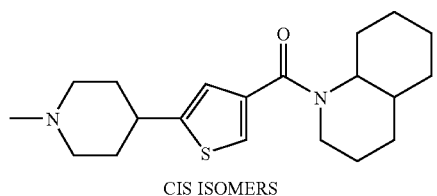 [SMILES: CN1CCC(c2cc(C(=O)N3CCCC4CCCCC43)cs2)CC1]<br>CIS ISOMERS |

-continued

| Code No. | Synthesis | Structure |
|---|---|---|
| CC-039 | 25 | CIS ENANTIOMER C |
| CC-040 | 25 | CIS ENANTIOMER D |
| CC-041 | 18 | 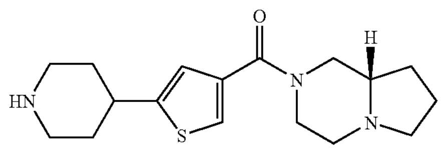 [SMILES: O=C(c1csc(C2CCNCC2)c1)N1CCN2CCC[C@H]2C1] |
| CC-042 | 18 | 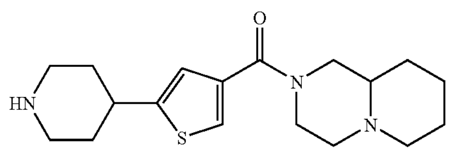 [SMILES: O=C(c1csc(C2CCNCC2)c1)N1CCN2CCCCC2C1] |
| CC-043 | 59 | 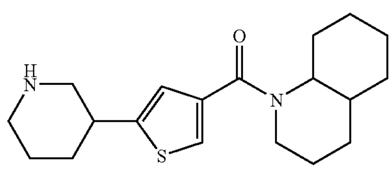 [SMILES: O=C(c1csc(C2CCCNC2)c1)N1CCCC2CCCCC21] |
| CC-044 | 22 | TRANS ENANTIOMER A |
| CC-045 | 22 | TRANS ENANTIOMER B |
| CC-046 | 65 | CIS ISOMERS |

-continued
| Code No. | Synthesis | Structure |
|---|---|---|
| CC-047 | 65 | 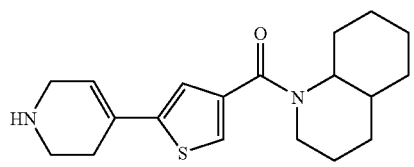<br>TRANS ISOMERS |
| CC-048 | 61 | 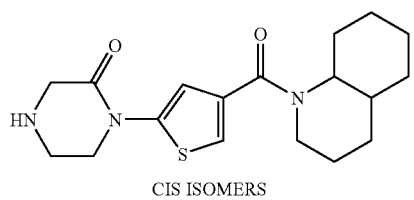<br>CIS ISOMERS |
| CC-049 | 61 | 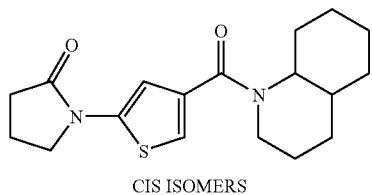 [SMILES: O=C1CCCN1c1cc(C(=O)N2CCCC3CCCCC32)cs1]<br>CIS ISOMERS |
| CC-050 | 61 | 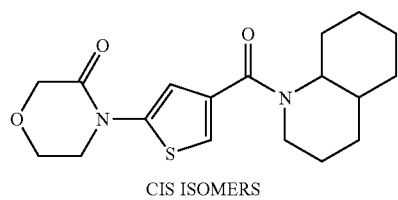 [SMILES: O=C1COCCN1c1cc(C(=O)N2CCCC3CCCCC32)cs1]<br>CIS ISOMERS |
| CC-051 | 26 | 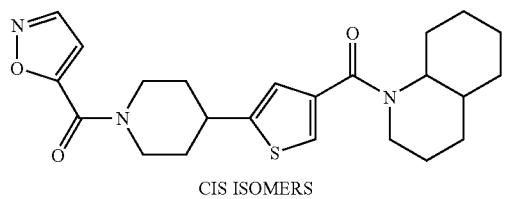 [SMILES: O=C(c1ccno1)N1CCC(c2cc(C(=O)N3CCCC4CCCCC43)cs2)CC1]<br>CIS ISOMERS |
| CC-052 | 26 | 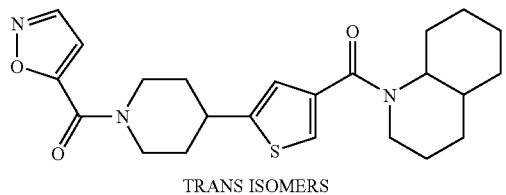 [SMILES: O=C(c1ccno1)N1CCC(c2cc(C(=O)N3CCCC4CCCCC43)cs2)CC1]<br>TRANS ISOMERS |
| CC-053 | 27 | 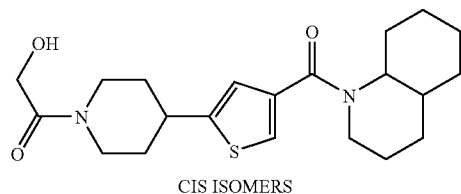 [SMILES: O=C(CO)N1CCC(c2cc(C(=O)N3CCCC4CCCCC43)cs2)CC1]<br>CIS ISOMERS |

-continued
| Code No. | Synthesis | Structure |
|---|---|---|
| CC-054 | 27 | 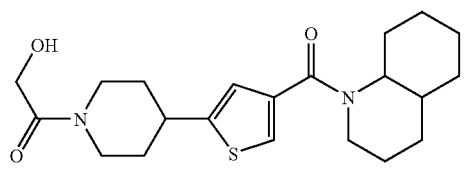<br>TRANS ISOMERS |
| CC-055 | 29 | 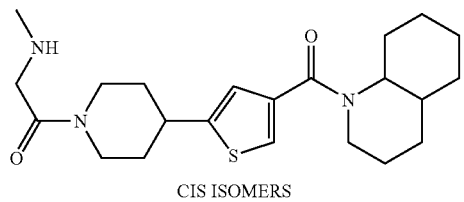 [SMILES: CNCC(=O)N1CCC(c2cc(C(=O)N3CCCC4CCCCC43)cs2)CC1]<br>CIS ISOMERS |
| CC-056 | 29 | 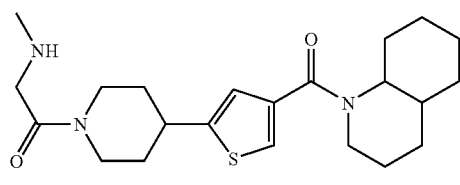<br>TRANS ISOMERS |
| CC-057 | 30 | 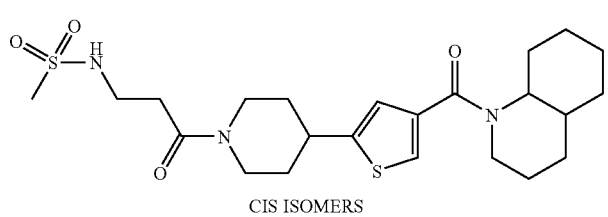 [SMILES: CS(=O)(=O)NCCC(=O)N1CCC(c2cc(C(=O)N3CCCC4CCCCC43)cs2)CC1]<br>CIS ISOMERS |
| CC-058 | 30 | 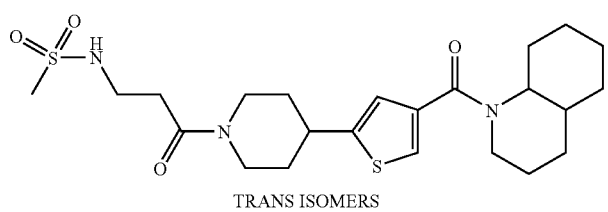 [SMILES: CS(=O)(=O)NCCC(=O)N1CCC(c2cc(C(=O)N3CCCC4CCCCC43)cs2)CC1]<br>TRANS ISOMERS |
| CC-059 | 28 | 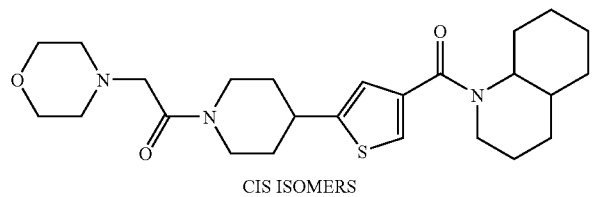 [SMILES: O=C(CN1CCOCC1)N1CCC(c2cc(C(=O)N3CCCC4CCCCC43)cs2)CC1]<br>CIS ISOMERS |
| CC-060 | 28 | 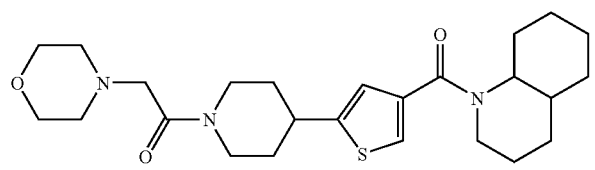<br>TRANS ISOMERS |

-continued
| Code No. | Synthesis | Structure |
|---|---|---|
| CC-061 | 28 | 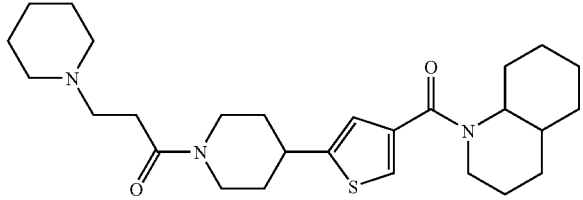<br>CIS ISOMERS |
| CC-062 | 28 | 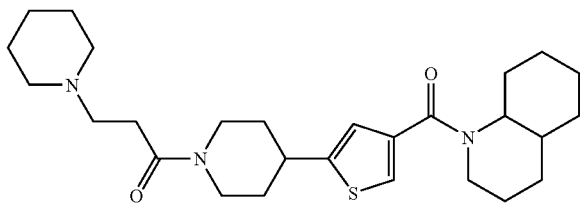<br>TRANS ISOMERS |
| CC-063 | 28 | 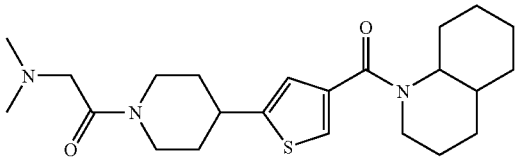<br>CIS ISOMERS |
| CC-064 | 28 | 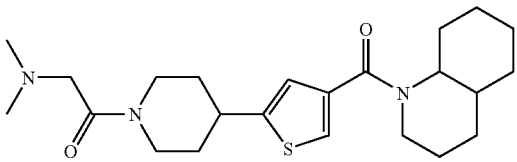<br>TRANS ISOMERS |
| CC-065 | 33 | 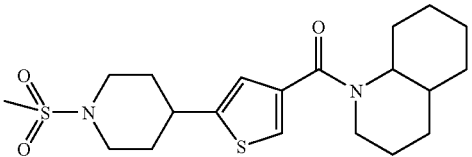<br>CIS ISOMERS |
| CC-066 | 32 | 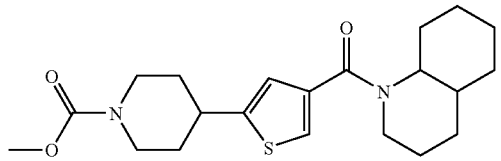<br>CIS ISOMERS |
| CC-067 | 32 | 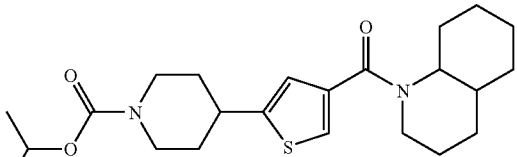<br>CIS ISOMERS |

| Code No. | Synthesis | Structure |
|---|---|---|
| CC-068 | 69 | 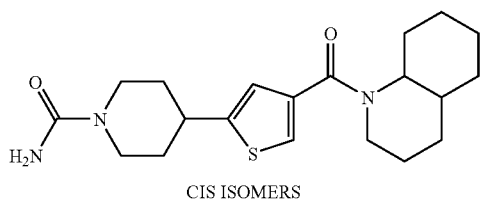<br>CIS ISOMERS |
| CC-069 | 4 | 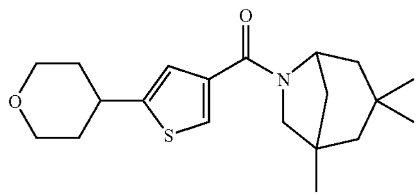 [SMILES: CC1(C)CC2CC(C)(CN2C(=O)c2csc(C3CCOCC3)c2)C1] |
| CC-070 | 5 | 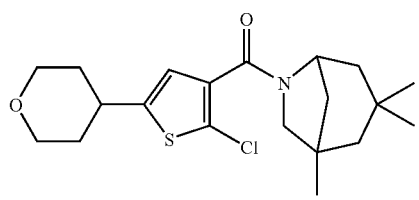 [SMILES: CC1(C)CC2CC(C)(CN2C(=O)c2cc(C3CCOCC3)sc2Cl)C1] |
| CC-071 | 13 | 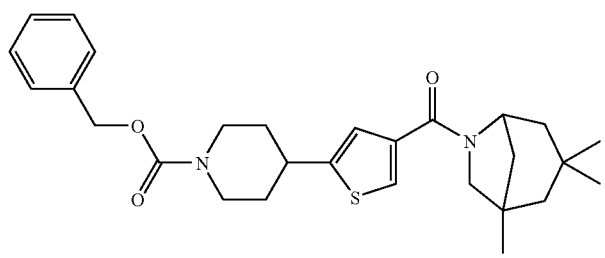 [SMILES: CC1(C)CC2CC(C)(CN2C(=O)c2csc(C3CCN(C(=O)OCc4ccccc4)CC3)c2)C1] |
| CC-072 | 18 | 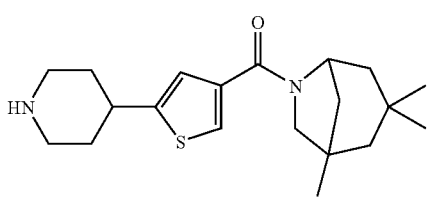 [SMILES: CC1(C)CC2CC(C)(CN2C(=O)c2csc(C3CCNCC3)c2)C1] |
| CC-073 | 59 | 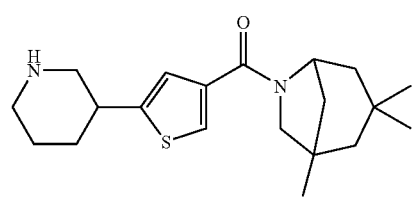 [SMILES: CC1(C)CC2CC(C)(CN2C(=O)c2csc(C3CCCNC3)c2)C1] |
| CC-074 | 65 | 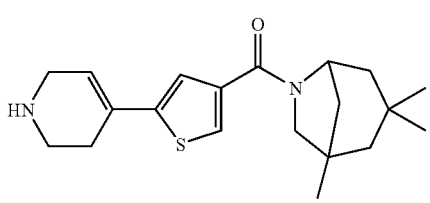 [SMILES: CC1(C)CC2CC(C)(CN2C(=O)c2csc(C3=CCNCC3)c2)C1] |

-continued
| Code No. | Synthesis | Structure |
|---|---|---|
| CC-075 | 72 | 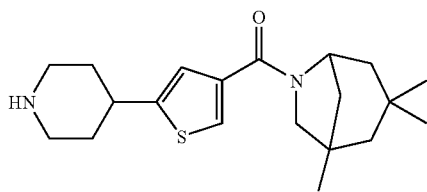 ENANTIOMER G |
| CC-076 | 72 | 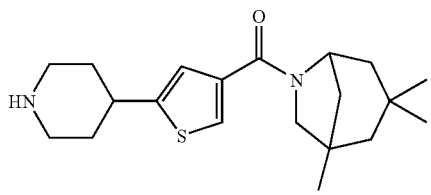 ENANTIOMER H |
| CC-077 | 4 | 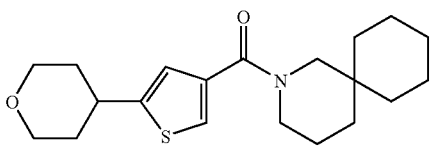 [SMILES: O=C(c1csc(C2CCOCC2)c1)N1CCCC2(CCCCC2)C1] |
| CC-078 | 13 | 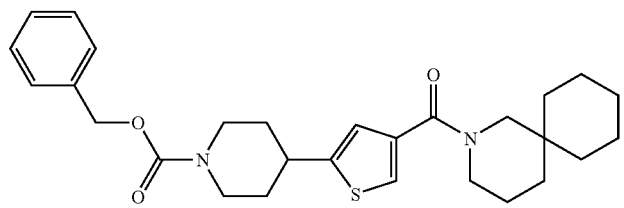 [SMILES: O=C(OCc1ccccc1)N1CCC(c2cc(C(=O)N3CCCC4(CCCCC4)C3)cs2)CC1] |
| CC-079 | 18 | 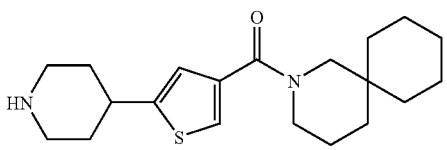 [SMILES: O=C(c1csc(C2CCNCC2)c1)N1CCCC2(CCCCC2)C1] |
| CC-080 | 59 | 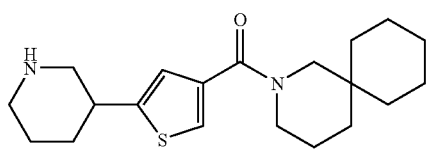 [SMILES: O=C(c1csc(C2CCCNC2)c1)N1CCCC2(CCCCC2)C1] |
| CC-081 | 26 | 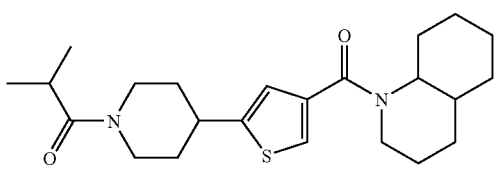 DHQ [CIS-M] |
| CC-082 | 28 | 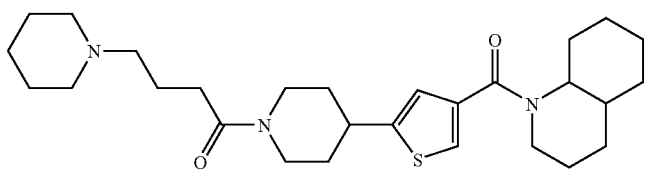 DHQ [CIS-M] |

-continued
| Code No. | Synthesis | Structure |
|---|---|---|
| CC-083 | 26 | 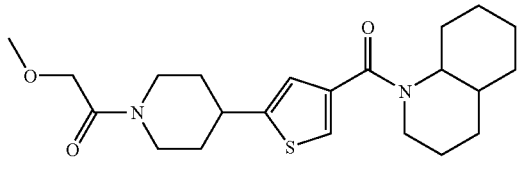<br>DHQ [CIS-M] |
| CC-084 | 26 | 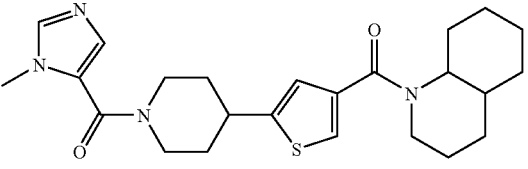<br>DHQ [CIS-M] |
| CC-085 | 28 | 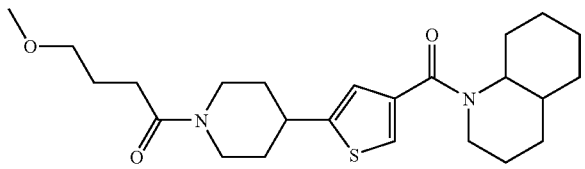<br>DHQ [CIS-M] |
| CC-086 | 66 | 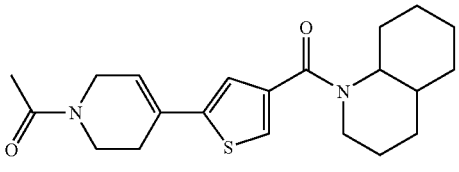<br>DHQ [CIS-M] |
| CC-087 | 31A | 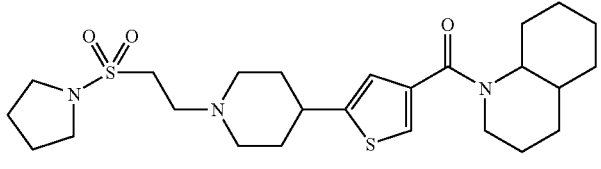<br>DHQ [CIS-M] |
| CC-088 | 31A | 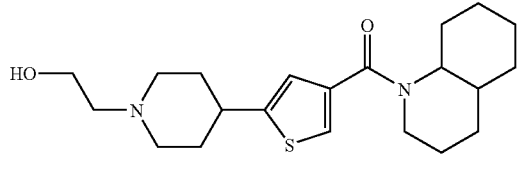<br>DHQ [CIS-M] |
| CC-089 | 31A | 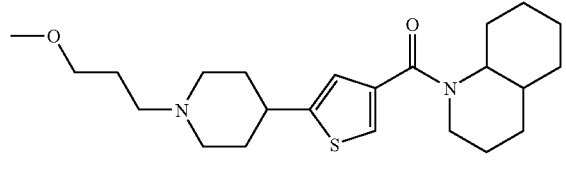<br>DHQ [CIS-M] |

-continued
| Code No. | Synthesis | Structure |
|---|---|---|
| CC-090 | 27 | 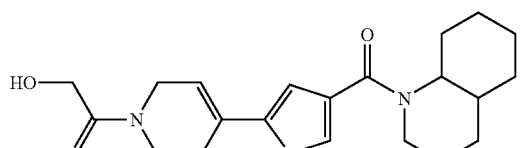<br>DHQ [CIS-M] |
| CC-091 | 30 | 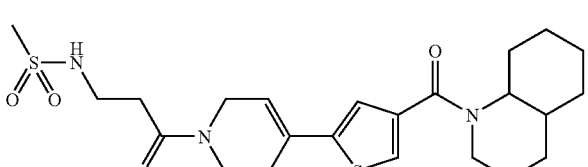<br>DHQ [CIS-M] |
| CC-092 | 33 | 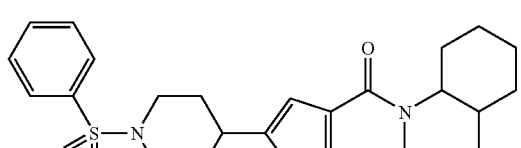<br>DHQ [CIS-M] |
| CC-093 | 33 | 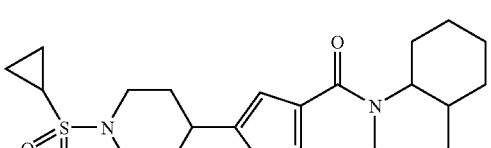<br>DHQ [CIS-M] |
| CC-094 | 32 | 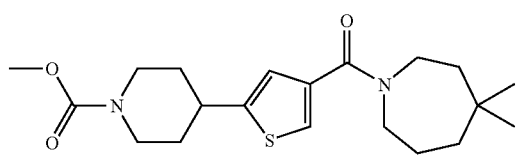 |
| CC-095 | 26 | 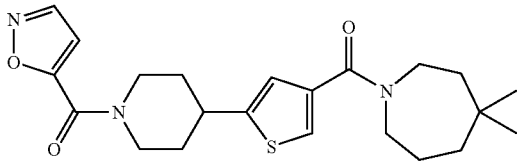 [SMILES: CC1(C)CCCN(C(=O)c2csc(C3CCN(C(=O)c4ccno4)CC3)c2)CC1] |
| CC-096 | 33 | 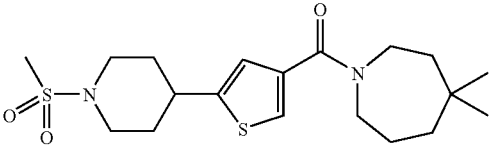 [SMILES: CC1(C)CCCN(C(=O)c2csc(C3CCN(S(C)(=O)=O)CC3)c2)CC1] |
| CC-097 | 28 | 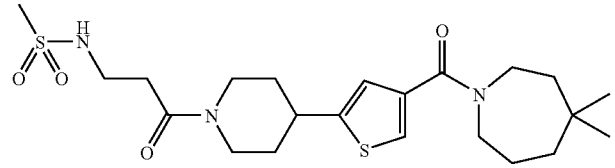 |

-continued
| Code No. | Synthesis | Structure |
|---|---|---|
| CC-098 | 26 | 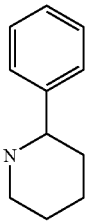 |
| CC-099 | 26 | 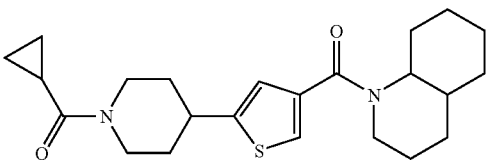<br>DHQ [CIS-M] |
| CC-100 | 26 | 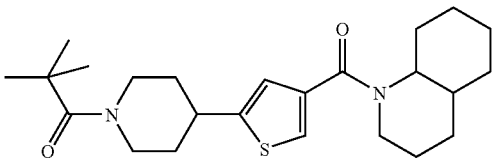<br>DHQ [CIS-M] |
| CC-101 | 27 | 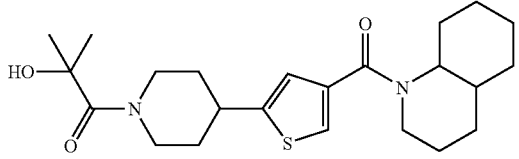<br>DHQ [CIS-M] |
| CC-102 | 27 | 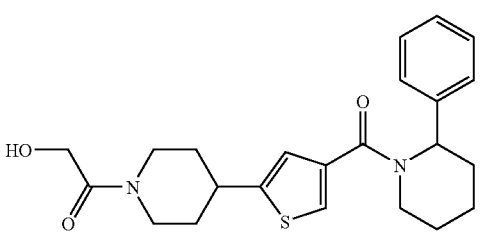 [SMILES: O=C(CO)N1CCC(c2cc(C(=O)N3CCCCC3c3ccccc3)cs2)CC1] |
| CC-103 | 28 | 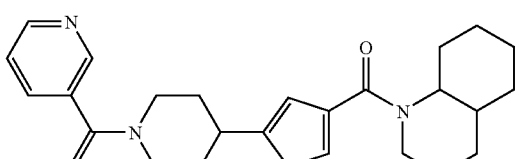<br>DHQ [CIS-M] |
| CC-104 | 33 | 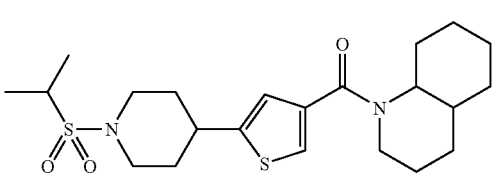<br>DHQ [CIS-M] |

-continued
| Code No. | Synthesis | Structure |
|---|---|---|
| CC-105 | 33 | 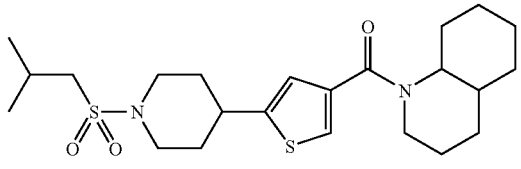<br>DHQ [CIS-M] |
| CC-106 | 32 | 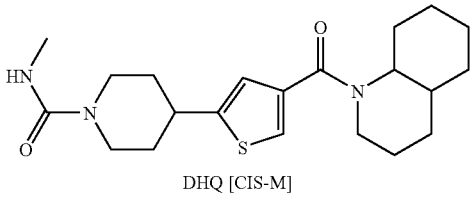 [SMILES: CNC(=O)N1CCC(c2cc(C(=O)N3CCCC4CCCCC43)cs2)CC1]<br>DHQ [CIS-M] |
| CC-107 | 18 | 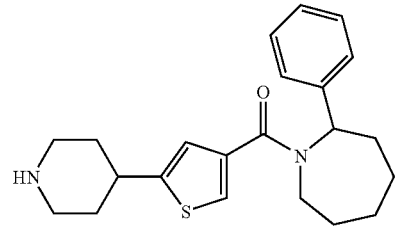 [SMILES: O=C(c1csc(C2CCNCC2)c1)N1CCCCCC1c1ccccc1] |
| CC-108 | 31A | 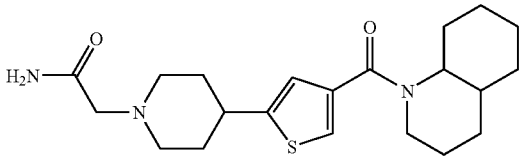<br>DHQ [CIS-M] |
| CC-109 | 28 | 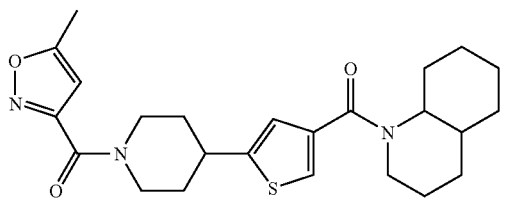<br>DHQ [CIS-M] |
| CC-110 | 28 | 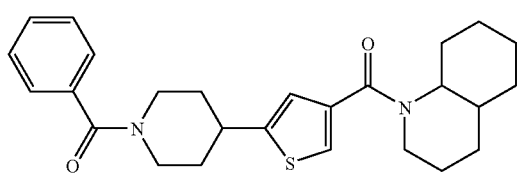<br>DHQ [CIS-M] |
| CC-111 | 82 | 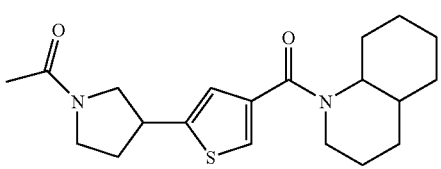<br>DHQ [CIS-S] |

-continued

| Code No. | Synthesis | Structure |
|---|---|---|
| CC-112 | 18 | 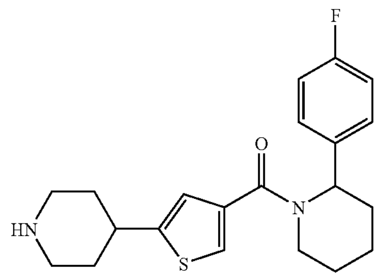 [SMILES: O=C(c1csc(C2CCNCC2)c1)N1CCCCC1c1ccc(F)cc1] |
| CC-113 | 27 | 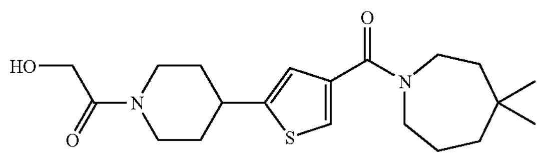 [SMILES: CC1(C)CCCN(C(=O)c2csc(C3CCN(C(=O)CO)CC3)c2)CC1] |
| CC-114 | 25A | DHQ [CIS ENANTIOMER C] |
| CC-115 | 25A | DNQ [CIS ENANTIOMER D] |
| CC-116 | 32 | DHQ [CIS-M] |
| CC-117 | 28 | DHQ [CIS-M] |
| CC-118 | 28 | DHQ [CIS-M] |

| Code No. | Synthesis | Structure |
| --- | --- | --- |
| CC-119 | 32 | 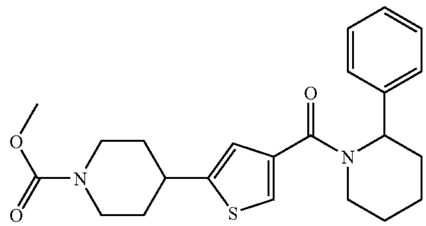 [SMILES: COC(=O)N1CCC(c2cc(C(=O)N3CCCCC3c3ccccc3)cs2)CC1] |
| CC-120 | 76 | DHQ [CIS-M] |
| CC-121 | 76 | DHQ [CIS-M] |
| CC-122 | 4 | 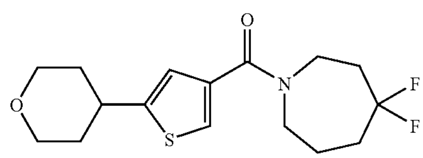 [SMILES: O=C(c1csc(C2CCOCC2)c1)N1CCCC(F)(F)CC1] |
| CC-123 | 65 | 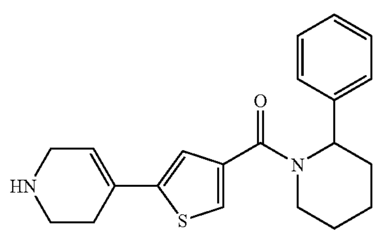 [SMILES: O=C(c1csc(C2=CCNCC2)c1)N1CCCCC1c1ccccc1] |
| CC-124 | 65 | 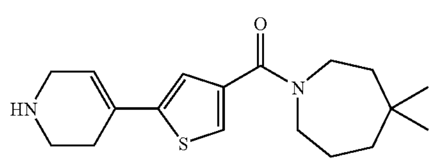 [SMILES: CC1(C)CCCN(C(=O)c2csc(C3=CCNCC3)c2)CC1] |
| CC-125 | 65 | 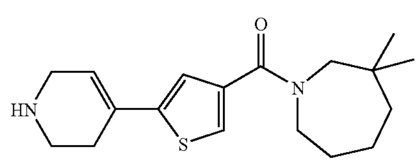 [SMILES: CC1(C)CCCCN(C(=O)c2csc(C3=CCNCC3)c2)C1] |
| CC-126 | 65 | 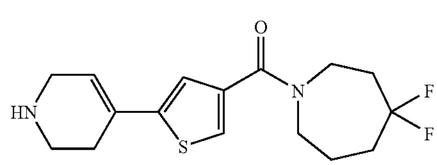 [SMILES: O=C(c1csc(C2=CCNCC2)c1)N1CCCC(F)(F)CC1] |

-continued
| Code No. | Synthesis | Structure |
|---|---|---|
| CC-127 | 75 | 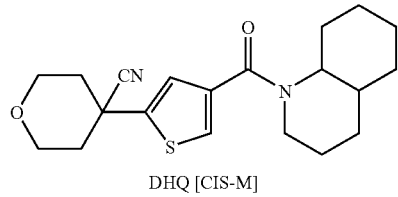 [SMILES: N#CC1(c2cc(C(=O)N3CCCC4CCCCC43)cs2)CCOCC1]<br>DHQ [CIS-M] |
| CC-128 | 30 | 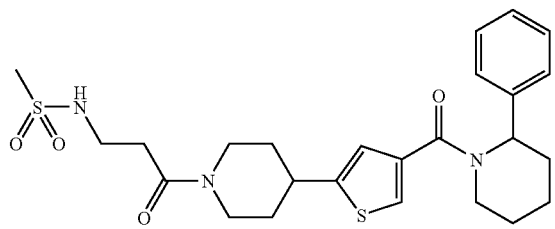 [SMILES: CS(=O)(=O)NCCC(=O)N1CCC(c2cc(C(=O)N3CCCCC3c3ccccc3)cs2)CC1] |
| CC-129 | 76 | 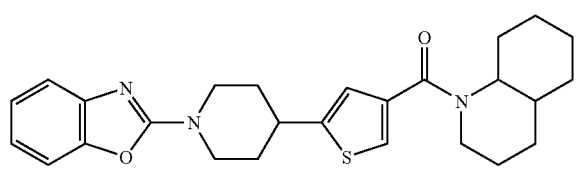<br>DHQ [CIS-M] |
| CC-130 | 18A | 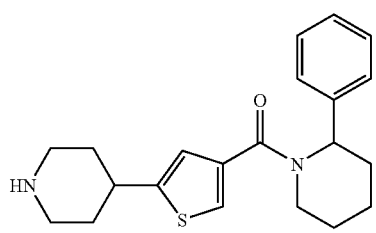<br>ENANTIOMER J |
| CC-131 | 18 | 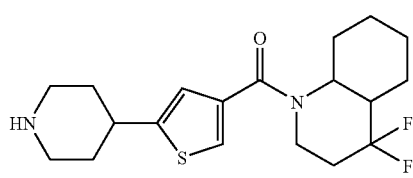<br>DHQ [CIS-M] |
| CC-132 | 32 | 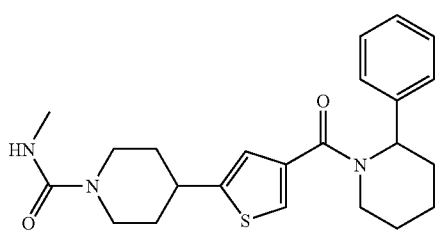 [SMILES: CNC(=O)N1CCC(c2cc(C(=O)N3CCCCC3c3ccccc3)cs2)CC1] |
| CC-133 | 28 | 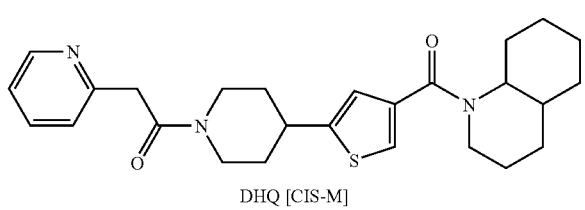<br>DHQ [CIS-M] |

-continued

| Code No. | Synthesis | Structure |
|---|---|---|
| CC-134 | 28 | DHQ [CIS-M] |
| CC-135 | 28 | DHQ [CIS-M] |
| CC-136 | 4 | DHQ [CIS-M] |
| CC-137 | 31B | 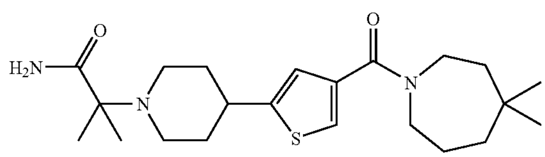 [SMILES: CC1(C)CCCN(C(=O)c2csc(C3CCN(C(C)(C)C(N)=O)CC3)c2)CC1] |
| CC-138 | 4B | DHQ [CIS-M] |
| CC-139 | 31A | 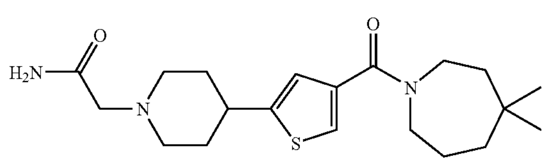 [SMILES: CC1(C)CCCN(C(=O)c2csc(C3CCN(CC(N)=O)CC3)c2)CC1] |
| CC-140 | 4A | DHQ [CIS ENANTOMER L] |
| CC-141 | 4A | DHQ [CIS ENANTIOMER K] |

-continued
| Code No. | Synthesis | Structure |
|---|---|---|
| CC-142 | 25A | 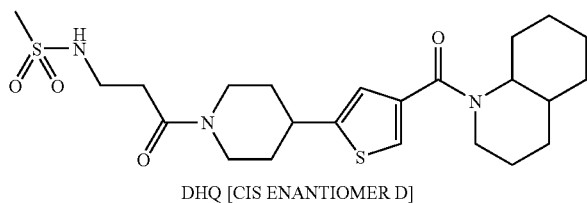 [SMILES: CS(=O)(=O)NCCC(=O)N1CCC(c2cc(C(=O)N3CCCC4CCCCC43)cs2)CC1]<br>DHQ [CIS ENANTIOMER D] |
| CC-143 | 25A | 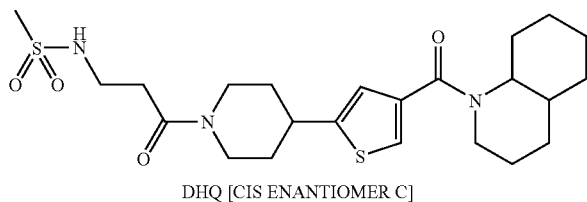 [SMILES: CS(=O)(=O)NCCC(=O)N1CCC(c2cc(C(=O)N3CCCC4CCCCC43)cs2)CC1]<br>DHQ [CIS ENANTIOMER C] |
| CC-144 | 25A | 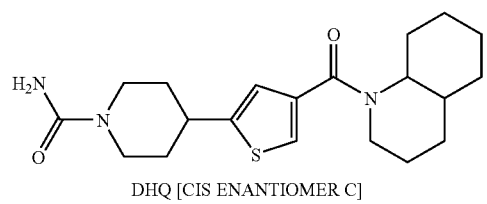 [SMILES: NC(=O)N1CCC(c2cc(C(=O)N3CCCC4CCCCC43)cs2)CC1]<br>DHQ [CIS ENANTIOMER C] |
| CC-145 | 25A | 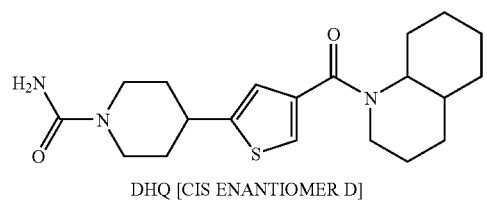 [SMILES: NC(=O)N1CCC(c2cc(C(=O)N3CCCC4CCCCC43)cs2)CC1]<br>DHQ [CIS ENANTIOMER D] |
| CC-146 | 25A | 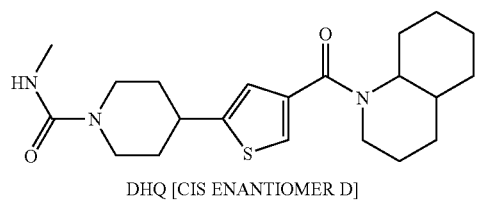 [SMILES: CNC(=O)N1CCC(c2cc(C(=O)N3CCCC4CCCCC43)cs2)CC1]<br>DHQ [CIS ENANTIOMER D] |
| CC-147 | 25A | 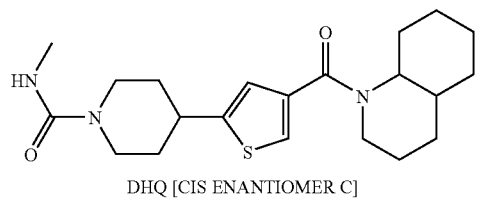 [SMILES: CNC(=O)N1CCC(c2cc(C(=O)N3CCCC4CCCCC43)cs2)CC1]<br>DHQ [CIS ENANTIOMER C] |
| CC-148 | 30 | 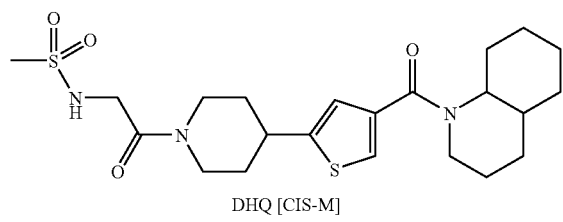 [SMILES: CS(=O)(=O)NCC(=O)N1CCC(c2cc(C(=O)N3CCCC4CCCCC43)cs2)CC1]<br>DHQ [CIS-M] |

-continued
| Code No. | Synthesis | Structure |
|---|---|---|
| CC-149 | 28 | 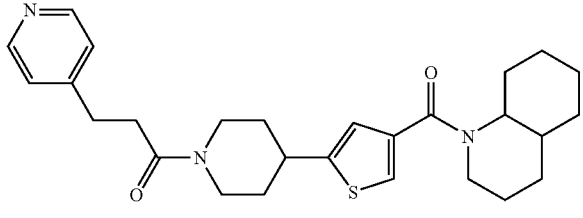<br>DHQ [CIS-M] |
| CC-150 | 31A | 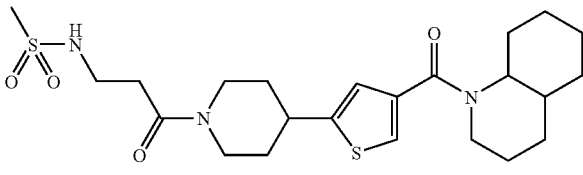<br>DHQ [CIS-M] |
| CC-151 | 28 | 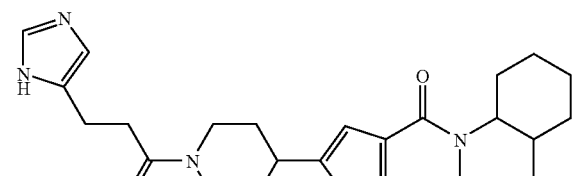<br>DHQ [CIS-M] |
| CC-152 | 77 | 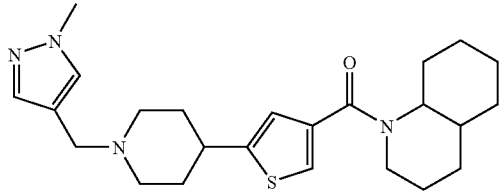<br>DHQ [CIS-M] |
| CC-153 | 31A | 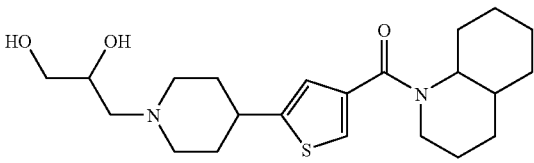<br>DHQ [CIS-M] |
| CC-154 | 77 | 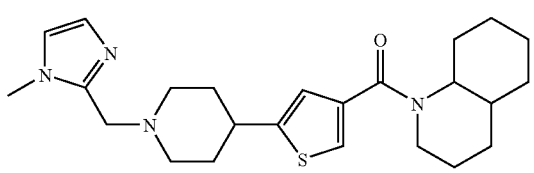<br>DHQ [CIS-M] |
| CC-155 | 23A | 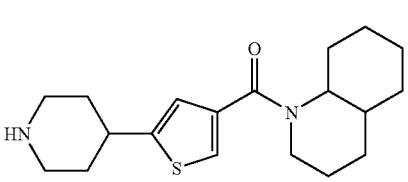<br>DHQ [CIS-R] |

-continued
| Code No. | Synthesis | Structure |
|---|---|---|
| CC-156 | 78 | 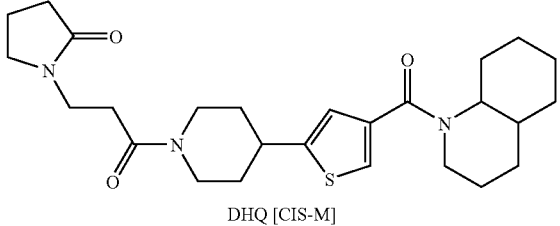 [SMILES: O=C1CCCN1CCC(=O)N1CCC(c2cc(C(=O)N3CCCC4CCCCC43)cs2)CC1]<br>DHQ [CIS-M] |
| CC-157 | 79 | 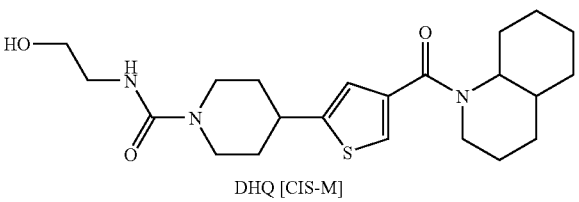 [SMILES: O=C(NCCO)N1CCC(c2cc(C(=O)N3CCCC4CCCCC43)cs2)CC1]<br>DHQ [CIS-M] |
| CC-158 | 31B | 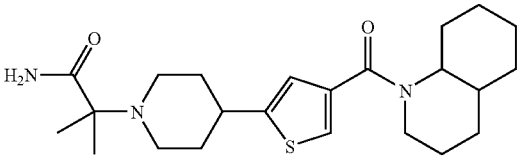<br>DHQ [CIS-M] |
| CC-159 | 23A | 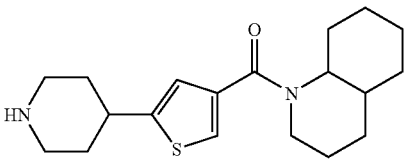<br>DHQ [CIS-S] |
| CC-160 | 79 | 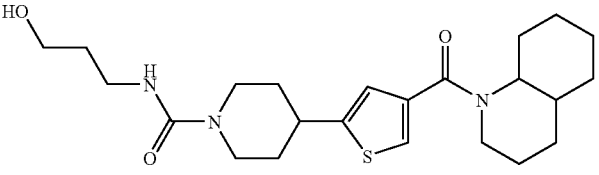<br>DHQ [CIS-S] |
| CC-161 | 79 | 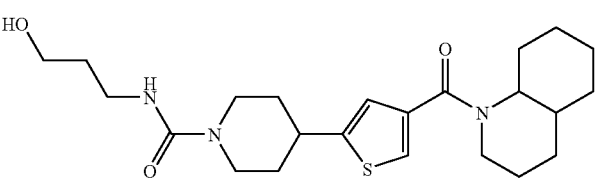<br>DHQ [CIS-R] |
| CC-162 | 79 | 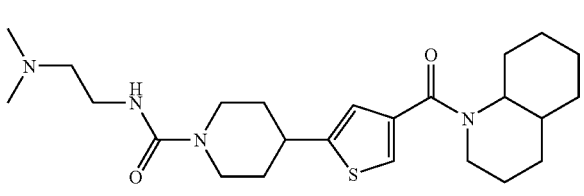<br>DHQ [CIS-S] |

-continued
| Code No. | Synthesis | Structure |
|---|---|---|
| CC-163 | 79 | 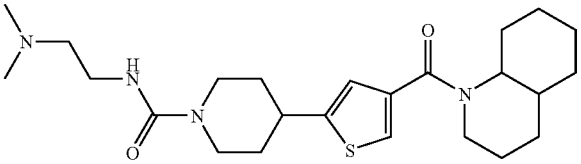<br>DHQ [CIS-R] |
| CC-164 | 79 | 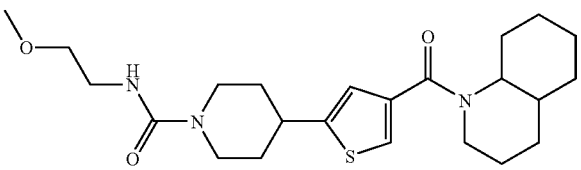<br>DHQ [CIS-R] |
| CC-165 | 79 | 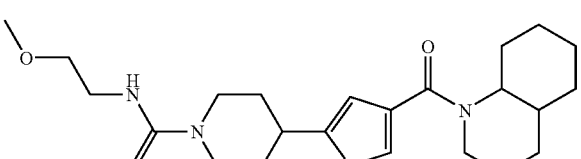<br>DHQ [CIS-S] |
| CC-166 | 79 | 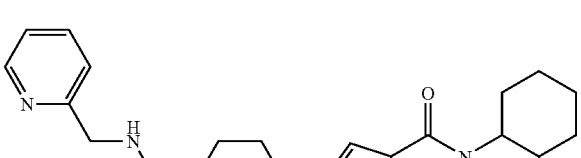<br>DHQ [CIS-R] |
| CC-167 | 79 | 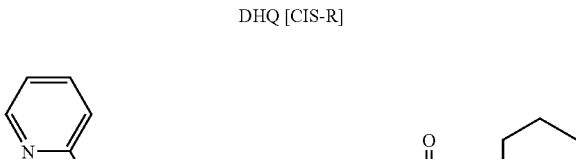<br>DHQ [CIS-S] |
| CC-168 | 80 | 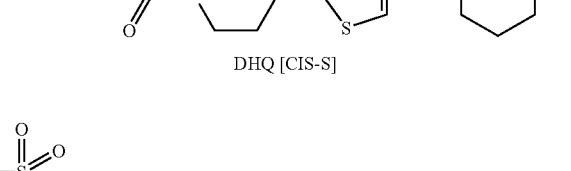<br>DHQ [CIS-S] |

-continued
| Code No. | Synthesis | Structure |
|---|---|---|
| CC-169 | 80 | 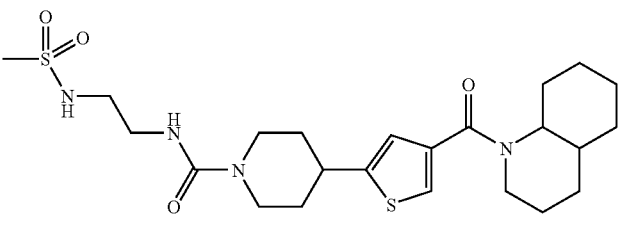<br>DHQ [CIS-R] |
| CC-170 | 31B | 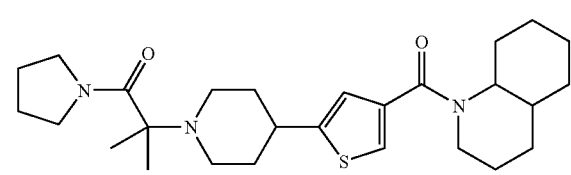<br>DHQ [CIS-S] |
| CC-171 | 31B | 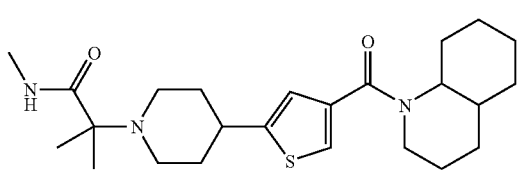<br>DHQ [CIS-S] |
| CC-172 | 83 | 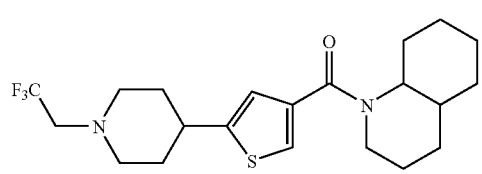<br>DHQ [CIS-S] |
| CC-173 | 79 | 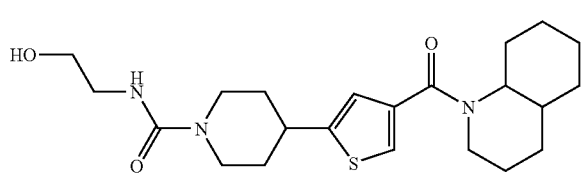<br>DHQ [CIS-S] |
| CC-174 | 31B | 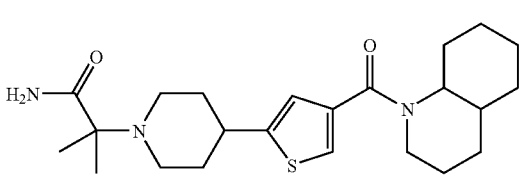<br>DHQ [CIS-S] |
| CC-175 | 79 | 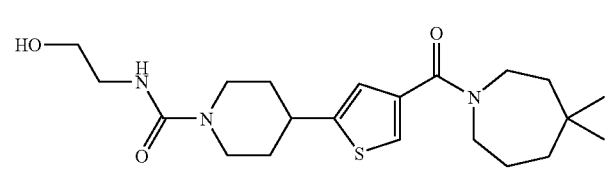 |

| Code No. | Synthesis | Structure |
|---|---|---|
| CC-176 | 65 | DHQ [CIS-S] |
| CC-177 | 4 | DHQ [CIS-S] |

In one embodiment, the compounds are selected from compounds of the following formulae and pharmaceutically acceptable salts, hydrates, and solvates thereof:

| Code No. | Synthesis | Structure |
|---|---|---|
| DD-001 | 54 | 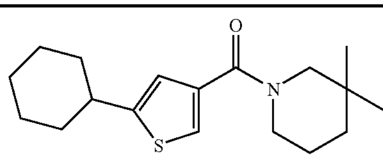 |
| DD-002 | 54 | 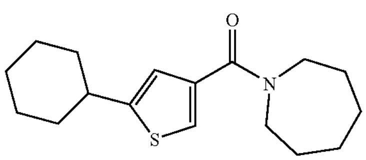 [SMILES: O=C(c1csc(C2CCCCC2)c1)N1CCCCCC1] |
| DD-003 | 54 | CIS ISOMERS |
| DD-004 | 54 | TRANS ISOMERS |
| DD-005 | 54 | 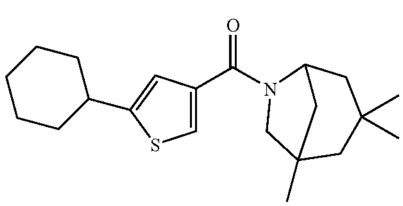 [SMILES: CC1(C)CC2CC(C)(CN2C(=O)c2csc(C3CCCCC3)c2)C1] |
| DD-006 | 54 | |

Substantially Purified Forms

One aspect of the present invention pertains to AMTP compounds, as described herein, in substantially purified form and/or in a form substantially free from contaminants.

In one embodiment, the compound is in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the compound is in a substantially purified form with an optical purity of at least 60% (i.e., 60% of the compound, on a molar basis, is the desired stereoisomer or enantiomer, and 40% is undesired stereoisomer(s) or enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

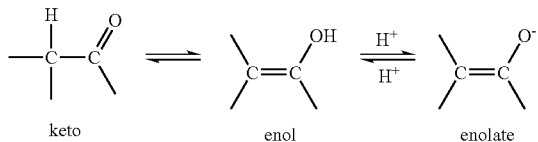

keto    enol    enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl(diphenylmethyl), or trityl(triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of AMTP compounds of the present invention are described herein. These and/or other well known methods may be modified and/or adapted in known ways in order to facilitate the synthesis of additional compounds within the scope of the present invention.

Compositions

One aspect of the present invention pertains to a composition (e.g., a pharmaceutical composition) comprising an AMTP compound, as described herein, and a pharmaceutically acceptable carrier, diluent, or excipient.

Another aspect of the present invention pertains to a method of preparing a composition (e.g., a pharmaceutical composition) comprising admixing an AMTP compound, as described herein, and a pharmaceutically acceptable carrier, diluent, or excipient.

Uses

The AMTP compounds, as described herein, are useful, for example, in the treatment of disorders (e.g., diseases) that are ameliorated by the inhibition of 11β-hydroxysteroid dehydrogenase type 1 (11β-HSD1), as described herein.

Use in Methods of Inhibiting 11β-Hydroxysteroid Dehydrogenase Type 1 (11β-HSD1)

One aspect of the present invention pertains to a method of inhibiting 11β-hydroxysteroid dehydrogenase type 1 in a cell, in vitro or in vivo, comprising contacting the cell with an effective amount of an AMTP compound, as described herein.

Suitable assays for determining 11β-hydroxysteroid dehydrogenase type 1 inhibition are described herein and/or are known in the art.

In one embodiment, the method is performed in vitro.

In one embodiment, the method is performed in vivo.

In one embodiment, the AMTP compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound inhibits 11β-hydroxysteroid dehydrogenase type 1. For example, suitable assays are described herein.

For example, a sample of cells may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to an AMTP compound, as described herein, for use in a method of treatment of the human or animal body by therapy.

Use in the Manufacture of Medicaments

Another aspect of the present invention pertains to use of an AMTP compound, as described herein, in the manufacture of a medicament for use in treatment.

In one embodiment, the medicament comprises the AMTP compound.

Methods of Treatment

Another aspect of the present invention pertains to a method of treatment comprising administering to a patient in need of treatment a therapeutically effective amount of an AMTP compound, as described herein, preferably in the form of a pharmaceutical composition.

Disorders Treated—Disorders Ameliorated by the Inhibition of 11β-Hydroxysteroid Dehydrogenase Type 1

In one embodiment (e.g., of use in methods of therapy, of use in the manufacture of medicaments, of methods of treatment), the treatment is treatment or prevention of a disorder (e.g., a disease) that is ameliorated by the inhibition of 11β-hydroxysteroid dehydrogenase type 1.

Disorders Treated—Disorders Characterised by Up-Regulation of 11β-HSD1 etc.

In one embodiment (e.g., of use in methods of therapy, of use in the manufacture of medicaments, of methods of treatment), the treatment is treatment or prevention of a disorder (e.g., a disease) that is characterised by one or more of: up-regulation of 11β-HSD1; up-regulation of glucocorticoid receptor mediated pathways; elevated PEPCK levels; other biochemical markers pertaining to glucocorticoid excess and insulin resistance.

Disorders Treated

In one embodiment (e.g., of use in methods of therapy, of use in the manufacture of medicaments, of methods of treatment), the treatment is treatment or prevention of one or more of the following:

(1) Cushing's syndrome;
(2) type 2 diabetes and impaired glucose tolerance;
(3) insulin resistance syndromes such as myotonic dystrophy, Prader Willi, lipodystrophies, gastrointestinal diabetes, etc.;
(4) obesity and being overweight;
(5) lipid disorders;
(6) atherosclerosis and its sequelae, including myocardial infarction and peripheral vascular disease;
(7) Metabolic Syndrome;
(8) steatohepatitis/fatty liver;
(9) cognitive impairment in type 2 diabetes, glucose intolerance and ageing, and in psychotic disorders and pre-schizophrenia;
(10) dementias such as Alheimer's disease, multi-infarct dementia, dementia with Lewy bodies, fronto-temporal dementia (including Pick's disease), progressive supranuclear palsy, Korsakoffs syndrome, Binswanger's disease, HIV-associated dementia, Creutzfeldt-Jakob disease (CJD), multiple sclerosis, motor neurone disease, Parkinson's disease, Huntington's disease, Niemann-Pick disease type C, normal pressure hydrocephalus, and Down's syndrome;
(11) mild cognitive impairment (cognitive impairment, no dementia);
(12) β-cell dysfunction in pancreatic disease;
(13) glaucoma;
(14) anxiety;
(15) depression and other affective disorders; typical (melancholic) and atypical depression; dysthymia; post-partum depression; bipolar affective disorder; drug-induced affective disorders; anxiety; posttraumatic stress disorder; panic; phobias;
(16) delirium and acute confusional state;
(17) inflammatory disease;
(18) osteoporosis;
(19) myocardial infarction, for example, to prevent left ventricular dysfunction after myocardial infarction; and
(20) stroke, for example, to limit ischaemic neuronal loss after cardiovascular accident.

In one embodiment (e.g., of use in methods of therapy, of use in the manufacture of medicaments, of methods of treatment), the treatment is treatment or prevention of one or more of the following:

(1) hyperglycaemia;
(2) glucose intolerance and impaired glucose tolerance;
(3) insulin resistance;
(4) hyperlipidaemia;
(5) hypertriglyceridaemia;
(6) hypercholesterolaemia;
(7) low HDL levels;
(8) high LDL levels;
(9) vascular restenosis;
(10) abdominal obesity;
(11) neurodegenerative disease;
(12) retinopathy;
(13) neuropathy;
(14) hypertension; and
(15) other diseases where insulin resistance is a component.

In one embodiment (e.g., of use in methods of therapy, of use in the manufacture of medicaments, of methods of treatment), the treatment is treatment or prevention of an adverse effect of glucocorticoids used to treat inflammatory diseases, such as asthma, chronic obstructive pulmonary disease, skin diseases, rheumatoid arthritis and other arthropathies, inflammatory bowel disease, and giant cell arthritis/polymyalgia rheumatica.

In one embodiment (e.g., of use in methods of therapy, of use in the manufacture of medicaments, of methods of treatment), the treatment is treatment or prevention of metabolic syndrome, which includes disorders such as type 2 diabetes and obesity, and associated disorders including insulin resistance, hypertension, lipid disorders and cardiovascular disorders such as ischaemic (coronary) heart disease.

In one embodiment (e.g., of use in methods of therapy, of use in the manufacture of medicaments, of methods of treatment), the treatment is treatment or prevention of a CNS disorder (e.g., a CNS disease) such as mild cognitive impairment and early dementia, including Alzheimer's disease.

Treatment

The term "treatment," as used herein in the context of treating a disorder, pertains generally to treatment and therapy, whether of a human or an animal (e.g., in veterinary applications), in which some desired therapeutic effect is achieved, for example, the inhibition of the progress of the disorder, and includes a reduction in the rate of progress, a halt in the rate of progress, alleviatiation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of metabolic syndrome, reducing the incidence of metabolic syndrome, alleviating the symptoms of metabolic syndrome, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more (e.g., 1, 2, 3, 4, etc.) additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Examples of additional agents/therapies that may be co-administered/combined with treatment with the AMTP compounds described herein include the following:

(1) insulin and insulin analogues;
(2) insulin sensitising agents, for example: PPAR-γ agonists; PPAR-α agonists; PPAR-α/γ dual agonists; biguanides;
(3) incretin and incretin mimetics;
(4) sulfonylureas and other insulin secretogogues;
(5) α-glucosidase inhibitors;
(6) glucagon receptor antagonists;
(7) GLP-1, GLP-1 analogues, and GLP-receptor agonists;
(8) GIP, GIP mimetics, and GIP receptor agonists;
(9) PACAP, PACAP mimetics, and PACAP receptor 3 agonists;
(10) agents that suppress hepatic glucose output, such as metformin;
(11) agents designed to reduce the absorption of glucose from the intestine, such as acarbose;
(12) phosphotyrosine phosphatase 1B inhibitors;
(13) glucose 6-phosphatase inhibitors;
(14) glucokinase activators;
(15) glycogen phosphorylase inhibitors;
(16) fructose 1,6-biphosphatase inhibitors;
(17) glutamine:fructose-6-phosphate amidotransferase inhibitors;
(18) anti-obesity agents, including: orilistat, sibutramine, fenfluramine, phentermine, dexfenfluramine, cannabinoid CB1 receptor antagonists or inverse agonists such as rimonobant, ghrelin antagonists, oxyntomodulin, neuropeptide Y1 or Y5 antagonists, melanocortin receptor agonists, and melanin-concentrating hormone receptor antagonists;
(19) anti-dyslipidaemia agents, including: HMG-CoA reductase inhibitors, PPAR-α agonists, PPAR-α/γ dual agonists, bile acid sequestrants, ileal bile acid absorption inhibitors, acyl CoA:cholesterol acyltransferase inhibitors, cholesterol absorption inhibitors, cholesterol ester transfer protein inhibitors, nicotinyl alcohol and its analogues, and anti-oxidants;
(20) anti-inflammatory agents, including: non-steroidal anti-inflammatory drugs such as aspirin; and steroidal anti-inflammatory agents such as hydrocortisone and dexamethasone;
(21) anti-hypertensive agents, including: β-blockers such as atenolol and inderal; calcium antagonists such as nifedipine; ACE inhibitors such as lisinopril, aptopril and captopril; angiotensin receptor antagonists such as candesartan, losartan and cilexetil; diuretic agents such as furosemide and benzthiazide; α-antagonists; centrally acting agents such as clonidine, methyl dopa, and indapamide; and vasodilators such as hydralazine;
(22) dipeptidyl peptidase IV (DPP-IV) inhibitors such as sitagliptin and saxagliptin.

Other Uses

The AMTP compounds described herein may also be used as cell culture additives to inhibit 11β-hydroxysteroid dehydrogenase type 1 (11β-HSD1), etc.

The AMTP compounds described herein may also be used as part of an in vitro assay, for example, in order to determine whether a candidate host is likely to benefit from treatment with the compound in question.

The AMTP compounds described herein may also be used as a standard, for example, in an assay, in order to identify other active compounds, other 11β-hydroxysteroid dehydrogenase type 1 (11β-HSD1) inhibitors, etc.

Kits

One aspect of the invention pertains to a kit comprising (a) an AMTP compound as described herein, or a composition comprising an AMTP compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The AMTP compound or pharmaceutical composition comprising the AMTP compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the AMTP compound to be administered alone, it is preferable to present it as a pharmaceutical formulation (e.g., composition, preparation, medicament) comprising at least one AMTP compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one AMTP compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the AMTP compounds, and compositions comprising the AMTP compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular AMTP compound, the route of administration, the time of administration, the rate of excretion of the AMTP compound, the duration of the treatment, other drugs, compounds, and/or materials used in combination, the severity of the disorder, and the species, sex, age, weight, condition, general health, and prior medical history of the patient. The amount of AMTP compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the AMTP compound is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Analytical Method 1:

The system consisted of a Waters LC system with a 1525 LC pump and a Higgins Clipeus 5 μm C18 100×3.0 mm column. Detection was achieved using a Micromass Platform LCT time of flight mass spectrometer (electrospray, positive ion), a Waters UV2488 dual wavelength UV detector at 254 nm and a Sedex ELS 85 evaporative light scattering detector. Mobile Phase A: 0.1% aqueous formic acid, Mobile Phase B: 0.1% formic acid in MeCN. Flow rate 1 mL/min: Gradient: 0-1 min 5% B; 1-15 min 5-95% B; 15-20 min 95% B; 20-22 min 95-5% B; 22-25 min 95% B.

Analytical Method 2:

The system consisted of a Hewlett Packard HP1100 LC system and a Higgins Clipeus 5 μm C18 100×3.0 mm column. Detection was achieved using a Micromass ZQ quadrupole electrospray (positive and negative ion), a UV detector at 254 nm and a Sedex ELS 85 evaporative light scattering detector. Mobile Phase A: 0.1% aqueous formic acid, Mobile Phase B: 0.1% formic acid in MeCN. Flow rate 1 mL/min: Gradient: 0-1 min 5% B; 1-15 min 5-95% B; 15-20 min 95% B; 20-22 min 95-5% B; 22-25 min 95% B.

Analytical Method 3:

The system consisted of a Waters HPLC and mass spectrometer system and an Agilent Scalar 5 μm C18 50×4.6 mm column. Detection was achieved using an electrospray ionization source (positive or negative ion), a UV detector at 254 nm and 215 nm. Mobile Phase A: 0.1% aqueous formic acid, Mobile Phase B: 0.1% formic acid in MeCN. Flow rate 2.5 mL/min: Gradient: 0-0.1 min 5% B; 0.1-5 min 5-95% B; 5-5.5 min 95% B; 5.5-5.6 min 95% B, flow increased to 3.5 mL/min; 5.6-6.6 95% B; 6.6-6.75 min 95-5% B; 6.75-6.9 min 5% B; 6.9-7 min 5% B, flow reduced to 2.5 mL/min.

Analytical Method 4:

The system consisted of Hewlett Packard HP1100 LC system and a Phenomenex Luna 3 μm C18 30×4.6 mm column. Detection was achieved using a Waters Platform LC quadrupole mass spectrometer (positive and negative ion), a UV diode array detector and a Sedex ELS 85 evaporative light scattering detector. Mobile Phase A: 0.1% aqueous formic acid, Mobile Phase B: 0.1% formic acid in MeCN. Flow rate 2 mL/min: Gradient: 0-0.5 min 5% B; 0.5-4.5 min 5-95% B; 4.5-5.5 min 95% B; 5.5-6 min 95-5% B.

Analytical Method 5:

The system consisted of an HPLC system and a ChiralPak IA 5 μm 250×21.2 mm column. Detection was achieved using a UV detector at 254 nm. The isocratic mobile phase used is stated in the text below. Flow rate 1 mL/min.

Analytical Method 6:

The system consisted of an HPLC system and a ChiralPak IA 5 μm 250×21.2 mm column. Detection was achieved using a UV detector at 254 nm. Mobile phase 10% EtOH/Heptane. Flow rate 0.9 mL/min.

Analytical Method 7:

The system consisted of an Agilent 1200 HPLC and mass spectrometer system and an Agilent Scalar 5 μm C18 50×4.6 mm column. Detection was achieved using an electrospray ionization source (positive or negative ion), a UV detector at 254 nm. Mobile Phase A: 0.1% aqueous formic acid, Mobile Phase B: 0.1% formic acid in MeCN. Flow rate 2.5 mL/min: Gradient: 0-0.1 min 5% B; 0.1-5min 5-95% B; 5-5.5min 95% B; 5.5-5.6 min 95% B, flow increased to 3.5 mL/min; 5.6-6.6 95% B; 6.6-6.75 min 95-5% B; 6.75-6.9 min 5% B; 6.9-7 min 5% B, flow rate reduced to 2.5 mL/min.

ABBREVIATIONS

DCE=Dichloroethane
DCM=Dichloromethane
DEA=Diethylamine
DEAD=Diethyl azodicarboxylate
DIPEA=Diisopropylethylamine
DME=1,2-Dimethoxyethane
DMF=Dimethylformamide
EDC=1-ethyl-3-(3-dimethylaminopropyl)carbodiimide.hydrochloride
HATU=(O-(7-Azabenzotriazol-1-yl)-N,N,N',N'-tetramethyluroniumhexafluorophosphate)
HCl=Hydrochloric acid
Herrmann's catalyst=trans-Di-μ-acetobis[2-(di-o-tolylphosphino)benzyl]-dipalladium (II)
NBS=N-bronnosuccinannide
NCS=N-chlorosuccinamide
IMS=Industrial methylated spirit
R.T.=retention time
TBAF=Tetrabutylammonium fluoride
TBDMSCl=t-Butyldimethylsilyl chloride
tBuONO=t-Butylnitrite
TEA=Triethylamine
TFA=Trifluoroacetic acid
THF=Tetrahydrofuran Compounds were named using Autonom.

Some compounds were isolated as formate salts following HPLC purification. These cases have been marked: FORMATE in the tables below.

Compounds containing chiral centres were prepared as racemic mixtures, unless stated otherwise.

Materials

Trans-decahydroquinoline (a 50:50 mixture of both trans-enantiomers) was obtained from TCI-Europe.

Decahydroquinoline (a mixture containing both of the cis- and both of the trans-enantiomers) was obtained from the Sigma-Aldrich Corporation.

Single cis-decahydroquinoline enantiomers were prepared from 3-(2-oxo-cyclohexyl)-propionic acid and (R)-(−)-2-phenylglycinol or from 3-(2-oxo-cyclohexyl)-propionic acid and (S)-(+)-2-phenylglycinol, using the method described in Amat et al., 2006, Chem. Eur. J., Vol. 12, No. 30, pp. 7872-7881.

Compounds containing decahydroquinolyl amides were prepared as:
(a) a mixture of the cis-diastereomers (referred to as DHQ [CIS-M] or CIS ISOMERS) or
(b) a mixture of the trans-diastereomers (referred to as DHQ [TRANS-M] or TRANS ISOMERS),
where, in certain instances as described below, the cis- or trans-diastereomeric mixtures were separated by chiral HPLC into the corresponding enantiomers, or (c) a single enantiomer of the cis-decahydroquinoline, prepared using (S)-(+)-2-phenylglycinol as a chiral auxiliary utilising the method outlined above (referred to as DHQ [CIS-S]), or (d) a single enantiomer of the cis-decahydroquinoline, prepared using (R)-(−)-2-phenylglycinol as a chiral auxiliary utilising the method outlined above (referred to as DHQ [CIS-R]).

It is predicted that the single enantiomer of cis-decahydroquinoline (DHQ [CIS-S]) prepared using (S)-(+)-2-phenyiglycinol as a chiral auxiliary is, or is predominantly, (4aS,8aS)-decahydroquinoline.

It is predicted that the single enantiomer of cis-decahydroquinoline (DHQ [CIS-R]) prepared using (R)-(−)-2-phenylglycinol as a chiral auxiliary is, or is predominantly, (4aR,8aR)-decahydroquinoline.

When thiophene-3-carboxylic acids are coupled using HATU to a mixture containing an excess of both of the cis- and both of the trans-isomers of decahydroquinoline, it was observed that the amide formed with the cis-decahydroquinoline is the major product. Decahydroquinolyl amides consisting of a mixture of cis-diastereomers (referred to as DHQ [CIS-M] or CIS ISOMERS) were prepared using this method.

Synthesis 1

2-Amino-5-(tetrahydro-pyran-4-yl)-thiophene-3-carboxylic acid ethyl ester

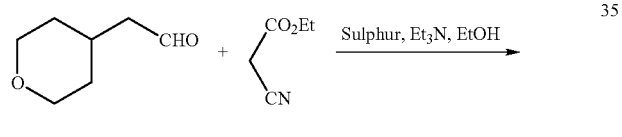

Tetrahydro-pyranyl-4-acetaldehyde (1.17 g, 9.1 mmol), ethyl cyanoacetate (9.1 mmol) and sulphur (9.1 mmol) were dissolved in ethanol (10 mL). Triethylamine (11.83 mmol) was added and the reaction heated to 80° C. overnight. The reaction was cooled to room temperature and the solvent removed under vacuum. The reaction was partitioned between ethyl acetate and sodium hydrogen carbonate. The organic solution was dried over magnesium sulphate, filtered and the solvent evaporated. The product was purified by column chromatography on silica, eluting with 0%-50% ethyl acetate in cyclohexane. The fractions containing the desired product were concentrated under vacuum to give the title compound (2.15 g). LCMS m/z 256 [M+H]+ RT=3.16 min (Analytical Method 4).

Synthesis 2

5-(Tetrahydro-pyran-4-yl)-thiophene-3-carboxylic acid ethyl ester

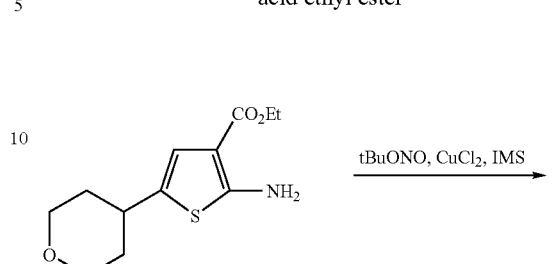

2-Amino-5-(tetrahydro-pyran-4-yl)-thiophene-3-carboxylic acid ethyl ester (1.79 g, 7 mmol) was added to a suspension of tert-butyl nitrite (10.5 mmol) and copper (II) chloride (7 mmol) in IMS (70 mL). The reaction was stirred for 15 minutes then saturated aqueous ammonium chloride (7 mL) was added and the mixture stirred for a further 15 minutes. The solvent was removed under vacuum and the residue partitioned between ethyl acetate and water. The organic layer was dried over magnesium sulphate, filtered and the solvent evaporated to give the title compound (1.02 g). LCMS m/z 241 [M+H]+ RT=3.44 min (Analytical Method 4).

Synthesis 3

5-(Tetrahydro-pyran-4-yl)-thiophene-3-carboxylic acid

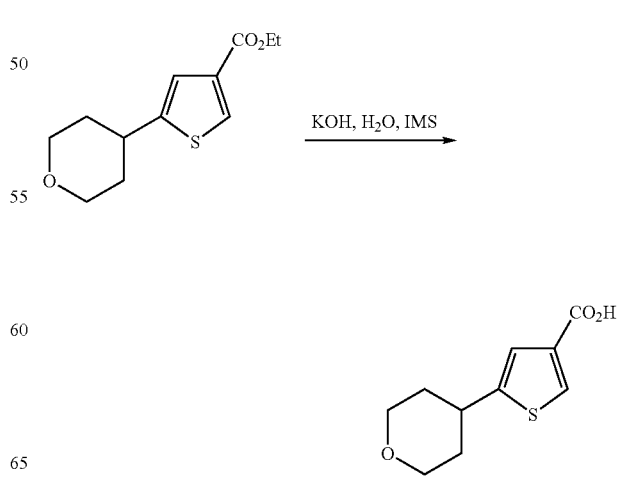

Potassium hydroxide (0.56 g, 10 mmol) in water (2 mL) was added to 5-(tetrahydro-pyran-4-yl)-thiophene-3-carboxylic acid ethyl ester (3.36 mmol) in IMS (6 mL). The reaction mixture was stirred for 1 hour then water was added and the mixture acidified to pH 7 with 1 N hydrochloric acid and then extracted with diethyl ether. The organic solution was dried over magnesium sulphate, filtered and the solvent evaporated to give the title compound (613 mg). LCMS m/z 211 [M−H]⁻ RT=2.53 min (Analytical Method 4).

Synthesis 4

Piperidin-1-yl-[5-(tetrahydro-pyran-4-yl)-thiophen-3-yl]-methanone (CC-001)

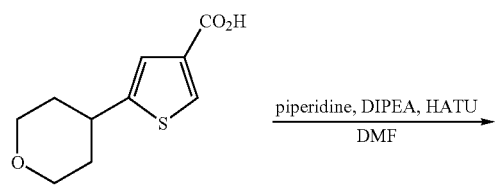

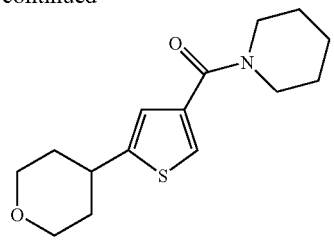

5-(Tetrahydro-pyran-4-yl)-thiophene-3-carboxylic acid (0.107 g, 0.5 mmol) was dissolved in DMF (2 mL). DIPEA (1.0 mmol), HATU (0.5 mmol) and piperidine (0.5 mmol) were added and the reaction stirred at room temperature for 1 hour. The reaction was then partitioned between ethyl acetate and water and the organic solution separated and dried over magnesium sulphate, filtered and the solvent evaporated. The product was purified by HPLC, eluting with 40%-90% acetonitrile in water (0.1% formic acid) over 30 minutes. The fractions containing the desired product were concentrated under vacuum to give the title compound (74 mg). LCMS m/z 280.22 [M+H]⁺ RT=8.77 min (Analytical Method 1). ¹H NMR δ (ppm)(CHCl₃-d): 7.25 (s, 1H), 6.9 (t, 1H), 4.1-4.0 (m, 2H), 3.6 (m, 4H), 3.5 (m, 2H), 3.1-3.0 (m, 1H), 1.95-1.6 (m, 10H).

The compounds in the following table were prepared using analogous methods:

| Code No. | Structure | ¹H NMR | Analytical Method | R.T. (min) | MS [m/z] |
|---|---|---|---|---|---|
| CC-004 | 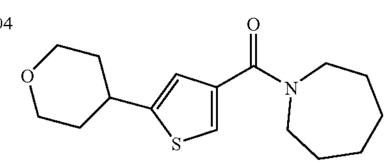 | 7.3 (s, 1H), 6.9 (s, 1H), 4.05 (m, 2H), 3.6 (t, 2H), 3.6-3.5 (m, 4H), 3.1-3.0 (m, 1H), 2.0-1.9 (m, 2H), 1.9-1.7 (m, 4H), 1.7 (s, 2H), 1.6 (m, 4H). | 1 | 9.39 | [M + H]⁺ 294.25 |
| CC-027 | CIS ISOMERS | 7.3 (s, 1H), 6.9 (s, 1H), 4.6 (m, 1H), 4.1 (m, 2H), 3.9-3.6 (m, 1H), 3.5 (m, 2H), 3.2-3.0 (m, 1H), 2.8 (m, 1H), 2.0-1.1 (m, 17H) | 2 | 11.24 | [M + H]⁺ 334.12 |
| CC-077 | 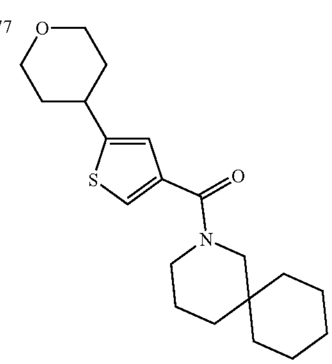 | 7.2 (s, 1H), 6.9 (s, 1H), 4.1 (m, 2H), 3.7-3.2 (m, 7H), 1.95 (m, 2H), 1.8 (m, 2H), 1.6-1.35 (m, 14H) | 1 | 14.39 | [M + H]⁺ 348.28 |

| Code No. | Structure | ¹H NMR | Analytical Method | R.T. (min) | MS [m/z] |
|---|---|---|---|---|---|
| CC-069 | 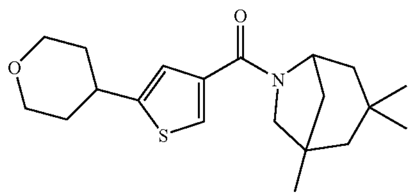 [SMILES: CC1(C)CC2CC(C)(CN2C(=O)c2csc(C3CCOCC3)c2)C1] | | 2 | 11.22 | [M + H]⁺ 348.17 |
| CC-002 | 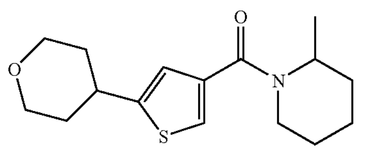 [SMILES: CC1CCCCN1C(=O)c1csc(C2CCOCC2)c1] | | 3 | 3.48 | [M + H]⁺ 294 |
| CC-003 | 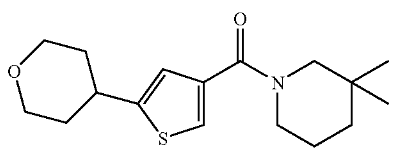 [SMILES: CC1(C)CCCN(C(=O)c2csc(C3CCOCC3)c2)C1] | | 3 | 3.74 | [M + H]⁺ 308 |
| CC-029 | 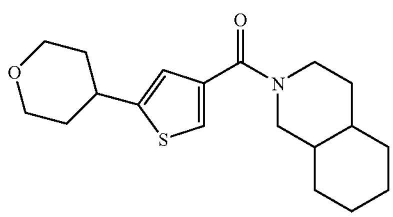 [SMILES: O=C(c1csc(C2CCOCC2)c1)N1CCC2CCCCC2C1] | | 3 | 4.26 | [M + H]⁺ 334 |
| CC-011 | 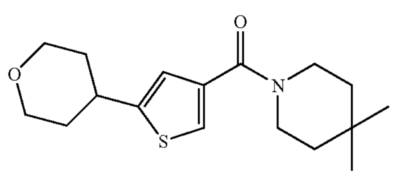 [SMILES: CC1(C)CCN(C(=O)c2csc(C3CCOCC3)c2)CC1] | 7.3 (s, 1H), 6.9 (s, 1H), 4.1 (m, 2H), 3.8-3.4 (m, 6H), 3.1 (m, 1H), 1.9 (m, 2H), 1.9-1.7 (m, 2H), 1.4 (m, 4H), 1.0 (s, 6H) | 2 | 10.15 | [M + H]⁺ 308.18 |
| CC-021 | 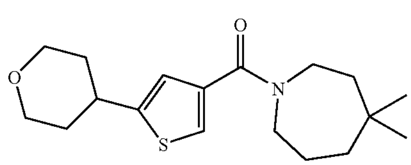 [SMILES: CC1(C)CCCN(C(=O)c2csc(C3CCOCC3)c2)CC1] | 7.2 (s, 1H), 6.9 (s, 1H), 4.1 (m, 2H), 3.7-3.4 (m, 6H), 3.1 (m, 1H), 2.0-1.4 (m, 10H), 1.0 (s, 3H), 0.9 (s, 3H) | 2 | 10.82 | [M + H]⁺ 322.15 |
| CC-022 | 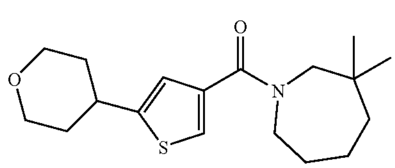 [SMILES: CC1(C)CCCCN(C(=O)c2csc(C3CCOCC3)c2)C1] | | 2 | 10.99 | [M + H]⁺ 322.17 |

| Code No. | Structure | ¹H NMR | Analytical Method | R.T. (min) | MS [m/z] |
|---|---|---|---|---|---|
| CC-028 | TRANS ISOMERS | | 2 | 11.44 | [M + H]⁺ 334.18 |
| CC-122 | 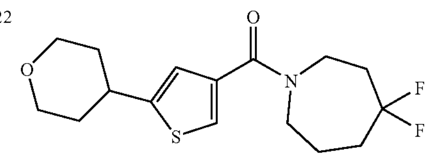 | | 2 | 9.04 | [M + H]⁺ 330.22 |

The compounds in the following table were prepared using analogous method to CC-001 but starting from (tetrahydro-thiopyran-4-yl)-acetaldehyde.

| Code No. | Structure | Analytical Method | R.T. (min) | MS [m/z] |
|---|---|---|---|---|
| CC-136 | DHQ [CIS-M] | 2 | 13.20 | [M + H]⁺ 350.21 |

The compound in the following table was prepared using analogous method to CC-001 but starting from 3-(2-oxo-ethyl)-pyrrolidine-1-carboxylic acid t-butyl ester.

| Code No. | Structure | Analytical Method | R.T. (min) | MS [m/z] |
|---|---|---|---|---|
| CC-177 | FORMATE SALT DHQ [CIS-S] | 2 | 6.38 | [M + H]⁺ 319.22 |

Synthesis 4A

Enantiomers of cis-(octahydro-quinolin-1-yl)-[5-(tetrahydro-pyran-4-yl)-thiophen-3-yl]-methanone (CC-027)

The diastereomeric mixture of cis-(octahydro-quinolin-1-yl)-[5-(tetrahydro-pyran-4-yl)-thiophen-3-yl]-methanone (0.150 g) was separated by chiral HPLC using a ChiralPak IA column with a mobile phase of ethanol/heptane (8:2) and a flow rate of 15 mL/min. Two fractions were obtained and the solvent was evaporated to give:

cis-(octahydro-quinolin-1-yl)-[5-(tetrahydro-pyran-4-yl)-thiophen-3-yl]-methanone

[Enantiomer K] (CC-141): 0.074 g RT=38.67 min; >95% e.e (Analytical Method 6; mobile phase: 10% EtOH/Heptane. RT=25.55 min. DHQ [CIS ENANTIOMER K]

cis-(octahydro-quinolin-1-yl)-[5-(tetrahydro-pyran-4-yl)-thiophen-3-yl]-methanone

[Enantiomer L] (CC-140): 0.060 g RT=43.57 min; >95% e.e (Analytical Method 6; mobile phase: 10% EtOH/Heptane. RT=27.31 min. DHQ [CIS ENANTIOMER L]

Synthesis 4B cis-[5-(1,1-Dioxo-hexahydro-thiopyran-4-yl)-thiophen-3-yl]-(octahydro-quinolin-1-yl)methanone (CC-138) DHQ [CIS-M]

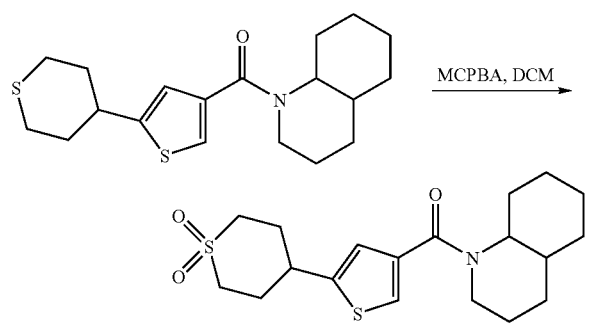

cis-(Octahydro-quinolin-1-yl)-[5-(tetrahydro-thiopyran-4-yl)-thiophen-3-yl]-methanone (0.12 g, 0.34 mmol) was dissolved in DCM (10 mL) and meta-chloroperbenzoic acid (0.17 g) was added. The mixture was stirred for one hour and the solvent evaporated to give a white solid which was purified by preparative HPLC, eluting with 20%-98% acetonitrile in water (0.1% formic acid). The fractions containing the desired product were concentrated under vacuum to give the title compound (0.034 g) as a colourless oil. LCMS m/z 382.19 [M+H]⁺ RT=9.69 min (Analytical Method 2).

Synthesis 5

Azepan-1-yl-[2-chloro-5-(tetrahydro-pyran-4-yl)-thiophen-3-yl]methanone (CC-006)

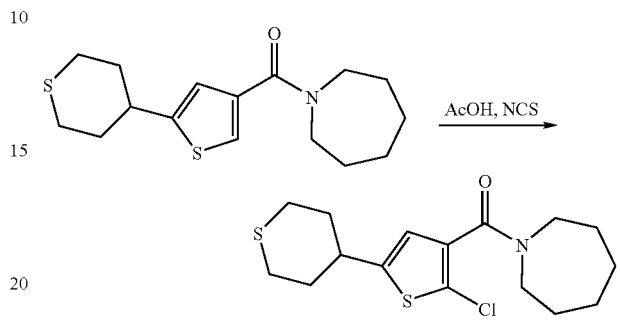

N-Chlorosuccinimide (0.024 g, 0.18 mmol) was added to a solution of azepan-1-yl-[5-(tetrahydro-pyran-4-yl)-thiophen-3-yl]-methanone (53 mg) in acetic acid (2 mL). The reaction mixture was heated to 100° C. for 3 minutes using microwave irradiation, then diluted with water and purified by HPLC, eluting with 20%-98% acetonitrile in water (0.1% formic acid). The fractions containing the desired product were concentrated under vacuum to give the title compound (38 mg). LCMS m/z 328.17 [M+H]⁺ RT=10.59 min (Analytical Method 1). ¹H NMR (400 MHz, CHCl₃-d): δ 6.6 (s, 1H), 4.05 (m, 2H), 3.7 (m, 2H), 3.5 (m, 2H), 3.4 (m, 2H), 2.9 (m, 1H), 1.9-1.5 (m, 12H).

The compounds in the following table were prepared using analogous methods:

| Code No. | Structure | Analytical Method | R.T. (min) | MS [m/z] |
|---|---|---|---|---|
| CC-030 | 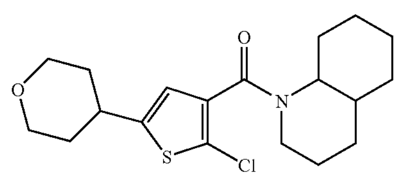 [SMILES: O=C(c1cc(C2CCOCC2)sc1Cl)N1CCCC2CCCCC21] | 1 | 12.72 | [M + H]⁺ 368.17 |
| CC-070 | 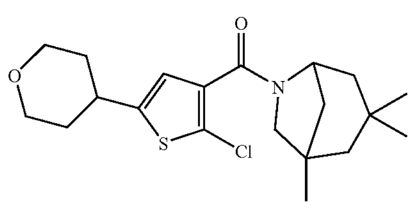 [SMILES: CC1(C)CC2CC(C)(CN2C(=O)c2cc(C3CCOCC3)sc2Cl)C1] | 1 | 12.80 | [M + H]⁺ 382.22 |
| CC-031 | 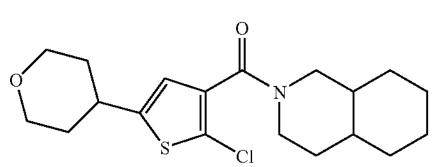 [SMILES: O=C(c1cc(C2CCOCC2)sc1Cl)N1CCC2CCCCC2C1] | 3 | 4.6, 4.7 | [M + H]⁺ 368 |

| Code No. | Structure | Analytical Method | R.T. (min) | MS [m/z] |
|---|---|---|---|---|
| CC-005 | 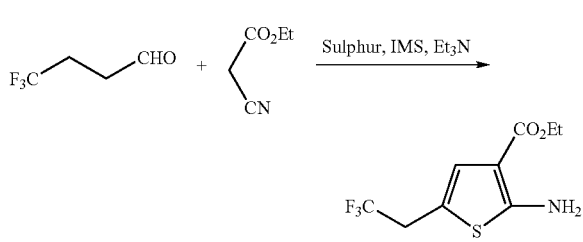 | 3 | 4.2 | [M + H]+ 342 |

Synthesis 6

2-Amino-5-(2,2,2-trifluoro-ethyl)-thiophene-3-carboxylic acid ethyl ester

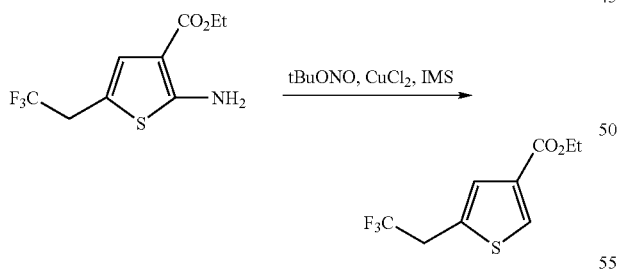

Trifluorobutyraldehyde (1.14 g, 10.3 mmol), ethyl cyanoacetate (9.9 mmol) and sulphur (10.3 mmol) were dissolved in IMS (10 mL). Triethylamine (14.42 mmol) was added and the reaction stirred for 1.5 hours. The solvent was removed under vacuum and the product purified by column chromatography on silica, eluting with 0%-50% ethyl acetate in cyclohexane. The fractions containing the desired product were concentrated under vacuum to give the title compound as a yellow oil (1.76 g). LCMS m/z 254.06 [M+H]+ RT=4.25 min (Analytical Method 4).

Synthesis 7

5-(2,2,2-Trifluoro-ethyl)-thiophene-3-carboxylic acid ethyl ester

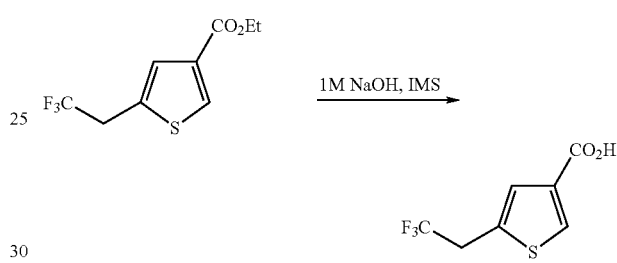

2-Amino-5-(2,2,2-trifluoro-ethyl)-thiophene-3-carboxylic acid ethyl ester (1.76 g, 6.96 mmol) was added to a suspension of t-butyl nitrite (10.4 mmol) and copper (II) chloride (26.8 mmol) in IMS (50 mL). The reaction mixture was stirred for 1.5 hours then quenched with saturated aqueous ammonium chloride (7 mL). The solvent was removed under vacuum and the residue partitioned between DCM and water. The organic solution was separated and dried over magnesium sulphate, filtered and the solvent evaporated. The product was purified by column chromatography on silica, eluting with 0%-35% t-butylmethylether in cyclohexane. The fractions containing the desired product were concentrated under vacuum to give the title compound (1.24 g). $^1$H NMR (400 MHz, CHCl$_3$-d): δ 8.05 (s, 1H), 7.45 (s, 1H), 4.3 (q, 2H), 3.6 (q, 2H), 1.37 (t, 3H).

Synthesis 8

5-(2,2,2-Trifluoro-ethyl)-thiophene-3-carboxylic acid

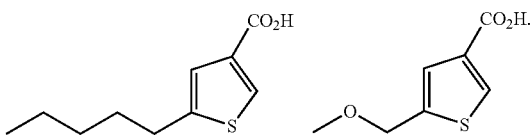

5-(2,2,2-Trifluoro-ethyl)-thiophene-3-carboxylic acid ethyl ester (1.24 g, 5.2 mmol) was dissolved in IMS (10 mL) and aqueous sodium hydroxide (1 M, 10 mL) was added. The reaction was heated to 140° C. using microwave irradiation for 20 minutes and then partitioned between water and DCM. The aqueous solution was separated, acidified with 1 N hydrochloric acid and then extracted with DCM. The organic solution was dried over magnesium sulphate, filtered and the solvent removed. The resulting oil was triturated with cyclohexane and minimal diethyl ether to give the title compound (0.22 g). $^1$H NMR (400 MHz, CHCl$_3$-d): δ 8.2 (s, 1H), 7.5 (s, 1H), 3.6 (q, 2H).

The following compounds were prepared using analogous methods from commercially available aldehydes:

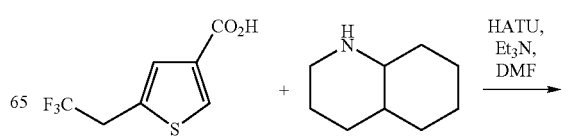

Synthesis 9 cis-(Octahydro-quinolin-1-yl)-[5-(2,2,2-trifluoro-ethyl)-thiophen-3-yl]-methanone (AA-012)

-continued

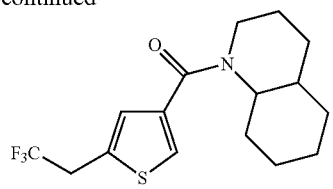

5-(2,2,2-Trifluoro-ethyl)-thiophene-3-carboxylic acid (0.05 g, 0.32 mol) was dissolved in DMF (2 mL). HATU (0.23 mmol), triethylamine (1.5 mmol) and decahydroquinoline (3:2 mixture of cis- and trans-isomers; 0.64 mmol) were added and the reaction stirred overnight. The reaction mixture was then diluted with water and acetonitrile and separated by HPLC, eluting with 10%-98% acetonitrile in water (0.1% formic acid). The fractions containing the desired product were concentrated under vacuum to give the title compound (21.2 mg). LCMS m/z 332.12 [M+H]$^+$ RT=11.62 min (Analytical Method 2). $^1$H NMR (400 MHz, CHCl$_3$-d): δ 7.4 (s, 1H), 7.1 (s, 1H), 4.6 (m, 1H), 3.8-3.7 (m, 1H), 3.6 (q, 2H), 3.1-2.8 (m, 1H), 2.0-1.1 (m, 13H).

The compounds in the following table were prepared using analogous methods:

| Code No. | Structure | $^1$H NMR | Analytical Method | R.T. (min) | MS [m/z] |
|---|---|---|---|---|---|
| AA-018 | 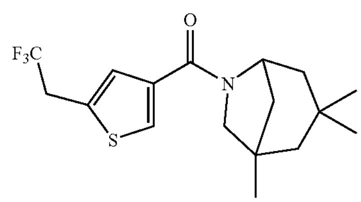 [SMILES: CC1(C)CC2CC(C)(CN2C(=O)c2csc(CC(F)(F)F)c2)C1] | | 2 | 11.78 | [M + H]$^+$ 346.13 |
| AA-017 | 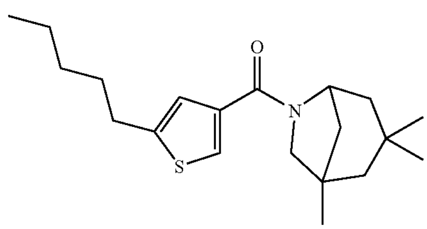 [SMILES: CCCCCc1cc(C(=O)N2CC3(C)CC2CC(C)(C)C3)cs1] | | 1 | 15.21 | [M + H]$^+$ 334.28 |
| AA-011 | 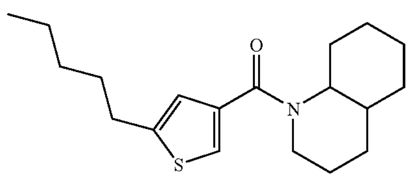 [SMILES: CCCCCc1cc(C(=O)N2CCCC3CCCCC32)cs1] | | 1 | 15.10 | [M + H]$^+$ 320.26 |
| BB-007 | 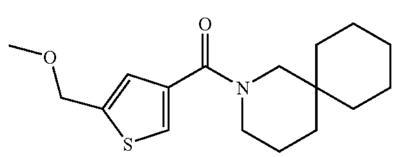 [SMILES: COCc1cc(C(=O)N2CCCC3(CCCCC3)C2)cs1] | 7.4 (s, 1H), 7.05 (s, 1H), 4.6 (s, 2H), 3.5 (m, 3H), 3.4 (s, 3H), 3.3 (m, 1H), 1.6 (m, 4H), 1.5-1.45 (m, 3H), 1.4 (s, 7H) | 1 | 11.34 | [M + H]$^+$ 308.22 |
| BB-005 | 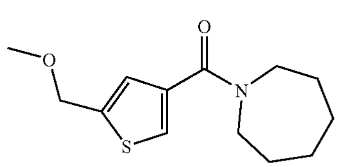 [SMILES: COCc1cc(C(=O)N2CCCCCC2)cs1] | 7.4 (s, 1H), 7.1 (s, 1H), 4.6 (s, 2H), 3.7 (t, 2H), 3.5 (t, 2H), 3.4 (s, 3H), 1.8 (m, 2H), 1.75-1.5 (m, 6H). | 1 | 8.48 | [M + H]$^+$ 254.16 |
| BB-006 | 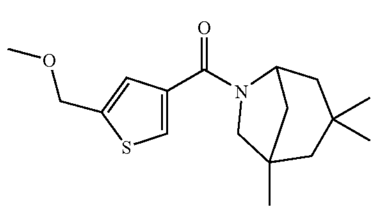 | | 1 | 10.80 | [M + H]$^+$ 308.22 |

Synthesis 10

4-(5-Amino-4-ethoxycarbonyl-thiophen-2-yl)-piperidine-1-carboxylic acid benzyl ester

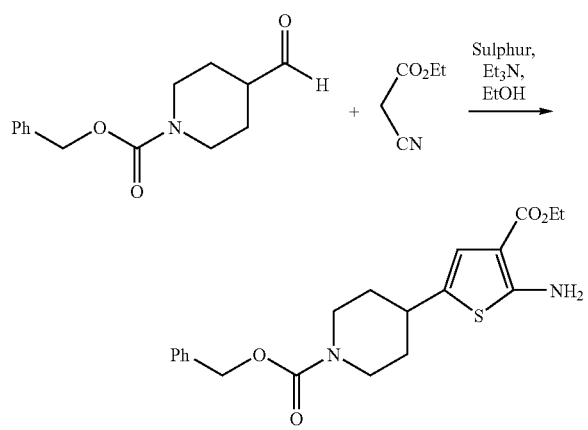

4-Formyl-piperidine-1-carboxylic acid benzyl ester (1.04 g, 4.12 mmol), ethyl cyanoacetate (4.12 mmol) and sulphur (4.12 mmol) were dissolved in ethanol (5 mL). Triethylamine (5.35 mmol) was added and the reaction stirred for 1.5 hours. The solvent was removed under vacuum and the product purified by column chromatography on silica, eluting with 0%-50% ethyl acetate in cyclohexane. The fractions containing the desired product were concentrated under vacuum to give the title compound (1.46 g). LCMS m/z 389 [M+H]+ RT=3.94 min (Analytical Method 4).

Synthesis 11

4-(4-Ethoxycarbonyl-thiophen-2-yl)-piperidine-1-carboxylic acid benzyl ester

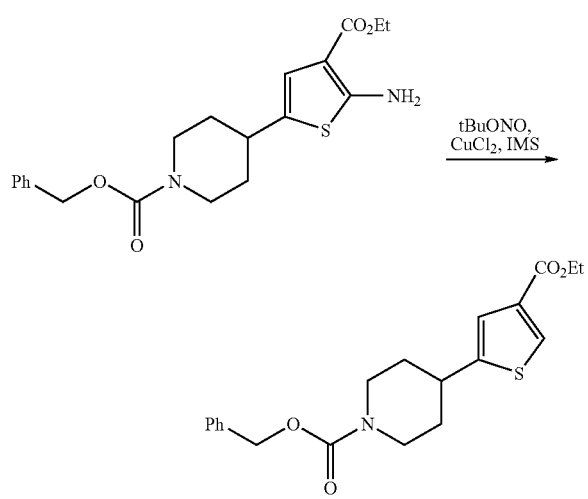

4-(5-Amino-4-ethoxycarbonyl-thiophen-2-yl)-piperidine-1-carboxylic acid benzyl ester (1.46 g, 3.76 mmol) was added to t-butyl nitrite (5.64 mmol) and copper(II)chloride (3.76 mmol) in IMS (40 mL). The reaction was stirred for 1.5 hours then saturated aqueous ammonium chloride (7 mL) was added and the resulting mixture stirred for a further 15 minutes. The solvent was removed under vacuum and product partitioned between ethyl acetate and water. The organic layer was dried over magnesium sulphate, filtered and the solvent removed to give the title compound (1.17 g). LCMS m/z 374 [M+H]+ RT=4.18 min (Analytical Method 4).

Synthesis 12

4-(4-Carboxy-thiophen-2-yl)-piperidine-1-carboxylic acid benzyl ester

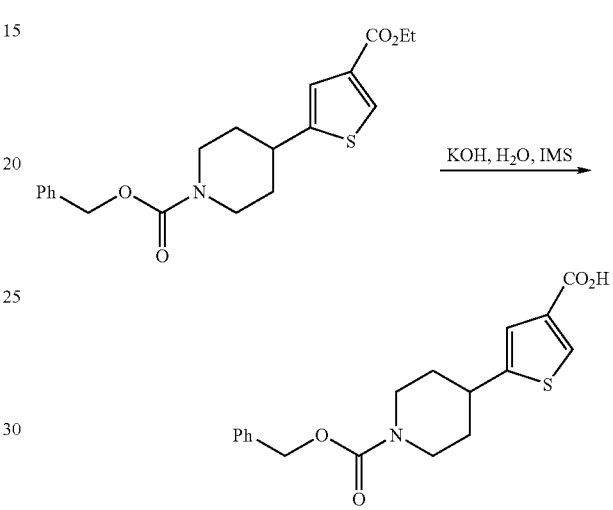

Potassium hydroxide (0.52 g, 9.0 mmol) in water (2 mL) was added to a solution of 4-(4-ethoxycarbonyl-thiophen-2-yl)-piperidine-1-carboxylic acid benzyl ester (3.0 mmol) in IMS (6 mL). The reaction was stirred for 1 hour then partitioned between diethyl ether and water. The aqueous layer was acidified to pH 7 and further extracted with diethyl ether. The organic solution was dried over magnesium sulphate, filtered and the solvent removed to give the title compound (0.92 g). LCMS m/z 346 [M+H]+ RT=3.43 min (Analytical Method 4).

Synthesis 13

4-[4-(Azepane-1-carbonyl)-thiophen-2-yl]-piperidine-1-carboxylic acid benzyl ester (CC-007)

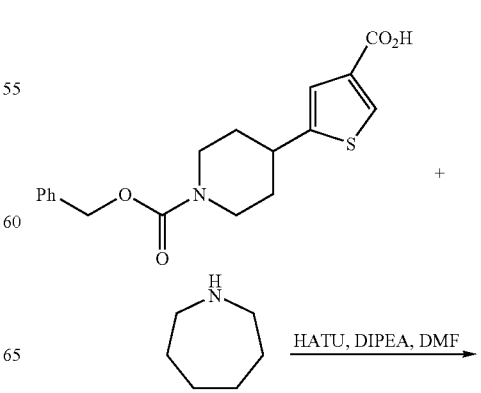

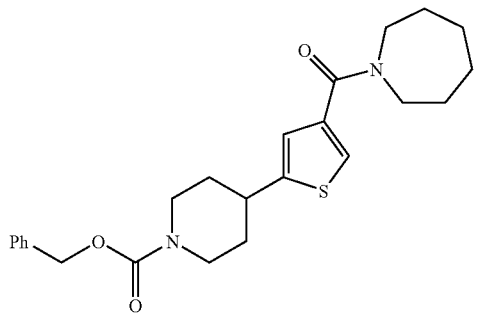

4-(4-Carboxy-thiophen-2-yl)-piperidine-1-carboxylic acid benzyl ester (0.095 g, 0.27 mmol) was dissolved in DMF (2 mL). DIPEA (0.54 mmol), HATU (0.27 mmol) and homopiperidine (0.27 mmol) were added and the reaction stirred at room temperature for 1 hour. The reaction mixture was partitioned between ethyl acetate and water. The organic solution was separated and dried with magnesium sulphate, filtered and the solvent removed under vacuum. The residue was purified by HPLC, eluting with 40%-90% acetonitrile in water (0.1% formic acid) over 30 minutes. The fractions containing the desired product were concentrated under vacuum to give the title compound (0.032 g). LCMS m/z 427.29 [M+H]$^+$ RT=12.22 min (Analytical Method 1). $^1$H NMR (400 MHz, CHCl$_3$-d): δ 7.4-7.35 (m, 4H), 7.35-7.3 (m, 1H), 7.25 (s, 1H), 6.9 (s, 1H), 5.15 (s, 2H), 4.3 (m, 2H), 3.6 (m, 2H), 3.5 (m, 2H), 3.00-2.90 (m, 3H), 2.0 (m, 2H), 1.8 (m, 2H), 1.75-1.5 (m, 8H).

The compounds in the following table were prepared using analogous methods:

| Code No. | Structure | Analytical Method | R.T. (min) | MS [m/z] |
|---|---|---|---|---|
| CC-032 | 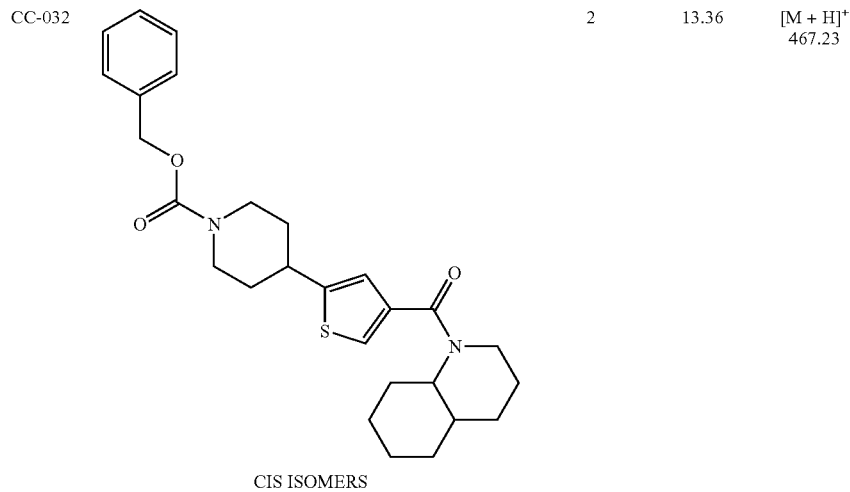 CIS ISOMERS | 2 | 13.36 | [M + H]$^+$ 467.23 |
| CC-078 | 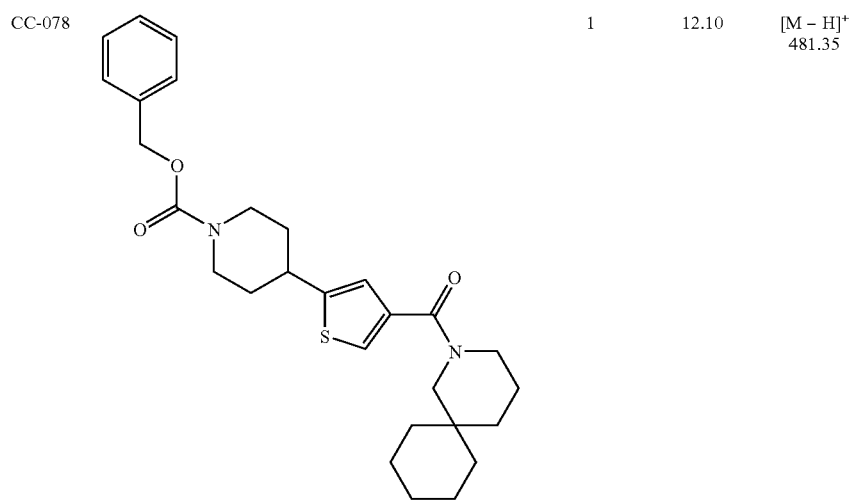 | 1 | 12.10 | [M − H]$^+$ 481.35 |

| Code No. | Structure | Analytical Method | R.T. (min) | MS [m/z] |
|---|---|---|---|---|
| CC-071 | 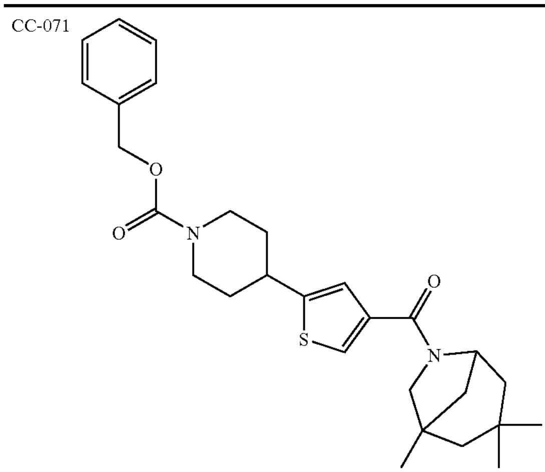 | 2 | 13.44 | [M + H]+ 481.25 |

Synthesis 14

Azepan-1-yl-(5-piperidin-4-yl-thiophen-3-yl)-methanone (CC-008)

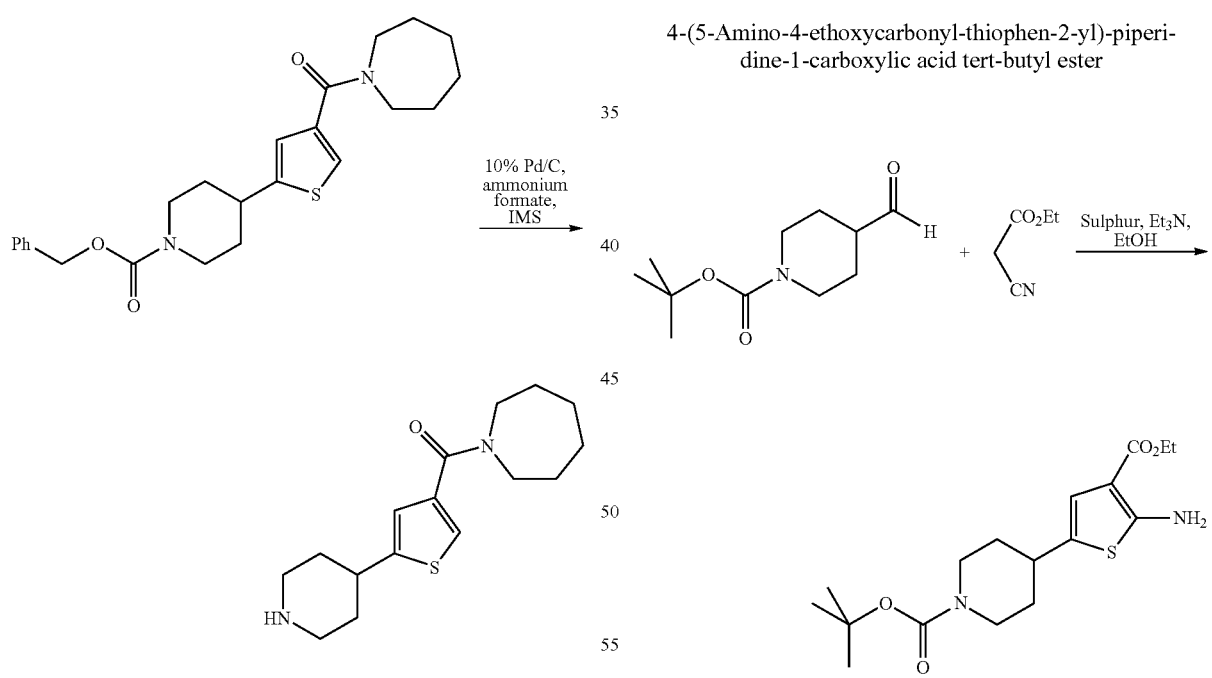

4-[Azepane-1-carbonyl)-thiophen-2-yl]-piperidine-1-carboxylic acid benzyl ester (0.26 g, 0.61 mmol) was added to a suspension of 10% palladium on charcoal (0.005 g) in a saturated solution of ammonium formate in IMS (10 mL). The reaction was stirred under argon for 3 hours, filtered and the solvent removed. The product was purified by flash chromatography on a SCX-2 cartridge, eluting with acetonitrile and then 2 M ammonia in methanol. The fractions containing the desired product were concentrated under vacuum to give the title compound (0.155 g). LCMS m/z 293.21 [M+H]+ RT=5.43 min (Analytical Method 1). $^1$H NMR (400 MHz, CHCl$_3$-d): δ 7.2 (s, 1H), 6.9 (s, 1H), 3.6 (m, 2H), 3.5 (m, 2H), 3.15 (m, 2H), 2.9 (m, 1H), 2.7 (m, 2H), 2.0 (m, 2H), 1.8-1.5 (m, 11H).

Synthesis 15

4-(5-Amino-4-ethoxycarbonyl-thiophen-2-yl)-piperidine-1-carboxylic acid tert-butyl ester 4-Formyl-piperidine-1-carboxylic acid t-butyl ester (10 g, 44 mmol), ethyl cyanoacetate (44 mmol) and sulphur (44 mmol) were dissolved in ethanol (50 mL). Triethylamine (53 mmol) was added and the reaction stirred overnight. The solvent was removed under vacuum and the product purified by column chromatography on silica, eluting with 0%-50% ethyl acetate in cyclohexane. The fractions containing the desired product were concentrated under vacuum to give the title compound (13.4 g). $^1$H NMR (400 MHz, CHCl$_3$-d): δ

6.65 (s, 1H), 5.8 (s, 2H), 4.25 (q, 2H), 4.2 (m, 2H), 2.8-2.6 (m, 3H), 1.9 (m, 2H), 1.6 (m, 2H), 1.4 (s, 9H), 1.3 (t, 3H).

Synthesis 16

4-(4-Ethoxycarbonyl-thiophen-2-yl)-piperidine-1-carboxylic acid tert-butyl ester

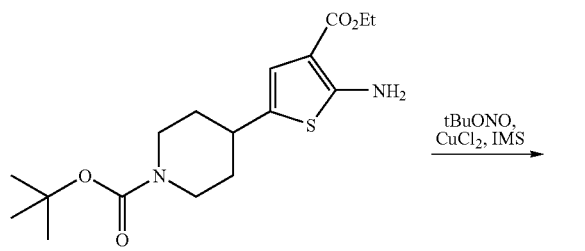

4-(5-Amino-4-ethoxycarbonyl-thiophen-2-yl)-piperidine-1-carboxylic acid butyl ester (13.4 g, 38 mmol) was added to t-butyl nitrite (56.4 mmol) and copper(II)chloride (38 mmol) in IMS (500 mL). The reaction was stirred for 1 hour then saturated aqueous ammonium chloride (70 mL) was added and the resulting mixture stirred for a further 15 minutes. The solution was filtered and the filtrate was evaporated under vacuum. The residue was then partitioned between DCM and water. The organic layer was separated and dried over magnesium sulphate, filtered and the solvent evaporated. The product was purified by column chromatography on silica, eluting with 0%-40% ethyl acetate in cyclohexane to give a clear oil (11.7 g). $^1$H NMR (400 MHz, CHCl$_3$-d): δ 7.9 (s, 1H), 7.2 (s, 1H), 4.3 (q, 2H), 4.2 (m, 2H), 2.9-2.7 (m, 3H), 2.0 (m, 2H), 1.7 (m, 2H), 1.5 (s, 9H), 1.4 (t, 3H).

Synthesis 17

4-(4-Carboxy-thiophen-2-yl)-piperidine-1-carboxylic acid tert-butyl ester

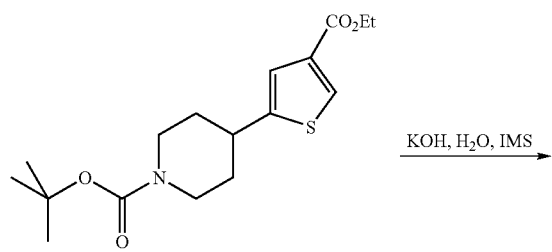

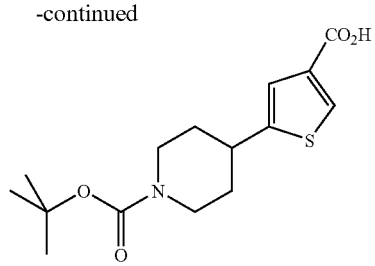

Aqueous sodium hydroxide (1 N, 10 mL) was added to a solution of 4-(4-ethoxycarbonyl-thiophen-2-yl)-piperidine-1-carboxylic acid t-butyl ester (1.0 g) in IMS (10 mL). The reaction was heated at 130° C. for 10 minutes by microwave irradiation. The solution was acidified to pH 7 and the resulting precipitate isolated by filtration and dried under vacuum to give the title compound as a white solid (0.81 g). $^1$H NMR (400 MHz, CHCl$_3$-d): δ 8.05 (s, 1H), 7.25 (s, 1H), 4.2 (m, 2H), 2.9 (m, 1H), 2.8 (m, 2H), 2.0 (m, 2H), 1.6 (m, 2H), 1.5 (s, 9H).

Synthesis 18

(2-Phenyl-piperidin-1-yl)-(5-piperidin-4-yl-thiophen-3-yl)methanone (CC-017)

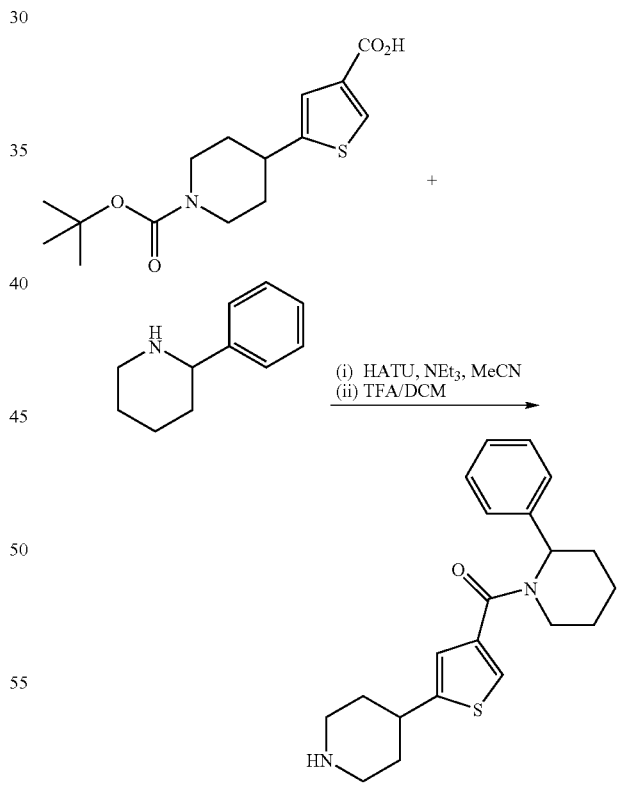

4-(4-Carboxy-thiophen-2-yl)-piperidine-1-carboxylic acid t-butyl ester (0.1 g, 0.32 mmol) was dissolved in acetonitrile (2 mL). Triethylamine (0.96 mmol), HATU (0.35 mmol) and 2-phenylpiperidine (0.35 mmol) were added and the reaction stirred at room temperature for 5 hours. The mixture was purified by HPLC, eluting with 10%-98% acetonitrile in water (0.1% formic acid) over 30 minutes. The fractions containing the desired product were concentrated under vacuum to give an oil which was dissolved in trifluoroacetic acid (3 mL) and DCM (5 mL) and stirred for 3 hours. The solvent was evaporated and the residue was purified by flash chromatography on an SCX-2 cartridge, washing with acetonitrile, then methanol and then eluting with 2 M ammonia in methanol. The fractions containing the desired product were concentrated under vacuum to give the title compound (0.058 g). LCMS m/z 355.18 [M+H]$^+$ RT=6.59 min (Analytical Method 2). $^1$H NMR (400 MHz, CHCl$_3$-d): δ 7.4 (m, 2H), 7.25 (m, 4H), 6.9 (s, 1H), 3.2 (d, 2H), 2.9 (m, 2H), 2.7 (m, 2H), 2.6 (m, 3H), 2.4 (d, 1H), 2.1-1.8 (m, 3H), 1.8-1.4 (m, 6H).

The compounds in the following table were prepared using analogous methods:

| Code No. | Structure | $^1$H NMR | Analytical Method | R.T. (min) | MS [m/z] |
|---|---|---|---|---|---|
| CC-012 | 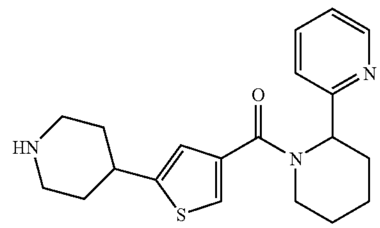 [SMILES: O=C(c1csc(C2CCNCC2)c1)N1CCCCC1c1ccccn1] | 8.6 (s, 1H), 7.7 (t, 1H), 7.3 (m, 2H), 7.1 (t, 1H), 6.9 (s, 1H), 3.6-2.6 (m, 11H), 2.1-1.4 (m, 8H) | 1 | 4.85 | [M + H]$^+$ 356.32 |
| CC-079 | 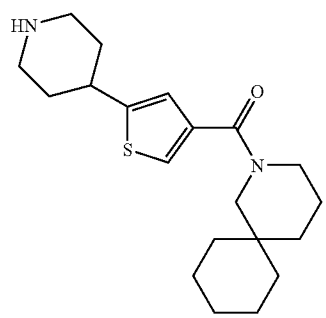 [SMILES: O=C(c1csc(C2CCNCC2)c1)N1CCCC2(CCCCC2)C1] | 7.3 (s, 1H), 6.9 (s, 1H), 3.8-3.3 (m, 4H), 3.2 (d, 2H), 2.9 (m, 1H), 2.7 (t, 2H), 2.1 (m, 2H), 2.05 (d, 2H), 1.7-1.1 (m, 15H) | 2 | 6.85 | [M + H]$^+$ 347.21 |
| CC-013 | 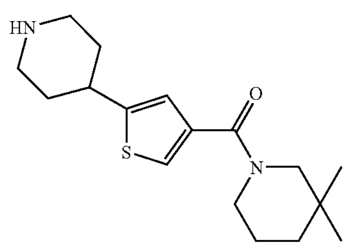 [SMILES: CC1(C)CCCN(C(=O)c2csc(C3CCNCC3)c2)C1] | 7.2 (s, 1H), 6.9 (s, 1H), 3.7-3.4 (m, 2H), 3.2 (m, 2H), 2.9 (m, 1H), 2.7 (m, 2H), 2.0 (m, 2H), 1.8-1.7 (m, 4H), 2.7-2.5 (m, 4H), 1.4 (m, 2H), 1.0-0.9 (m, 6H) | 2 | 5.78 | [M + H]$^+$ 307.17 |
| CC-072 | 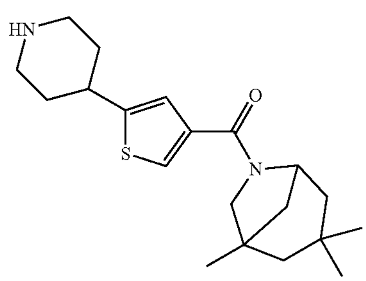 [SMILES: CC1(C)CC2CC(C)(CN2C(=O)c2csc(C3CCNCC3)c2)C1] | | 2 | 6.67 | [M + H]$^+$ 347.21 |

| Code No. | Structure | ¹H NMR | Analytical Method | R.T. (min) | MS [m/z] |
|---|---|---|---|---|---|
| CC-018 | 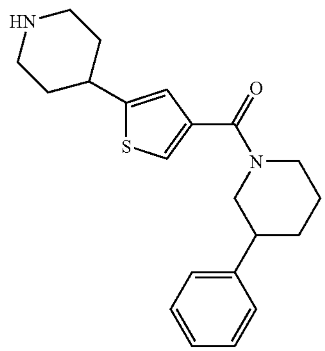 [SMILES: O=C(c1csc(C2CCNCC2)c1)N1CCCC(c2ccccc2)C1] | 7.4-7.2 (m, 6H), 6.9 (s, 1H), 4.8 (m, 1H), 3.2-2.6 (m, 8H), 2.2-1.5 (m, 10H) | 2 | 6.61 | [M + H]⁺ 355.13 |
| CC-020 | 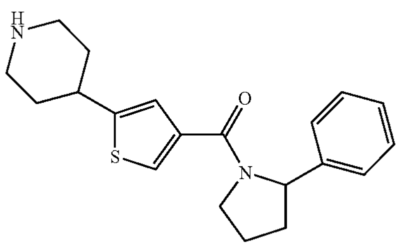 [SMILES: O=C(c1csc(C2CCNCC2)c1)N1CCCC1c1ccccc1] | | 2 | 6.14 | [M + H]⁺ 341.11 |
| CC-024 | 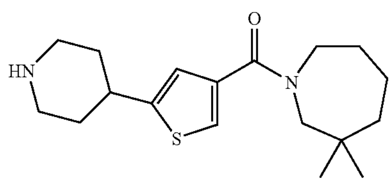 [SMILES: CC1(C)CCCCN(C(=O)c2csc(C3CCNCC3)c2)C1] | | 2 | 6.08 | [M + H]⁺ 321.18 |
| CC-023 | 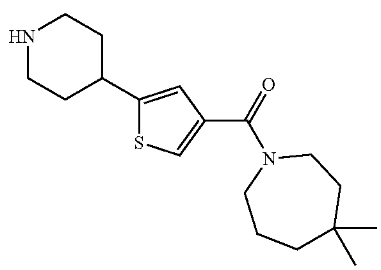 [SMILES: CC1(C)CCCN(C(=O)c2csc(C3CCNCC3)c2)CC1] | | 2 | 6.06 | [M + H]⁺ 321.18 |
| CC-019 | 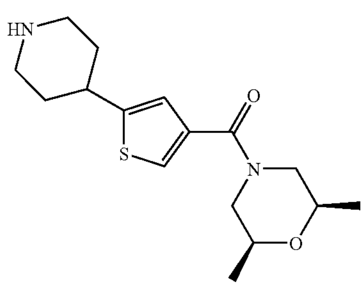 [SMILES: C[C@@H]1CN(C(=O)c2csc(C3CCNCC3)c2)C[C@H](C)O1] | 7.3 (s, 1H), 6.9 (s, 1H), 4.5 (m, 1H), 3.6 (m, 2H), 3.2 (m, 2H), 2.9 (m, 1H), 2.8 (m, 3H), 2.5 (m, 3H), 2.05 (m, 2H), 1.7 (m, 2H), 1.2 (m, 6H) | 2 | 4.52 | [M + H]⁺ 309.11 |

-continued

| Code No. | Structure | ¹H NMR | Analytical Method | R.T. (min) | MS [m/z] |
|---|---|---|---|---|---|
| CC-041 | 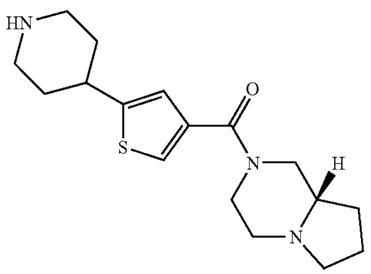 [SMILES: O=C(c1csc(C2CCNCC2)c1)N1CCN2CCC[C@H]2C1] | 7.3 (s, 1H), 6.9 (s, 1H), 4.7 (m, 1H), 4.0 (m, 1H), 3.3-2.4 (m, 10H), 2.2-1.6 (m, 10H), 1.4 (m, 1H) | 2 | 0.92 | [M + H]⁺ 320.10 |
| CC-042 | 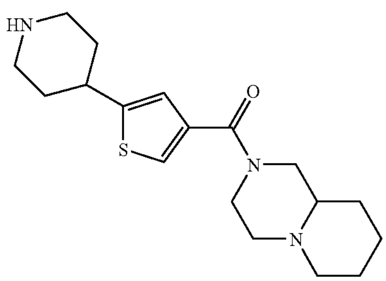 [SMILES: O=C(c1csc(C2CCNCC2)c1)N1CCN2CCCCC2C1] | | 2 | 0.77 | [M + H]⁺ 334.10 |
| CC-107 | 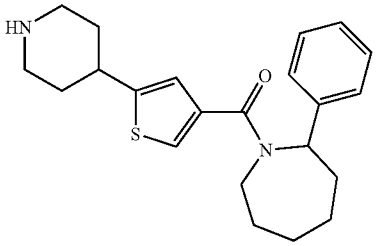 [SMILES: O=C(c1csc(C2CCNCC2)c1)N1CCCCCC1c1ccccc1] | | 2 | 6.97 | [M + H]⁺ 369.13 |
| CC-112 | 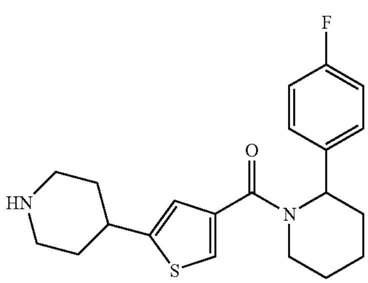 [SMILES: O=C(c1csc(C2CCNCC2)c1)N1CCCCC1c1ccc(F)cc1] | | 2 | 7.20 | [M + H]⁺ 373.26 |
| CC-131 | DHQ [CIS-M] | | 2 | 6.29 | [M + H]⁺ 369.27 |

Synthesis 18A cis-(2-Phenyl-piperidin-1-yl)-(5-piperidin-4-yl-thiophen-3-yl) methanone [ENANTIOMER J] (CC-130)

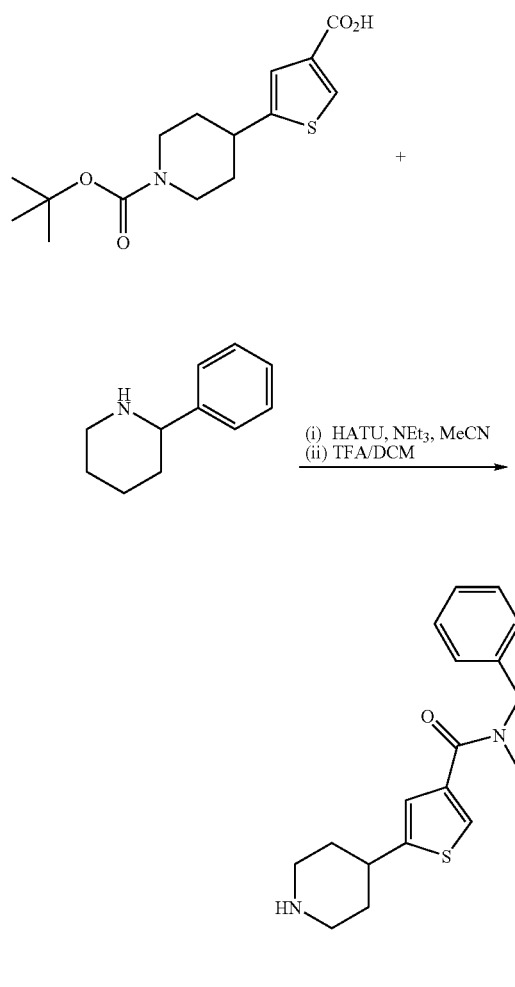

4-(4-Carboxy-thiophen-2-yl)-piperidine-1-carboxylic acid t-butyl ester (0.4 g, 1.28 mmol) was dissolved in acetonitrile (6 mL). Triethylamine (3.8 mmol), HATU (1.4 mmol) and 2-phenylpiperidine (1.4 mmol) were added and the reaction stirred at room temperature for 12 hours. The solvent was evaporated and the residue was purified by flash chromatography on a silica column, eluting with 0-50% ethyl acetate in cyclohexane. The fractions containing the desired product were concentrated under vacuum to give a pale yellow oil (0.62 g).

The diastereomeric mixture of cis-4-[4-(2-phenyl-piperidine-1-carbonyl)-thiophen-2-yl]-piperidine-1-carboxylic acid t-butyl ester was separated by chiral HPLC using a ChiralPak IA prep column with a mobile phase of IPA/heptane (8:2) containing DEA (0.1% v/v). Two fractions were obtained and the solvent was evaporated from the first fraction to give: cis-4-[4-(2-phenyl-piperidine-1-carbonyl)-thiophen-2-yl]-piperidine-1-carboxylic acid t-butyl ester [Enantiomer J] which was dissolved in trifluoroacetic acid (3 mL) and DCM (5 mL) and stirred for 3 hours. The solvent was evaporated and the residue was purified by flash chromatography on an SCX-2 cartridge, washing with acetonitrile, then methanol and then eluting with 2 M ammonia in methanol. The fractions containing the desired product were concentrated under vacuum to give the title compound (0.049 g). LCMS m/z 355.28 [M+H]$^+$ RT=6.72 min (Analytical Method 2).

Synthesis 19

1-{4-[4-(Octahydro-pyrido[1,2-a]pyrazine-2-carbonyl)-thiophen-2-yl]-piperidin-1-yl}-ethanone (CC-025)

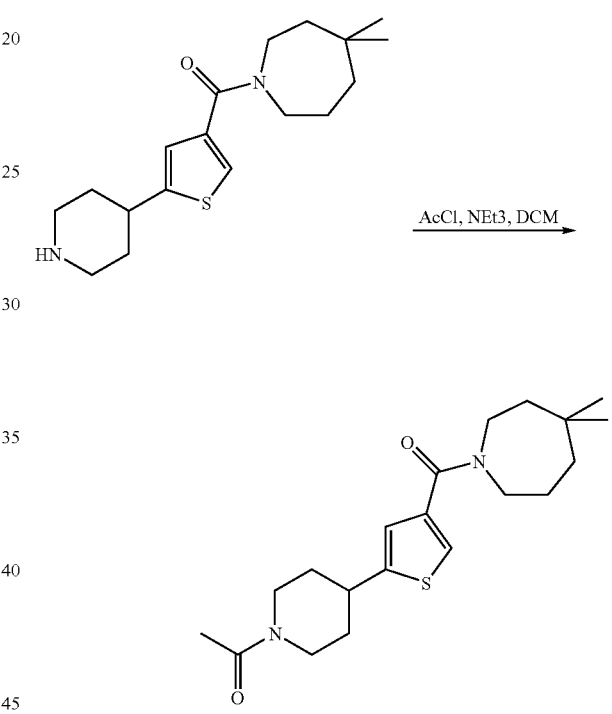

(4,4-Dimethyl-azepan-1-yl)-(5-piperidin-4-yl-thiophen-3-yl)-methanone (0.02 g) was dissolved in DCM (2 mL) and triethylamine (0.1 mL). Acetyl chloride (0.1 mL) was added and the mixture stirred for 1 hour. The organic solution was washed with 1 N hydrochloric acid, dried over anhydrous magnesium sulphate, filtered and evaporated to give a colourless oil. The oil was purified by flash chromatography on silica eluting with 10% methanol in ethyl acetate. The fractions containing the desired product were concentrated under vacuum to give the title compound (38 mg) as a clear oil. LCMS m/z 363.13 [M+H]$^+$RT=9.40 min (Analytical Method 2). $^1$H NMR (400 MHz, CHCl$_3$-d): δ 7.3 (s, 1H), 6.9 (s, 1H), 4.4 (m, 1H), 3.9 (m, 1H), 3.7-3.4 (m, 4H), 3.2 (m, 1H), 3.0 (m, 1H), 2.6 (m, 1H), 2.15 (s, 3H), 2.1-2.0 (m, 2H), 1.8-1.4 (m, 9H), 1.0 (s, 3H), 0.9 (s, 3H).

The compounds in the following table were prepared using analogous methods:

| Code No. | Structure | ¹H NMR | Analytical Method | R.T. (min) | MS [m/z] |
|---|---|---|---|---|---|
| CC-026 | 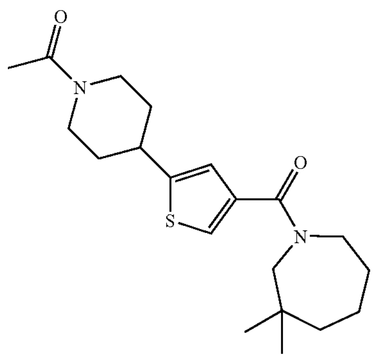 [SMILES: CC(=O)N1CCC(c2cc(C(=O)N3CCCCC(C)(C)C3)cs2)CC1] | 7.3 (s, 1H), 6.9 (s, 1H), 4.7 (m, 1H), 3.8 (m, 1H), 3.7-3.3 (m, 4H), 3.2 (m, 1H), 3.0 (m, 1H), 2.7 (m, 1H), 2.1-2.0 (m, 4H), 1.9-1.4 (m, 9H), 1.0-0.9 (m, 6H) | 2 | 9.51 | [M + H]⁺ 363.13 |
| CC-037 | 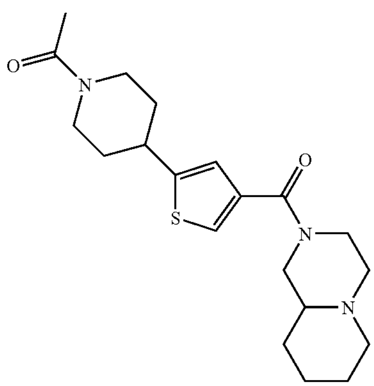 [SMILES: CC(=O)N1CCC(c2cc(C(=O)N3CCN4CCCCC4C3)cs2)CC1] | | 2 | 4.42 | [M + H]⁺ 376.14 |

Synthesis 20 trans-4-[4-(Octahydro-quinoline-1-carbonyl)-thiophen-2-yl]-piperidine-1-carboxylic acid tert-butyl ester

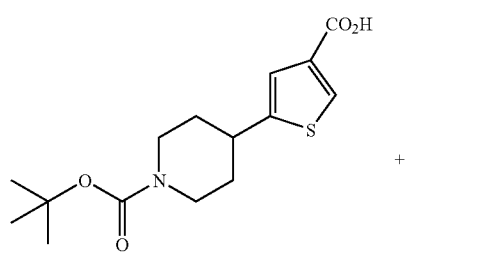

+

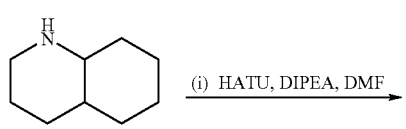

(i) HATU, DIPEA, DMF

-continued

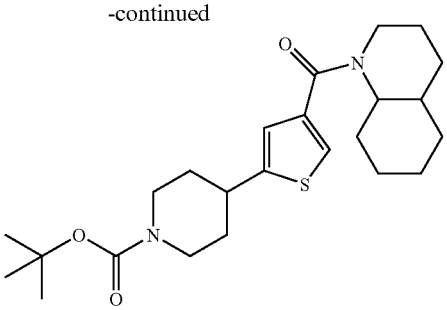

4-(4-Carboxy-thiophen-2-yl)-piperidine-1-carboxylic acid t-butyl ester (0.1 g, 0.32 mmol) was dissolved in acetonitrile (2 mL). Triethylamine (0.96 mmol), trans-decahydroquinoline (1:1 mixture of the trans-isomers; 0.35 mmol) and HATU (0.35 mmol) were added and the reaction stirred at room temperature for 5 hours. The solvent was evaporated and the residue was purified by HPLC, eluting with 10%-90% acetonitrile in water (0.1% formic acid). The fractions containing the desired product were concentrated under vacuum to give the title compound (0.09 g). ¹H NMR (400 MHz, CHCl₃-d): δ 7.2 (s, 1H), 6.9 (s, 1H), 4.2 (m, 2H), 3.7 (m, 1H), 3.5-3.3 (m, 2H), 3.0-2.7 (m, 3H), 2.25 (m, 1H), 2.0 (m, 2H), 1.8-1.5 (m, 8H) 1.5 (s, 9H), 1.4-1.0 (m, 6H).

Synthesis 21 trans-(Octahydro-quinolin-1-yl)-(5-piperidin-4-yl-thiophen-3-yl)-methanone (CC-034)

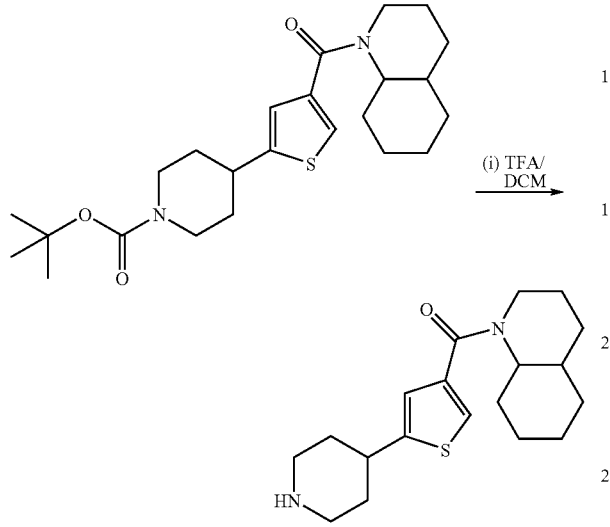

trans-4-[4-(Octahydro-quinoline-1-carbonyl)-thiophen-2-yl]-piperidine-1-carboxylic acid t-butyl ester (0.09 g, 0.32 mmol) was dissolved in DCM (2 mL) and TFA (1 mL) and the reaction stirred at room temperature for 6 hours. The solvent was evaporated and the residue product was purified by flash chromatography on an SCX-2 cartridge, washing with acetonitrile and then eluting with 2 M ammonia in methanol. The fractions containing the desired product were concentrated under vacuum to give the title compound (0.074 g). LCMS m/z 333.20 [M+H]$^+$ RT=6.23 min (Analytical Method 2). $^1$H NMR (400 MHz, CHCl$_3$-d): δ 7.2 (s, 1H), 6.9 (s, 1H), 3.7 (m, 1H), 3.5 (m, 1H), 3.4 (m, 1H), 3.2 (m, 2H), 2.9 (m, 1H), 2.7 (m, 2H), 2.2 (m, 1H), 2.0-1.9 (m, 4H) 1.8-1.0 (m, 13H).

Synthesis 22

Enantiomers of trans-(octahydro-quinolin-1-yl)-(5-piperidin-4-yl-thiophen-3-yl)-methanone The diastereomeric mixture of trans-(octahydro-quinolin-1-yl)-(5-piperidin-4-yl-thiophen-3-yl)-methanone (0.07 g) was separated by chiral HPLC using a ChiralPak IA column with a mobile phase of ethanol/heptane (8:2) containing DEA (0.1% v/v). Two fractions were obtained and the solvent was evaporated to give:

trans-(Octahydro-quinolin-1-yl)-(5-piperidin-4-yl-thiophen-3-yl)-methanone [Enantiomer A] (CC-044): 0.019 g RT=20.05 min; >95% e.e (Analytical Method 5; mobile phase: ethanol/heptane (8:2). LCMS m/z 333.18 [M+H]$^+$ RT=6.39 min (Analytical Method 2). $^1$H NMR (400 MHz, CHCl$_3$-d): δ 7.3 (s, 1H), 6.9 (s, 1H), 3.6 (m, 1H), 3.5 (m, 1H), 3.4 (m, 1H), 3.2 (m, 2H), 2.9 (m, 1H), 2.7 (m, 2H), 2.3 (m, 1H), 2.0 (m, 2H), 1.9-1.1 (m, 15H).

trans-(Octahydro-quinolin-1-yl)-(5-piperidin-4-yl-thiophen-3-yl)-methanone [Enantiomer B] (CC-045): 0.015 g RT=23.86 min; >95% e.e (Analytical Method 5; mobile phase: ethanol/heptane (8:2). LCMS m/z 333.18 [M+H]$^+$ RT=6.49 min (Analytical Method 2). $^1$H NMR (400 MHz, CHCl$_3$-d): δ 7.3 (s, 1H), 6.9 (s, 1H), 3.6 (m, 1H), 3.5 (m, 1H), 3.4 (m, 1H), 3.2 (m, 2H), 2.9 (m, 1H), 2.7 (m, 2H), 2.3 (m, 1H), 2.0 (m, 2H), 1.9-1.1 (m, 15H).

Synthesis 23 cis-4-[4-(Octahydro-quinoline-1-carbonyl)-thiophen-2-yl]-piperidine-1-carboxylic acid tert-butyl ester

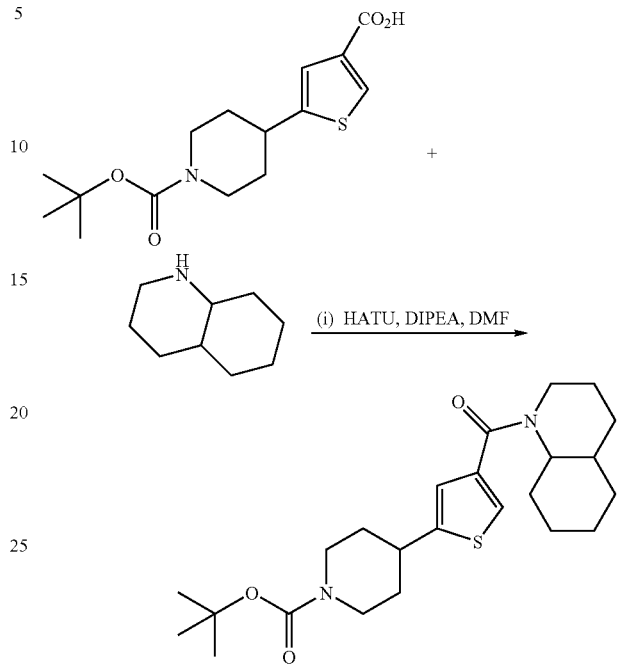

4-(4-Carboxy-thiophen-2-yl)-piperidine-1-carboxylic acid t-butyl ester (0.1 g, 0.32 mmol) was dissolved in acetonitrile (2 mL). Triethylamine (0.96 mmol), HATU (0.35 mmol) and decahydroquinoline (3:2 mixture of cis/trans-isomers; 2.5 mmol) were added and the reaction stirred at room temperature for 3 hours. The solvent was evaporated and the residue product was purified by flash chromatography on silica, eluting with 0-50% ethyl acetate in cyclohexane. The fractions containing the desired product were concentrated under vacuum to give the title compound (0.14 g). $^1$H NMR (400 MHz, CHCl$_3$-d): δ 7.2 (s, 1H), 6.85 (s, 1H), 4.7 (m, 1H), 4.2 (m, 2H), 3.7 (m, 1H), 3.1-2.7 (m, 4H), 2.0-1.4 (m, 26H).

Synthesis 23A cis-(Octahydro-quinolin-1-yl)-(5-piperidin-4-yl-thiophen-3-yl)-methanone (CC-033)

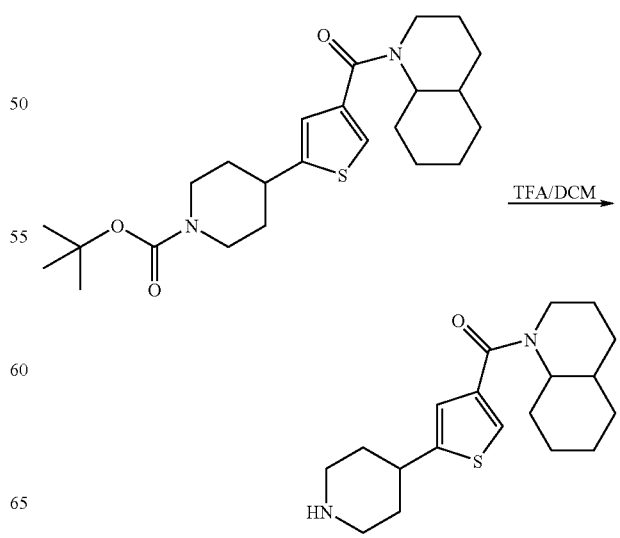

cis-4-[4-(octahydro-quinoline-1-carbonyl)-thiophen-2-yl]-piperidine-1-carboxylic acid t-butyl ester (0.06 g, 0.14 mmol) was dissolved in DCM (3 mL) and TFA (3 mL) and the reaction stirred at room temperature for 5 hours. The solvent was evaporated and the residue product was purified by flash chromatography on a SCX-2 cartridge, washing with acetonitrile and then eluting with 2 M ammonia in methanol. The fractions containing the desired product were concentrated under vacuum to give the title compound (0.036 g). LCMS m/z 333.20 [M+H]+ RT=6.44 min (Analytical Method 2). $^1$H NMR (400 MHz, CHCl$_3$-d): δ 7.2 (s, 1H), 6.9 (s, 1H), 4.6 (m, 1H), 3.8 (m, 1H), 3.2 (m, 2H), 3.1 (m, 1H), 2.9 (m, 1H), 2.7 (m, 2H), 2.0-1.1 (m 18H).

The compounds in the following table were prepared using analogous methods:

| Code No. | Structure | $^1$H NMR | Analytical Method | R.T. (min) | MS [m/z] |
|---|---|---|---|---|---|
| CC-159 | DHQ [CIS-S] | | 2 | 6.44 | [M + H]+ 333.35 |
| CC-155 | DHQ [CIS-R] | | 2 | 6.40 | [M + H]+ 333.33 |

Synthesis 24

Enantiomers of cis-4-[4-(octahydro-quinoline-1-carbonyl)-thiophen-2-yl]-piperidine-1-carboxylic acid tert-butyl ester The diastereomeric mixture of cis-4-[4-(octahydro-quinoline-1-carbonyl)-thiophen-2-yl]-piperidine-1-carboxylic acid t-butyl ester (0.120 g) was separated by chiral HPLC using a ChiralPak IA column with a mobile phase of ethanol/heptane (8:2) containing DEA (0.1% v/v). Two fractions were obtained after evaporation of the solvent:

Enantiomer C: (0.061 g), >95% e.e, RT=19.26 min (Analytical Method 5: mobile phase: ethanol/heptane (9:1)). $^1$H NMR (400 MHz, CHCl$_3$-d): δ 7.2 (s, 1H), 6.85 (s, 1H), 4.7 (m, 1H), 4.2 (m, 2H), 3.7 (m, 1H), 3.1-2.6 (m, 4H), 2.0-1.4 (m, 26H).

Enantiomer D: (0.59 g), >90% e.e, RT=25.43 min (Analytical Method 5: mobile phase: ethanol/heptane (9:1)). $^1$H NMR (400 MHz, CHCl$_3$-d): δ 7.2 (s, 1H), 6.85 (s, 1H), 4.7 (m, 1H), 4.2 (m, 2H), 3.7 (m, 1H), 3.1-2.6 (m, 4H), 2.0-1.4 (m, 26H).

Synthesis 25

Enantiomer C of cis-(octahydro-quinolin-1-yl)-(5-piperidin-4-yl-thiophen-3-yl)-methanone (CC-039)

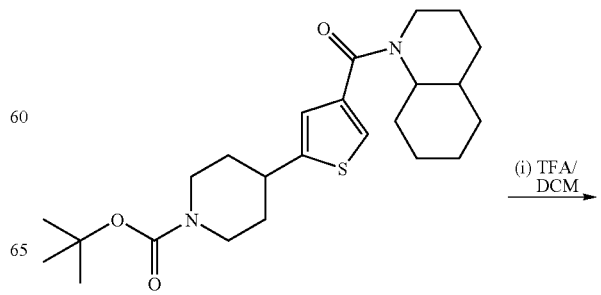

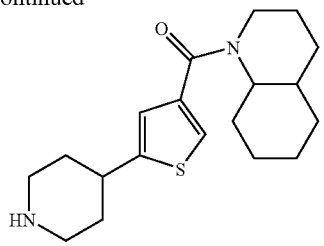

Enantiomer C of cis-4-[4-(octahydro-quinoline-1-carbonyl)-thiophen-2-yl]-pipendine-1-carboxylic acid tert-butyl ester [Enantiomer C] (0.06 g, 0.14 mmol) was dissolved in DCM (3 mL) and TFA (3 mL) and the reaction stirred at room temperature for 5 hours. The solvent was evaporated and the residue product was purified by flash chromatography on a SCX-2 cartridge, washing with acetonitrile and then eluting with 2 M ammonia in methanol. The fractions containing the desired product were concentrated under vacuum to give the title compound (0.056 g). LCMS m/z 333.20 [M+H]$^+$ RT=6.44 min (Analytical Method 2). $^1$H NMR (400 MHz, CHCl$_3$-d): δ 7.2 (s, 1H), 6.9 (s, 1H), 4.6 (m, 1H), 3.8 (m, 1H), 3.2 (m, 2H), 3.1 (m, 1H), 2.9 (m, 1H), 2.7 (m, 2H), 2.0-1.1 (m 18H).

The compound in the following table was prepared using analogous methods:

| Code No. | Structure | $^1$H NMR | Analytical Method | R.T. (min) | MS [m/z] |
|---|---|---|---|---|---|
| CC-040 | CIS ENANTIOMER D | 7.2 (s, 1H), 6.9 (s, 1H), 4.6 (m, 1H), 3.8 (m, 1H), 3.2 (m, 2H), 3.1 (m, 1H, 2.9 (m, 1H), 2.7 (m, 2H), 2.0-1.1 (m 18H) | 2 | 6.48 | [M + H]$^+$ 333.21 |

Synthesis 25A cis-1-{4-[4-(Octahydro-quinoline-1-carbonyl)-thiophen-2-yl]-piperidin-1-yl}-ethanone (CC-114) DHQ [CIS ENANTIOMER C]

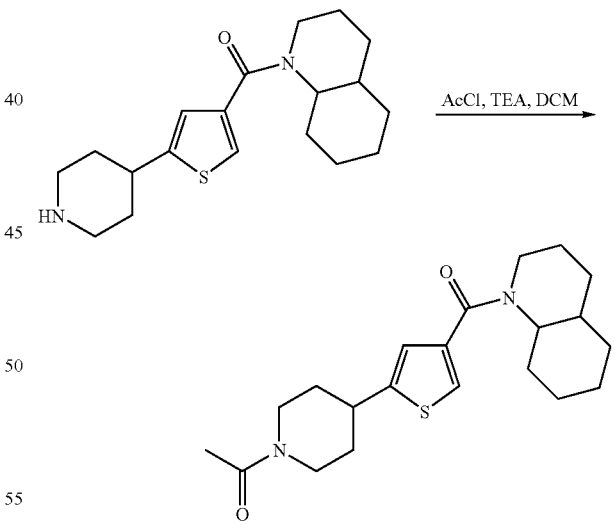

To a solution of cis-(octahydro-quinolin-1-yl)-(5-piperidin-4-yl-thiophen-3-yl)-methanone [Enantiomer C] (CC-039) (0.150 g, 0.45 mmol) in DCM (2 mL) was added polymer supported morpholine (2.5 equivalents) and acetyl chloride (0.51 mmol). The reaction mixture was stirred for 3 hours, filtered and then the solvent evaporated. The product was purified by HPLC, eluting with 10%-98% acetonitrile in water (0.1% formic acid). The fractions containing the desired product were concentrated under vacuum to give the title compound as a colourless oil (0.095 g). LCMS m/z 375.27 [M+H]$^+$ RT=9.71 min (Analytical Method 2).

The compounds in the following table were prepared using analogous methods:
| Code No. | Structure | Analytical Method | R.T. (min) | MS [m/z] |
|---|---|---|---|---|
| CC-115 | 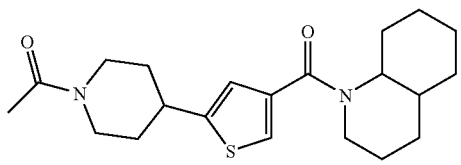 DHQ [CIS ENANTIOMER D] | 2 | 9.80 | [M + H]⁺ 375.28 |
| CC-142 | 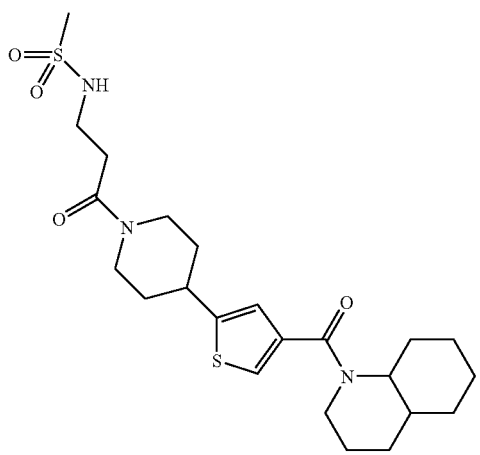 DHQ [CIS ENANTIOMER D] | 7 | 3.51 | [M + H]⁺ 482 |
| CC-143 | 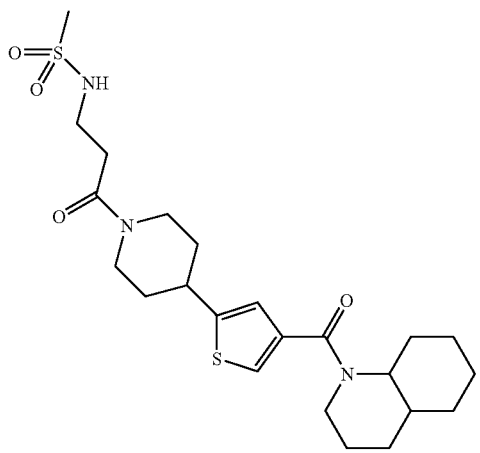 DHQ [CIS ENANTIOMER C] | 7 | 3.51 | [M + H]⁺ 482 |

| Code No. | Structure | Analytical Method | R.T. (min) | MS [m/z] |
|---|---|---|---|---|
| CC-144 | 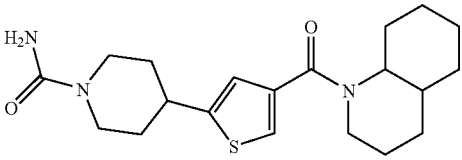 DHQ [CIS ENANTIOMER C] | 7 | 3.32 | [M + H]+ 376 |
| CC-145 | 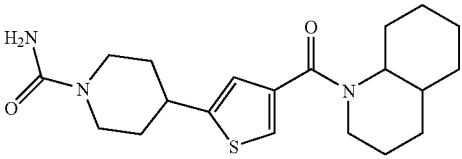 DHQ [CIS ENANTIOMER D] | 7 | 3.32 | [M + H]+ 376 |
| CC-146 | 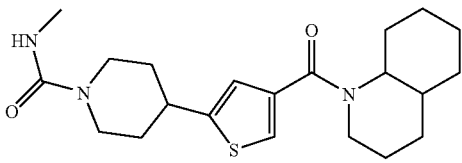 DHQ [CIS ENANTIOMER D] | 7 | 3.50 | [M + H]+ 390 |
| CC-147 | 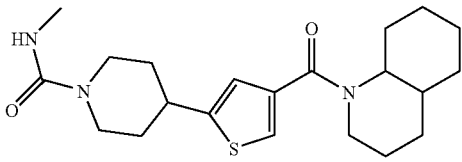 DHQ [CIS ENANTIOMER C] | 7 | 3.50 | [M + H]+ 390 |

Synthesis 26 cis-1-{4-[4-(Octahydro-quinoline-1-carbonyl)-thiophen-2-yl]-piperidin-1-yl}-ethanone (CC-035)

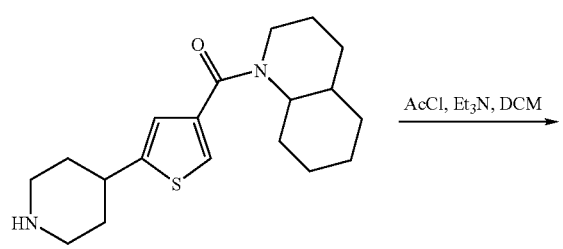

AcCl, Et₃N, DCM →

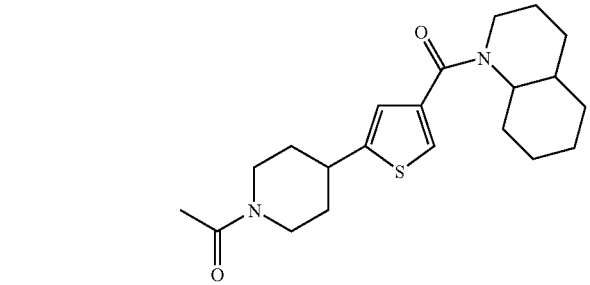

To a solution of cis-(octahydro-quinolin-1-yl)-(5-piperidin-4-yl-thiophen-3-yl)-methanone (CC-033) (0.026 g, 0.08 mmol) in DCM (1 mL) was added triethylamine (0.27 mmol) and acetyl chloride (0.11 mmol). The reaction mixture was stirred for 1 hour, and then the solvent evaporated. The product was purified by HPLC, eluting with 10%-98% acetonitrile in water (0.1% formic acid). The fractions containing the desired product were concentrated under vacuum to give the title compound as a colourless oil (0.02 g). LCMS m/z 375.15 [M+H]+ RT=9.73 min (Analytical Method 2). ¹H NMR (400 MHz, CHCl₃-d): δ 7.3 (s, 1H), 6.9 (s, 1H), 4.7 (m, 2H), 3.90-3.7 (m, 2H), 3.2-3.10 (m, 3H), 2.9-2.6 (m, 2H), 2.2 (s, 3H), 2.1-1.1 (m, 16H).

The compounds in the following table were prepared using analogous methods:

| Code No. | Structure | Analytical Method | R.T. (min) | MS [m/z] |
|---|---|---|---|---|
| CC-081 | DHQ [CIS-M] | 2 | 11.19 | [M + H]+ 403.20 |
| CC-083 | DHQ [CIS-M] | 2 | 9.66 | [M + H]+ 405.18 |
| CC-084 | FORMATE SALT DHQ [CIS-M] | 2 | 7.25 | [M + H]+ 441.13 |
| CC-099 | DHQ [CIS-M] | 2 | 10.86 | [M + H]+ 401.13 |

| Code No. | Structure | Analytical Method | R.T. (min) | MS [m/z] |
|---|---|---|---|---|
| CC-100 | DHQ [CIS-M] | 2 | 12.19 | [M + H]⁺ 417.21 |
| CC-051 | CIS ISOMERS | 2 | 10.71 | [M + H]⁺ 428.14 |

The compounds in the following table were prepared using analogous methods but starting from trans-(octahydro-quinolin-1-yl)-(5-piperidin-4-yl-thiophen-3-yl)-methanone (CC-034).

| Code No. | Structure | Analytical Method | R.T. (min) | MS [m/z] |
|---|---|---|---|---|
| CC-036 | TRANS ISOMERS | 2 | 9.92 | [M + H]⁺ 375.15 |
| CC-052 | TRANS ISOMERS | 2 | 10.90 | [M + H]⁺ 428.15 |

The compound in the following table was prepared using analogous methods but starting from (4,4-dimethyl-azepan-1-yl)-(5-piperidin-4-yl-thiophen-3-yl)-methanone (CC-023).

| Code No. | Structure | Analytical Method | R.T. (min) | MS [m/z] |
|---|---|---|---|---|
| CC-095 | 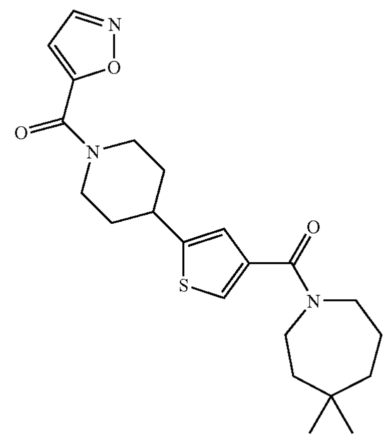 [SMILES: CC1(C)CCCN(C(=O)c2csc(C3CCN(C(=O)c4ccno4)CC3)c2)CC1] | 2 | 10.34 | [M + H]+ 416.20 |

The compound in the following table was prepared using analogous methods but starting from (2-phenyl-piperidin-1-yl)-(5-piperidin-4-yl-thiophen-3-yl)-methanone (CC-017).

| Code No. | Structure | Analytical Method | R.T. (min) | MS [m/z] |
|---|---|---|---|---|
| CC-098 | 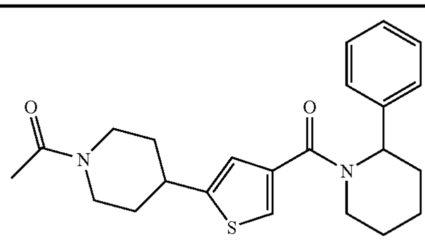 | 2 | 9.86 | [M + H]+ 397.11 |

Synthesis 27 cis-2-Hydroxy-1-{4-[4-(octahydro-quinoline-1-carbonyl)-thiophen-2-yl]-piperidin-1-yl}-ethanone (CC-053)

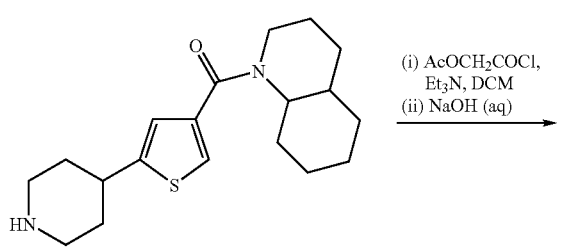

(i) AcOCH₂COCl, Et₃N, DCM
(ii) NaOH (aq)

-continued

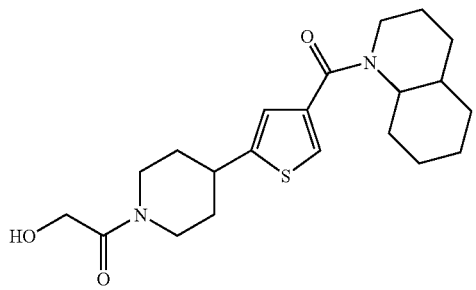

To a solution of cis-(octahydro-quinolin-1-yl)-(5-piperidin-4-yl-thiophen-3-yl)-methanone (CC-033) (0.061 g, 0.18 mmol) in DCM (1 mL) was added triethylamine (0.55 mmol) and glycolic acid chloride acetate (0.24 mmol). The reaction mixture was stirred for 1 hour, and then the solvent evaporated. Methanol (1 mL) and sodium methoxide (0.91 mmol) were added and the reaction mixture was stirred overnight.

The solvent was removed by evaporation and the product was purified by HPLC, eluting with 10%-98% acetonitrile in water (0.1% formic acid). The fractions containing the desired product were concentrated under vacuum to give the title compound as a colourless oil (0.018 g). LCMS m/z 391.11 [M+H]⁺ RT=9.24 min (Analytical Method 2).

The compounds in the following table were prepared using analogous methods:

| Code No. | Structure | Analytical Method | R.T. (min) | MS [m/z] |
|---|---|---|---|---|
| CC-054 | 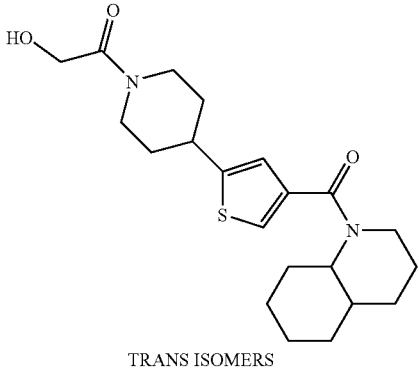 [SMILES: O=C(CO)N1CCC(c2cc(C(=O)N3CCCC4CCCCC43)cs2)CC1] TRANS ISOMERS | 2 | 9.42 | [M + H]⁺ 391.11 |
| CC-101 | 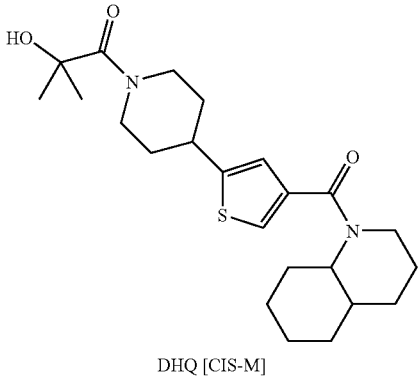 DHQ [CIS-M] | 2 | 10.10 | [M + H]⁺ 463.14 |

The compound in the following table was prepared using analogous methods but starting from cis-(octahydro-quinolin-1-yl)-[5-(1,2,3,6-tetrahydro-pyridin-4-yl)-thiophen-3-yl]-methanone (CC-046).

| Code No. | Structure | Analytical Method | R.T. (min) | MS [m/z] |
|---|---|---|---|---|
| CC-090 | 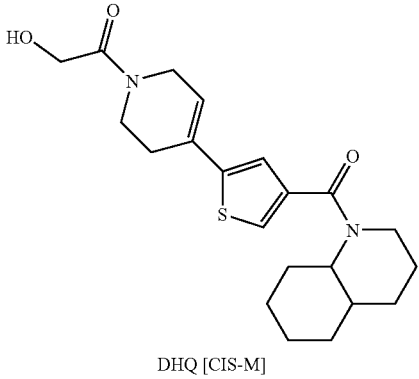 [SMILES: O=C(CO)N1CC=C(c2cc(C(=O)N3CCCC4CCCCC43)cs2)CC1] DHQ [CIS-M] | 2 | 9.27 | [M + H]⁺ 389.11 |

The compound in the following table was prepared using analogous methods but starting from (2-phenyl-piperidin-1-yl)-(5-piperidin-4-yl-thiophen-3-yl)-methanone (CC-017).

| Code No. | Structure | Analytical Method | R.T. (min) | MS [m/z] |
|---|---|---|---|---|
| CC-102 | 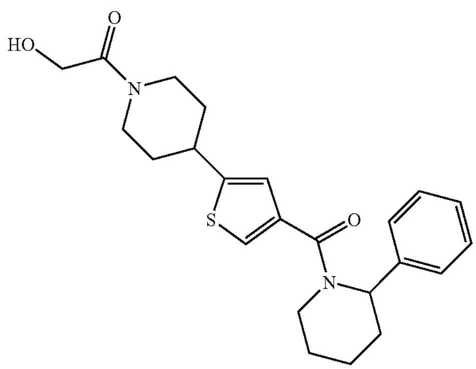 [SMILES: O=C(CO)N1CCC(c2cc(C(=O)N3CCCCC3c3ccccc3)cs2)CC1] | 2 | 9.40 | [M + H]⁺ 413:06 |

The compound in the following table was prepared using analogous methods but starting from (4,4-dimethyl-azepan-1-yl)-(5-piperidin-4-yl-thiophen-3-yl)-methanone (CC-023).

| Code No. | Structure | Analytical Method | R.T. (min) | MS [m/z] |
|---|---|---|---|---|
| CC-113 | 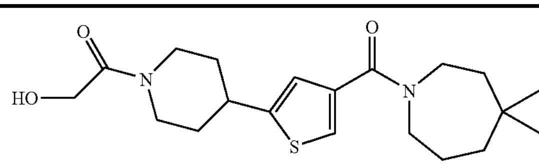 | 2 | 8.93 | [M + H]⁺ 379.09 |

Synthesis 28 cis-1-{4-[4-(Octahydro-quinoline-1-carbonyl)-thiophen-2-yl]-piperidin-1-yl}-3-piperidin-1-yl-propan-1-one (CC-061)

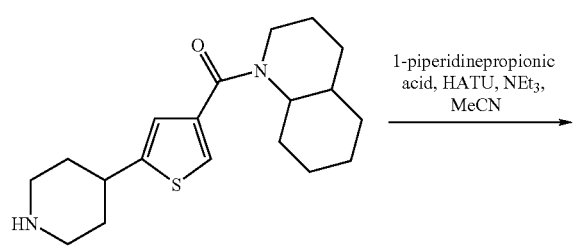

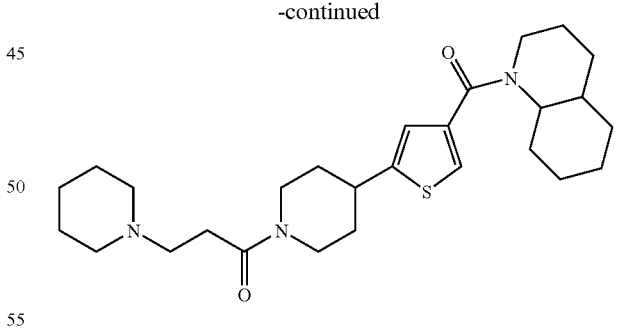

To a solution of cis-(octahydro-quinolin-1-yl)-(5-piperidin-4-yl-thiophen-3-yl)-methanone (CC-033) (0.061 g, 0.18 mmol) in acetonitrile (1 mL) was added triethylamine (0.55 mmol), HATU (0.21 mmol) and 1-piperidinepropionic (0.21 mmol). The reaction mixture was stirred for 4 hours, and then water (1 mL) was added and the resulting solution was purified by HPLC, eluting with 10%-98% acetonitrile in water (containing 20 mM triethylamine). The fractions containing the desired product were concentrated under vacuum to give the title compound as a colourless oil (0.013 g). LCMS m/z 472.00 [M+H]⁺ RT=7.07 min (Analytical Method 2).

The compounds in the following table were prepared using analogous methods:
| Code No. | Structure | Analytical Method | R.T. (min) | MS [m/z] |
|---|---|---|---|---|
| CC-059 | 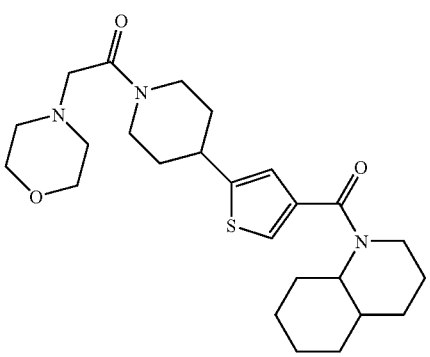<br>CIS ISOMERS | 2 | 6.89 | $[M + H]^+$ 460.17 |
| CC-063 | 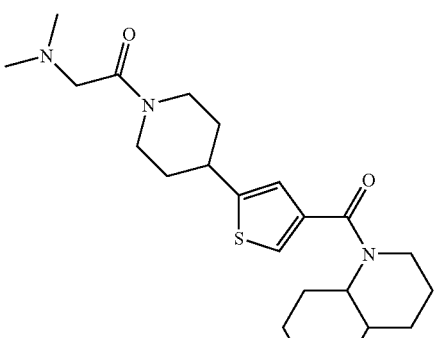<br>CIS ISOMERS | 2 | 6.71 | $[M + H]^+$ 418.32 |
| CC-085 | 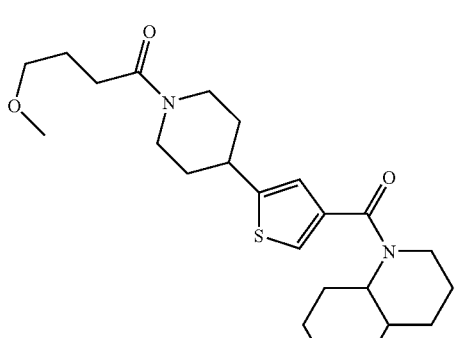<br>DHQ [CIS-M] | 2 | 10.33 | $[M + H]^+$ 433.14 |
| CC-103 | 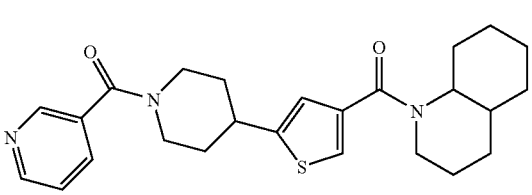<br>DHQ [CIS-M] | 2 | 9.23 | $[M + H]^+$ 438.16 |

-continued

| Code No. | Structure | Analytical Method | R.T. (min) | MS [m/z] |
|---|---|---|---|---|
| CC-109 | DHQ [CIS-M] | 2 | 11.28 | [M + H]+ 442.06 |
| CC-110 | DHQ [CIS-M] | 2 | 11.74 | [M + H]+ 437.20 |
| CC-133 | DHQ [CIS-M] | 2 | 7.70 | [M + H]+ 452.27 |
| CC-134 | DHQ [CIS-M] | 2 | 7.41 | [M + H]+ 452.28 |
| CC-135 | DHQ [CIS-M] | 2 | 10.99 | [M + H]+ 468.28 |

-continued

| Code No. | Structure | Analytical Method | R.T. (min) | MS [m/z] |
|---|---|---|---|---|
| CC-082 | DHQ [CIS-M] | 2 | 7.42 | [M + H]⁺ 486.31 |
| CC-117 | DHQ [CIS-M] | 2 | 7.14 | [M + H]⁺ 455.24 |
| CC-118 | DHQ [CIS-M] | 2 | 9.19 | [M + H]⁺ 502.26 |
| CC-149 | DHQ [CIS-M] | 2 | 7.24 | [M + H]⁺ 466.31 |

| Code No. | Structure | Analytical Method | R.T. (min) | MS [m/z] |
|---|---|---|---|---|
| CC-151 | 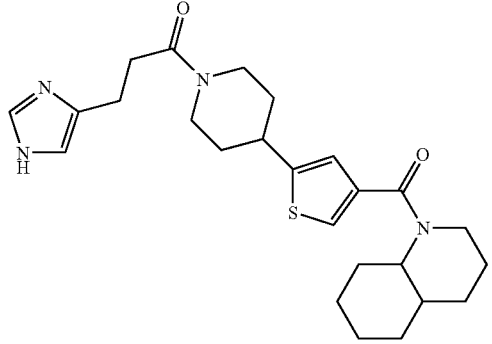 DHQ [CIS-M] | 2 | 6.95 | [M + H]+ 455.32 |
The compounds in the following table were prepared using analogous methods but starting from trans-(octahydro-quinolin-1-yl)-(5-piperidin-4-yl-thiophen-3-yl)-methanone (CC-034).
| Code No. | Structure | Analytical Method | R.T. (min) | MS [m/z] |
|---|---|---|---|---|
| CC-062 | 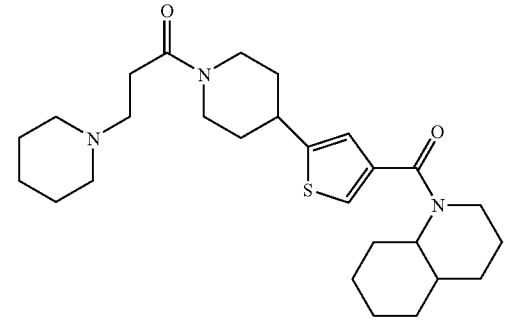 TRANS ISOMERS | 2 | 7.41 | [M + H]+ 472.26 |
| CC-060 | 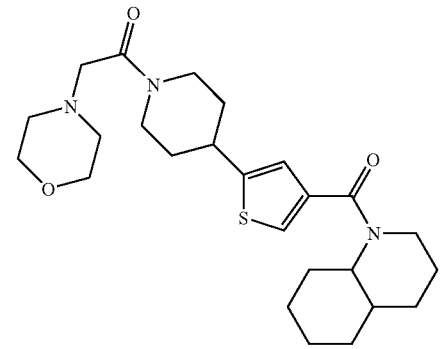 TRANS ISOMERS | 2 | 7.10 | [M + H]+ 460.26 |

-continued

| Code No. | Structure | Analytical Method | R.T. (min) | MS [m/z] |
|---|---|---|---|---|
| CC-064 | TRANS ISOMERS | 2 | 6.89 | [M + H]+ 418.13 |

The compound in the following table was prepared using analogous methods but starting from (4,4-dimethyl-azepan-1-yl)-(5-piperidin-4-yl-thiophen-3-yl)-methanone (CC-023).

| Code No. | Structure | Analytical Method | R.T. (min) | MS [m/z] |
|---|---|---|---|---|
| CC-097 | 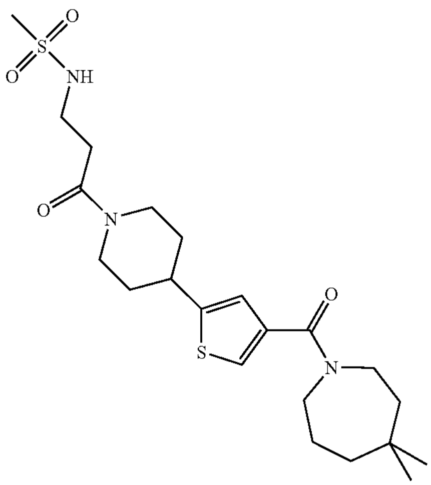 | 2 | 9.22 | [M + H]+ 470.17 |

Synthesis 29 cis-2-Methylamino-1-{4-[4-(octahydro-quinoline-1-carbonyl)-thiophen-2-yl]-piperidin-1-yl}-ethanone (CC-055)

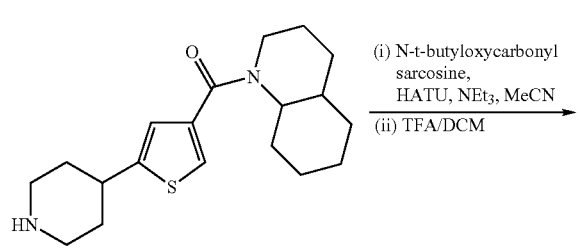

(i) N-t-butyloxycarbonyl sarcosine, HATU, NEt₃, MeCN
(ii) TFA/DCM

-continued

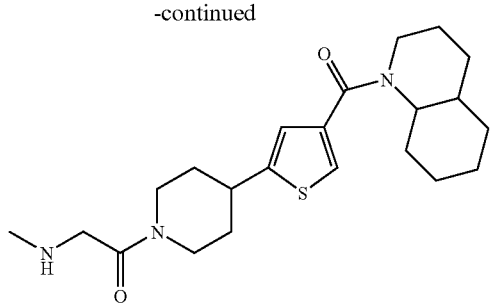

To a solution of cis-(octahydro-quinolin-1-yl)-(5-piperidin-4-yl-thiophen-3-yl)-methanone (CC-033) (0.065 g, 0.20 mmol) in acetonitrile (1 mL) was added triethylamine (0.59 mmol), HATU (0.22 mmol) and N-t-butyloxycarbonyl sarcosine (0.22 mmol). The reaction mixture was stirred for 4 hours, and then water (1 mL) added and the resulting solution purified by HPLC, eluting with 10%-98% acetonitrile in water (0.1% formic acid). The fractions containing methyl-(2-{4-[4-(octahydro-quinoline-1-carbonyl)-thiophen-2-yl]-piperidin-1-yl}-2-oxo-ethyl)-carbamic acid tert-butyl ester were concentrated under vacuum to give an oil (0.03 g). The oil was dissolved in TFA (1 mL) and DCM (1 mL) and the reaction mixture stirred for 2 hours. The solvent was evaporated and the residue purified by flash chromatography on a SCX-2 cartridge, eluting with acetonitrile followed by 2 M ammonia in methanol. The fractions containing the desired product were concentrated under vacuum to give the title compound as a colourless oil (0.034 g). LCMS m/z 404.22 [M+H]$^+$ RT=6.72 min (Analytical Method 2).

The compound in the following table was prepared using analogous methods:

| Code No. | Structure | Analytical Method | R.T. (min) | MS [m/z] |
|---|---|---|---|---|
| CC-056 | 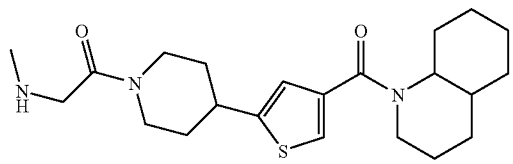 [SMILES: CNCC(=O)N1CCC(c2cc(C(=O)N3CCCC4CCCCC43)cs2)CC1] | 2 | 6.97 | [M + H]$^+$ 404.18 |

Synthesis 30 cis-N-(3-{4-[4-(Octahydro-quinoline-1-carbonyl)-thiophen-2-yl]-piperidin-1-yl}-3-oxo-propyl)-methanesulfonamide (CC-057)

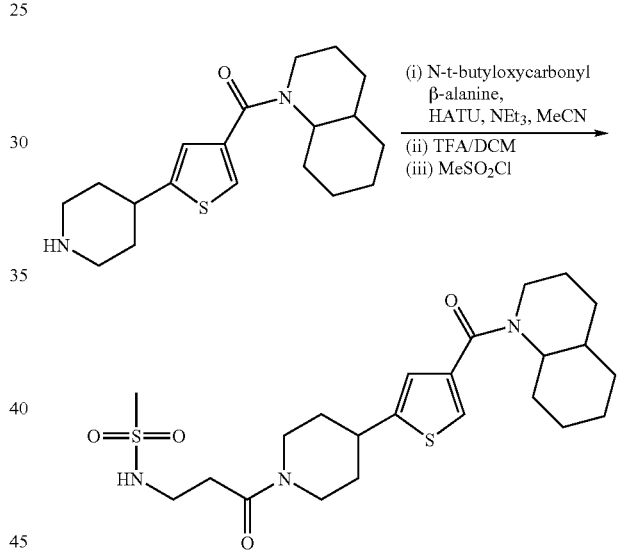

To a solution of cis-(octahydro-quinolin-1-yl)-(5-piperidin-4-yl-thiophen-3-yl)-methanone (CC-033) (0.065 g, 0.20 mmol) in acetonitrile (1 mL) was added triethylamine (0.59 mmol), HATU (0.22 mmol) and N-t-butyloxycarbonyl β-alanine (0.22 mmol). The reaction mixture was stirred for 4 hours, and then the solvent was removed by evaporation. The residue was dissolved in TFA (2 mL) and DCM (2 mL) and the reaction mixture stirred for 2 hours. The solvent was evaporated and the residue purified by flash chromatography on an SCX-2 cartridge, eluting with acetonitrile and then 2 M ammonia in methanol. The fractions containing 3-amino-1-{4-[4-(octahydro-quinoline-1-carbonyl)-thiophen-2-yl]-piperidin-1-yl}-propan-1-one were concentrated under vacuum to a colourless oil (0.089 g). The oil was dissolved in DCM (1 mL) and triethylamine (0.33 mmol) and methanesulphonyl chloride (0.22 mmol) were added. The mixture was stirred for 18 hours and then diluted with water and DCM. The organic solution was separated, dried and the solvent evaporated. The residue was purified by HPLC, eluting with 10%-98% acetonitrile in water (0.1% formic acid). The fractions containing the desired product were concentrated under vacuum to give the title compound as a colourless oil (0.047 g). LCMS mk 482.09 [M+H]$^+$ RT=9.52 min (Analytical Method 2).

The compounds in the following table were prepared using analogous methods:

| Code No. | Structure | Analytical Method | R.T. (min) | MS [m/z] |
|---|---|---|---|---|
| CC-058 | 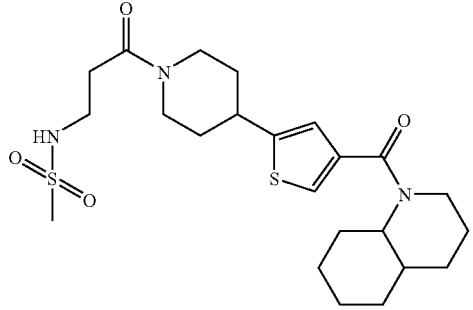<br>TRANS ISOMERS | 2 | 9.69 | [M + H]⁺ 482.23 |
| CC-148 | 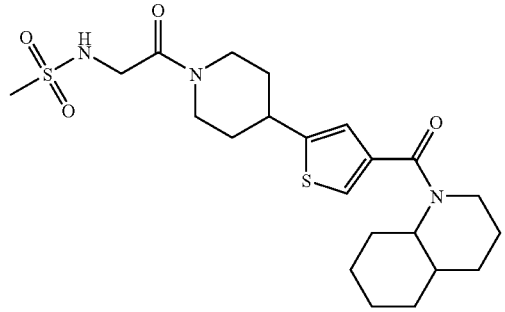<br>DHQ [CIS-M] | 2 | 9.66 | [M + H]⁺ 468.24 |

The compound in the following table was prepared using analogous methods but starting from cis-(octahydro-quinolin-1-yl)-[5-(1,2,3,6-tetrahydro-pyridin-4-yl)-thiophen-3-yl]-methanone (CC-046).

| Code No. | Structure | Analytical Method | R.T. (min) | MS [m/z] |
|---|---|---|---|---|
| CC-091 | 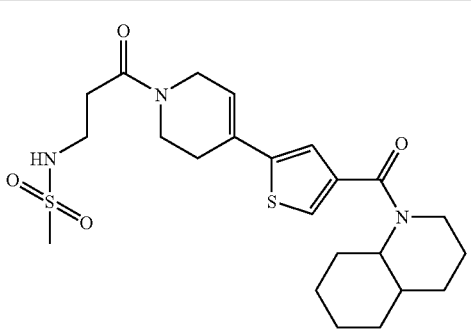<br>DHQ [CIS-M] | 2 | 9.62 | [M + H]⁺ 480.08 |

The compound in the following table was prepared using analogous methods but starting from (2-phenyl-piperidin-1-yl)-(5-piperidin-4-yl-thiophen-3-yl)-methanone (CC-017).

| Code No. | Structure | Analytical Method | R.T. (min) | MS [m/z] |
|---|---|---|---|---|
| CC-128 | 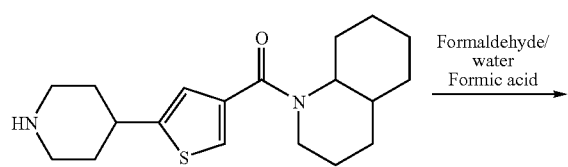 | 2 | 9.65 | [M + H]+ 504.18 |

Synthesis 31 cis-[5-(1-Methyl-piperidin-4-yl)-thiophen-3-yl]-(octahydro-quinolin-1-yl)-methanone (CC-038)

Synthesis 31A cis-1-(2-Hydroxy-ethyl)-4-[4-(octahydro-quinoline-1-carbonyl)-thiophen-2-yl]-piperidinium formate (CC-088) DHQ [CIS-M]

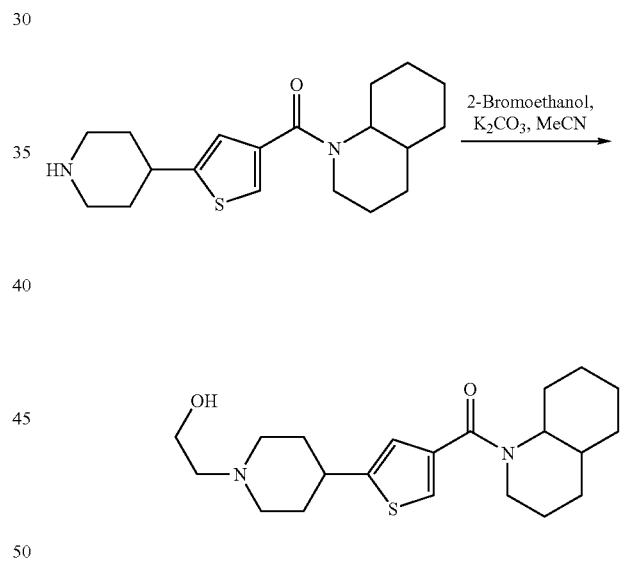

cis-(Octahydro-quinolin-1-yl)-(5-piperidin-4-yl-thiophen-3-yl)-methanone (CC-033) (0.070 g, 0.21 mmol) was dissolved in aqueous formaldehyde (37% w/w; 0.1 mL) and formic acid (1 mL). The reaction was heated to 150° C. using microwave irradiation for 5 minutes. The product was purified by flash chromatography on a SCX-2 cartridge, eluting with acetonitrile and then 2 M ammonia in methanol. The residue was further purified by flash chromatography on a NH$_2$-SPE cartridge, eluting with 0%-100% ethyl acetate in cyclohexane. The fractions containing the desired product were concentrated under vacuum to give the title compound (0.035 g). LCMS m/z 347.21 min [M+H]+ RT=6.68 min (Analytical Method 1). $^1$H NMR (400 MHz, CHCl$_3$-d): δ 7.2 (s, 1H), 6.85 (s, 1H), 4.7 (m, 1H), 3.8 (m, 1H), 3.1 (m, 1H), 2.9 (m, 1H), 2.8-2.7 (m, 1H), 2.30 (s, 3H), 2.1-1.1 (m, 20H).

cis-(Octahydro-quinolin-1-yl)-(5-piperidin-4-yl-thiophen-3-yl)-methanone (0.029 g, 0.087 mmol) was dissolved MeCN (1 mL) and potassium carbonate (36 mmol) was added followed by 2-bromoethanol (22 mg). The reaction was heated to 60° C. and stirred for 5 hours. The product was purified by flash chromatography on a SCX-2 cartridge, eluting with acetonitrile and then 2 M ammonia in methanol. The residue was further purified by HPLC, eluting with 10%-98% acetonitrile in water (0.1% formic acid). The fractions containing the desired product were concentrated under vacuum to give the title compound (0.046 g). LCMS m/z 377.17 min [M+H]+ RT=6.45 min (Analytical Method 2).

The compounds in the following table were prepared using analogous methods:
| Code No. | Structure | Analytical Method | R.T. (min) | MS [m/z] |
|---|---|---|---|---|
| CC-087 | 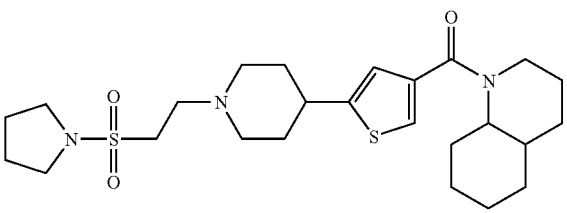<br>FORMATE SALT<br>DHQ [CIS-M] | 2 | 7.37 | [M + H]⁺ 494.17 |
| CC-089 | 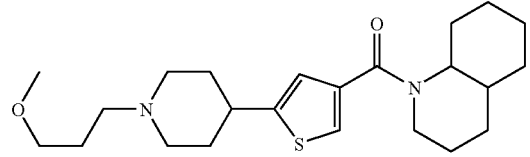<br>FORMATE SALT<br>DHQ [CIS-M] | 2 | 6.96 | [M + H]⁺ 405.19 |
| CC-108 | 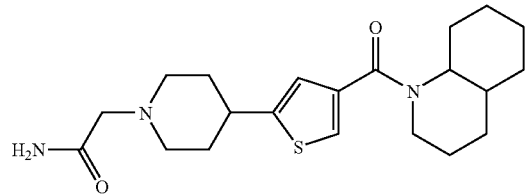<br>FORMATE SALT<br>DHQ [CIS-M] | 2 | 6.38 | [M + H]⁺ 390.10 |
| CC-150 | 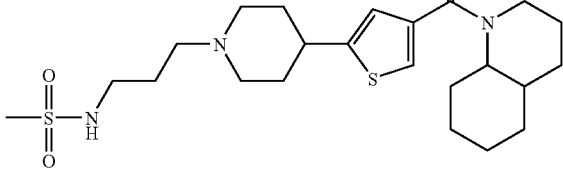<br>FORMATE SALT<br>DHQ [CIS-M] | 2 | 6.65 | [M + H]⁺ 468.20 |
| CC-153 | 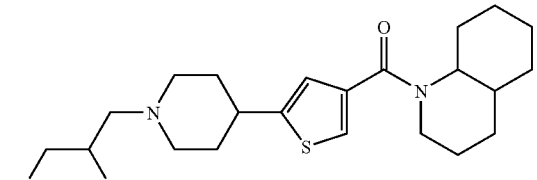<br>FORMATE SALT<br>DHQ [CIS-M] | 2 | 6.32 | [M + H]⁺ 407.30 |
(MS values rendered with LaTeX superscripts: $[M+H]^+$)

The compound in the following table was prepared using analogous methods but starting from (4,4-dimethyl-azepan-1-yl)-(5-piperidin-4-yl-thiophen-3-yl)-methanone (CC-023).

| Code No. | Structure | Analytical Method | R.T. (min) | MS [m/z] |
|---|---|---|---|---|
| CC-139 | 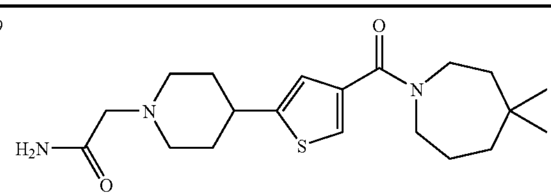 | 2 | 6.16 | [M + H]⁺ 378.30 |

Synthesis 31 B cis-2-{4-[4-(Octahydro-quinoline-1-carbonyl)-thiophen-2-yl]-piperidin-1-yl}-isobutyramide (CC-158) DHQ [CIS-M]

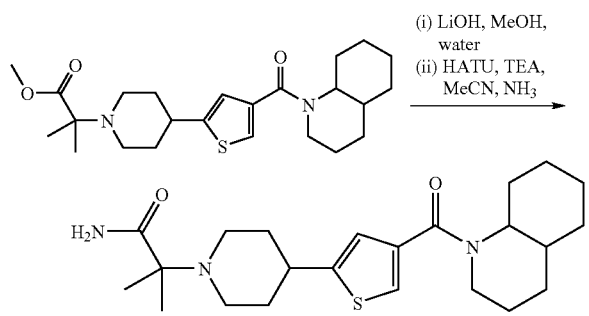

(i) LiOH, MeOH, water
(ii) HATU, TEA, MeCN, NH₃ cis-2-Methyl-2-{4-[4-(octahydro-quinoline-1-carbonyl)-thiophen-2-yl]-piperidin-1-yl}-propionic acid methyl ester was prepared using a similar synthetic route to that described in Synthesis 31A. The ester (0.150 g, 0.35 mmol) was dissolved in methanol (1 mL) and water (1 mL) and lithium hydroxide monohydrate (1.6 mmol) added. The mixture was refluxed for 8 hours and then the solvent evaporated and the residue taken up in water (5 mL). The mixture was acidified with 1N hydrochloric acid and extracted with DCM. The organic solution was dried with magnesium sulphate, filtered and the solvent removed by evaporation to give a light brown gum. The gum was dissolved in acetonitrile (2 mL) and triethylamine (0.1 mL) and then HATU (0.4 mmol) was added. The mixture was stirred for 15 minutes and then saturated aqueous ammonia (0.2 mL) was added and the mixture stirred for another hour. The solvent was removed by evaporation and the residue dissolved in DCM (5 mL) which was washed with saturated aqueous sodium hydrogencarbonate solution. The organic solution was dried with magnesium sulphate, filtered and evaporated to give a brown gum which was then purified by preparative HPLC eluting with 10%-98% acetonitrile in water (0.1% formic acid). The fractions containing the desired product were concentrated under vacuum to give the title compound as a white solid (0.062 g). LCMS m/z 418.31 [M+H]⁺ RT=6.48 min (Analytical Method 2).

The compounds in the following table were prepared using analogous methods

| Code No. | Structure | Analytical Method | R.T. (min) | MS [m/z] |
|---|---|---|---|---|
| CC-170 | DHQ [CIS-S] | 2 | 7.25 | [M + H]⁺ 472.18 |
| CC-171 | DHQ [CIS-S] | 2 | 6.63 | [M + H]⁺ 432.20 |

-continued

| Code No. | Structure | Analytical Method | R.T. (min) | MS [m/z] |
|---|---|---|---|---|
| CC-174 | 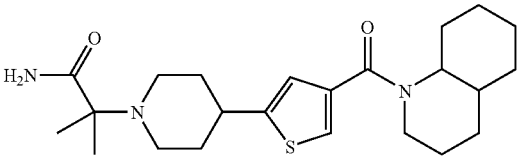<br>DHQ [CIS-S] | 2 | 6.62 | [M + H]+ 418.20 |

The compound in the following table was prepared using analogous methods but starting from (4,4-dimethyl-azepan-1-yl)-(5-piperidin-4-yl-thiophen-3-yl)-methanone (CC-023).

| Code No. | Structure | Analytical Method | R.T. (min) | MS [m/z] |
|---|---|---|---|---|
| CC-137 | 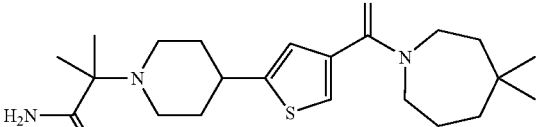<br>FORMATE SALT | 2 | 6.38 | [M + H]+ 406.20 |

Synthesis 32 cis-4-[4-(Octahydro-quinoline-1-carbonyl)-thiophen-2-yl]-piperidine-1-carboxylic acid methyl ester (CC-066)

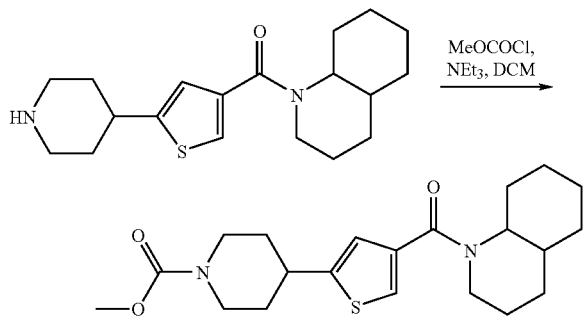

cis-(Octahydro-quinolin-1-yl)-(5-piperidin-4-yl-thiophen-3-yl)-methanone (CC-033) (0.04 g, 0.12 mmol) was dissolved in dichloromethane (2 mL) and triethylamine (0.37 mmol). Methyl chloroformate (0.25 mmol) was added and the mixture stirred for 2 hours and then the solvent removed by evaporation. The residue was purified by HPLC, eluting with 10%-98% acetonitrile in water (0.1% formic acid). The fractions containing the desired product were concentrated under vacuum to give the title compound as a colourless oil (0.023 g). LCMS m/z 391.15 min [M+H]+ RT=11.55 min (Analytical Method 2). $^1$H NMR (400 MHz, CHCl$_3$-d): δ 7.2 (s, 1H), 6.9 (s, 1H), 4.6 (m, 1H), 4.3 (m, 2H), 3.8 (m, 1H), 3.7 (s, 3H), 3.1-2.7 (m, 4H), 2.1-1.1 (m, 17H).

The compounds in the following table were prepared using analogous methods:

| Code No. | Structure | Analytical Method | R.T. (min) | MS [m/z] |
|---|---|---|---|---|
| CC-067 | 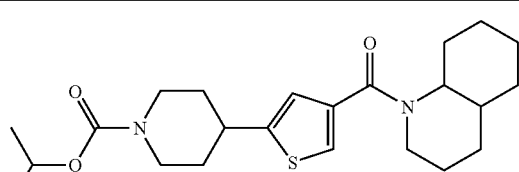<br>CIS ISOMERS | 2 | 13.07 | [M + H]+ 419.19 |

-continued

| Code No. | Structure | Analytical Method | R.T. (min) | MS [m/z] |
|---|---|---|---|---|
| CC-106 | 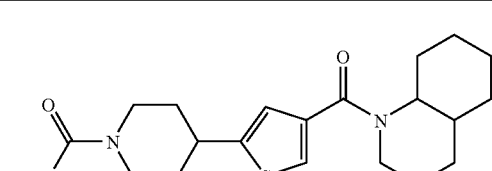<br>DHQ [CIS-M] | 2 | 9.39 | [M + H]+ 390.18 |
| CC-116 | <br>DHQ [CIS-M] | 2 | 11.40 | [M + H]+ 430.30 |

The compound in the following table was prepared using analogous methods but starting from (4,4-dimethyl-azepan-1-yl)-(5-piperidin-4-yl-thiophen-3-yl)-methanone (CC-023).

| Code No. | Structure | Analytical Method | R.T. (min) | MS [m/z] |
|---|---|---|---|---|
| CC-094 | 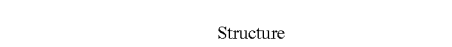 | 2 | 11.13 | [M + H]+ 379.14 |

The compounds in the following table were prepared using analogous methods but starting from (2-phenyl-piperidin-1-yl)-(5-piperidin-4-yl-thiophen-3-yl)-methanone (CC-017).

| Code No. | Structure | Analytical Method | R.T. (min) | MS [m/z] |
|---|---|---|---|---|
| CC-119 | 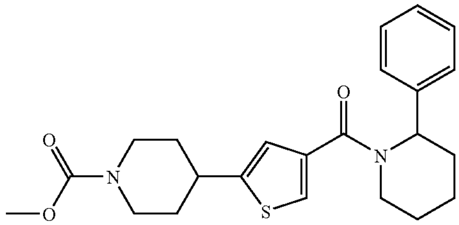 [SMILES: COC(=O)N1CCC(c2cc(C(=O)N3CCCCC3c3ccccc3)cs2)CC1] | 2 | 11.52 | [M + H]+ 413.22 |

| Code No. | Structure | Analytical Method | R.T. (min) | MS [m/z] |
|---|---|---|---|---|
| CC-132 | 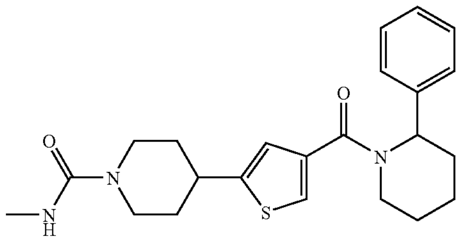 [SMILES: CNC(=O)N1CCC(c2cc(C(=O)N3CCCCC3c3ccccc3)cs2)CC1] | 2 | 9.56 | [M + H]+ 412.26 |

Synthesis 33 cis-[5-(1-Methanesulfonyl-piperidin-4-yl)-thiophen-3-yl]-(octahydro-quinolin-1-yl)-methanone (CC-065)

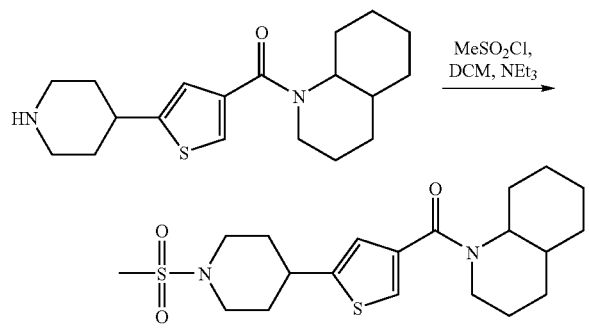

cis-(Octahydro-quinolin-1-yl)-(5-piperidin-4-yl-thiophen-3-yl)-methanone (CC-033) (0.04 g, 0.12 mmol) was dissolved in dichloromethane (2 mL) and triethylamine (0.37 mmol). Methylsulphonyl chloride (0.25 mmol) was added and the mixture stirred for 2 hours and then the solvent removed by evaporation. The residue was purified by HPLC, eluting with 10%-98% acetonitrile in water (0.1% formic acid). The fractions containing the desired product were concentrated under vacuum to give the title compound as a colourless oil (0.022 g). LCMS m/z 411.11 min [M+H]+ RT=10.84 min (Analytical Method 2). $^1$H NMR (400 MHz, CHCl$_3$-d): δ 7.2 (s, 1H), 6.9 (s, 1H), 4.6 (m, 1H), 3.9-3.6 (m, 3H), 3.1-2.7 (m, 2H), 2.7 (s, 3H), 2.1-1.1 (m, 19H).

The compounds in the following table were prepared using analogous methods:

| Code No. | Structure | Analytical Method | R.T. (min) | MS [m/z] |
|---|---|---|---|---|
| CC-092 | DHQ [CIS-M] | 2 | 12.95 | [M + H]+ 473.11 |
| CC-104 | DHQ [CIS-M] | 2 | 11.90 | [M + H]+ 439.18 |
| CC-105 | DHQ [CIS-M] | 2 | 12.68 | [M + H]+ 453.19 |

-continued

| Code No. | Structure | Analytical Method | R.T. (min) | MS [m/z] |
|---|---|---|---|---|
| CC-093 | DHQ [CIS-M] | 2 | 11.66 | [M + H]+ 437.16 |

The compound in the following table was prepared using analogous methods but starting from (4,4-dimethyl-azepan-1-yl)-(5-piperidin-4-yl-thiophen-3-yl)-methanone (CC-023).

microwave irradiation. The product was purified by HPLC, eluting with 20%-98% acetonitrile in water (0.1% formic acid). The fractions containing the desired product were concentrated under vacuum to give the title compound (0.027 g).

| Code No. | Structure | Analytical Method | R.T. (min) | MS [m/z] |
|---|---|---|---|---|
| CC-096 | 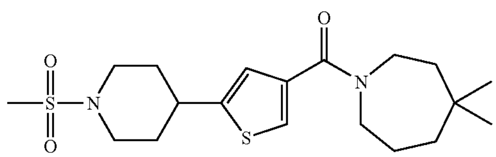 | 2 | 10.45 | [M + H]+ 399.13 |

Synthesis 34

4-[4-(Azepane-1-carbonyl)-5-chloro-thiophen-2-yl]-piperidine-1-carboxylic acid benzyl ester (CC-009)

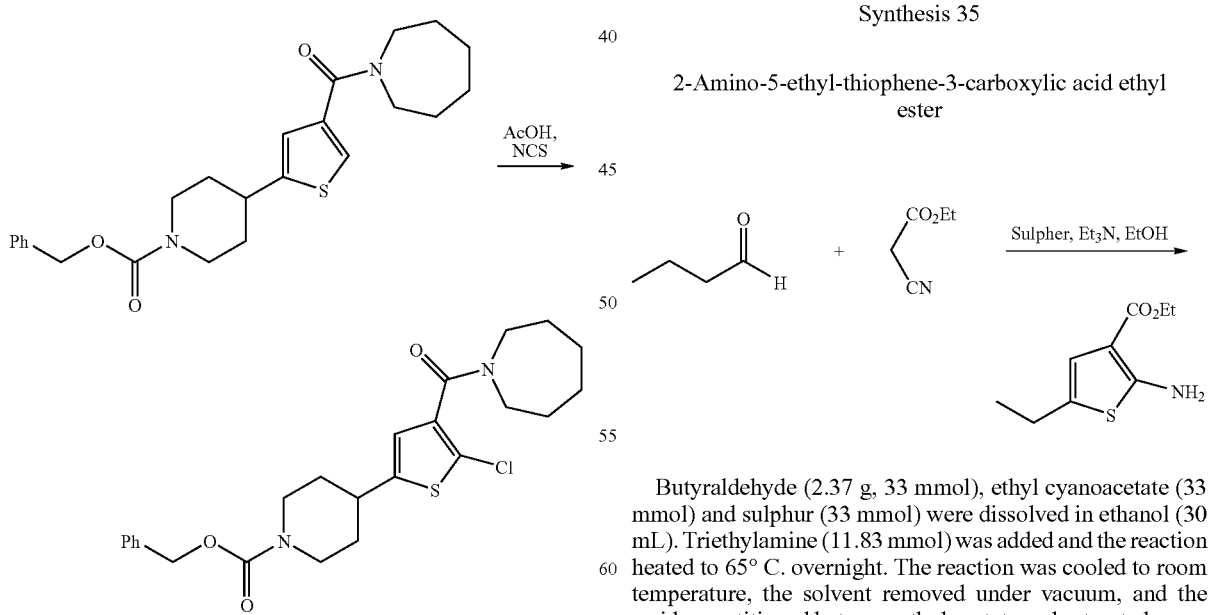

4-[4-(Azepane-1-carbonyl)-thiophen-2-yl]-piperidine-1-carboxylic acid benzyl ester (0.037 g, 0.087 mmol) was dissolved in acetic acid. N-chlorosuccinimide (0.09 mmol) was added and the reaction heated to 100° C. for 2.5 minutes using LCMS m/z 461.24 [M+H]+ RT=13.23 min (Analytical Method 1). $^1$H NMR (400 MHz, CHCl$_3$-d): δ 7.4-7.25 (m, 5H), 6.6 (m, 1H), 5.1 (s, 2H), 4.3 (m, 2H), 3.65 (m, 2H), 3.35 (t, 2H), 2.9-2.8 (m, 3H), 2.0-1.9 (m, 2H), 1.85-1.75 (m, 2H), 1.7-1.6 (m, 8H).

Synthesis 35

2-Amino-5-ethyl-thiophene-3-carboxylic acid ethyl ester

Butyraldehyde (2.37 g, 33 mmol), ethyl cyanoacetate (33 mmol) and sulphur (33 mmol) were dissolved in ethanol (30 mL). Triethylamine (11.83 mmol) was added and the reaction heated to 65° C. overnight. The reaction was cooled to room temperature, the solvent removed under vacuum, and the residue partitioned between ethyl acetate and saturated aqueous sodium hydrogen carbonate. The organic solution was dried over magnesium sulphate, filtered and the solvent removed. The product was purified by column chromatography on silica, eluting with 0%-25% ethyl acetate in cyclohexane. The fractions containing the desired product were concentrated under vacuum to give the title compound (4.9 g). LCMS m/z 200.11 [M+H]+ RT=3.54 min (Analytical Method 4).

Synthesis 36

5-Ethyl-thiophene-3-carboxylic acid ethyl ester

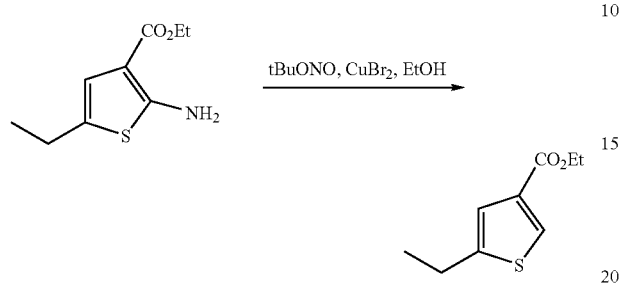

2-Amino-5-ethyl-thiophene-3-carboxylic acid ethyl ester (2.5 g, 12.5 mmol) was added to a suspension of t-butyl nitrite (18.8 mmol) and copper (II) bromide (15.1 mmol) in ethanol (120 mL). The reaction mixture was stirred for 15 minutes then saturated aqueous ammonium chloride (7 mL) was added and the mixture stirred for a further 15 minutes. The solvent was removed under vacuum and product partitioned between diethyl ether and water. The organic layer was dried over magnesium sulphate, filtered and the solvent removed. The product was purified by column chromatography on silica, eluting with 0%-10% ethyl acetate in cyclohexane. The fractions containing the desired product were concentrated under vacuum to give the title compound (1.2 g). $^1$H NMR (400 MHz, CHCl$_3$-d): δ 7.9 (s, 1H), 7.2 (s, 1H), 3.4 (q, 2H), 2.8 (q, 2H), 1.4 (m, 6H).

Synthesis 36A

5-Ethyl-thiophene-3-carboxylic acid

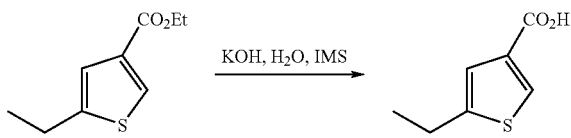

Potassium hydroxide (1.02 g, 18.3 mmol) in water (3 mL) was added to a solution of 5-ethyl-thiophene-3-carboxylic acid ethyl ester (6.1 mmol) in IMS (9 mL). The reaction was stirred for 1 hour then partitioned between diethyl ether and water. The aqueous layer was acidified to pH 7 with concentrated hydrochloric acid and extracted with diethyl ether. The organic solution was dried over magnesium sulphate, filtered and the solvent removed to give the title compound (0.78 g). $^1$H NMR (400 MHz, CHCl$_3$-d): δ 8.0 (s, 1H), 7.2 (s, 1H), 2.8 (q, 2H), 1.3 (t, 3H).

Synthesis 37

(5-Ethyl-thiophen-3-yl)-(1,3,3-trimethyl-6-aza-bicyclo[3.2.1]oct-6-yl)-methanone (AA-014)

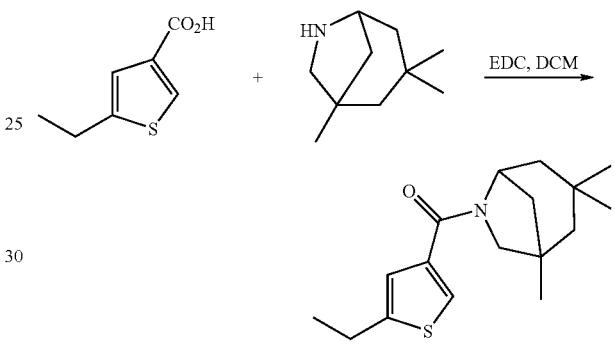

1-Ethyl-3-(3-dimethylaminopropyl)carbodiimide hydrochloride (0.06 g; 1.2 eq) was added to a solution of 5-ethyl-thiophene-3-carboxylic acid (0.04 g; 1 eq.) in DCM (1 mL/100 mg of starting material). This mixture was stirred at room temperature for 5 minutes, then 1,3,3-trimethyl-6-aza-bicyclo[3.2.1]octane (0.043 g; 1.1 eq.) added and the mixture allowed to stir for 18 hours. Water (1 mL/100 mg of starting material) was then added and the organic layer separated, dried and evaporated to give the crude product which was purified by column chromatography (EtOAc/iso-hexane) to give the title compound (0.046 g). LCMS m/z 292 [M+H]+ RT=4.28 min (Analytical Method 3).

The compounds in the following table were prepared using analogous methods:

| Code No. | Structure | Analytical Method | R.T. (min) | MS [m/z] |
|---|---|---|---|---|
| AA-009 | 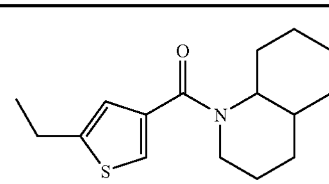 | 2 | 12.21 | [M + H]+ 278.18 |

| Code No. | Structure | Analytical Method | R.T. (min) | MS [m/z] |
|---|---|---|---|---|
| AA-010 | 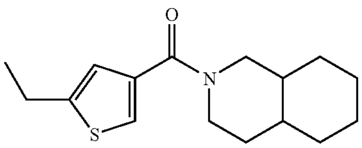 [SMILES: CCc1cc(C(=O)N2CCC3CCCCC3C2)cs1] | 3 | 4.35, 4.45 | [M + H]⁺ 278 |
| AA-015 | 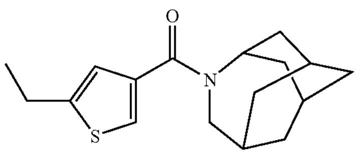 [SMILES: CCc1cc(C(=O)N2CC3CC4CC(C3)CC2C4)cs1] | 3 | 4.17 | [M + H]⁺ 290 |
| AA-016 | 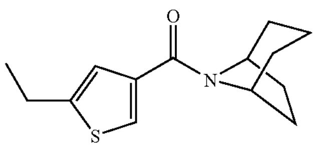 [SMILES: CCc1cc(C(=O)N2C3CCCC2CC3)cs1] | 3 | 3.4 | [M + H]⁺ 250 |
| AA-019 | 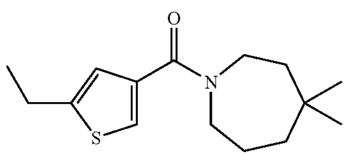 [SMILES: CCc1cc(C(=O)N2CCCC(C)(C)CC2)cs1] | 2 | 11.90 | [M + H]⁺ 266.29 |
| AA-020 | 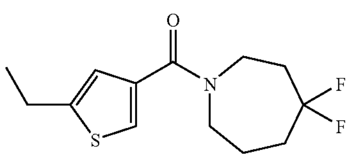 [SMILES: CCc1cc(C(=O)N2CCCC(F)(F)CC2)cs1] | 2 | 10.02 | [M + H]⁺ 274.22 |
| AA-021 | 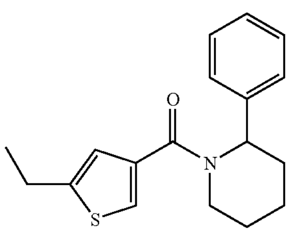 [SMILES: CCc1cc(C(=O)N2CCCCC2c2ccccc2)cs1] | 2 | 12.31 | [M + H]⁺ 300.25 |

Synthesis 38

2-Bromo-5-ethyl-thiophene-3-carboxylic acid ethyl ester

5-Ethyl-thiophene-3-carboxylic acid ethyl ester (1.2 g, 6.52 mmol) was dissolved in acetic acid (10 mL). N-Bromosuccinimide (7.1 mmol) was added and the reaction was stirred for 4 hours. The solvent was removed under vacuum and the product purified by flash chromatography on silica, eluting with 0%-30% t-butylmethylether in cyclohexane. The fractions containing the desired product were concentrated under vacuum to give the title compound (0.7 g). ¹H NMR (400 MHz, CHCl₃-d): δ 7.05 (s, 1H), 4.3 (q, 2H), 2.75 (q, 2H), 1.4 (t, 3H), 1.3 (t, 3H).

Synthesis 39

2-Bromo-5-ethyl-thiophene-3-carboxylic acid

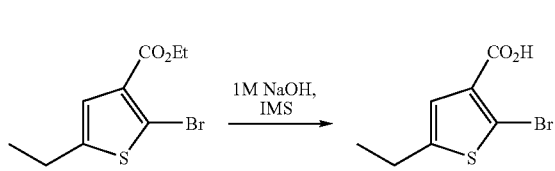

2-Bromo-5-ethyl-thiophene-3-carboxylic acid ethyl ester (0.7 g, 2.65 mmol) was dissolved in IMS (4 mL) and aqueous sodium hydroxide (1 M, 6 mL) was added. The reaction was heated to 140° C. using microwave irradiation for 10 minutes. Water (5 mL) was added and the white precipitate formed was isolated by filtration, washed with water and then dried under vacuum to give the title compound (0.44 g). ¹H NMR (400 MHz, CHCl₃-d): δ 7.1 (s, 1H), 2.7 (q, 2H), 1.25 (t, 3H).

Synthesis 40

(2-Bromo-5-ethyl-thiophen-3-yl)-piperidin-1-yl-methanone (AA-002)

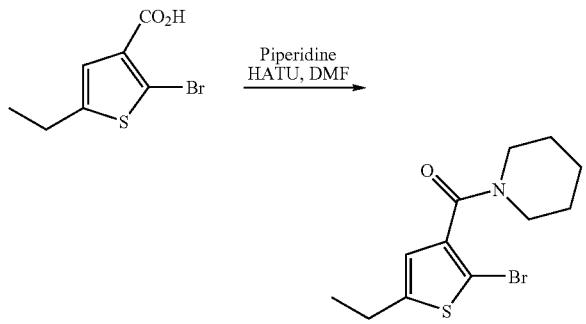

2-Bromo-5-ethyl-thiophene-3-carboxylic acid (0.44 g, 1.88 mmol) was dissolved in DMF (10 mL). HATU (1.88 mmol) and piperidine (10 mmol) were added and the reaction mixture stirred for 3 hours. The mixture was diluted with water and acetonitrile and the product was purified by HPLC, eluting with 0%-95% acetonitrile in water (0.1% formic acid) over 30 minutes. The fractions containing the desired product were concentrated under vacuum to give the title compound (0.36 g). LCMS m/z 304.00 [M+H]$^+$ RT=10.91 min (Analytical Method 2). $^1$H NMR (400 MHz, CHCl$_3$-d): δ 6.6 (s, 1H), 3.7 (m, 2H), 3.35 (m, 2H), 2.75 (q, 2H), 1.65 (m, 4H), 1.55 (m, 2H), 1.27 (t, 3H).

The compound in the following table was prepared using analogous methods:

| Code No. | Structure | $^1$H NMR | Analytical Method | R.T. (min) | MS [m/z] |
|---|---|---|---|---|---|
| AA-005 | 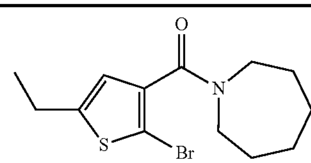 | 6.6 (s, 1 H), 3.7 (m, 2 H), 3.4 (m, 2 H), 2.80-2.75 (q, 2 H), 1.8 (m, 2 H), 1.65-1.55 (m, 6 H), 1.3 (t, 3 H) | 1 | 11.73 | [M + H]$^+$ 316.08 |

Synthesis 41

5-Ethyl-3-(piperidine-1-carbonyl)-thiophene-2-carbonitrile (AA-003)

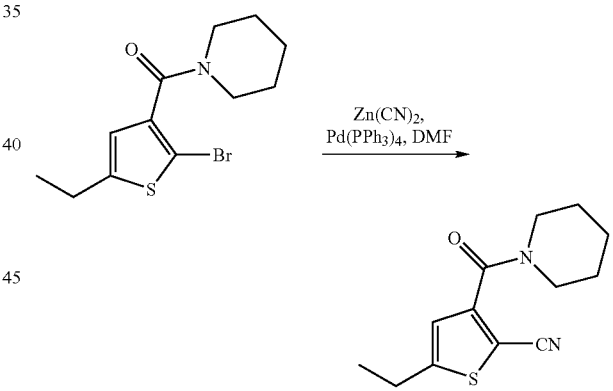

(2-Bromo-5-ethyl-thiophen-3-yl)-piperidin-1-yl-methanone (0.1 g, 0.33 mmol) was dissolved in DMF (3 mL). Zinc cyanide (0.34 mmol) and tetrakis-(triphenylphosphine) palladium (0) (0.017 mmol) were added and the reaction mixture heated at 100° C. for 4 hours. The mixture was cooled to ambient temperature and the reaction quenched with a mixture of 5% aqueous sodium thiosulphate and saturated aqueous potassium carbonate (1:1, 5 mL) and extracted with diethyl ether. The organic solution was dried over magnesium sulphate, filtered and the solvent removed. The product was purified by HPLC, eluting with 20%-95% acetonitrile in water (0.1% formic acid) over 30 minutes. The fractions containing the desired product were concentrated under vacuum and freeze-dried to give the title compound (0.26 mg). LCMS m/z 249.14 [M+H]$^+$ RT=9.75 min (Analytical Method 1). $^1$H NMR (400 MHz, CHCl$_3$-d): δ 6.85 (t, 1H), 3.70 (m, 2H), 3.4 (m, 2H), 2.9 (m, 2H), 1.7 (m, 4H), 1.6 (s, 2H), 1.3 (t, 3H).

The compound in the following table was prepared using analogous methods:

| Code No. | Structure | ¹H NMR | Analytical Method | R.T. (min) | MS [m/z] |
|---|---|---|---|---|---|
| AA-006 | 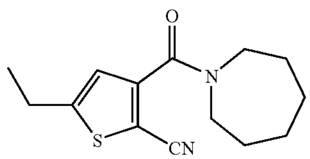 [SMILES: CCc1cc(C(=O)N2CCCCCC2)c(C#N)s1] | 6.8 (s, 1H), 3.7-3.6 (m, 2H), 3.4 (t, 2H), 2.9 (q, 2H), 1.8 (m, 2H), 1.7-1.55 (m, 6H), 1.3 (t, 3H). | 1 | 10.20 | [M + H]⁺ 263.17 |

Synthesis 43

2-Chloro-5-ethyl-thiophene-3-carboxylic acid ethyl ester

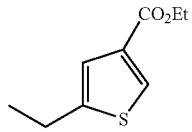 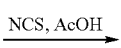 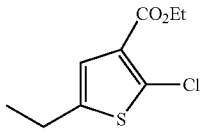

N-Chlorosuccinimide (0.8 g, 5.9 mmol) was added to a solution of 5-ethyl-thiophene-3-carboxylic acid ethyl ester (1 g, 5.43 mmol) in acetic acid (10 mL) and stirred overnight. The reaction was filtered and the solvent removed under vacuum. The product was purified by flash chromatography on silica, eluting with 0%-100% t-butylmethyl ether in cyclohexane. The fractions containing the desired product were concentrated under vacuum to give the title compound (0.83 g). ¹H NMR (400 MHz, CHCl₃-d): δ 7.05 (s, 1H), 4.3 (q, 2H), 2.75 (q, 2H), 1.4 (t, 3H), 1.3 (t, 3H).

Synthesis 44

2-Chloro-5-ethyl-thiophene-3-carboxylic acid

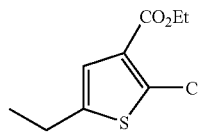 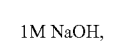 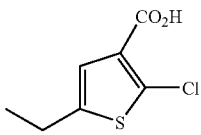

5-Ethyl-thiophene-3-carboxylic acid ethyl ester (0.83 g, 3.8 mmol) was dissolved in a solution of aqueous sodium hydroxide (1 M, 6 mL) and ethanol (4 mL). The mixture was then heated to 140° C. for 10 minutes using microwave irradiation. The reaction mixture was acidified with 1 N hydrochloric acid and the resulting precipitate was isolated by filtration, washed with water and then dried under vacuum to give the title compound (0.53 g). ¹H NMR (400 MHz, DMSO-d6): δ 7.05 (s, 1H), 2.75 (q, 2H), 1.4 (t, 3H), 1.2 (t, 3H).

Synthesis 45

(2-Chloro-5-ethyl-thiophen-3-yl)-piperidin-1-yl-methanone (AA-001)

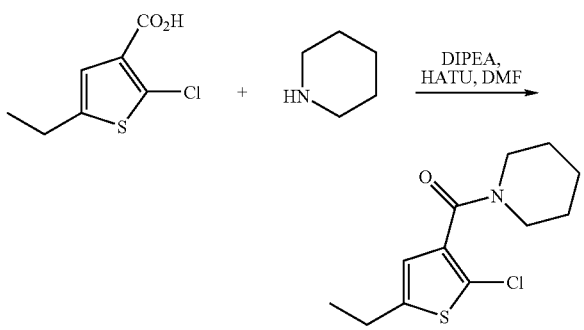

2-Chloro-5-ethyl-thiophene-3-carboxylic acid (0.04 g, 0.21 mmol) was dissolved in DMF (6 mL). DIPEA (0.63 mmol), HATU (0.21 mmol) and piperidine (2.0 mmol) were added and the reaction stirred overnight. The mixture was diluted with acetonitrile and water and the product purified by HPLC, eluting with 20%-95% acetonitrile in water (0.1% formic acid) over 30 minutes. The fractions containing the desired product were concentrated under vacuum to give the title compound (0.023 g). LCMS m/z 358.08 [M+H]⁺ RT=10.84 min (Analytical Method 2). ¹H NMR (400 MHz, CHCl₃-d): δ 6.6 (s, 1H), 3.7 (s, 2H), 3.35 (s, 2H), 2.75 (q, 2H), 1.6 (s, 6H), 1.3 (t, 3H).

The compounds in the following table were prepared using analogous methods:

| Code No. | Structure | ¹H NMR | Analytical Method | R.T. (min) | MS [m/z] |
|---|---|---|---|---|---|
| AA-004 | 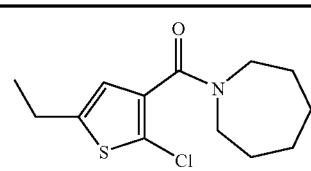 | 6.6 (s, 1H), 3.65 (m, 2H), 3.4 (m, 2H), 2.75 (q, 2H), 1.85-1.75 (m, 2H), 1.7-1.5 (m, 6H), 1.25 (t, 3H) | 2 | 11.38 | [M + H]⁺ 272.10 |

| Code No. | Structure | ¹H NMR | Analytical Method | R.T. (min) | MS [m/z] |
|---|---|---|---|---|---|
| AA-013 | 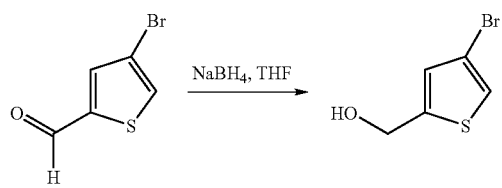 | | 2 | 13.40 | [M + H]⁺ 312.12 |
| AA-008 | 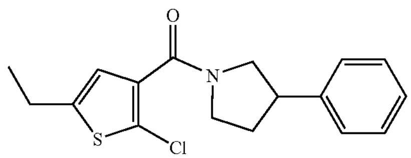 [SMILES: CCc1cc(C(=O)N2CCC(c3ccccc3)C2)c(Cl)s1] | | 2 | 12.06 | [M + H]⁺ 320.09 |

Synthesis 46

(4-Bromo-thiophen-2-yl)-methanol

4-Bromo-thiophene-2-carbaldehyde (14.2 g, 74.5 mmol) was dissolved in tetrahydrofuran (160 mL). To this was added sodium borohydride (82 mmol) and the reaction was stirred for 45 minutes. The reaction was quenched with saturated aqueous sodium hydrogen carbonate and extracted with diethyl ether. The organic solvent was dried over magnesium sulphate, filtered and the solvent removed to give the title compound (13.2 g). $^1$H NMR (400 MHz, CHCl$_3$-d): δ 7.2 (s, 1H), 6.9 (s, 1H), 4.8 (d, 2H).

Synthesis 47

(4-Bromo-thiophen-2-ylmethoxy)-tert-butyl-dimethyl-silane

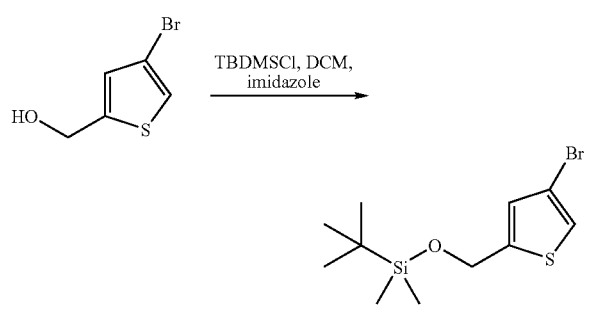

To a solution of (4-bromo-thiophen-2-yl)-methanol (13.2 g, 72 mmol) in DCM (140 mL) was added t-butyldimethylsilyl chloride (79.2 mmol) and imidazole (79.2 mmol). The reaction was stirred for 1 hour, then quenched with 1 M HCl and extracted into DCM. The organic solution was dried over magnesium sulphate, filtered and the solvent removed to give the title compound as a yellow oil, which was used without further purification.

Synthesis 48

[5-(tert-Butyl-dimethyl-silanyloxymethyl)-thiophen-3-yl]-piperidin-1-yl-methanone

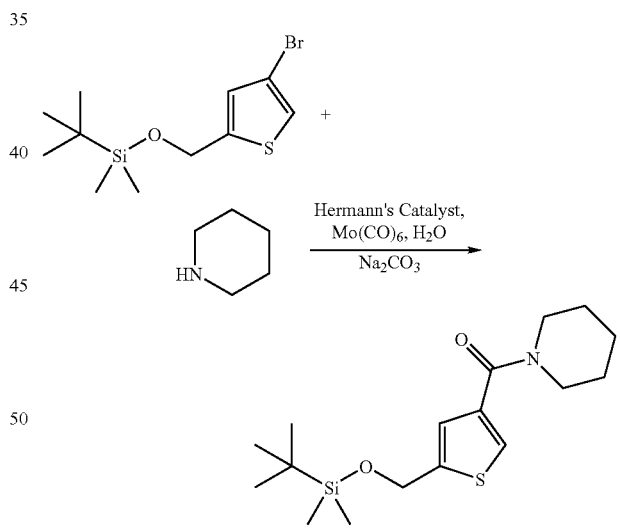

(4-Bromo-thiophen-2-ylmethoxy)-tert-butyl-dimethyl-silane (0.46 g, 1.5 mmol), Hermann's catalyst (0.05 mmol), molybdenumhexacarbonyl (0.5 mmol), piperidine (1 mmol) and sodium carbonate (3 mmol) were added to water (2 mL). The reaction mixture was heated to 170° C. for 10 minutes using microwave irradiation, and then quenched with water. The mixture was extracted with ethyl acetate, and the organic solution dried over magnesium sulphate, filtered and the solvent evaporated. The product was purified by flash chromatography on silica, eluting with ethyl acetate in pentane. The fractions containing the desired product were concentrated

Synthesis 49

(5-Hydroxymethyl-thiophen-3-yl)-piperidin-1-yl-methanone

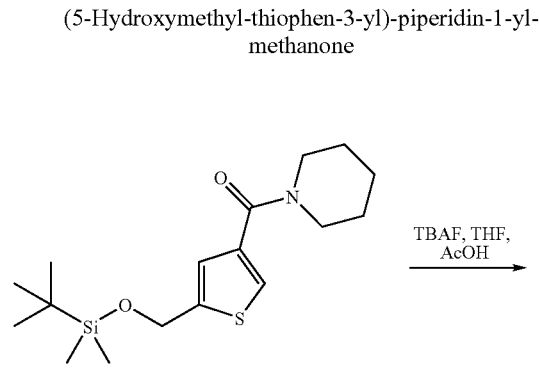

[5-(tert-Butyl-dimethyl-silanyloxymethyl)-thiophen-3-yl]-piperidin-1-yl-methanone (0.96 g, 2.83 mmol) was dissolved in tetrahydrofuran (15 mL) and t-butylammonium fluoride (1 M in THF; 3.12 mL) and acetic acid (1 mL) were added. The reaction mixture was stirred overnight then partitioned between diethyl ether and saturated aqueous sodium hydrogen carbonate. The organic solution was separated and dried over magnesium sulphate, filtered and the solvent removed. The residue was purified by flash chromatography on silica, eluting with 30% ethyl acetate in pentane. The fractions containing the desired product were concentrated under vacuum to give the title compound as a clear oil (0.41 g). LCMS m/z 226 [M+H]+ RT=6.15 min (Analytical Method 4).

Synthesis 50

Piperidin-1-yl-(5-o-tolyloxymethyl-thiophen-3-yl)-methanone (BB-002)

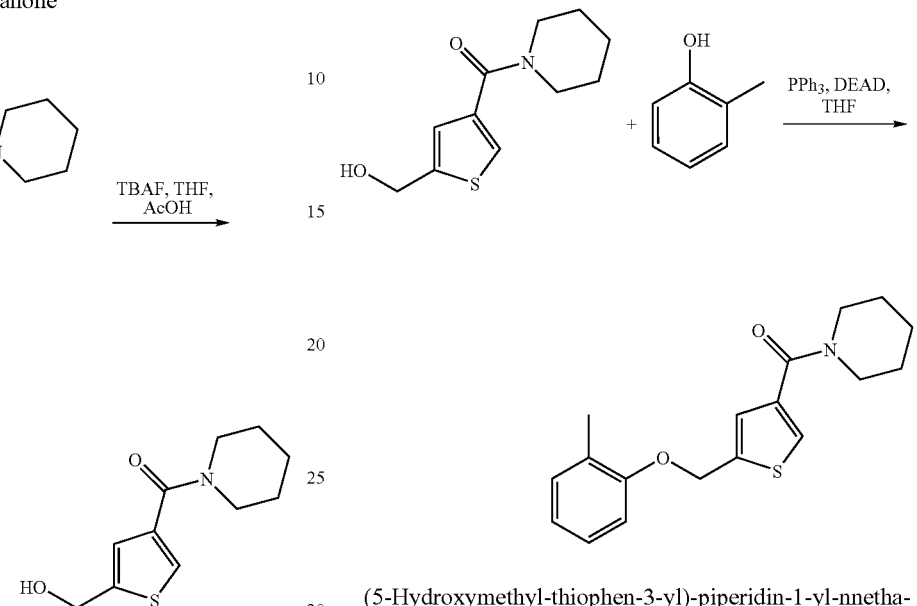

(5-Hydroxymethyl-thiophen-3-yl)-piperidin-1-yl-nnethanone (0.068 g, 0.3 mmol) was dissolved in THF (5 mL). Triphenylphosphine (0.3 mmol), diethylazodicarboxylate (0.3 mmol) and 2-methyl-phenol (0.3 mmol) were added and the reaction stirred overnight. The reaction was quenched with saturated aqueous ammonium chloride and the solvent was reduced under vacuum. The residue was partitioned between DCM and water and the organic solution separated, dried over magnesium sulphate, filtered and the solvent evaporated. The product was purified by HPLC, eluting with acetonitrile in water (0.1% formic acid). The fractions containing the desired product were concentrated under vacuum to give the title compound (20 mg). LCMS m/z 316.20 [M+H]+RT=11.75 min (Analytical Method 1). $^1$H NMR (400 MHz, CHCl$_3$-d): δ 7.45 (s, 1H), 7.2-7.1 (m, 3H), 6.9 (m, 2H), 5.2 (s, 2H), 3.6 (m, 4H), 2.25 (s, 3H), 1.7-1.6 (m, 6H).

The compounds in the following table were prepared using analogous methods:

| Code No. | Structure | $^1$H NMR | Analytical Method | R.T. (min) | MS [m/z] |
|---|---|---|---|---|---|
| BB-001 | | 7.45 (s, 1H), 7.3-7.25 (m, 2H), 7.15 (s, 1H), 7.0-6.9 (m, 3H), 5.2 (s, 2H), 3.6 (m, 4H), 1.7-1.60 (m, 6H) | 1 | 10.78 | [M + H]+ 302.15 | under vacuum to give the title compound (0.24 g). LCMS m/z 340 [M+H]+ RT=4.46 min (Analytical Method 4).

| Code No. | Structure | ¹H NMR | Analytical Method | R.T. (min) | MS [m/z] |
|---|---|---|---|---|---|
| BB-004 | 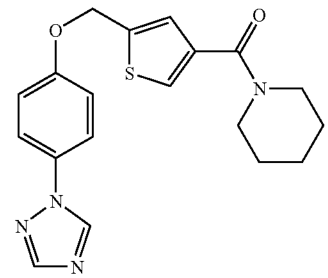 [SMILES: O=C(c1csc(COc2ccc(-n3cncn3)cc2)c1)N1CCCCC1] | 8.45 (s, 1H), 8.1 (s, 1H), 7.6 (m, 2H), 7.5 (s, 1H), 7.2 (s, 1H), 7.1-7.05 (m, 2H), 5.3 (s, 2H), 3.6 (m, 4H), 1.7-1.55 (m, 6H) | 1 | 8.90 | [M + H]⁺ 369.23 |
| BB-003 | 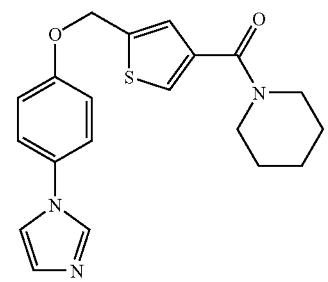 [SMILES: O=C(c1csc(COc2ccc(-n3ccnc3)cc2)c1)N1CCCCC1] | 7.8 (s, 1H), 7.5 (s, 1H), 7.35-7.3 (m, 2H), 7.2 (m, 3H), 7.1-7.05 (m, 2H), 5.5 (s, 2H), 3.6 (m, 4H), 1.7-1.6 (m, 6H) | 1 | 6.17 | [M + H]⁺ 368.24 |

Synthesis 51

2-Amino-5-(cyclohexyl)-thiophene-3-carboxylic acid ethyl ester

Synthesis 52

5-(Cyclohexyl)-thiophene-3-carboxylic acid ethyl ester

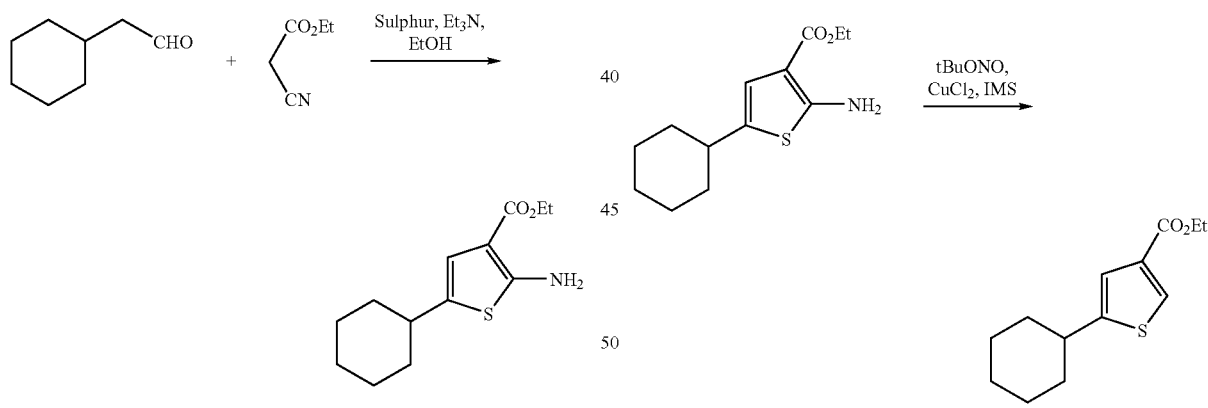

Cyclohexyl-acetaldehyde (0.98 g, 7.8 mmol), ethyl cyanoacetate (8.5 mmol) and sulphur (8.5 mmol) were dissolved in ethanol (10 mL). Triethylamine (11.83 mmol) was added and the reaction heated to 65° C. for 1 hour. The reaction was cooled to room temperature and the solvent removed under vacuum. The residue was purified by column chromatography on silica, eluting with 0%-40% ethyl acetate in cyclohexane. The fractions containing the desired product were concentrated under vacuum to give the title compound as a pale yellow oil (1.78 g). LCMS m/z 254.08 [M+H]⁺ RT=4.37 min (Analytical Method 4).

2-Amino-5-(cyclohexyl)-thiophene-3-carboxylic acid ethyl ester (1.79 g, 7 mmol) was added to a mixture of t-butyl nitrite (10.5 mmol) and copper (II) chloride (7 mmol) in IMS (100 mL). The reaction mixture was stirred for 30 minutes then saturated aqueous ammonium chloride (7 mL) was added and the resulting solution stirred overnight. The solvent was then evaporated under vacuum and the residue partitioned between ethyl acetate and water. The organic solution was separated and dried with magnesium sulphate, filtered and the solvent evaporated to give the title compound as an orange oil (1.28 g). ¹H NMR δ (ppm) (CHCl₃-d): 7.9 (s, 1H), 7.2 (s, 1H), 4.3 (q, 2H), 2.8 (m, 1H), 2.1 (m, 2H), 1.9 (m, 2H), 1.7-1.2 (m, 9H).

Synthesis 53

5-(Cyclohexyl)-thiophene-3-carboxylic acid

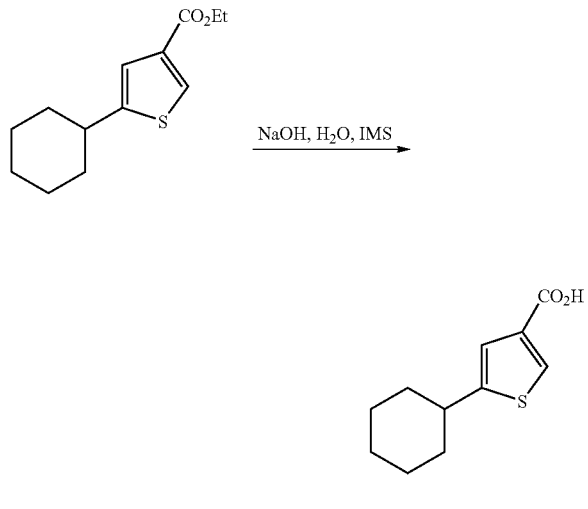

Sodium hydroxide (1 N, 2.5 mL) was added to 5-(cyclohexyl)-thiophene-3-carboxylic acid ethyl ester (0.485 g) in IMS (3 mL). The reaction was irradiated in a microwave at 140° C. for 10 minutes. Water was added (5 mL) and the mixture washed with DCM. The aqueous layer was acidified to pH 1 and extracted with DCM. The organic solution was dried over magnesium sulphate, filtered and the solvent removed to give the title compound (460 mg, 86%). Recrystallisation from IMS/water gave a red solid (0.2 g). LCMS m/z 210.99 [M+H]$^+$ RT=3.75 min (Analytical Method 4).

Synthesis 54

Azepan-1-yl-(5-cyclohexyl-thiophen-3-yl)-methanone (DD-002)

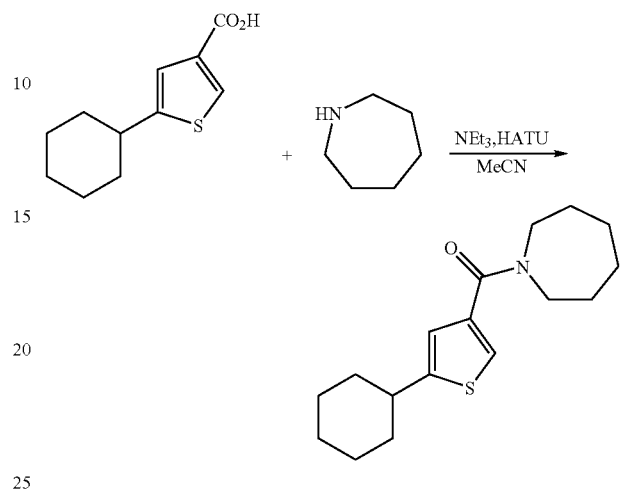

5-(Cyclohexyl)-thiophene-3-carboxylic acid (0.03 g, 0.14 mmol) was dissolved in acetonitrile (2 mL). Triethylamine (0.42 mmol), HATU (0.15 mmol) and azepane (0.14 mmol) were added and the reaction stirred at room temperature overnight. The resulting solution was purified directly by HPLC, eluting with 10%-98% acetonitrile in water (0.1% formic acid) over 30 minutes. The fractions containing the desired product were concentrated under vacuum to give the title compound (0.022 g). LCMS m/z 292.22 [M+H]$^+$ RT=13.57 min (Analytical Method 1). $^1$H NMR δ (ppm) (CHCl$_3$-d): 7.2 (s, 1H), 6.95 (s, 1H), 3.7-3.4 (m, 4H), 2.8 (m, 1H), 2.1 (m, 2H), 1.9-1.2 (m, 16H).

The compounds in the following table were prepared using analogous methods:

| Code No. | Structure | $^1$H NMR | Analytical Method | R.T. (min) | MS [m/z] |
|---|---|---|---|---|---|
| DD-001 | cyclohexyl-thiophene with 3,3-dimethylpiperidine amide | 7.2 (s, 1H), 6.8 (s, 1H), 3.7-3.1 (m, 4H), 2.8 (m, 1H), 2.1 (m, 2H), 1.8 (m, 2H), 1.7 (m, 1H), 1.6, (m, 2H), 1.5-1.2 (m, 7H), 0.9 (m, 6H) | 1 | 14.32 | [M + H]$^+$ 306.18 |
| DD-003 | cyclohexyl-thiophene with decahydroquinoline amide (CIS ISOMERS) | 7.2 (s, 1H), 6.9 (s, 1H), 4.8-4.5 (m, 1H), 3.9-3.7 (m, 1H), 3.1 (m, 1H), 2.8 (m, 2H), 2.1-1.1 (m, 22H) | 2 | 14.78 | [M + H]$^+$ 332.23 |

| Code No. | Structure | ¹H NMR | Analytical Method | R.T. (min) | MS [m/z] |
|---|---|---|---|---|---|
| DD-004 | TRANS ISOMERS | 7.2 (s, 1H), 6.9 (s, 1H), 3.7 (m, 1H), 3.5 (m, 1H), 3.4 (m, 1H), 2.8 (m, 1H), 2.3 (m, 1H), 2.1 (m, 2H), 1.8-1.0 (m, 20H) | 2 | 15.32 | [M + H]⁺ 332.17 |
| DD-005 | 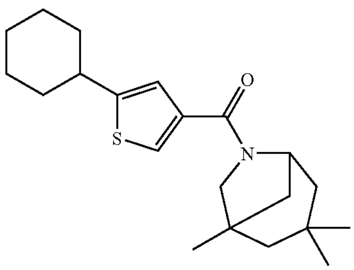 [SMILES: CC1(C)CC2CC(C)(CN2C(=O)c2csc(C3CCCCC3)c2)C1] | | 2 | 14.78 | [M + H]⁺ 346.20 |
| DD-006 | 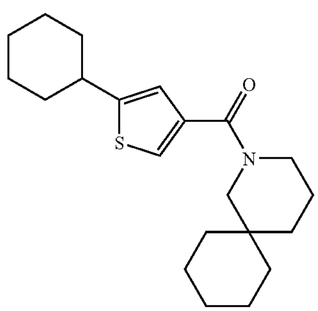 [SMILES: O=C(c1csc(C2CCCCC2)c1)N1CCCC2(CCCCC2)C1] | 7.2 (s, 1H), 6.9 (s, 1H), 3.7-3.2 (m, 4H), 2.8 (m, 1H), 2.1 (m, 2H), 1.8 (m, 2H), 1.7-1.1 (m, 20H) | 2 | 15.38 | [M + H]⁺ 346.22 |

Synthesis 55

3-(5-Amino-4-ethoxycarbonyl-thiophen-2-yl)-piperidine-1-carboxylic acid tert-butyl ester

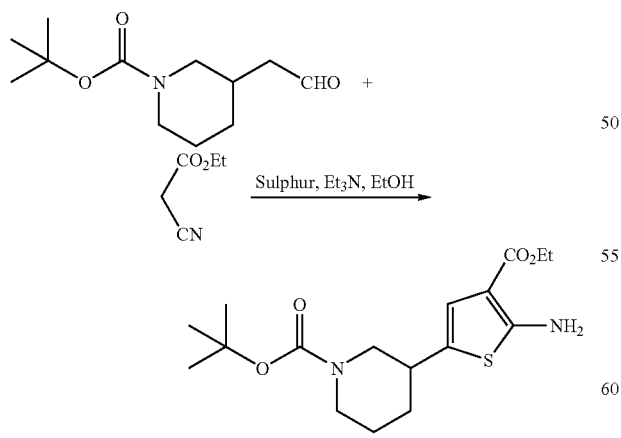

3-(2-Oxo-ethyl)-piperidine-1-carboxylic acid tert-butyl ester (1.0 g, 4.4 mmol), ethyl cyanoacetate (4.8 mmol) and sulphur (4.8 mmol) were dissolved in ethanol (5 mL). Triethylamine (6.5 mmol) was added and the reaction heated to 70° C. for 2 hours. The reaction was cooled to room temperature and the solvent removed under vacuum. The residue was purified by column chromatography on silica, eluting with 0%-40% ethyl acetate in cyclohexane. The fractions containing the desired product were concentrated under vacuum to give the title compound as a pale yellow solid (1.5 g). LCMS m/z 355.26 [M+H]⁺ RT=4.04 min (Analytical Method 4).

Synthesis 56

3-(4-Carboxy-thiophen-2-yl)-piperidine-1-carboxylic acid tert-butyl ester

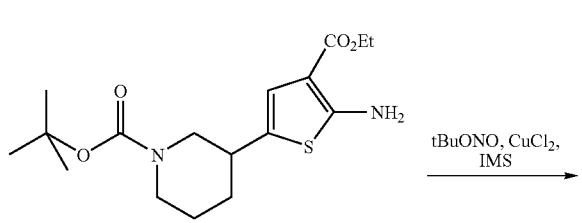

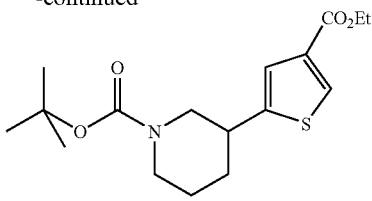

3-(5-Amino-4-ethoxycarbonyl-thiophen-2-yl)-piperidine-1-carboxylic acid tert-butyl ester (1.45 g, 4.1 mmol) was added to a suspension of t-butyl nitrite (6.1 mmol) and copper (II) chloride (4.1 mmol) in IMS (100 mL). The reaction was stirred for 30 minutes. Saturated aqueous ammonium chloride (7 mL) was added and the mixture stirred overnight. The solvent was removed under vacuum and product partitioned between ethyl acetate and water. The organic layer was dried over magnesium sulphate, filtered and the solvent removed. The residue was purified by column chromatography on silica, eluting with 0%-40% ethyl acetate in cyclohexane. The fractions containing the desired product were concentrated under vacuum to give the title compound as a pale yellow oil (1.08 g). LCMS m/z 362.20 [M+Na]+ RT=4.30 min (Analytical Method 4).

Synthesis 57

3-(4-Carboxy-thiophen-2-yl)-piperidine-1-carboxylic acid tert-butyl ester

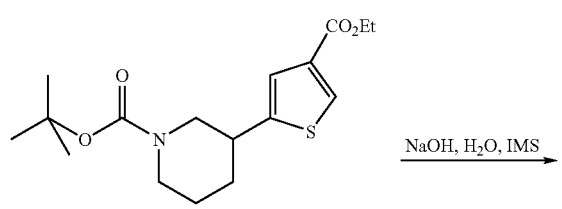

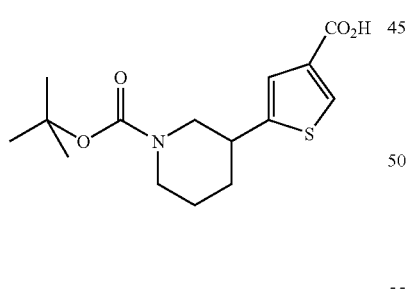

Sodium hydroxide (1 N, 4.5 mL) was added to a 3-(4-carboxy-thiophen-2-yl)-piperidine-1-carboxylic acid tert-butyl ester (1.08 g) in IMS (6 mL). The reaction mixture was irradiated in a microwave at 140° C. for 15 minutes. Water was added (5 mL) and the mixture washed with DCM. The aqueous layer was acidified with saturated aqueous citric acid and extracted with DCM. The organic solution was dried over magnesium sulphate, filtered and the solvent removed to give the title compound (0.77 g). LCMS m/z 312.18 [M+H]+ RT=3.52 min (Analytical Method 4).

Synthesis 58

3-[4-(Azepane-1-carbonyl)-thiopen-2-yl]-piperidine-1-carboxylic acid tert-butyl ester

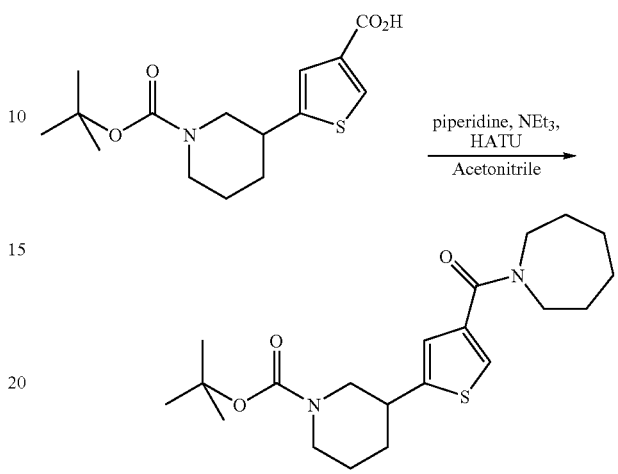

3-(4-Carboxy-thiophen-2-yl)-piperidine-1-carboxylic acid tert-butyl ester (0.075 g, 0.24 mmol) was dissolved in DMF (2 mL). Triethylamine (0.72 mmol), HATU (0.26 mmol) and homopiperidine (0.26 mmol) were added and the reaction stirred at room temperature overnight. The reaction mixture was purified directly by HPLC, eluting with 10%-98% acetonitrile in water (0.1% formic acid) over 30 minutes. The fractions containing the desired product were concentrated under vacuum to give the title compound (0.066 g). LCMS m/z 393.26 [M+H]+ RT=4.05 min (Analytical Method 4).

Synthesis 59

Azepan-1-yl-(5-piperidin-3-yl-thiophen-3-yl)-methanone (CC-015)

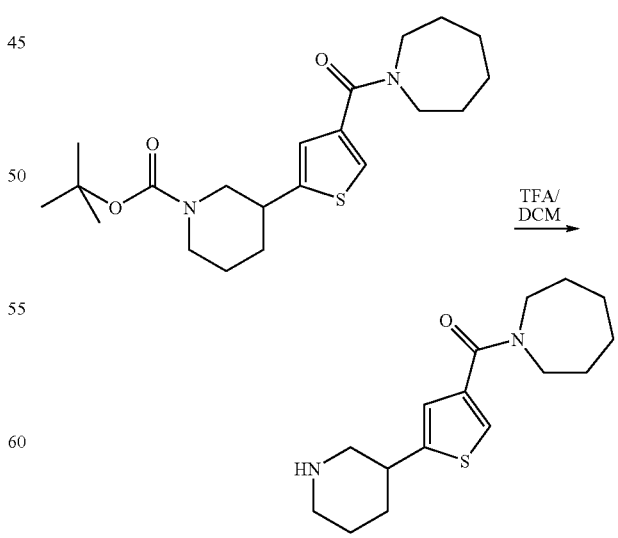

3-[4-(Azepane-1-carbonyl)-thiophen-2-yl]-piperidine-1-carboxylic acid tert-butyl ester (0.066 g) was dissolved in TFA/DCM (1:1, 5 mL) and stirred for 1 hour. The solvent was then evaporated and the residue dissolved in DCM and purified using a SCX-2 column. After washing with methanol and acetonitrile, the desired compound was washed from the column with ammonia (2 M in MeOH). Evaporation gave the title compound as a clear colourless oil (0.052 g). LCMS m/z 293.14 [M+H]$^+$ RT=5.27min (Analytical Method 2). $^1$H NMR δ (ppm)(CHCl$_3$-d): 7.3 (s, 1H), 6.9 (s, 1H), 3.8 (m, 2H), 3.5 (m, 2H), 3.3 (d, 1H), 3.1 (d, 1H), 2.9 (m, 1H), 2.7-2.6 (m, 3H), 2.1 (m, 1H), 1.8-1.5 (m, 11H).

The compounds in the following table were prepared using analogous methods:

| Code No. | Structure | $^1$H NMR | Analytical Method | R.T. (min) | MS [m/z] |
|---|---|---|---|---|---|
| CC-073 | 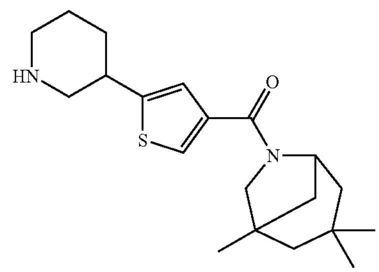 [SMILES: CC1(C)CC2CC(C)(CN2C(=O)c2csc(C3CCCNC3)c2)C1] | | 2 | 6.71 | [M + H]$^+$ 347.21 |
| CC-043 | 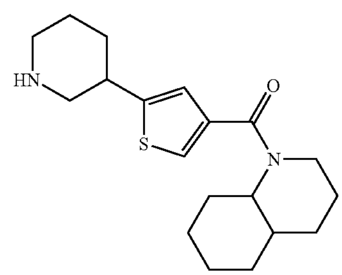 [SMILES: O=C(c1csc(C2CCCNC2)c1)N1CCCC2CCCCC21] | | 2 | 6.55 | [M + H]$^+$ 333.19 |
| CC-080 | 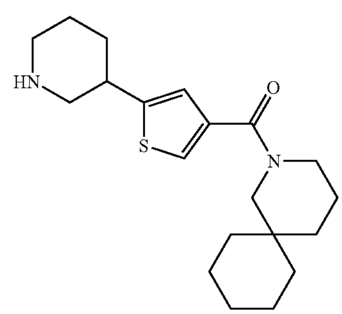 [SMILES: O=C(c1csc(C2CCCNC2)c1)N1CCCC2(CCCCC2)C1] | 7.3 (s, 1H), 6.9 (s, 1H), 3.8-3.2 (m, 3H), 3.1 (d, 1H), 2.9 (m, 1H), 2.6 (m, 2H), 2.3-2.1 (m, 3H), 1.8(m, 1H), 1.6-1.0 (m, 17H). | 2 | 6.78 | [M + H]$^+$ 347.23 |
| CC-014 | 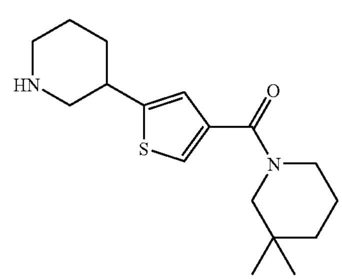 [SMILES: CC1(C)CCCN(C(=O)c2csc(C3CCCNC3)c2)C1] | 7.3 (S, 1H), 6.9 (s, 1H), 3.8-2.9 (m, 7H), 2.7 (m, 2H), 2.3-2.1 (m, 3H), 1.8-1.4 (m, 7H), 0.9 (m, 5H) | 2 | 5.82 | [M + H]$^+$ 307.15 |

Synthesis 60 cis-(5-Bromo-thiophen-3-yl)-(octahydro-quinolin-1-yl)-methanone

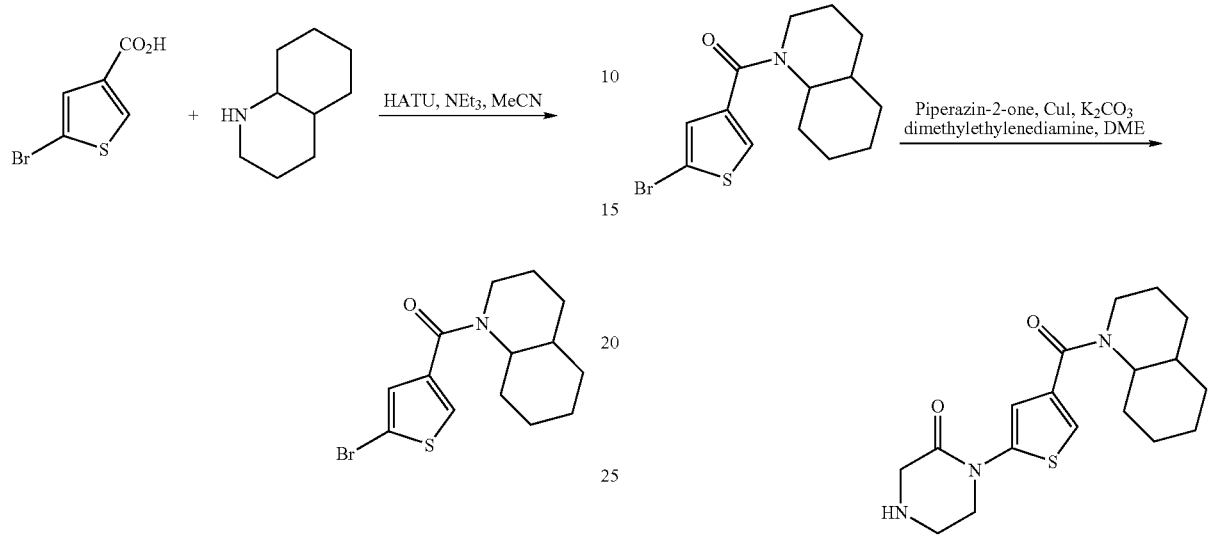

5-Bromothiophene-3-carboxylic acid (0.5 g, 2.4 mmol) was dissolved in acetonitrile (10 mL) and triethylamine (7.1 mmol). Decahydroquinoline (3:2 mixture of cis- and trans-isomers; 4.8 mmol) and HATU (2.4 mmol) were added and the reaction stirred at room temperature overnight. The solvent was evaporated and the residue dissolved in DCM and washed with water. After drying with anhydrous magnesium sulphate, the solution was filtered and evaporated and the residue purified by flash chromatography on silica, eluting with 0-40% ethyl acetate in cyclohexane. The fractions containing the desired product were combined and evaporated to give the title compound as a white crystalline solid (0.39 g). LCMS m/z 330.11 [M+H]$^+$ RT=4.07 min (Analytical Method 4).

Synthesis 61 cis-1-[4-(Octahydro-quinoline-1-carbonyl)-thiophen-2-yl]-piperazin-2-one (CC-048)

cis-(5-Bromo-thiophen-3-yl)-(octahydro-quinolin-1-yl)-methanone (0.05 g, 0.15 mmol) was dissolved in DME (1 mL) and piperazin-2-one (0.3 mmol), potassium carbonate (0.15 mmol), copper (I) iodide (0.003 g) and dimethylethylenediamine (0.0013 g) were added. The mixture was heated to 120° C. for 65 hours. The mixture was diluted with DCM (10 mL) and the organic solution washed with water, then evaporated to give a brown oil. The residue was purified by flash chromatography on silica, eluting with 0-40% methanol in DCM. The fractions containing the desired product were combined and evaporated to give the title compound as a pale brown oil (0.032 g). LCMS m/z 348.05 [M+H]$^+$ RT=6.24 min (Analytical Method 2). $^1$H NMR δ (ppm)(CHCl$_3$-d): 7.0 (s, 1H), 6.7 (s, 1H), 4.6 (m, 1H), 4.0-3.6 (m, 5H), 3.3 (m, 2H), 3.0 (m, 1H), 2.0-1.0 (m, 16H).

The compounds in the following table were prepared using analogous methods:

| Code No. | Structure | $^1$H NMR | Analytical Method | R.T. (min) | MS [m/z] |
|---|---|---|---|---|---|
| CC-050 | (structure shown) | 7.0 (s, 1H), 6.7 (s, 1H), 4.6 (m, 1H), 4.4 (s, 2H), 4.1 (t, 2H), 4.0-3.8 (m, 3H), 3.0 (m, 1H), 2.0-1:2 (m, 13H) | 2 | 9.48 | [M + H]$^+$ 349.04 |

CIS ISOMERS

| Code No. | Structure | $^1$H NMR | Analytical Method | R.T. (min) | MS [m/z] |
|---|---|---|---|---|---|
| CC-049 | 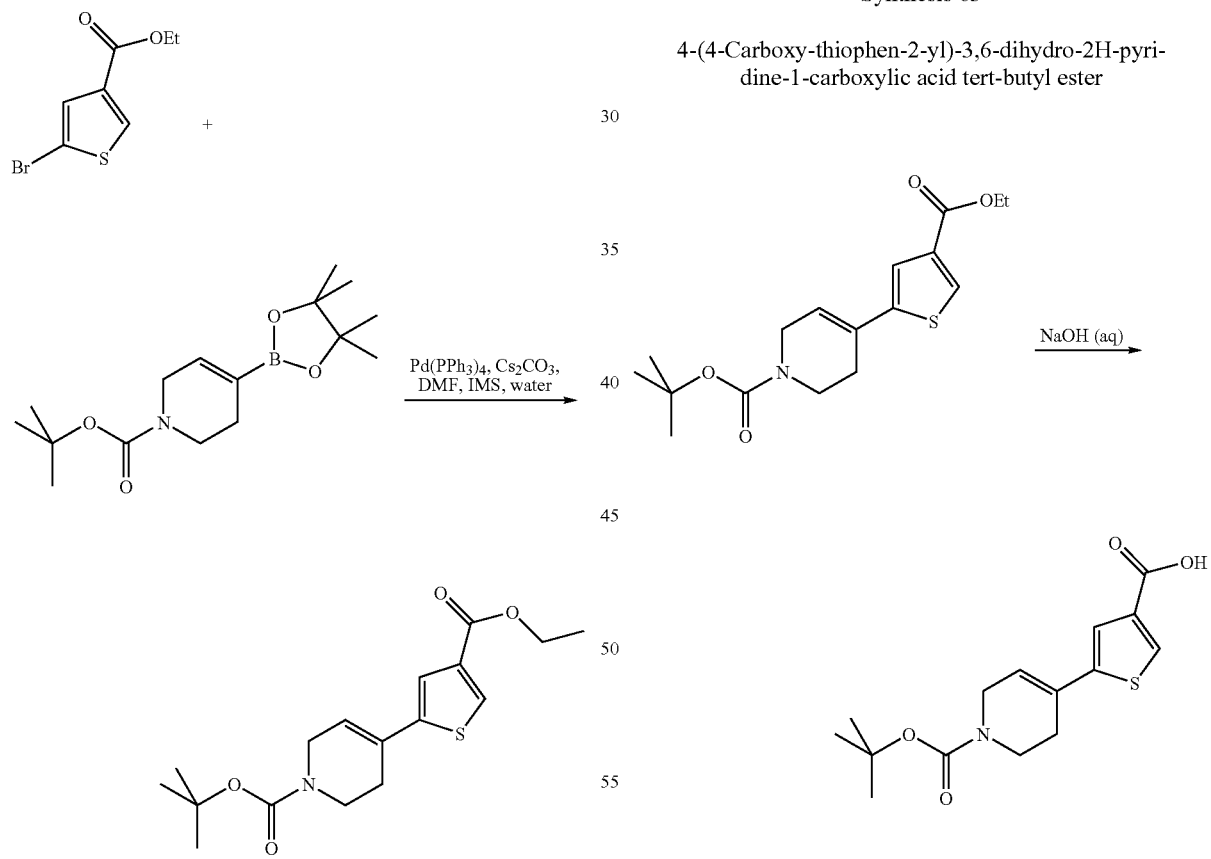 CIS ISOMERS | 6.9 (s, 1H), 6.6 (s, 1H), 4.6 (m, 1H), 3.9 (m, 3H), 3.0 (m, 1H), 2.6 (t, 2H), 2.3 (m, 2H), 2.0-1.2 (m, 14H) | 2 | 9.71 | [M + H]$^+$ 333.10 |

Synthesis 62

4-(4-Ethoxycarbonyl-thiophen-2-yl)-3,6-dihydro-2H-pyridine-1-carboxylic acid tert-butyl ester 2-Bromothiophene-4-carboxylic acid ethyl ester (1.0 g, 5.26 mmol) and 4-(3,3,4,4-tetramethyl-borolan-1-yl)-3,6-dihydro-2H-pyridine-1-carboxylic acid tert-butyl ester (5.26 mmol) were dissolved in DME (40 mL), IMS (20 mL) and water (10 mL). Palladium tetrakis-triphenylphoshine (0.53 mmol) and caesium carbonate (7.9 mmol) were then added and the mixture heated to 120° C. for 20 minutes using microwave radiation. The solvent was then evaporated and the residue purified by flash chromatography on silica, eluting with 0-40% ethyl acetate in cyclohexane. The fractions containing the desired product were combined and evaporated to give the title compound as a clear oil (1.0 g). LCMS m/z 238.06 [M+H]$^+$ RT=4.33min (Analytical Method 4).

Synthesis 63

4-(4-Carboxy-thiophen-2-yl)-3,6-dihydro-2H-pyridine-1-carboxylic acid tert-butyl ester 4-(4-Ethoxycarbonyl-thiophen-2-yl)-3,6-dihydro-2H-pyridine-1-carboxylic acid tert-butyl ester (1.0 g, 3 mmol) was dissolved in IMS (10 mL) and aqueous sodium hydroxide (1 M, 8 mmol) was added and the mixture stirred at 130° C. for 10 minutes. The solution was then cooled, filtered and acidified with 1 N hydrochloric acid to pH 4. The resulting precipitate was isolated by filtration and dried under vacuum to give the title compound as a white solid (0.47 g). LCMS m/z 308.48 [M−H]⁻ RT=3.45 min (Analytical Method 4).

Synthesis 64

4-[4-(Azepane-1-carbonyl)-thiophen-2-yl]-3,6-dihydro-2H-pyridine-1-carboxylic acid tert-butyl ester

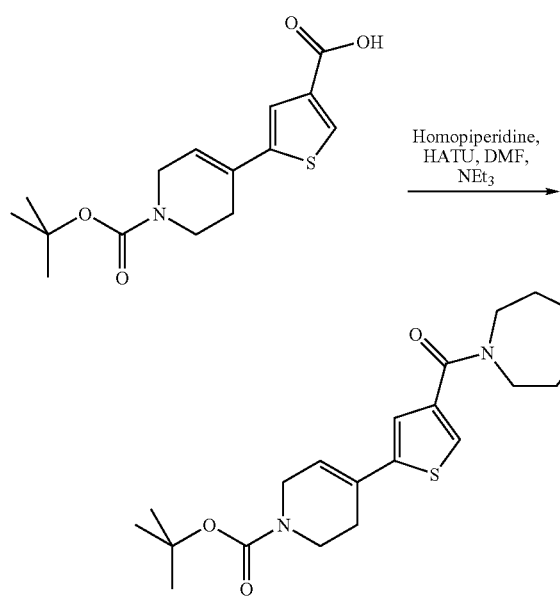

4-(4-Carboxy-thiophen-2-yl)-3,6-dihydro-2H-pyridine-1-carboxylic acid tert-butyl ester (0.1 g, 0.35 mmol) was dissolved in DMF (2 mL) and triethylamine (1.0 mmol). Homopiperidine (1.4 mmol) was added with HATU (0.35 mmol) and the mixture stirred for 2 hours. The mixture was diluted with DCM (20 mL) and washed with water. The organic solution was separated, dried with anhydrous magnesium sulphate, filtered and evaporated. The residue was then purified by HPLC, eluting with 10%-98% acetonitrile in water (0.1% formic acid) over 30 minutes. The fractions containing the desired product were concentrated under vacuum to give the title compound (0.095 g). LCMS m/z 391.56 [M+H]⁺ RT=4.09min (Analytical Method 4).

Synthesis 65

Azepan-1-yl-[5-(1,2,3,6-tetrahydro-pyridin-4-yl)-thiophen-3-yl]-methanone

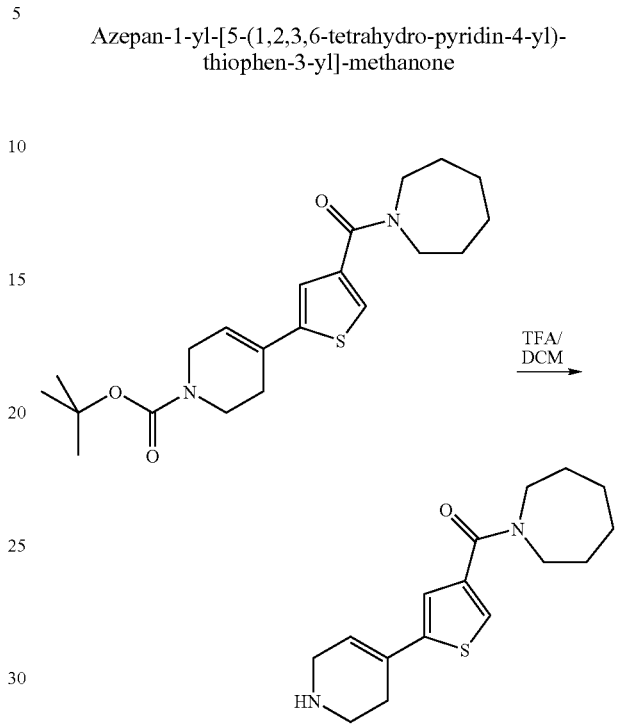

4-[4-(Azepane-1-carbonyl)-thiophen-2-yl]-3,6-dihydro-2H-pyridine-1-carboxylic acid tert-butyl ester (0.094 g) was dissolved in TFA (1 mL) and DCM (1 mL). The mixture was stirred for 1 hour and then the solvent evaporated. The residue was purified using a SCX-2 column. After washing with methanol and acetonitrile, the desired compound was washed from the column with ammonia (2 M in MeOH). Evaporation gave the title compound as a clear colourless oil (0.068 g). LCMS m/z 291.07 [M+H]⁺ RT=5.14 min (Analytical Method 2).

The compounds in the following table were prepared using analogous methods:

| Code No. | Structure | Analytical Method | R.T. (min) | MS [m/z] |
|---|---|---|---|---|
| CC-046 | CIS ISOMERS | 2 | 6.34 | [M + H]⁺ 331.14 |
| CC-047 | TRANS ISOMERS | 2 | 6.45 | [M + H]⁺ 331.13 |

-continued
| Code No. | Structure | Analytical Method | R.T. (min) | MS [m/z] |
|---|---|---|---|---|
| CC-074 | 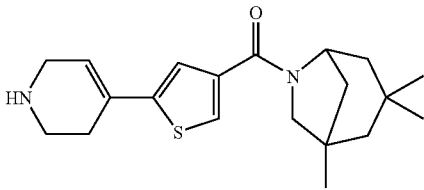 [SMILES: CC1(C)CC2CC(C)(CN2C(=O)c2csc(C3=CCNCC3)c2)C1] | 2 | 6.69 | [M + H]+ 345.14 |
| CC-123 | 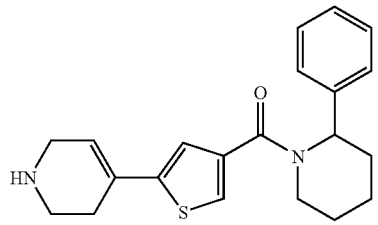 [SMILES: O=C(c1csc(C2=CCNCC2)c1)N1CCCCC1c1ccccc1] | 2 | 6.60 | [M + H]+ 353.24 |
| CC-124 | 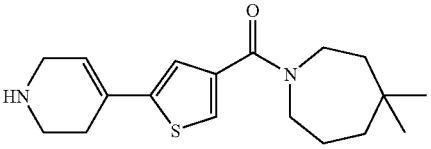 [SMILES: CC1(C)CCCN(C(=O)c2csc(C3=CCNCC3)c2)CC1] | 2 | 6.36 | [M + H]+ 319.26 |
| CC-125 | 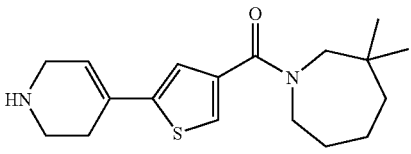 [SMILES: CC1(C)CCCCN(C(=O)c2csc(C3=CCNCC3)c2)C1] | 2 | 9.33 | [M + H]+ 319.25 |
| CC-126 | 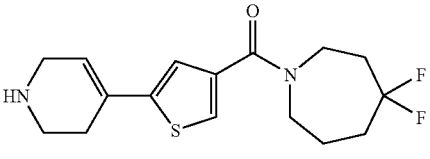 | 2 | 5.30 | [M + H]+ 327.24 |
| CC-176 | 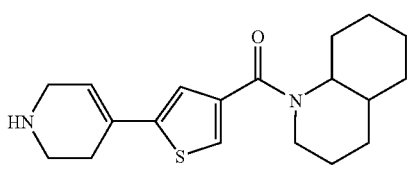 DHQ [CIS-S] | 2 | 6.56 | [M + H]+ 373.17 |

Synthesis 66

1-{4-[4-(Azepane-1-carbonyl)-thiophen-2-yl]-3,6-dihydro-2H-pyridin-1-yl}-ethanone (CC-016)

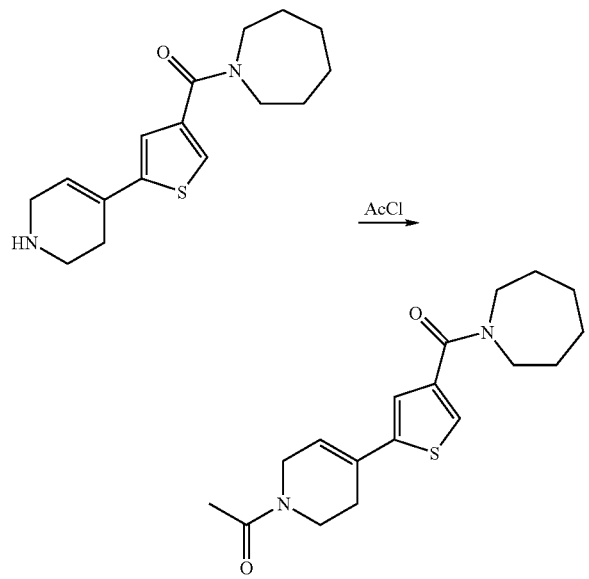

To a solution of azepan-1-yl-[5-(1,2,3,6-tetrahydro-pyridin-4-yl)-thiophen-3-yl]-methanone (0.023 g, 0.08 mmol) in DCM (1 mL) was added triethylamine (0.27 mmol) and acetyl chloride (0.11 mmol). The reaction mixture was stirred for 1 hour, and then the solvent evaporated. The product was purified by HPLC, eluting with 10%-98% acetonitrile in water (0.1% formic acid). The fractions containing the desired product were concentrated under vacuum to give the title compound as a colourless oil (0.009 g). LCMS m/z 333.11 [M+H]$^+$ RT=8.18 min (Analytical Method 2).

The compound in the following table was prepared using analogous methods:

| Code No. | Structure | Analytical Method | R.T. (min) | MS [m/z] |
|---|---|---|---|---|
| CC-086 | 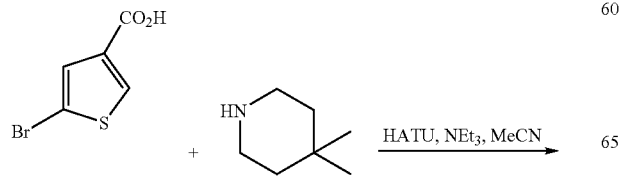 | 2 | 9.85 | [M + H]$^+$ 373.10 |

Synthesis 67

(5-Bromo-thiophen-3-yl)-(3,3-dimethyl-piperidin-1-yl)-methanone

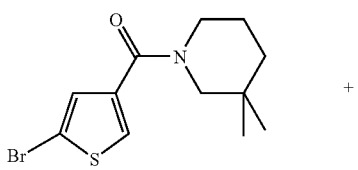

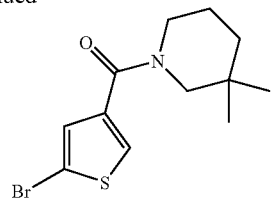

5-Bromothiophene-3-carboxylic acid (0.5 g, 2.4 mmol) was dissolved in acetonitrile (10 mL) and triethylamine (7.1 mmol). 3,3-Dimethylpiperidine (2.4 mmol) and HATU (2.4 mmol) were added and the reaction stirred at room temperature overnight. The solvent was evaporated and the residue dissolved in DCM and washed with water. After drying with anhydrous magnesium sulphate, the solution was filtered and evaporated and the residue purified by flash chromatography on silica, eluting with 0-40% ethyl acetate in cyclohexane. The fractions containing the desired product were combined and evaporated to give the title compound as a white crystalline solid (0.475 g). $^1$H NMR δ (ppm)(CHCl$_3$-d): 7.4 (s, 1H), 7.1 (s, 1H), 3.6-3.1 (m, 4H), 1.7 (m, 2H), 1.4 (m, 2H), 0.9 (s, 6H).

Synthesis 68

(3,3-Dimethyl-piperidin-1-yl)-(5-morpholin-4-yl-thiophen-3-yl)-methanone (CC-010)

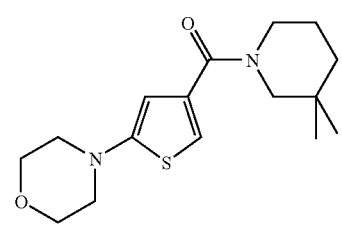

(5-Bromo-thiophen-3-yl)-(3,3-dimethyl-piperidin-1-yl)-Methanone (0.1 g) was dissolved in N,N-dimethylethanol (0.5 mL). Copper (I) iodide (0.003 g), copper powder (0.001 g), morpholine (0.045 mL) and potassium phosphate tribasic (0.001 g) were added. The mixture was heated to 70° C. and stirred overnight then diluted with water (2 mL) and the solvent evaporated. The residue was purified by flash chromatography on silica, eluting with 0-60% ethyl acetate in cyclohexane. The fractions containing the desired product were combined and evaporated to give the title compound as a gum (0.008 g). LCMS m/z 309.15 [M+H]+ RT=9.77 min (Analytical Method 1). $^1$H NMR δ (ppm)(CHCl$_3$-d): 6.7 (s, 1H), 6.2 (s, 1H), 4.8 (m, 4H), 3.6-3.5 (m, 2H), 3.3 (m, 2H), 3.1 (m, 4H), 1.6 (m, 2H), 1.5 (m, 2H), 0.9 (s, 6H).

Synthesis 69 cis-4-[4-(Octahydro-quinoline-1-carbonyl)-thiophen-2-yl]-piperidine-1-carboxylic acid amide (CC-068)

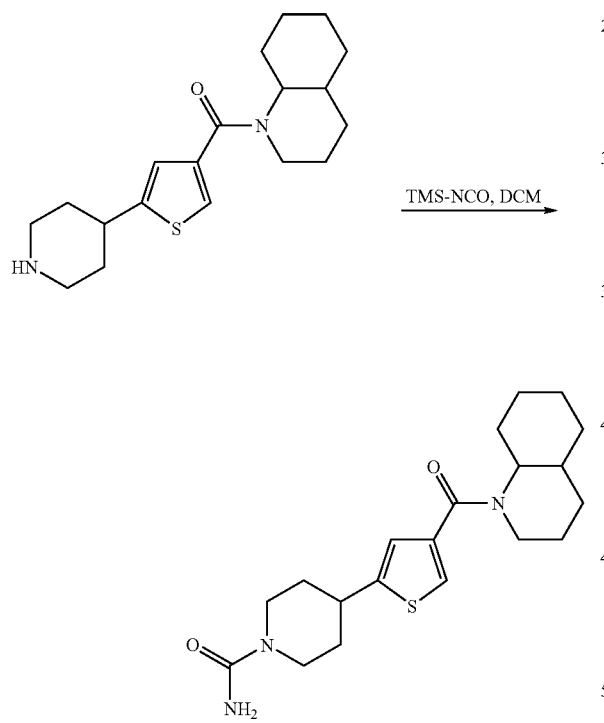

To a solution of cis-(octahydro-quinolin-1-yl)-(5-piperidin-4-yl-thiophen-3-yl)-methanone (CC-033) (0.053 g, 0.16 mmol) in DCM (1 mL) was added trimethylsilylisocyanate (1.6 mmol). The mixture was stirred at room temperature overnight and then more trimethylsilylisocyanate (1.6 mmol) was added and the mixture stirred for a further 5 hours. The solution was diluted with DCM (10 mL) and washed with water. The resulting organic solution was dried and the solvent evaporated. The resulting oil was purified by HPLC, eluting with 10%-98% acetonitrile in water (0.1% formic acid). The fractions containing the desired product were concentrated under vacuum to give the title compound as a colourless oil (0.014 g). LCMS m/z 376.12 [M+H]+ RT=8.89 min (Analytical Method 2). $^1$H NMR (400 MHz, CHCl$_3$-d): δ 7.25 (s, 1H), 6.9 (s, 1H), 4.7 (s, 2H), 4.6 (m, 1H), 4.1 (m, 2H), 3.8 (m, 1H), 3.2-2.7 (m, 4H), 2.1-1.05 (m, 17H).

Synthesis 70

4-[4-(1,3,3-Trimethyl-6-aza-bicyclo[3.2.1]octane-6-carbonyl)-thiophen-2-yl]-piperidine-1 carboxylic acid tert-butyl ester

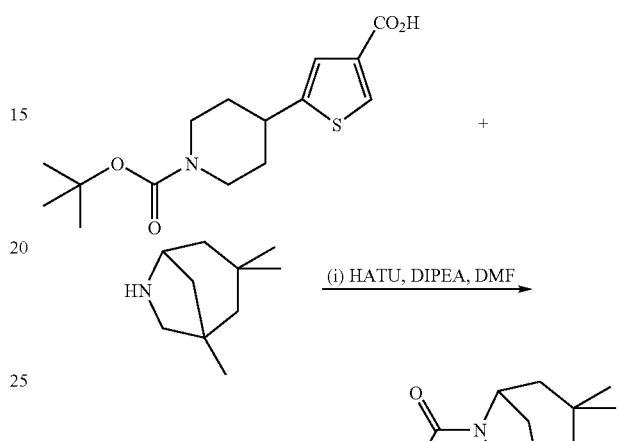

4-(4-Carboxy-thiophen-2-yl)-piperidine-1-carboxylic acid t-butyl ester (0.1 g, 0.32 mmol) was dissolved in acetonitrile (2 mL). Triethylamine (0.96 mmol), 1,3,3-trimethyl-6-aza-bicyclo[3.2.1]octane (0.35 mmol) and HATU (0.35 mmol) were added and the reaction stirred at room temperature for 18 hours. The solvent was evaporated and the residue was purified by flash chromatography, eluting with 0-50% ethyl acetate in cyclohexane. The fractions containing the desired product were concentrated under vacuum to give the title compound (0.132 g). $^1$H NMR (400 MHz, CHCl$_3$-d; 80° C.); □ 7.6 (s, 1H), 7.0 (s, 1H), 4.3 (m, 1H), 4.0 (m, 2H), 3.4 (m, 1H), 3.2 (m, 1H), 3.0 (m, 1H), 2.9 (m, 1.9 (m, 2H), 1.7 (m, 1H), 1.6-0.9 (m, 26H).

Synthesis 71

Enantiomers of 4-[4-(1,3,3-trimethyl-6-aza-bicyclo [3.2.1]octane-6-carbonyl)-thiophen-2-yl]-piperidine-1 carboxylic acid tert-butyl ester The diastereomeric mixture of 4-[4-(1,3,3-trimethyl-6-aza-bicyclo[3.2.1]octane-6-carbonyl)-thiophen-2-yl]-piperidine-1 carboxylic acid tert-butyl ester (0.13 g) was separated by chiral HPLC using a ChiralPak IA column with a mobile phase of ethanol/heptane (14:86). Two fractions were obtained and the solvent was evaporated to give:
4-[4-(1,3,3-Trimethyl-6-aza-bicyclo[3.2.1]octane-6-carbonyl)-thiophen-2-yl]-piperidine-1 carboxylic acid t-butyl ester [Enantiomer E]: 0.064 g; RT=13.52 min; >98% e.e (Analytical Method 5; mobile phase: ethanol/heptane (14:86).

4-[4-(1,3,3-Trimethyl-6-aza-bicyclo[3.2.1]octane-6-carbonyl)-thiophen-2-yl]-piperidine-1 carboxylic acid t-butyl ester [Enantiomer F]: 0.05 g; RT=16.94 min; >92% e.e (Analytical Method 5; mobile phase: ethanol/heptane (14:86).

Synthesis 72

(5-Piperidin-4-yl-thiophen-3-yl)-(1,3,3-trimethyl-6-aza-bicyclo[3.2.1]oct-6-yl)-methanone [Enantiomer G] (CC-075)

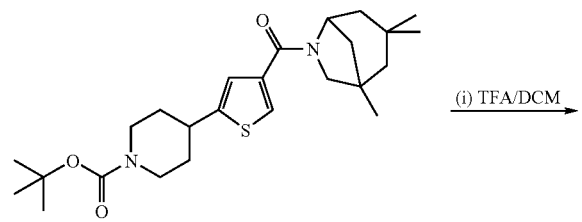

4-[4-(1,3,3-Trimethyl-6-aza-bicyclo[3.2.1]octane-6-carbonyl)-thiophen-2-yl]-piperidine-1 carboxylic acid tert-butyl ester [Enantiomer E] (0.06 g) was dissolved in DCM (2 mL) and TFA (1 mL) and the reaction stirred at room temperature for 2 hours. The solvent was evaporated and the residue product was purified by flash chromatography on a SCX-2 cartridge, washing with acetonitrile and then eluting with 2 M ammonia in methanol. The fractions containing the desired product were concentrated under vacuum to give the title compound (0.038 g). LCMS m/z 347.17 [M+H]⁺ RT=6.63 min (Analytical Method 2).

(5-Piperidin-4-yl-thiophen-3-yl)-(1,3,3-trimethyl-6-aza-bicyclo[3.2.1]oct-6-yl)-methanone [Enantiomer H] (CC-076) was similarly prepared from 4-[4-(1,3,3-trimethyl-6-azabicyclo[3.2.1]octane-6-carbonyl)-thiophen-2-yl]-piperidine-1 carboxylic acid tert-butyl ester [Enantiomer F].

Synthesis 73 cis-Cyano-[4-(octahydro-quinoline-1-carbonyl)-thiophen-2-yl]-acetic acid ethyl ester DHQ [CIS-M]

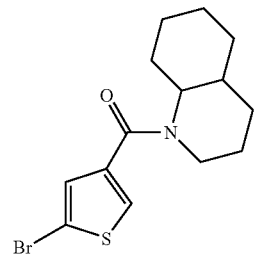

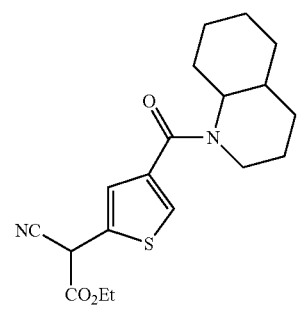

Sodium hydride (60% dispersion in mineral oil; 400 mg) was added to a solution of ethylcyanoacetate (0.450 g) in THF (10 mL) and the mixture stirred for 10 minutes. A solution of (5-bromo-thiophen-3-yl)-(octahydro-quinolin-1-yl)-methanone (0.326 g) and PdCl₂(PPh₃)₂ (0.035 g) in THF (2 mL) was then added dropwise and the mixture heated to 60° C. overnight. The solvent was evaporated and the residue purified by flash chromatography on silica, washing with cyclohexane and ethyl acetate. The fractions containing the desired product were concentrated under vacuum to give the title

| Code No. | Structure | ¹H NMR | Analytical Method | R.T. (min) | MS [m/z] |
|---|---|---|---|---|---|
| CC-076 | 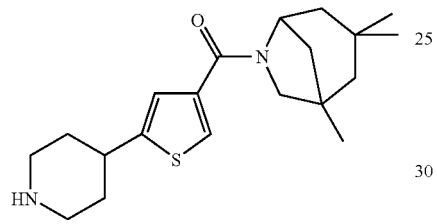<br>ENANTIOMER H | | 2 | 6.58 | [M + H]⁺ 347.16 |

Synthesis 74 cis-[4-(Octahydro-quinoline-1-carbonyl)-thiophen-2-yl]-acetonitrile (AA-022) DHQ [CIS-M]

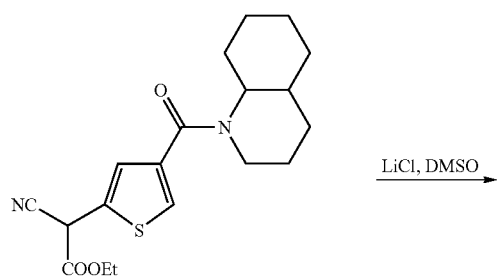

cis-Cyano-[4-(octahydro-quinoline-1-carbonyl)-thiophen-2-yl]-acetic acid ethyl ester (0.168 g, 0.46 mmol) and lithium chloride (0.5 mmol) were dissolved in DMSO (5 mL) and heated to 160° C. by microwave irradiation for one minute. The solution was diluted with DCM (10 mL) and washed with water. The resulting organic solution was dried and the solvent evaporated to give an oil which was purified by HPLC, eluting with 10%-98% acetonitrile in water (0.1% formic acid). The fractions containing the desired product were concentrated under vacuum to give the title compound as a colourless oil (0.025 g). LCMS m/z 289.25 [M+H]$^+$ RT=10.02 min (Analytical Method 2).

Synthesis 75 cis-4-[4-(Octahydro-quinoline-1-carbonyl)-thiophen-2-yl]-tetrahydro-pyran-4-carbonitrile (CC-127) DHQ [CIS-M]

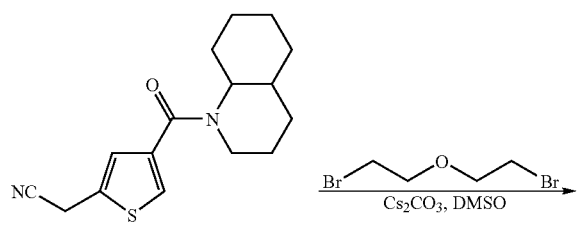

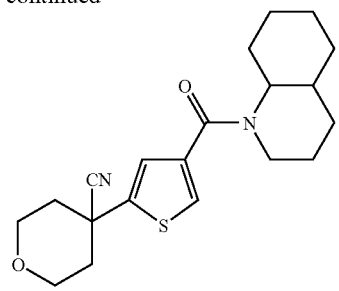

cis-[4-(Octahydro-quinoline-1-carbonyl)-thiophen-2-yl]-acetonitrile (0.049 g, 0.17 mmol) and 1-bromo-2-(2-bromo-ethoxy)-ethane (0.04 g, 0.17 mmol) and caesium carbonate (1.0 mmol) in DMSO (2 mL) was stirred for 12 hr at room temperature. The mixture was diluted with water (5 mL) and DCM (5 mL). The organic layer was filtered and then evaporated to give an oil which was purified by HPLC eluting with 10%-98% acetonitrile in water (0.1% formic acid). The fractions containing the desired product were concentrated under vacuum to give the title compound as a colourless oil (0.02 g). LCMS m/z 359.24 [M+H]$^+$ RT=10.70 min (Analytical Method 2).

Synthesis 76 cis-(Octahydro-quinolin-1-yl)-[5-(1-pyrimidin-2-yl-piperidin-4-yl)-thiophen-3-yl]-methanone (CC-121) DHQ [CIS-M]

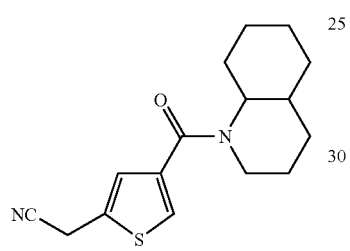

cis-(Octahydro-quinolin-1-yl)-(5-piperidin-4-yl-thiophen-3-yl)-methanone (0.054 g, 0.16 mmol) was dissolved DMSO (1 mL) and cesium carbonate (0.5 mmol) was added followed by 2-chloropyrimidine (0.18 mmol). The reaction was heated to 180° C. by microwave irradiation for 45 minutes. The reaction mixture was diluted with MeCN (1 mL) and the mixture was filtered to remove any insoluble material. The filtrate was diluted with water and the mixture separated by HPLC, eluting with 10%-98% acetonitrile in water (0.1% formic acid). The fractions containing the desired product were concentrated under vacuum to give the title compound as a pale yellow oil (0.015 g). LCMS m/z 411.25 [M+H]$^+$ RT=12.36 min (Analytical Method 2).

The compound in the following table was prepared using analogous methods:

| Code No. | Structure | Analytical Method | R.T. (min) | MS [m/z] |
|---|---|---|---|---|
| CC-120 | 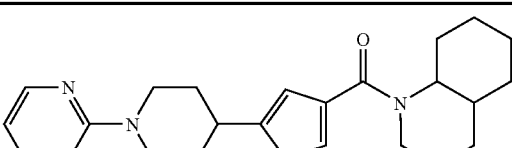 DHQ [CIS-M] | 2 | 7.47 | [M + H]+ 410.27 |
| CC-129 | 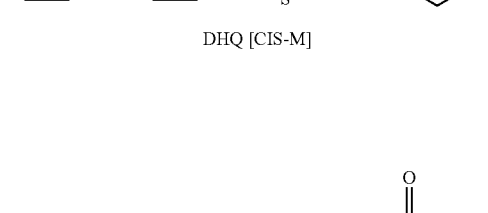 DHQ [CIS-M] | 2 | 13.07 | [M + H]+ 450.30 |

Synthesis 77 cis-1-(1-Methyl-1H-pyrazol-4-ylmethyl)-4-[4-(octahydro-quinoline-1-carbonyl)-thiophen-2-yl]-piperidinium formate (CC-152) DHQ [CIS-M]

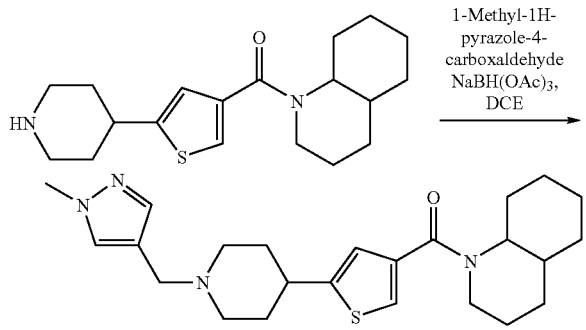

cis-(Octahydro-quinolin-1-yl)-(5-piperidin-4-yl-thiophen-3-yl)-methanone (CC-033) (0.072 g, 0.21 mmol) and 1-methyl-1H-pyrazole-4-carboxaldehyde (0.33 mmol) were dissolved in DCE (3 mL). Sodium triacetoxyborohydride (0.33 mmol) was added and the mixture stirred for 6 hours. A second portion of sodium triacetoxyborohydride was added and the mixture stirred for 72 hours. DCM (25 mL) was added and the organic solution was washed with saturated sodium carbonate solution then brine, and then dried with anhydrous magnesium sulphate. The solvent was removed under vacuum and the resulting gum purified by HPLC eluting with 10%-98% acetonitrile in water (0.1% formic acid). The fractions containing the desired product were concentrated under vacuum to give the title compound (0.047 g). LCMS m/z 427.31 [M+H]+ RT=6.70 min (Analytical Method 2).

The compound in the following table was prepared using analogous methods:

| Code No. | Structure | Analytical Method | R.T. (min) | MS [m/z] |
|---|---|---|---|---|
| CC-154 |  FORMATE SALT DHQ [CIS-M] | 2 | 6.44 | [M + H]+ 427.31 |

Synthesis 78 cis-{1-(3-{4-[4-(Octahydro-quinoline-1-carbonyl)-thiophen-2-yl]-piperidin-1-yl}-propyl)-pyrrolidin-2-one (CC-156) DHQ [CIS-M]

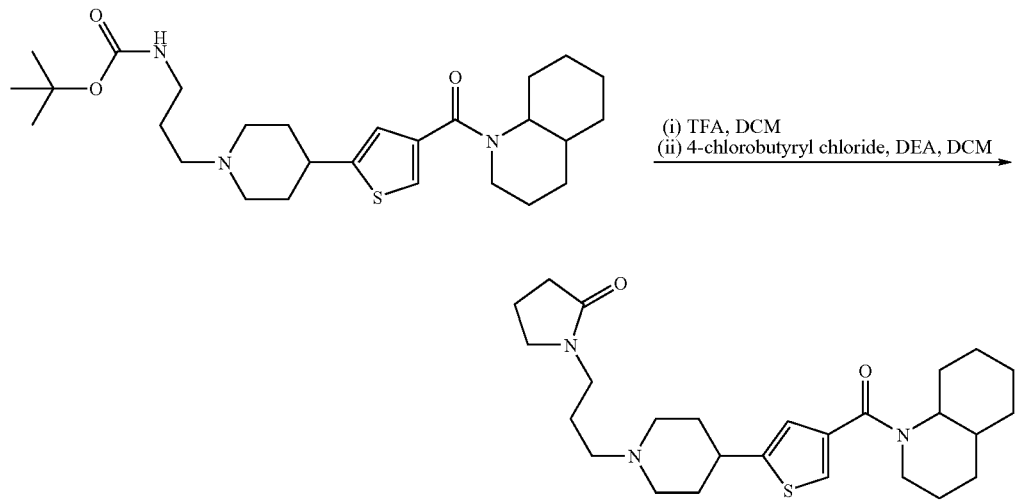 [SMILES: CC(C)(C)OC(=O)NCCCN1CCC(c2cc(C(=O)N3CCCC4CCCCC43)cs2)CC1 ; O=C1CCCN1CCCN1CCC(c2cc(C(=O)N3CCCC4CCCCC43)cs2)CC1]

cis-(3-{4-[4-(Octahydro-quinoline-1-carbonyl)-thiophen-2-yl]-piperidin-1-yl}-propyl)-carbamic acid t-butyl ester was prepared using a similar synthetic route to that described in Synthesis 31A and then dissolved in TFA/DCM (1:1, 2 mL). After 30 minutes the solvent was evaporated to give a brown gum. The solid was dissolved in DCM (3 mL) and TEA (0.5 mmol) and the resulting mixture cooled in an ice bath. 4-Chlorobutyryl chloride (0.11 mmol) in DCM (1 mL) was then added and the mixture allowed to warm to room temperature. After 1 hour the mixture was diluted with DCM (30 mL) and washed with saturated aqueous sodium hydrogen carbonate and then brine. After drying with magnesium sulphate the mixture was filtered and the solvent evaporated to give a brown gum. The gum was dissolved in dry THF and sodium hydride (60% disp. in mineral oil; 0.012 g) was added and the mixture refluxed under argon. The solvent was evaporated and the solid dissolved in DCM. The organic solution was washed with saturated aqueous sodium hydrogen carbonate and then brine. After drying with magnesium sulphate, the mixture was filtered and the solvent evaporated and the resulting gum purified by HPLC eluting with 10%-98% acetonitrile in water (0.1% formic acid). The fractions containing the desired product were concentrated under vacuum to give the title compound (0.029 g). LCMS m/z 458.3 [M+H]+ RT=6.77 min (Analytical Method 2).

Synthesis 79 cis-4-[4-(Octahydro-quinoline-1-carbonyl)-thiophen-2-yl]-piperidine-1-carboxylic acid(2-hydroxy-ethyl)-amide (CC-157) DHQ [CIS-M]

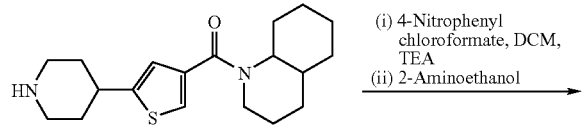

(i) 4-Nitrophenyl chloroformate, DCM, TEA
(ii) 2-Aminoethanol

-continued cis-(octahydro-quinolin-1-yl)-(5-piperidin-4-yl-thiophen-3-yl)-methanone (CC-033) (0.095 g, 0.28 mmol) and 4-nitrophenyl chloroformate (0.29 mmol) were dissolved in DCM (4 mL) and TEA (0.3 mmol) and the resulting mixture stirred overnight. The mixture was diluted with DCM (25 mL) and washed with aqueous citric acid (10% w/v) and saturated aqueous sodium hydrogen carbonate and then brine. After drying with magnesium sulphate, the mixture was filtered and the solvent evaporated to give a clear gum. DCM (3 mL) was added together with 2-aminoethanol (0.26 mmol). The mixture was refluxed overnight and then diluted with DCM (10 mL) and washed with aqueous citric acid (10% w/v) and 2M aqueous sodium carbonate and then brine. After drying with magnesium sulphate, the mixture was filtered and the solvent evaporated to give a yellow gum which was purified by HPLC eluting with 10%-98% acetonitrile in water (0.1% formic acid). The fractions containing the desired product were concentrated under vacuum to give the title compound (0.055 g). LCMS m/z 420.30 [M+H]+ RT=8.68 min (Analytical Method 2).

The compounds in the following table were prepared using analogous methods but starting from cis-(octahydro-quinolin-1-yl)-(5-piperidin-4-yl-thiophen-3-yl)-methanone (CC-155).

| Code No. | Structure | Analytical Method | R.T. (min) | MS [m/z] |
|---|---|---|---|---|
| CC-161 | DHQ [CIS-R] | 2 | 8.89 | [M + H]+ 434.17 |
| CC-163 | DHQ [CIS-R] | 2 | 6.95 | [M + H]+ 447.20 |
| CC-164 | DHQ [CIS-R] | 2 | 9.58 | [M + H]+ 434.20 |
| CC-166 | DHQ [CIS-R] | 2 | 7.35 | [M + H]+ 467.16 |

The compounds in the following table were prepared using analogous methods but starting from cis-(octahydro-quinolin-1-yl)-(5-piperidin-4-yl-thiophen-3-yl)-methanone (CC-159).

| Code No. | Structure | Analytical Method | R.T. (min) | MS [m/z] |
|---|---|---|---|---|
| CC-160 | DHQ [CIS-S] | 2 | 8.88 | [M + H]+ 478.13 |

-continued

| Code No. | Structure | Analytical Method | R.T. (min) | MS [m/z] |
|---|---|---|---|---|
| CC-165 | DHQ [CIS-S] | 2 | 9.58 | [M + H]+ 434.19 |
| CC-167 | DHQ [CIS-S] | 2 | 7.41 | [M + H]+ 467.13 |
| CC-173 | DHQ [CIS-S] | 2 | 8.78 | [M + H]+ 420.14 |
| CC-162 | DHQ [CIS-S] | 2 | 6.95 | [M + H]+ 447.19 |

The compound in the following table was prepared using analogous methods but starting from (4,4-dimethyl-azepan-1-yl)-(5-piperidin-4-yl-thiophen-3-yl)-methanone (CC-023).

| Code No. | Structure | Analytical Method | R.T. (min) | MS [m/z] |
|---|---|---|---|---|
| CC-175 | DHQ [CIS-S] | 2 | 8.53 | [M + H]+ 408.18 |

Synthesis 80 cis-4-[4-(Octahydro-quinoline-1-carbonyl)-thiophen-2-yl]-piperidine-1-carboxylic acid(2-methanesulfonylamino-ethyl)-amide (CC-168) DHQ [CIS-S]

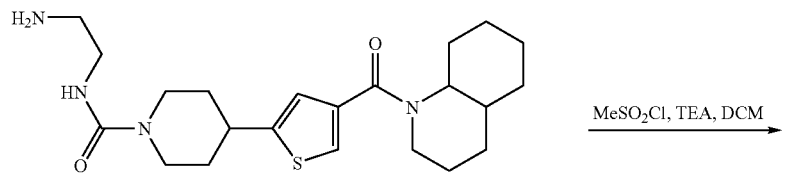

MeSO₂Cl, TEA, DCM

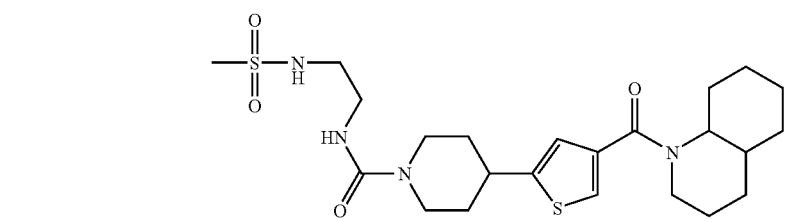

cis-4-[4-(Octahydro-quinoline-1-carbonyl)-thiophen-2-yl]-piperidine-1-carboxylic acid(2-amino-ethyl)-amide (0.058 g, 0.14 mmol) was prepared using the method described above to prepare CC-157 and dissolved in DCM (4 mL). DIPEA (0.042 mL) and methylsulphonyl chloride (0.02 mL) was added and the mixture stirred for 2 hours in an ice bath. The solvent evaporated and the resulting gum was purified by HPLC eluting with 10%-98% acetonitrile in water (0.1% formic acid). The fractions containing the desired product were concentrated under vacuum to give the title compound (0.05 g). LCMS m/z 497.09 [M+H]⁺ RT=9.27 min (Analytical Method 2).

The compounds in the following table were prepared using analogous methods but starting from cis-(octahydro-quinolin-1-yl)-(5-piperidin-4-yl-thiophen-3-yl)-methanone (CC-155) DHQ [CIS-R].

Synthesis 81

4,4-Difluoro-azepane hydrochloride

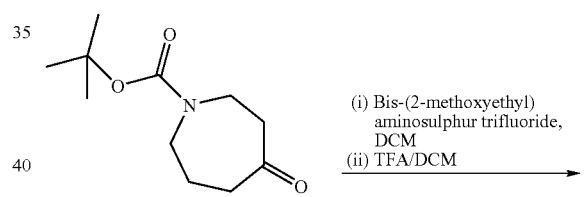

(i) Bis-(2-methoxyethyl) aminosulphur trifluoride, DCM
(ii) TFA/DCM

| Code No. | Structure | Analytical Method | R.T. (min) | MS [m/z] |
|---|---|---|---|---|
| CC-169 | ![structure] DHQ [CIS-R] | 2 | 9.24 | [M + H]⁺ 497.12 |

-continued

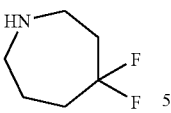

To N-t-butyloxycarbonyl-azopin-4-one (5 g, 23.5 mmol) in DCM (50 mL) was added bis-(2-methoxyethyl)amino sulphur trifluoride (8 mL) and the mixture stirred for 48 hours. The mixture was washed carefully with saturated aqueous cesium carbonate solution and then evaporated. The residue was purified by flash chromatography on silica eluting with 0-3% t-butyl methyl ether in cyclohexane. The fractions containing the desired product were concentrated under vacuum to give an oil which was treated with a solution of hydrochloric acid in dioxane (4M, 40 mL). After 30 minutes the solvent was evaporated and the resulting solid triturated with ether to give the title compound as an off-white solid.

Synthesis 82 cis-1-{3-[4-(Octahydro-quinoline-1-carbonyl)-thiophen-2-yl]-pyrrolidin-1-yl}ethanone (CC-111) DHQ [CIS-S]

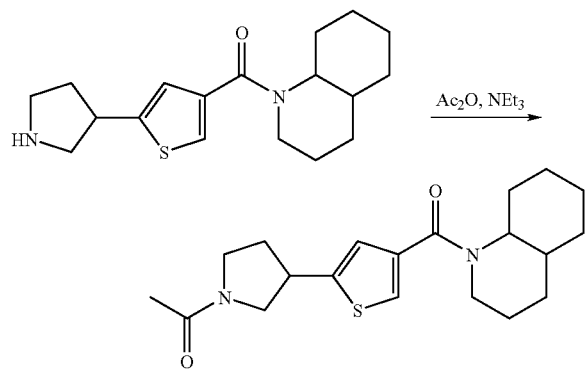

cis-(Octahydro-quinolin-1-yl)-(5-pyrrolidin-3-yl-thiophen-3-yl)-methanone (CC-177) (0.065 g, 0.19 mmol) was dissolved in triethylamine (2 mL) and acetic anhydride was added and the resulting mixture stirred for 20 minutes. The solvent was evaporated and the resulting gum was purified by HPLC eluting with 10%-98% acetonitrile in water (0.1% formic acid). The fractions containing the desired product were concentrated under vacuum to give the title compound (0.029 g). LCMS m/z 361.20[M+H]+ RT=9.24 min (Analytical Method 2).

Synthesis 83 cis-(Octahydro-quinolin-1-yl)-{5-[1-(2,2,2-trifluoro-ethyl)-piperidin-4-yl]-thiophen-3-yl}-methanone (CC-172) (DHQ [CIS-S]

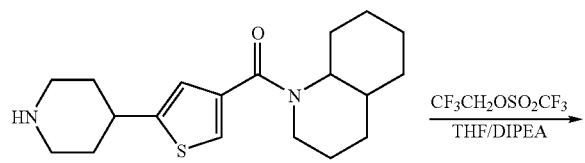

-continued

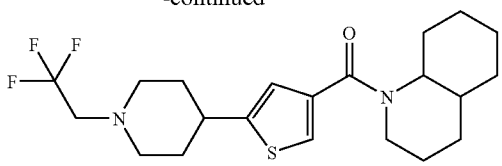

cis-(Octahydro-quinolin-1-yl)-(5-piperidin-4-yl-thiophen-3-yl)-methanone (CC-159) (0.072 g, 0.21 mmol) was dissolved in dry THF (5 mL) and DIPEA (0.66 mmol) was added followed by 2,2,2-trifluoroethyltrifluoromethanesulphonate (0.26 mmol) and the resulting mixture stirred for 2 hours. 2,2,2-Trifluoroethyltrifluoromethanesulphonate (0.26 mmol) was added and the mixture refluxed overnight. The solvent was evaporated and the resulting gum was purified by HPLC eluting with 10%-98% acetonitrile in water (0.1% formic acid). The fractions containing the desired product were concentrated under vacuum to give the title compound (0.06 g). LCMS m/z 415.13 [M+H]+ RT=12.16 min (Analytical Method 2).

Biological Methods

Cellular In Vitro 11β-HSD1 Enzyme Inhibition Assay

Compounds were assessed by a Scintillation Proximity Assay (SPA) performed according to the following protocol:

HEK293 cells were stably transfected with a construct containing the full-length gene coding for the human 11β-HSD1 enzyme to create HEK293/11β-HSD1 cells. Cells were routinely cultured in DMEM containing 10% calf foetal serum, 1% glutamine, and 1% penicillin and streptomycin. Prior to assay, cells were plated at $2 \times 10^4$ cells/well in 96-well poly-D-Lys coated flat-bottomed microplates and incubated in 5% $CO_2$, 95% $O_2$ at 37° C. for 24 hours. The media in each well was removed immediately before assay.

Compounds to be tested were dissolved in DMSO at 10 mM and serially diluted into water containing 10% DMSO. Diluted compounds at a volume of 10 μL were added to wells of a 96-well V-bottomed microplate. A solution of DMEM, 1% glutamine, 1% penicillin and streptomycin, and 22 nM tritiated cortisone was prepared and 90 μL added to each well of the assay plate. This solution (100 μL/well) was transferred to the plate containing the cells. The plate was then incubated in 5% $CO_2$, 95% $O_2$ at 37° C. for 2 hours.

Following this incubation, 50 μL of the assay solution was transferred to each well of a 96-well scintillation microplate. A mixture consisting of anti-mouse YSi SPA beads, premixed with anti-cortisol antibody in assay buffer (50 mM Tris.HCl, pH 7.0; 300 mM NaCl; 1 mM EDTA, 5% glycerol) was prepared and 50 μL added to each well of the scintillation microplate. An adhesive strip was applied to the microplate and the plate gently shaken for at least 2 hours at room temperature, and then spun briefly on a low speed centrifuge. The plate was read on a scintillation counter suitable for 96-well microplates. For the calculation of percentage inhibition, a series of wells were added to the plate that represented the assay maximum and the assay minimum: one set that contained substrate without cells (mimimum) and another set that contained substrate and cells without any compound (maximum).

The calculation of median inhibitory concentration ($IC_{50}$) values for the compounds was performed using GraphPad Prism® software. Dose-response curves for each compound were plotted as fractional inhibition and data fitted to the four parameter logistic equation.

Cellular In Vitro 11β-HSD2 Enzyme Inhibition Assay

For measurement of inhibition of 11β-HSD2, CHO cells stably transfected with the full-length gene coding for human 11β-HSD2 were used. Assays were carried out in 96-well microplates containing $1 \times 10^5$ cells/well. Controls and compounds were plated as above, so that the final DMSO concentration in each well was 1%. To initiate the assay, 90 µL of a solution of HAMS F-12 medium containing 1% glutamine, 1% penicillin and streptomycin, and 22 nM tritiated cortisol was added to each well of the assay plate. The plate was then incubated in 5% $CO_2$, 95% $O_2$ at 37° C. for 16 hours.

The assay solutions were transferred to glass tubes and 20 µL ethyl acetate added to each tube. Each tube was vortexed thoroughly and the upper layer containing the tritiated steroid transferred to a fresh glass tube. The solvent was evaporated by placing the tubes in a heating block at 65° C. under a stream of Nitrogen gas. 20 µL ethanol was added to each of the dried samples and vortexed briefly. Each sample was applied to a silica TLC plate and the plate dried. The plate was placed vertically in a glass tank containing 92% chloroform: 8% ethanol and the solvent allowed to rise up the plate. The plate was dried, placed in an imaging cassette, and overlayed with a tritium imaging plate for 1-2 days. The amount of enzyme inhibition in each sample was determined by measuring the intensity of the substrate and product spots using a phosphoimager.

$IC_{50}$ values for inhibitors were determined as described for 11β-HSD1.

Biological Data

Cellular In Vitro Enzyme Inhibition Data

The following compounds were tested using the cellular in vitro enzyme inhibition assays described above: AA-001 through AA-006; AA-008 through AA-022; BB-001 through BB-007; CC-001 through CC-177 and DD-001 through DD-006.

All of the compounds tested have an $IC_{50}$ for 11β-HSD1 (HEK293) of less than about 30 µM, often less than about 1 µM, and in many cases less than about 100 nM.

All of the compounds tested have an $IC_{50}$ for 11β-HSD2 (CHO) of greater than 10,000 nM.

Generally, the $IC_{50}$ ratio for 11β-HSD2 to 11β-HSD1 is at least about five or greater, and in many cases ten or greater. For example, data for some of the compounds is shown in the following table.

TABLE 1

In vitro Enzyme Inhibition Data

| Code No. | $IC_{50}$ for 11β-HSD1 (HEK293) (nM) | $IC_{50}$ for 11β-HSD2 (CHO) (nM) |
| --- | --- | --- |
| AA-001 | 281 | >10,000 |
| AA-014 | 4 | >10,000 |
| BB-007 | 68 | >10,000 |
| CC-003 | 150 | >10,000 |
| CC-033 | 127 | >10,000 |
| CC-106 | 96 | >10,000 |
| CC-111 | 20 | >10,000 |
| CC-119 | 61 | >10,000 |
| CC-168 | 77 | >10,000 |
| CC-175 | 23 | >10,000 |
| DD-002 | 882 | >10,000 |

The following compounds have an $IC_{50}$ for 11β-HSD1 (HEK293) of less than or equal to 1000 nM (1 µM): AA-001, AA-002, AA-004, AA-005, AA-009, AA-011, AA-012, AA-013, AA-014, AA-015, AA-016, AA-017, AA-018, AA-019, AA-021, AA-022, BB-002, BB-006, BB-007, CC-003, CC-004, CC-005, CC-006, CC-007, CC-017, CC-021, CC-022, CC-025, CC-026, CC-027, CC-028, CC-030, CC-031, CC-033, CC-035, CC-040, CC-044, CC-046, CC-047, CC-049, CC-050, CC-051, CC-053, CC-054, CC-057, CC-058, CC-059, CC-065, CC-066, CC-068, CC-069, CC-070, CC-072, CC-073, CC-074, CC-075, CC-077, CC-081, CC-083, CC-084, CC-086, CC-090, CC-091, CC-097, CC-099, CC-101, CC-103, CC-106, CC-108, CC-111, CC-113, CC-114, CC-115, CC-116, CC-119, CC-123, CC-126, CC-127, CC-130, CC-132, CC-133, CC-134, CC-135, CC-136, CC-137, CC-138, CC-140, CC-141, CC-142, CC-143, CC-144, CC-145, CC-146, CC-147, CC-148, CC-149, CC-151, CC-154, CC-157, CC-158, CC-159, CC-160, CC-161, CC-164, CC-165, CC-166, CC-167, CC-168, CC-169, CC-170, CC-171, CC-173, CC-174, CC-175, CC-176, CC-177, DD-001, DD-002, DD-005.

The following compounds have an $IC_{50}$ for 11β-HSD1 (HEK293) of more than 1000 nM (1.0 µM) and less than or equal to 30 µM: AA-003, AA-006, AA-008, AA-010, AA-020, BB-001, BB-003, BB-004, BB-005, CC-001, CC-002, CC-008, CC-009, CC-010, CC-011, CC-012, CC-013, CC-014, CC-015, CC-016, CC-018, CC-019, CC-020, CC-023, CC-024, CC-029, CC-032, CC-034, CC-036, CC-037, CC-038, CC-039, CC-041, CC-042, CC-043, CC-045, CC-048, CC-052, CC-055, CC-056, CC-060, CC-061, CC-062, CC-063, CC-064, CC-067, CC-071, CC-076, CC-078, CC-079, CC-080, CC-082, CC-085, CC-087, CC-088, CC-089, CC-092, CC-093, CC-094, CC-095, CC-096, CC-100, CC-102, CC-104, CC-105, CC-107, CC-109, CC-110, CC-112, CC-117, CC-120, CC-121, CC-122, CC-124, CC-125, CC-128, CC-129, CC-131, CC-139, CC-150, CC-152, CC-153, CC-155, CC-156, CC-162, CC-163, CC-172, CC-098, DD-003, DD-004, DD-006.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Andersen et al., 2006, "Pharmaceutical Use of Substituted Amides", US patent publication number US 2006/0111366 A1, published 25 May 2006.

Andrews, R. C., et al., 2003, "Effects of the 11beta-hydroxysteroid dehydrogenase inhibitor carbenoxolone on insulin sensitivity in men with type 2 diabetes," *J. Clin. Endocrinol. Metab.*, Vol. 88, pp. 285-291.

Barton et al., 2005, "N-Acylated 3-(benzoyl)-pyrrolidines as 11-Beta-HSD1 Inhibitors useful for the treatment of metabolic disorders", international patent publication number WO 2005/047250 A1, published 26 May 2005.

Barton et al., 2005, "Substituted piperidines fro the treatment of metabolic syndrome", international patent publication number WO 2005/046685 A1, published 26 May 2005.

Christy, C., et al., 2003, "Glucocorticoid action in mouse aorta; localisation of 11β-hydroxysteroid dehydrogenase type 2 and effects on responses to glucocorticoids in vitro," Hypertension, Vol. 42, pp. 580-587.

Cooper, M. S., et al., 2000, "Expression and functional consequences of 11β-hydroxysteroid dehydrogenase activity in human bone," Bone, Vol. 27, pp. 375-381.

Hadoke, P. W. F., et al., 2001, "Endothelial cell dysfunction in mice after transgenic knockout of type 2, but not type 1, 11β-hydroxysteroid dehydrogenase," Circulation, Vol. 104, pp. 2832-2837.

Kotelevtsev, Y. V., et al., 1997, "11β-Hydroxysteroid dehydrogenase type 1 knockout mice show attenuated glucocorticoid inducible responses and resist hyperglycaemia on obesity and stress," Proc. Natl. Acad. Sci., Vol. 94, pp. 14924-14929

Lee et al., 2005, "Heterocyclic Antiviral Compounds", international patent publication number WO 2005/121145 A2, published 22 Dec. 2005.

Masuzaki, H., et al., 2001, "A Transgenic Model of Visceral Obesity and the Metabolic Syndrome," Science, Vol. 294, pp. 2166-2170.

Moisan, M. P., et al., 1990, "11 beta-hydroxysteroid dehydrogenase bioactivity and messenger RNA expression in rat forebrain: localization in hypothalamus, hippocampus, and cortex," Endocrinology, Vol. 127, pp. 1450-1455.

Morton, N. M., et al., 2001, "Improved lipid and lipoprotein profile, hepatic insulin sensitivity, and glucose tolerance in 11β-hydroxysteroid dehydrogenase type 1 null mice," J. Biol. Chem., Vol. 276, pp. 41293-41300.

Morton, N. M., et al., 2004, "Novel adipose tissue-mediated resistance to diet-induced visceral obesity in 11β-hydroxysteroid dehydrogenase type 1 deficient mice," Diabetes, Vol. 53, pp. 931-938.

Paterson, J. M., et al., 2004, "Metabolic syndrome without obesity: hepatic overexpression of 11β-hydroxysteroid dehydrogenase type 1 in transgenic mice," Proc. Natl. Acad. Sci., Vol. 101, pp. 7088-7093).

Rask, E., et al., 2001, "Tissue-specific dysregulation of cortisol metabolism in human obesity," J. Clin. Endocrinol. Metab., Vol. 86, pp. 1418-1421.

Rauz, S., et al., 2001, "Expression and putative role of 11 beta-hydroxysteroid dehydrogenase isozymes within the human eye," Investigative Opthalmology & Visual Science, Vol. 42, pp. 2037-2042.

Sandeep, T. C., et al., 2004, "11β-hydroxysteroid dehydrogenase inhibition improves cognitive function in healthy elderly men and type 2 diabetics," Proc. Natl. Acad. Sci. Vol. 101, pp. 6734-6739.

Seckl, J. R., Walker, B. R., 2001, "11β-Hydroxysteroid dehydrogenase type 1—a tissue-specific amplifier of glucocorticoid action," Endocrinology, Vol. 142, pp. 1371-1376.

Small, G. R., et al., 2005, "Preventing local regeneration of glucocorticoids by 11β-hydroxysteroid dehydrogenase type 1 enhances angiogenesis," Proc. Natl. Acad. Sci., Vol. 102, pp. 12165-12170.

Walker, B. R., et al., 1991, "11β-Hydroxysteroid dehydrogenase in vascular smooth muscle and heart: implications for cardiovascular responses to glucocorticoids," Endocrinology, Vol. 129, pp. 3305-3312.

Walker, B. R., et al., 1995, "Carbenoxolone increases hepatic insulin sensitivity in man: a novel role for 11-oxosteroid reductase in enhancing glucocorticoid receptor activation," J. Clin. Endocrinol. Metab., Vol. 80, pp. 3155-3139.

Yau, J. L. W., et al., 2001, "Lack of tissue glucocorticoid reactivation in 11β-hydroxysteroid dehydrogenase type 1 knockout mice ameliorates age-related learning impairments," Proc. Natl. Acad. Sci., Vol. 98, pp. 4716-4721.

The invention claimed is:

1. A compound selected from compounds of the following formula, and pharmaceutically acceptable salts thereof:

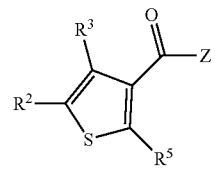

wherein:
— $R^2$ is independently
— $R^3$ is independently —H;
— $R^5$ is independently —H; and
≦Z is independently -$J_1$, -$J^2$, or -$J^3$;
with the proviso that:
if: — $R^2$ is — $R^{2A}$, then: —Z is independently -$J^2$ or -$J^3$;
wherein:
— $R^{2A}$ is independently — $R^{2A1}$, $R^{2A2}$ or — $R^{2A3}$;
— $R^{2A1}$ is independently saturated aliphatic $C_{1-6}$alkyl;
— $R^{2A2}$ is independently saturated aliphatic $C_{1-6}$alkyl substituted with one or more fluorine atoms;
— $R^{2A3}$ is independently saturated aliphatic $C_{1-6}$alkyl substituted with —CN;
— $R^{2B}$ is independently — $R^{2BL}$-M-$R^{2BR}$;
$R^{2BL}$ is independently saturated aliphatic $C_{1-4}$alkylene;
-M- is independently —O;
— $R^{2BR}$ is independently — $R^{2B1}$;
— $R^{2B1}$ is independently saturated aliphatic $C_{1-6}$alkyl, and is optionally substituted;
— $R^{2C}$ is independently non-aromatic $C_{4-7}$heterocyclyl, and is optionally substituted;
-$J^1$ is independently a monocyclic non-aromatic heterocyclyl group having from 4 to 8 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said non-aromatic heterocyclyl group is optionally substituted;
-$J^2$ is independently a fused bicyclic non-aromatic heterocyclyl group having from 9 to 12 ring atoms, wherein: exactly 1 of said ring atoms is a ring heteroatom, and is N;
or exactly 2 of said ring atoms are ring heteroatoms, and are both N; or exactly 2 of said ring atoms are ring heteroatoms, and are N and O; or exactly 2 of said ring atoms are ring heteroatoms, and are N and S; or exactly 3 of said ring atoms are ring heteroatoms, wherein one ring heteroatom is N, and the other two ring heteroatoms are selected from N, O, and S; and wherein said fused bicyclic non-aromatic heterocyclyl group is optionally substituted; and
-$J^3$ is independently a bridged non-aromatic heterocyclyl group having from 7 to 11 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said bridged non-aromatic heterocyclyl group is optionally substituted.

2. A compound according to claim 1, wherein —R² is independently —R²ᴬ.

3. A compound according to claim 1, wherein —R² is independently —R²ᴮ.

4. A compound according to claim 1, wherein —R² is independently —R²ᶜ.

5. A compound according to claim 1, wherein —Z is independently -J¹.

6. A compound according to claim 1, wherein —Z is independently -J².

7. A compound according to claim 1, wherein —Z is independently -J³.

8. A compound according to claim 1, wherein —R²ᴬ is independently —R²ᴬ¹.

9. A compound according to claim 1, wherein —R²ᴬ is independently —R²ᴬ².

10. A compound according to claim 1, wherein —R²ᴬ is independently —R²ᴬ³.

11. A compound according to claim 1, wherein:
—R²ᴬ¹ is independently -Me, -Et, -nPr, -iPr, -nBu, -sBu, -tBu, or -nPentyl;
—R²ᴬ² is independently —CF₃ or —CH₂CF₃; and
—R²ᴬ³ is independently saturated aliphatic C₁₋₄alkyl substituted with —CN.

12. A compound according to claim 1, wherein:
—R²ᴮᴸ— is independently —CH₂—; and —R²ᴮ¹ is independently saturated aliphatic C₁₋₄alkyl, and is optionally substituted.

13. A compound according to claim 4, wherein —R²ᶜ is independently azetidinyl, oxitanyl, pyrrolidinyl, tetrahydrofuranyl, piperidinyl, tetrahydropyridinyl, tetrahydropyranyl, piperazinyl, morpholinyl, thiomorpholinyl, azepanyl, diazepanyl, or oxazepanyl, and is optionally substituted.

14. A compound according to claim 4, wherein —R²ᶜ is independently tetrahydropyranyl, and is optionally substituted.

15. A compound according to claim 4, wherein —R²ᶜ is independently tetrahydropyran-4-yl, and is optionally substituted.

16. A compound according to claim 4, wherein —R²ᶜ is independently piperidinyl, and is optionally substituted.

17. A compound according to claim 4, wherein —R²ᶜ is independently piperidin-4-yl, and is optionally substituted.

18. A compound according to claim 4, wherein —R²ᶜ is independently selected from:

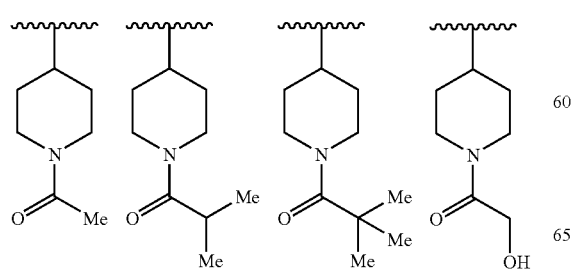

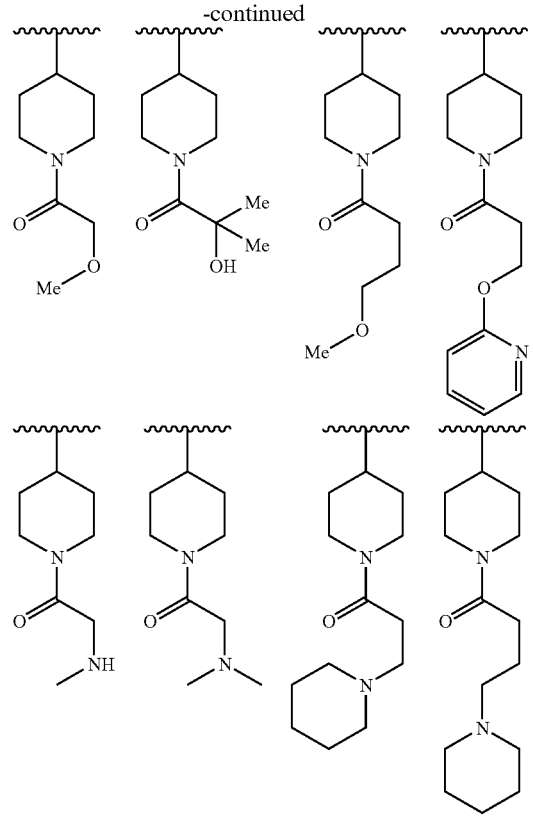

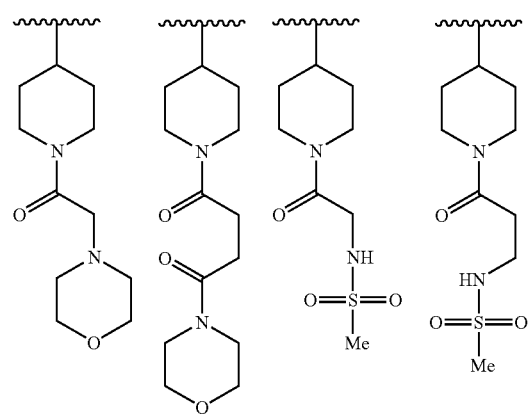

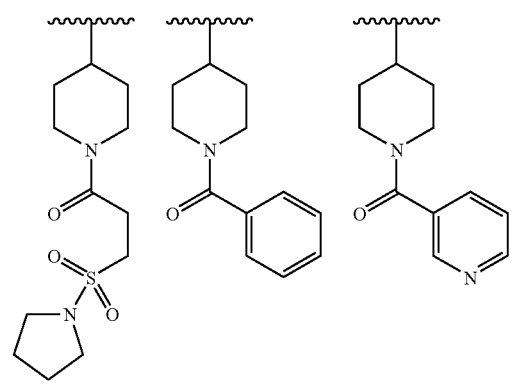

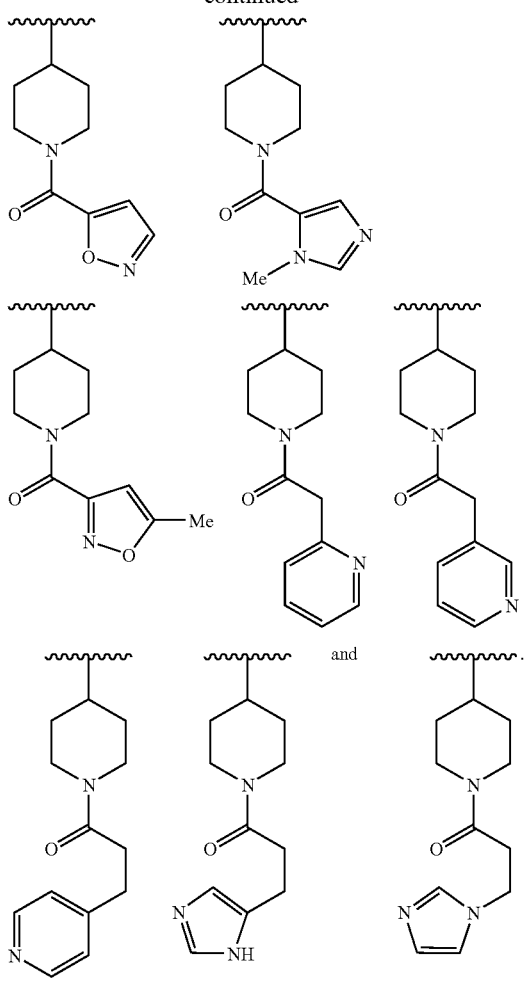

19. A compound according to claim 4, wherein —R$^{2C}$ is independently selected from:

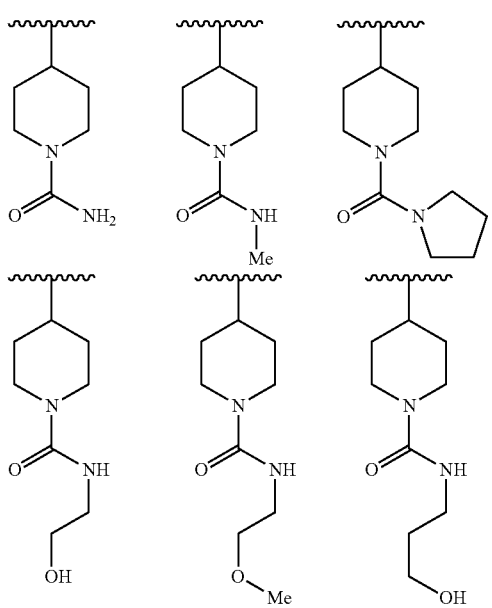

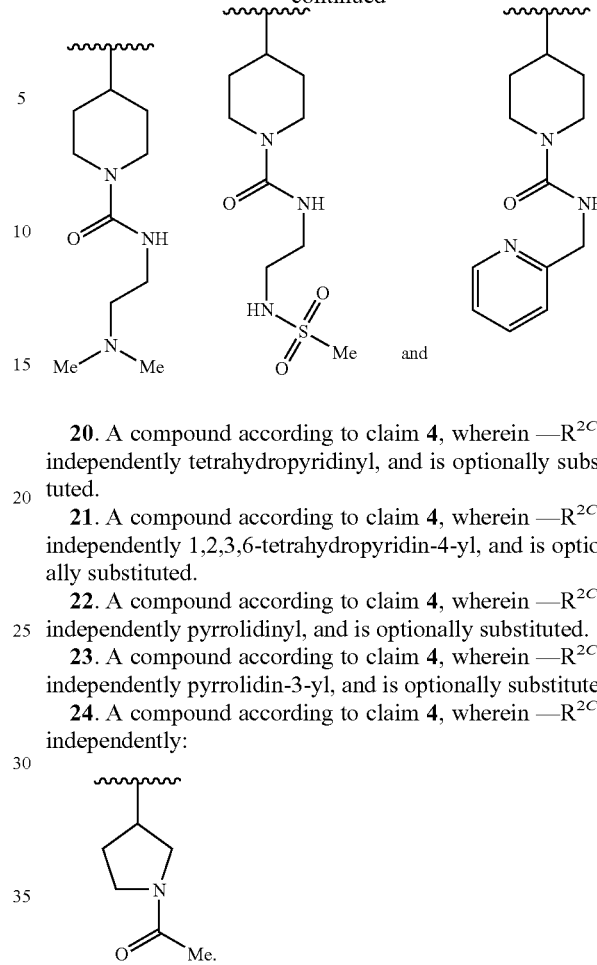

20. A compound according to claim 4, wherein —R$^{2C}$ is independently tetrahydropyridinyl, and is optionally substituted.

21. A compound according to claim 4, wherein —R$^{2C}$ is independently 1,2,3,6-tetrahydropyridin-4-yl, and is optionally substituted.

22. A compound according to claim 4, wherein —R$^{2C}$ is independently pyrrolidinyl, and is optionally substituted.

23. A compound according to claim 4, wherein —R$^{2C}$ is independently pyrrolidin-3-yl, and is optionally substituted.

24. A compound according to claim 4, wherein —R$^{2C}$ is independently:

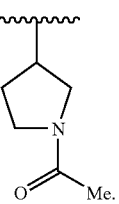

25. A compound according to claim 4, wherein —R$^{2C}$ is independently azetidinyl, and is optionally substituted.

26. A compound according to claim 5, wherein -J$^1$ is independently selected from the following groups and corresponding groups having one or more substituents selected from saturated aliphatic C$_{1-3}$alkyl, phenyl, and pyridyl:

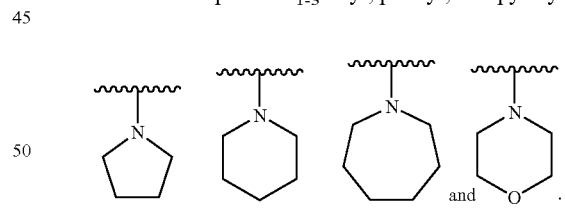

27. A compound according to claim 5, wherein -J$^1$, is independently selected from:

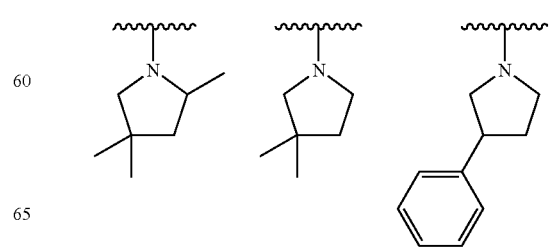

-continued

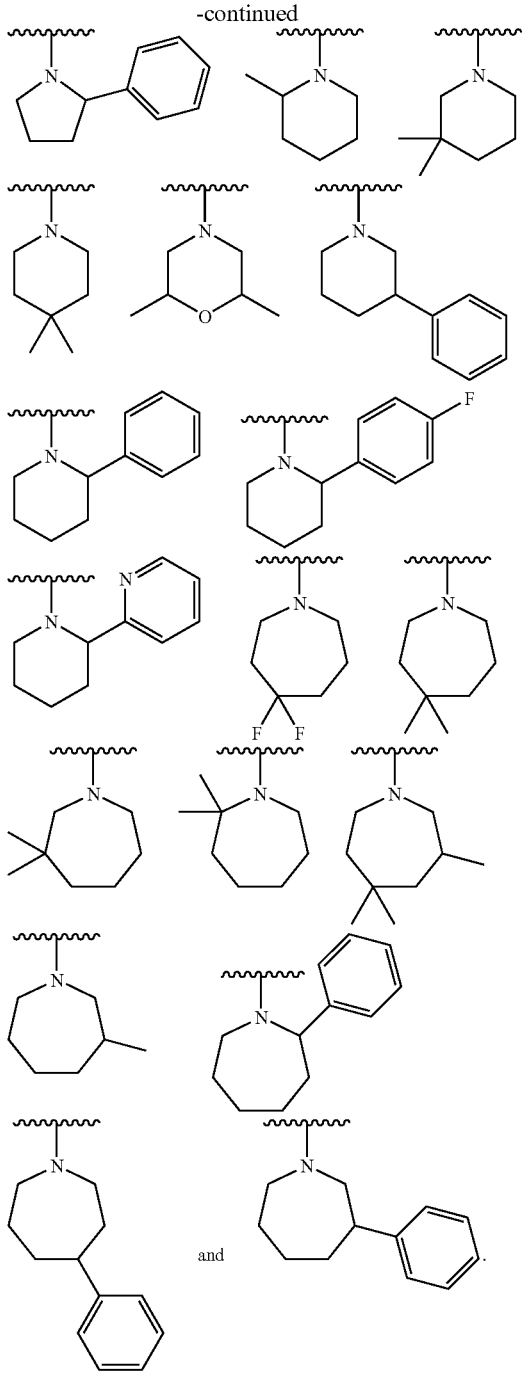

28. A compound according to claim 6, wherein -J² is independently selected from the following groups and corresponding groups having one or more substituents selected from saturated aliphatic $C_{1-3}$alkyl:

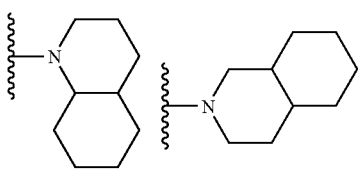

-continued

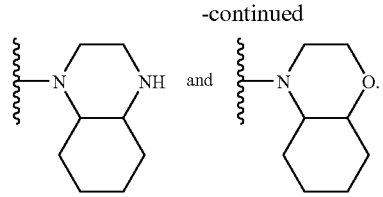 and

29. A compound according to claim 6, wherein -J² is independently selected from the following group and corresponding groups having one or more substituents selected from saturated aliphatic $C_{1-3}$alkyl:

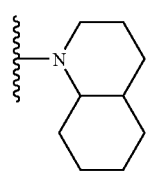

30. A compound according to claim 6, wherein -J² is independently:

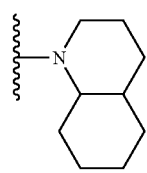

31. A compound according to claim 6, wherein -J² is independently selected from:

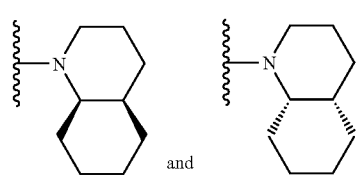

32. A compound according to claim 7, wherein -J³ is independently selected from the following groups and corresponding groups having one or more substituents selected from saturated aliphatic $C_{1-3}$alkyl:

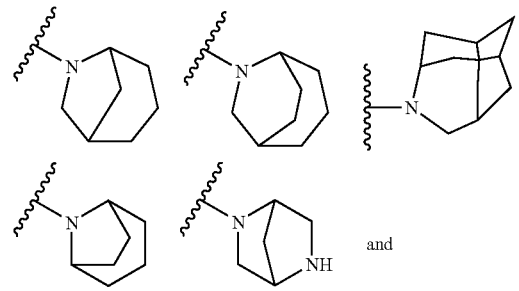

-continued

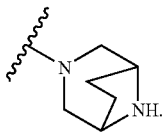

33. A compound according to claim 7, wherein -J³ is independently:

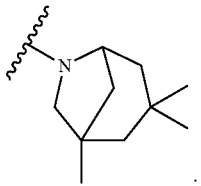 [SMILES: *N1CC2(C)CC1CC(C)(C)C2]

34. A compound according to claim 7, wherein -J³ is independently selected from:

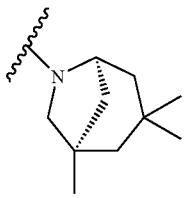 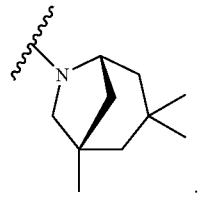

and

35. A compound according to claim 4, wherein optional substituents on —R$^{2C}$ are independently selected from:
substituents on carbon, independently selected from:
—R$^Q$,
—R$^R$,
—R$^L$—R$^R$,
—F, —Cl, —Br,
=O
—OH, —R$^L$—OH, —O—R$^L$—OH, —NH—R$^L$—OH, —NR$^P$—R$^L$—OH,
—OR$^P$, —R$^L$—OR$^P$, —O—R$^L$—OR$^P$, —NH—R$^L$—OR$^P$, —NR$^P$—R$^L$—OR$^P$,
—NH$_2$, —NHR$^P$, —NR$^P$$_2$, —R$^M$,
—R$^L$—NH$_2$, —R$^L$—NHR$^P$, —R$^L$—NR$^P$$_2$, —R$^L$—R$^M$,
—O—R$^L$—NH$_2$, —O—R$^L$—NHR$^P$, —O—R$^L$—NR$^P$$_2$, —O—R$^L$—R$^M$,
—NH—R$^L$—NH$_2$, —NH—R$^L$—NHR$^P$, —NH—R$^L$—NR$^P$$_2$, —NH—R$^L$—R$^M$,
—NR$^P$—R$^L$—NH$_2$, —NR$^P$—R$^L$—NHR$^P$, —NR$^P$—R$^L$—NR$^P$$_2$, —NR$^P$—R$^L$—R$^M$,
—S(=O)$_2$NH$_2$, —S(=O)$_2$NHR$^P$, —S(=O)$_2$NR$^P$$_2$, —S(=O)$_2$R$^M$,
—R$^L$—S(=O)$_2$NH$_2$, —R$^L$—S(=O)$_2$NHR$^P$, —R$^L$—S(=O)$_2$NR$^P$$_2$, —R$^L$—S(=O)$_2$R$^M$,
—O—R$^L$—S(=O)$_2$NH$_2$, —O—R$^L$—S(=O)$_2$NHR$^P$, —O—R$^L$—S(=O)$_2$NR$^P$$_2$, —O—R$^L$—S(=O)$_2$R$^M$,
—NHS(=O)$_2$R$^P$, —NR$^P$S(=O)$_2$R$^P$, —NHS(=O)$_2$R$^M$, —NR$^P$S(=O)$_2$R$^M$,
—R$^L$—NHS(=O)$_2$R$^P$, —R$^L$—NR$^P$S(=O)$_2$R$^P$, —R$^L$—NHS(=O)$_2$R$^M$, —R$^L$—NR$^P$S(=O)$_2$R$^M$,
—O—R$^L$—NHS(=O)$_2$R$^P$, —O—R$^L$—NR$^P$S(=O)$_2$R$^P$, —S(=O)$_2$R$^P$,
—R$^L$—S(=O)$_2$R$^P$,
—O—R$^L$—S(=O)$_2$R$^P$,
—SR$^P$,
—C(=O)OH, —C(=O)OR$^P$,
—R$^L$—C(=O)OH, —R$^L$—C(=O)OR$^P$,
—C(=O)NH$_2$, —C(=O)NHR$^P$, —C(=O)NR$^P$$_2$,
—C(=O)R$^M$,
—R$^L$—C(=O)NH$_2$, —R$^L$—C(=O)NHR$^P$, —R$^L$—C(=O)NR$^P$$_2$, —R$^L$—C(=O)R$^M$,
—C(=O)R$^P$,
—CN,
—NHC(=O)R$^P$, —NR$^P$C(=O)R$^P$,
—R$^L$—NHC(=O)R$^P$, —R$^L$—NR$^P$C(=O)R$^P$,
—NHC(=O)—OR$^P$, —NR$^P$C(=O)—OR$^P$,
—NHC(=O)—R$^L$—OH, —NHC(=O)—R$^L$—OR$^P$,
—NR$^P$C(=O)—R$^L$—OH, —NR$^P$C(=O)—R$^L$—OR$^P$,
—NHC(=O)—NH$_2$, —NHC(=O)—NHR$^P$, —NHC(=O)—NR$^P$$_2$, —NHC(=O)—R$^M$,
—NR$^P$C(=O)—NH$_2$, —NR$^P$C(=O)—NHR$^P$, —NR$^P$C(=O)—NR$^P$$_2$, —NR$^P$C(=O)—R$^M$,
—NHC(=O)—R$^L$—NH$_2$, —NHC(=O)—R$^L$—NHR$^P$,
—NHC(=O)—R$^L$—NR$^P$$_2$, —NHC(=O)—R$^L$—R$^M$,
—NR$^P$C(=O)—R$^L$—NH$_2$, —NR$^P$C(=O)—R$^L$—NHR$^P$,
—NR$^P$C(=O)—R$^L$—NR$^P$$_2$, —NR$^P$C(=O)—R$^L$—R$^M$,
—NHC(=O)—R$^L$—NHS(=O)$_2$R$^P$, —NHC(=O)—R$^L$—NR$^P$S(=O)$_2$R$^P$,
—NR$^P$C(=O)—R$^L$—NHS(=O)$_2$R$^P$, —NR$^P$C(=O)—R$^L$—NR$^P$S(=O)$_2$R$^P$,
—NHC(=O)—R$^L$—NHS(=O)$_2$R$^M$, —NHC(=O)—R$^L$—NR$^P$S(=O)$_2$R$^M$,
—NR$^P$C(=O)—R$^L$—NHS(=O)$_2$R$^M$, —NR$^P$C(=O)—R$^L$—NR$^P$S(=O)$_2$R$^M$,
—NHC(=O)—R$^L$—S(=O)$_2$NH$_2$, —NR$^P$C(=O)—R$^L$—S(=O)$_2$NH$_2$,
—NHC(=O)—R$^L$—S(=O)$_2$NHR$^P$, —NR$^P$C(=O)—R$^L$—S(=O)$_2$NHR$^P$,
—NHC(=O)—R$^L$—S(=O)$_2$NR$^P$$_2$, —NR$^P$C(=O)—R$^L$—S(=O)$_2$NR$^P$$_2$,
—NHC(=O)—R$^L$—S(=O)$_2$R$^M$, —NR$^P$C(=O)—R$^L$—S(=O)$_2$R$^M$,
—NHS(=O)$_2$NH$_2$, —NHS(=O)$_2$NHR$^P$, —NHS(=O)$_2$NR$^P$$_2$, —NHS(=O)$_2$R$^M$,
—NR$^P$S(=O)$_2$NH$_2$, —NR$^P$S(=O)$_2$NHR$^P$, —NR$^P$S(=O)$_2$NR$^P$$_2$, —NR$^P$S(=O)$_2$R$^M$,
—NH—R$^L$—NHS(=O)$_2$R$^P$, —NH—R$^L$—NR$^P$S(=O)$_2$R$^P$,
—NR$^P$—R$^L$—NHS(=O)$_2$R$^P$, —NR$^P$—R$^L$—NR$^P$S(=O)$_2$R$^P$,
—NH—R$^L$—S(=O)$_2$NH$_2$, —NR$^P$—R$^L$—S(=O)$_2$NH$_2$,
—NH—R$^L$—S(=O)$_2$NHR$^P$, —NR$^P$—R$^L$—S(=O)$_2$NHR$^P$,
—NH—R$^L$—S(=O)$_2$NR$^P$$_2$, —NR$^P$—R$^L$—S(=O)$_2$NR$^P$$_2$,
—NH—R$^L$—S(=O)$_2$R$^M$, —NR$^P$—R$^L$—S(=O)$_2$R$^M$,
—NH—R$^L$—S(=O)$_2$R$^P$, and —NR$^P$—R$^L$—S(=O)$_2$R$^P$;
substituents on nitrogen, independently selected from:
—R$^Q$,
—R$^R$,
—R$^L$—R$^R$,
—C(=O)R$^Q$, —C(=O)R$^R$, —C(=O)—R$^L$—R$^R$,
—C(=O)—R$^L$—OH, —C(=O)—R$^L$—OR$^P$,
—C(=O)—R$^L$—NH$_2$, —C(=O)—R$^L$—NHR$^P$,
—C(=O)—R$^L$—NR$^P$$_2$, —C(=O)—R$^L$—R$^M$,
—C(=O)—R$^L$—C(=O)—NH$_2$, —C(=O)—R$^L$—C(=O)—NHR$^P$,
—C(=O)—R$^L$—C(=O)—NR$^P$$_2$, —C(=O)—R$^L$—C(=O)—R$^M$, —C(=O)—R$^L$—NH—C(=O)R$^P$, —C(=O)—R$^L$—NR$^P$—C(=O)R$^P$,
—C(=O)—R$^L$—NHS(=O)$_2$R$^P$, —C(=O)—R$^L$—NR$^P$S(=O)$_2$R$^P$,
—C(=O)—R$^L$—NHS(=O)$_2$R$^M$, —C(=O)—R$^L$—NR$^P$S(=O)$_2$R$^M$,
—C(=O)—R$^L$—S(=O)$_2$NH$_2$, —C(=O)—R$^L$—S(=O)$_2$NHR$^P$,
—C(=O)—R$^L$—S(=O)$_2$NR$^P$$_2$, —C(=O)—R$^L$—S(=O)$_2$R$^M$,
—C(=O)OR$^Q$, —C(=O)OR$^R$, —C(=O)O—R$^L$—R$^R$,
—C(=O)NH$_2$, —C(=O)NHR$^P$, —C(=O)NR$^P$$_2$, —C(=O)R$^M$,
—C(=O)NH—R$^L$—R$^R$, —C(=O)NR$^P$—R$^L$—R$^R$,
—C(=O)NH—R$^L$—OH, —C(=O)NR$^P$—R$^L$—OH,
—C(=O)NH—R$^L$—OR$^P$, —C(=O)NR$^P$—R$^L$—OR$^P$,
—C(=O)NH—R$^L$—NH$_2$, —C(=O)NR$^P$—R$^L$—NH$_2$,
—C(=O)NH—R$^L$—NHR$^P$, —C(=O)NR$^P$—R$^L$—NHR$^P$,
—C(=O)NH—R$^L$—NR$^P$$_2$, —C(=O)NR$^P$—R$^L$—NR$^P$$_2$,
—C(=O)NH—R$^L$—R$^M$, —C(=O)NR$^P$—R$^L$—R$^M$,
—C(=O)NH—R$^L$—NH—S(O)$_2$R$^P$, —C(=O)NR$^P$—R$^L$—NH—S(O)$_2$R$^P$,
—C(=O)NH—R$^L$—NR$^P$—S(O)$_2$R$^P$, —C(=O)NR$^P$—R$^L$—NR$^P$—S(O)$_2$R$^P$,
—S(=O)$_2$NH$_2$, —S(=O)$_2$NHR$^P$, —S(=O)$_2$NR$^P$$_2$, —S(=O)$_2$R$^M$,
—S(=O)$_2$R$^P$,
—R$^L$—OH, —R$^L$—OR$^P$,
—R$^L$—CH(OH)—R$^L$—OH, —R$^L$—CH(OH)—R$^L$—OR$^P$,
—R$^L$—CH(OR$^P$)—R$^L$—OH, —R$^L$—CH(OR$^P$)—R$^L$-OR$^P$,
—R$^L$—C(=O)NH$_2$, —R$^L$—C(=O)NHR$^P$, —R$^L$—C(=O)NR$^P$$_2$, —R$^L$—C(=O)R$^M$,
—R$^L$—NH$_2$, —R$^L$—NHR$^P$, —R$^L$—NR$^P$$_2$, —R$^L$—R$^M$,
—R$^L$—NH(C=O)R$^P$, —R$^L$—NR$^P$C(=O)R$^P$,
—R$^L$—NHS(=O)$_2$R$^P$, —R$^L$—NR$^P$S(=O)$_2$R$^P$,
—R$^L$—S(=O)$_2$NH$_2$, —R$^L$—S(=O)$_2$NHR$^P$, —R$^L$—S(=O)$_2$NR$^P$$_2$, —R$^L$—S(=O)$_2$R$^M$, and
—R$^L$—S(=O)$_2$R$^P$;

wherein:
each —R$^P$ is independently —R$^Q$ or —R$^R$;
each —R$^Q$ is independently saturated aliphatic C$_{1-4}$alkyl or saturated C$_{3-6}$cycloalkyl, and is optionally substituted with one or more fluorine atoms;
each —R$^R$ is independently phenyl or C$_{5-10}$heteroaryl, and is optionally substituted with one or more substitutents independently selected from:
—F, —Cl, —Br,
—R$^{K1}$, —CF$_3$,
—OH, —OR$^{K1}$, —OCF$_3$,
—NH$_2$, —NHR$^{K1}$, —NR$^{K1}$$_2$,
—NHC(=O)R$^{K1}$, —NR$^{K1}$C(=O)R$^{K1}$,
—C(=O)OH, —C(=O)OR$^{K1}$,
—C(=O)NH$_2$, —C(=O)NHR$^{K1}$, —C(=O)NR$^{K1}$$_2$,
—NO$_2$, and
—CN;
wherein each —R$^{K1}$ is independently saturated aliphatic C$_{1-4}$alkyl;
each —R$^M$ is independently azetidino, pyrrolidino, piperidino, piperazino, morpholino, azepino, or diazepino, and is optionally substituted with one or more substitutents independently selected from:
—F, —R$^{K2}$, —OH, —OR$^{K2}$, —OCF$_3$, —CN, and =O; and on nitrogen with one or more substitutents independently selected from:
—C(=O)R$^{K2}$, —R$^{K2}$, —C(=O)Ph, —S(=O)$_2$R$^{K2}$,
—S(=O)$_2$Ph, —S(=O)$_2$NH$_2$,
—S(=O)$_2$NHR$^{K2}$, —S(=O)$_2$NR$^{K2}$$_2$, and —S(=O)$_2$NHPh;
wherein each —R$^{K2}$ is independently saturated aliphatic C$_{1-4}$alkyl; and
each —R$^L$— is independently saturated aliphatic C$_{1-4}$alkylene.

36. A compound according to claim 35, wherein optional substituents on —R$^{2C}$ are selected from:

substituents on carbon, independently selected from:
—R$^Q$,
—R$^R$,
—R$^L$—R$^R$
—F,
—OH, —R$^L$—OH,
—OR$^P$, —R$^L$—OR$^P$,
—C(=O)NHR$^P$, —C(=O)NR$^P$$_2$,
—NHC(=O)R$^P$, —NR$^P$C(=O)R$^P$,
—CN, and
=O; and substituents on nitrogen, independently selected from:
—C(=O)R$^Q$, —C(=O)R$^R$, —C(=O)—R$^L$—R$^R$,
—C(=O)—R$^L$—OH, —C(=O)—R$^L$—OR$^P$,
—C(=O)—R$^L$—NH$_2$, —C(=O)—R$^L$—NHR$^P$,
—C(=O)—R$^L$—NR$^P$$_2$, —C(=O)—R$^L$—R$^M$,
—C(=O)—R$^L$—C(=O)—NH$_2$, —C(=O)—R$^L$—C(=O)—NHR$^P$,
—C(=O)—R$^L$—C(=O)—NR$^P$$_2$, —C(=O)—R$^L$—C(=O)—R$^M$,
—C(=O)—R$^L$—NH—C(=O)R$^P$, —C(=O)—R$^L$—NR$^P$—C(=O)R$^P$,
—C(=O)—R$^L$—NHS(=O)$_2$R$^P$, —C(=O)—R$^L$—NR$^P$S(=O)$_2$R$^P$,
—C(=O)—R$^L$—NHS(=O)$_2$R$^M$, —C(=O)—R$^L$—NR$^P$S(=O)$_2$R$^M$,
—C(=O)—R$^L$—S(=O)$_2$NH$_2$, —C(=O)—R$^L$—S(=O)$_2$NHR$^P$,
—C(=O)—R$^L$—S(=O)$_2$NR$^P$$_2$, —C(=O)—R$^L$—S(=O)$_2$R$^M$,
—C(=O)OR$^Q$, —C(=O)OR$^R$, —C(=O)O—R$^L$—R$^R$,
—C(=O)NH$_2$, —C(=O)NHR$^P$, —C(=O)NR$^P$$_2$, —C(=O)R$^M$,
—C(=O)NH—R$^L$—R$^R$, —C(=O)NR$^P$—R$^L$—R$^R$,
—C(=O)NH—R$^L$—OH, —C(=O)NR$^P$—R$^L$—OH,
—C(=O)NH—R$^L$—OR$^P$, —C(=O)NR$^P$—R$^L$—OR$^P$,
—C(=O)NH—R$^L$—NH$_2$, —C(=O)NR$^P$—R$^L$—NH$_2$,
—C(=O)NH—R$^L$—NHR$^P$, —C(=O)NR$^P$—R$^L$—NHR$^P$,
—C(=O)NH—R$^L$—NR$^P$$_2$, —C(=O)NR$^P$—R$^L$—NR$^P$$_2$,
—C(=O)NH—R$^L$—R$^M$, —C(=O)NR$^P$—R$^L$—R$^M$,
—C(=O)NH—R$^L$—NH—S(O)$_2$R$^P$, —C(=O)NR$^P$—R$^L$—NH—S(O)$_2$R$^P$,
—C(=O)NH—R$^L$—NR$^P$—S(O)$_2$R$^P$, —C(=O)NR$^P$—R$^L$—NR$^P$—S(O)$_2$R$^P$,
—S(=O)$_2$NH$_2$, —S(=O)$_2$NHR$^P$, —S(=O)$_2$NR$^P$$_2$, —S(=O)$_2$R$^M$,
—S(=O)$_2$R$^P$,
—R$^R$,
—R$^L$—R$^R$,
—R$^L$—OH, —R$^L$—OR$^P$,
—R$^L$—C(=O)NH$_2$, —R$^L$—C(=O)NHR$^P$, —R$^L$—C(=O)NR$^P$$_2$, —R$^L$—C(=O)R$^M$,
—R$^L$—NH$_2$, —R$^L$—NHR$^P$, —R$^L$—NR$^P$$_2$, —R$^L$—R$^M$,
—R$^L$—NHC(=O)R$^P$, —R$^L$—NR$^P$C(=O)R$^P$, —$R^L$—NHS(=O)$_2R^P$, —$R^L$—NR$^P$S(=O)$_2R^P$,
—$R^L$—S(=O)$_2$NH$_2$, —$R^L$—S(=O)$_2$NHR$^P$, —$R^L$—S(=O)$_2$NR$^P_2$, —$R^L$—S(=O)$_2R^M$, and
—$R^L$—S(=O)$_2R^P$.

37. A compound according to claim 1, wherein optional substituents on each of -J$^1$, -J$^2$, and -J$^3$ are independently selected from:

substituents on carbon, independently selected from:
- —$R^Q$,
- —$R^R$,
- —F, —Cl, —Br,
- —OH, —$R^L$—OH, —O—$R^L$—OH,
- —OR$^P$, —$R^L$—OR$^P$, —O—$R^L$—OR$^P$,
- —SR$^P$,
- —NH$_2$, —NHR$^P$, —NR$^P_2$, —$R^M$,
- —NHC(=O)R$^P$, —NR$^P$C(=O)R$^P$,
- —C(=O)NH$_2$, —C(=O)NHR$^P$, —C(=O)NR$^P_2$, —C(=O)R$^M$,
- —C(=O)OH, —C(=O)OR$^P$,
- —S(=O)$_2$NH$_2$, —S(=O)$_2$NHR$^P$, —S(=O)$_2$NR$^P_2$, —S(=O)$_2$R$^M$,
- —NHS(=O)$_2$R$^P$, —NR$^P$S(=O)$_2$R$^P$, —NHS(=O)$_2$R$^M$, —NR$^P$S(=O)$_2$R$^M$,
- —CN,
- —$R^L$—S(=O)$_2$NH$_2$, —$R^L$—S(=O)$_2$NHR$^P$, —$R^L$—S(=O)$_2$NR$^P_2$, —$R^L$—S(=O)$_2$R$^M$,
- —$R^L$—NH$_2$, —$R^L$—NHR$^P$, —$R^L$—NR$^P_2$, —$R^L$—R$^M$,
- —$R^L$—NHC(=O)R$^P$, —$R^L$—NR$^P$C(=O)R$^P$,
- —$R^L$—NHS(=O)$_2$R$^P$, —$R^L$—NR$^P$S(=O)$_2$R$^P$, —$R^L$—NHS(=O)$_2$R$^M$, —$R^L$—NR$^P$S(=O)$_2$R$^M$,
- —$R^L$—C(=O)OH, —$R^L$—C(=O)OR$^P$,
- —$R^L$—C(=O)NH$_2$, —$R^L$—C(=O)NHR$^P$, —$R^L$—C(=O)NR$^P_2$, —$R^L$—C(=O)R$^M$, and
- =O; and substituents on nitrogen, independently selected from:
- —$R^Q$,
- —$R^R$,
- —$R^L$—$R^R$,
- —C(=O)OR$^Q$, —C(=O)OR$^R$, —C(=O)O—$R^L$—$R^R$,
- —C(=O)R$^Q$, —C(=O)R$^R$, —C(=O)—$R^L$—$R^R$,
- —C(=O)—$R^L$—OH, —C(=O)—$R^L$—OR$^P$,
- —C(=O)NH$_2$, —C(=O)NHR$^P$, —C(=O)NR$^P_2$, —C(=O)R$^M$,
- —C(=O)—$R^L$—NH$_2$, —C(=O)—$R^L$—NHR$^P$, —C(=O)—$R^L$—NR$^P_2$, —C(=O)—$R^L$—R$^M$,
- —C(=O)—$R^L$—NHS(=O)$_2$R$^P$, —C(=O)—$R^L$—NR$^P$S(=O)$_2$R$^P$,
- —C(=O)—$R^L$—NHS(=O)$_2$R$^M$, —C(=O)—$R^L$—NR$^P$S(=O)$_2$R$^M$,
- —C(=O)—$R^L$—S(=O)$_2$NH$_2$, —C(=O)—$R^L$—S(=O)$_2$NHR$^P$,
- —C(=O)—$R^L$—S(=O)$_2$NR$^P_2$, —C(=O)—$R^L$—S(=O)$_2$R$^M$,
- —S(=O)$_2$NH$_2$, —S(=O)$_2$NHR$^P$, —S(=O)$_2$NR$^P_2$, —S(=O)$_2$R$^M$,
- —S(=O)$_2$R$^P$,
- —$R^L$—OH, —$R^L$—OR$^P$,
- —$R^L$—NH$_2$, —$R^L$—NHR$^P$, —$R^L$—NR$^P_2$, —$R^L$—R$^M$,
- —$R^L$—NHS(=O)$_2$R$^P$, —$R^L$—NR$^P$S(=O)$_2$R$^P$,
- —$R^L$—S(=O)$_2$NH$_2$, —$R^L$—S(=O)$_2$NHR$^P$, —$R^L$—S(=O)$_2$NR$^P_2$, —$R^L$—S(=O)$_2$R$^M$, and
- —$R^L$—S(=O)$_2$R$^P$; and substituents on sulfur, independently selected from:
=O and (=O)$_2$;

wherein:
each —$R^P$ is independently —$R^Q$ or —$R^R$;
each —$R^Q$ is independently saturated aliphatic C$_{1-4}$alkyl or saturated C$_{3-7}$cycloalkyl, and is optionally substituted with one or more fluorine atoms;
each —$R^R$ is independently phenyl or C$_{5-10}$heteroaryl, and is optionally substituted with one or more substitutents independently selected from:
- —F, —Cl, —Br,
- —R$_{K1}$, —CF$_3$,
- —OH, —OR$^{K1}$, —OCF$_3$,
- —NH$_2$, —NHR$^{K1}$, —NR$^{K1}_2$,
- —NHC(=O)R$^{K1}$, —NR$^{K1}$C(=O)R$^{K1}$,
- —C(=O)OH, —C(=O)OR$^{K1}$,
- —C(=O)NH$_2$, —C(=O)NHR$^{K1}$, —C(=O)NR$^{K1}_2$,
- —NO$_2$, and
- —CN;

wherein each —$R^{K1}$ is independently saturated aliphatic C$_{1-4}$alkyl;
each —$R^M$ is independently azetidino, pyrrolidino, piperidino, piperazino, morpholino, azepino, or diazepino, and is optionally substituted with one or more substitutents independently selected from:
—F, —R$^{K2}$, —OH, —OR$^{K2}$, —OCF$_3$, —CN, and =O;
and
on nitrogen with one or more substituents independently selected from:
- —C(=O)R$^{K2}$, —R$^{K2}$, —C(=O)Ph, —S(=O)$_2$R$^{K2}$, —S(=O)$_2$Ph, —S(=O)$_2$NH$_2$,
- —S(=O)$_2$NHR$^{K2}$, —S(=O)$_2$NR$^{K2}_2$, and —S(=O)$_2$NHPh;

wherein each —$R^{K2}$ is independently saturated aliphatic C$_{1-4}$alkyl; and
each —$R^L$— is independently saturated aliphatic C$_{1-4}$alkylene.

38. A compound according to claim 37, wherein optional substituents on each of -J$^1$, -J$^2$, and -J$^3$ are independently selected from:

substituents on carbon, independently selected from:
- —$R^R$,
- —$R^Q$,
- —F,
- —OH, —$R^L$—OH,
- —OR$^P$, —$R^L$—OR$^P$,
- —NHC(=O)R$^P$, —NR$^P$C(=O)R$^P$,
- —C(=O)NH$_2$, —C(=O)NHR$^P$, —C(=O)NR$^P_2$, —C(=O)R$^M$,
- —CN,
- —$R^L$—S(=O)$_2$NH$_2$, —$R^L$—S(=O)$_2$NHR$^P$, —$R^L$—S(=O)$_2$NR$^P_2$, —$R^L$—S(=O)$_2$R$^M$,
- —$R^L$—NHC(=O)R$^P$, —$R^L$—NR$^P$C(=O)R$^P$,
- —$R^L$—NHS(=O)$_2$R$^P$, —$R^L$—NR$^P$S(=O)$_2$R$^P$, —$R^L$—NHS(=O)$_2$R$^M$, —$R^L$—NR$^P$S(=O)$_2$R$^M$,
- —$R^L$—C(=O)OH, —$R^L$—C(=O)OR$^P$,
- —$R^L$—C(=O)NH$_2$, —$R^L$—C(=O)NHR$^P$, —$R^L$—C(=O)NR$^P_2$, and —$R^L$—C(=O)R$^M$; and substituents on nitrogen, independently selected from:
- —$R^Q$,
- —$R^R$,
- —$R^L$—$R^R$,
- —C(=O)OR$^Q$, —C(=O)OR$^R$, —C(=O)O—$R^L$—$R^R$,
- —C(=O)R$^Q$, —C(=O)R$^R$, —C(=O)—$R^L$—$R^R$,
- —C(=O)—$R^L$—OH, —C(=O)—$R^L$—OR$^P$,
- —C(=O)NH$_2$, —C(=O)NHR$^P$, —C(=O)NR$^P_2$, —C(=O)R$^M$,
- —C(=O)—$R^L$—NH$_2$, —C(=O)—$R^L$—NHR$^P$,
- —C(=O)—$R^L$—NR$^P_2$, —C(=O)—$R^L$—R$^M$, —C(=O)—R$^L$—NHS(=O)$_2$R$^P$, —C(=O)—R$^L$—NR$^P$S(=O)$_2$R$^P$,
—C(=O)—R$^L$—NHS(=O)$_2$R$^M$, —C(=O)—R$^L$—NR$^P$S(=O)$_2$R$^M$,
—C(=O)—R$^L$—S(=O)$_2$NH$_2$, —C(=O)—R$^L$—S(=O)$_2$NHR$^P$,
—C(=O)—R$^L$—S(=O)$_2$NR$^P{}_2$, —C(=O)—R$^L$—S(=O)$_2$R$^M$,
—S(=O)$_2$NH$_2$, —S(=O)$_2$NHR$^P$, —S(=O)$_2$NR$^P{}_2$, —S(=O)$_2$R$^M$,
—S(=O)$_2$R$^P$,
—R$^L$—OH, —R$^L$—OR$^P$,
—R$^L$—NH$_2$, —R$^L$—NHR$^P$, —R$^L$—NR$^P{}_2$, —R$^L$—R$^M$,
—R$^L$—NHS(=O)$_2$R$^P$, —R$^L$—NR$^P$S(=O)$_2$R$^P$,
—R$^L$—S(=O)$_2$NH$_2$, —R$^L$—S(=O)$_2$NHR$^P$, —R$^L$—S(=O)$_2$NR$^P{}_2$, —R$^L$—S(=O)$_2$R$^M$, and
—R$^L$—S(=O)$_2$R$^P$.

39. A compound according to claim 37, wherein optional substituents on each of -J$^1$, -J$^2$, and -J$^3$ are independently selected from:
  substituents on carbon, independently selected from:
    —F, —OH, —OR$^X$, —R$^X$, —CF$_3$, —CN, phenyl, and pyridinyl, wherein phenyl and pyridinyl are optionally substituted with one or more groups selected from —F, —Cl, —Br, —OH, —OR$^X$, and —R$^X$; and
  substituents on nitrogen, independently selected from:
    —R$^X$, —S(=O)$_2$R$^X$ and —C(=O)R$^X$;
  wherein each —R$^X$ is independently saturated aliphatic C$_{1-4}$alkyl.

40. A compound according to claim 37, wherein optional substituents on each of -J$^1$, -J$^2$, and -J$^3$, are independently selected from:
  substituents on carbon, independently selected from:
    —F, —OH, —OMe, -Me, —CF$_3$, —CN, phenyl, and pyridinyl; and
  substituents on nitrogen, independently selected from:
    -Me, —S(=O)$_2$Me and —C(=O)Me.

41. A compound according to claim 1, wherein:
  -J$^1$ is independently unsubstituted;
  -J$^2$ is independently unsubstituted; and
  -J$^3$ is independently unsubstituted.

42. A compound according to claim 1, selected from the following compounds, and pharmaceutically acceptable salts thereof:

1. 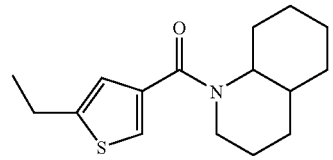 [SMILES: CCc1cc(C(=O)N2CCCC3CCCCC32)cs1] AA-009

2. 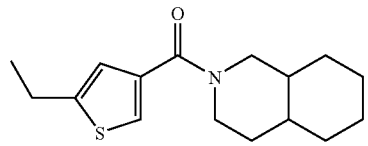 [SMILES: CCc1cc(C(=O)N2CCC3CCCCC3C2)cs1] AA-010

3. 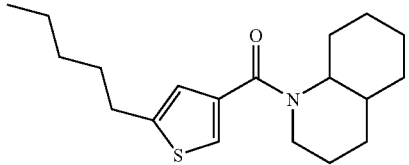 [SMILES: CCCCCc1cc(C(=O)N2CCCC3CCCCC32)cs1] AA-011

4. 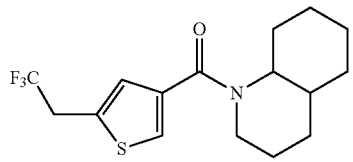 AA-012

CIS ISOMERS

5. 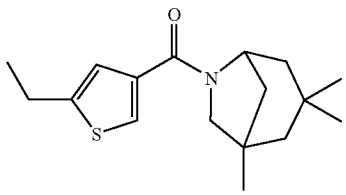 [SMILES: CCc1cc(C(=O)N2CC3(C)CC2CC(C)(C)C3)cs1] AA-014

-continued
| 6. | 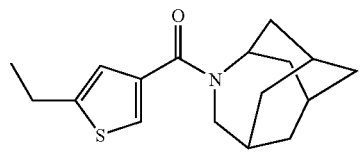 [SMILES: CCc1cc(C(=O)N2CC3CC4CC(C3)CC2C4)cs1] | AA-015 |
| 7. | 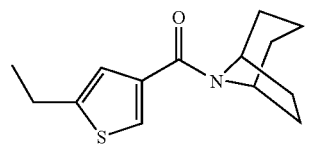 [SMILES: CCc1cc(C(=O)N2C3CCCC2CC3)cs1] | AA-016 |
| 8. | 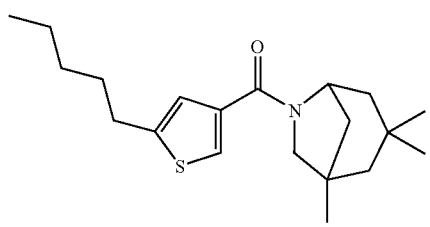 [SMILES: CCCCCc1cc(C(=O)N2CC3(C)CC2CC(C)(C)C3)cs1] | AA-017 |
| 9. | 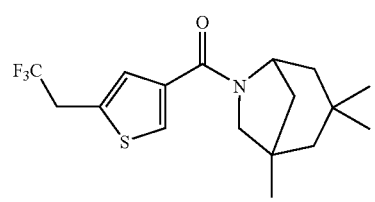 [SMILES: CC1(C)CC2CC(C)(CN2C(=O)c2csc(CC(F)(F)F)c2)C1] | AA-018 |
| 10. | 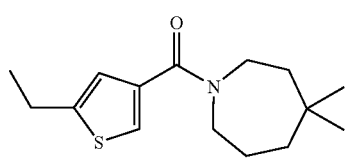 [SMILES: CCc1cc(C(=O)N2CCCC(C)(C)CC2)cs1] | AA-019 |
| 11. | 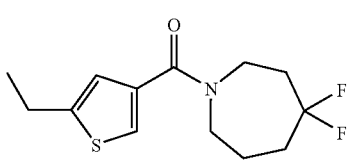 | AA-020 |
| 12. | 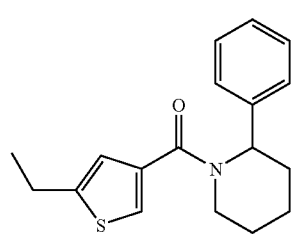 | AA-021 |
| 13. | 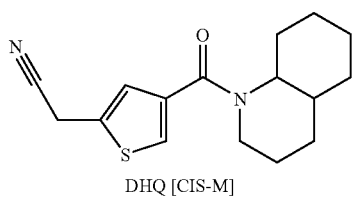 [SMILES: N#CCc1cc(C(=O)N2CCCC3CCCCC32)cs1]<br>DHQ [CIS-M] | AA-022 |

-continued
| | | |
|---|---|---|
| 14. | 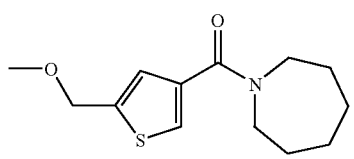 [SMILES: COCc1cc(C(=O)N2CCCCCC2)cs1] | BB-005 |
| 15. | 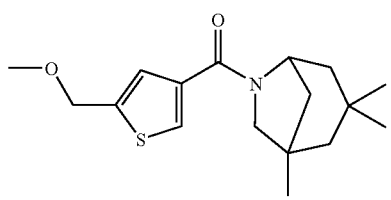 | BB-006 |
| 16. | 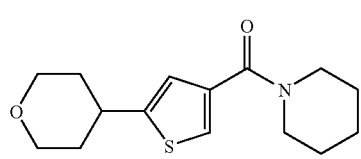 [SMILES: O=C(c1csc(C2CCOCC2)c1)N1CCCCC1] | CC-001 |
| 17. | 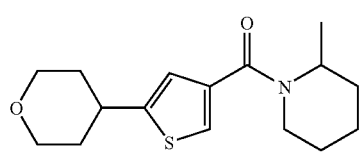 [SMILES: CC1CCCCN1C(=O)c1csc(C2CCOCC2)c1] | CC-002 |
| 18. | 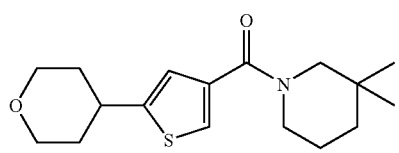 [SMILES: CC1(C)CCCN(C(=O)c2csc(C3CCOCC3)c2)C1] | CC-003 |
| 19. | 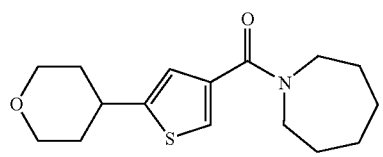 | CC-004 |
| 20. | 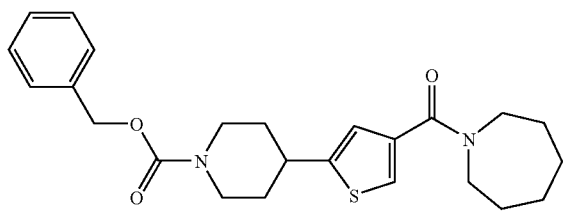 | CC-007 |
| 21. | 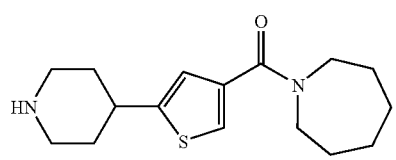 [SMILES: O=C(c1csc(C2CCNCC2)c1)N1CCCCCC1] | CC-008 |
| 22. | 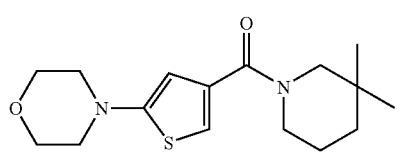 [SMILES: CC1(C)CCCN(C(=O)c2csc(N3CCOCC3)c2)C1] | CC-010 |

| | | |
|---|---|---|
| 23. | 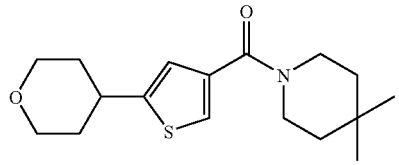 [SMILES: CC1(C)CCN(C(=O)c2csc(C3CCOCC3)c2)CC1] | CC-011 |
| 24. | 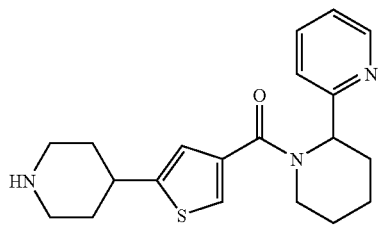 [SMILES: O=C(c1csc(C2CCNCC2)c1)N1CCCCC1c1ccccn1] | CC-012 |
| 25. | 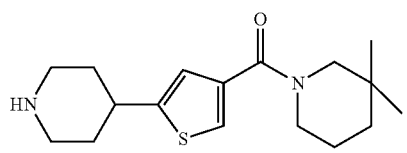 [SMILES: CC1(C)CCCN(C(=O)c2csc(C3CCNCC3)c2)C1] | CC-013 |
| 26. | 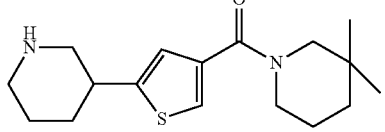 | CC-014 |
| 27. | 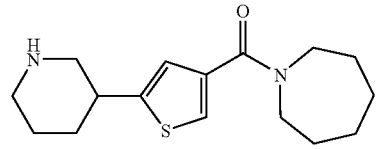 [SMILES: O=C(c1csc(C2CCCNC2)c1)N1CCCCCC1] | CC-015 |
| 28. | 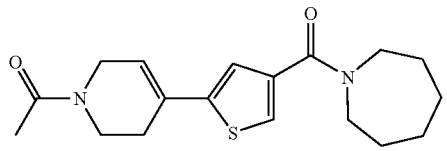 [SMILES: CC(=O)N1CC=C(c2cc(C(=O)N3CCCCCC3)cs2)CC1] | CC-016 |
| 29. | 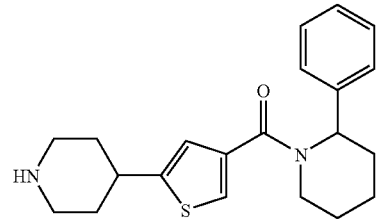 | CC-017 |
| 30. | 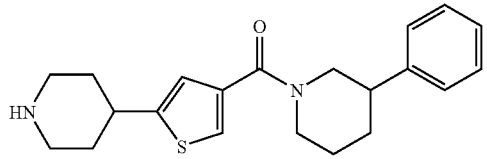 [SMILES: O=C(c1csc(C2CCNCC2)c1)N1CCCC(c2ccccc2)C1] | CC-018 |

-continued
| | | |
|---|---|---|
| 31. | 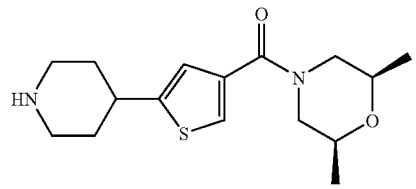 [SMILES: C[C@@H]1CN(C(=O)c2csc(C3CCNCC3)c2)C[C@H](C)O1] | CC-019 |
| 32. | 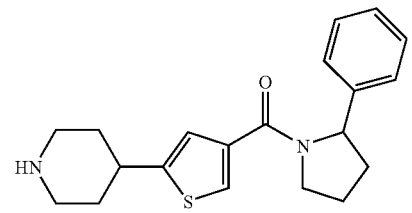 [SMILES: O=C(c1csc(C2CCNCC2)c1)N1CCCC1c1ccccc1] | CC-020 |
| 33. | 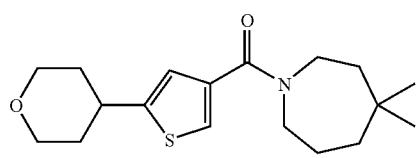 [SMILES: CC1(C)CCCN(C(=O)c2csc(C3CCOCC3)c2)CC1] | CC-021 |
| 34. | 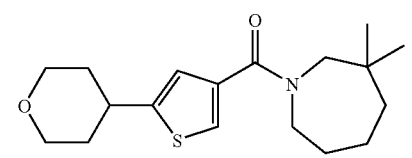 [SMILES: CC1(C)CCCCN(C(=O)c2csc(C3CCOCC3)c2)C1] | CC-022 |
| 35. | 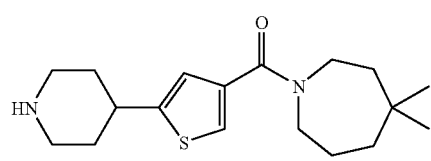 | CC-023 |
| 36. | 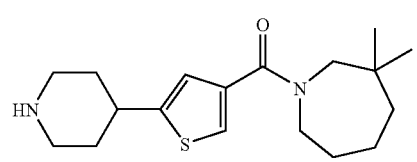 [SMILES: CC1(C)CCCCN(C(=O)c2csc(C3CCNCC3)c2)C1] | CC-024 |
| 37. | 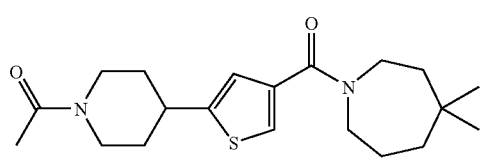 [SMILES: CC(=O)N1CCC(c2cc(C(=O)N3CCCC(C)(C)CC3)cs2)CC1] | CC-025 |
| 38. | 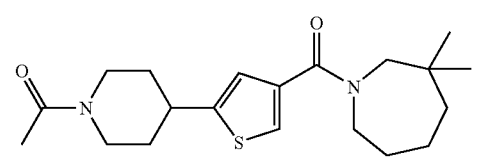 [SMILES: CC(=O)N1CCC(c2cc(C(=O)N3CCCCC(C)(C)C3)cs2)CC1] | CC-026 |
| 39. | 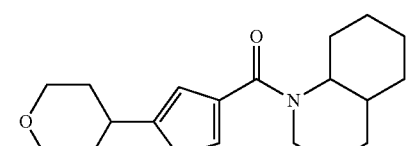 | CC-027 |

-continued
| | | |
|---|---|---|
| 40. | 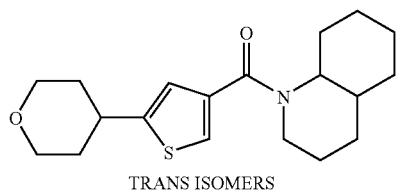 [SMILES: O=C(c1csc(C2CCOCC2)c1)N1CCCC2CCCCC21]  TRANS ISOMERS | CC-028 |
| 41. | 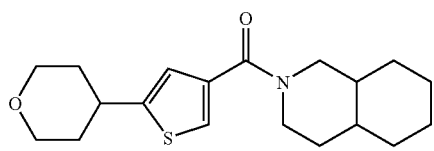 [SMILES: O=C(c1csc(C2CCOCC2)c1)N1CCC2CCCCC2C1] | CC-029 |
| 42. | 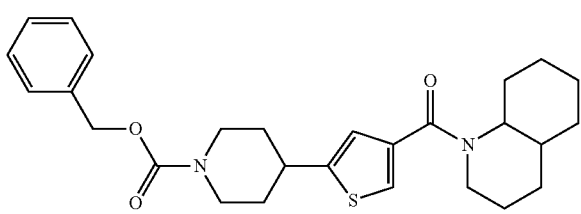 [SMILES: O=C(OCc1ccccc1)N1CCC(c2cc(C(=O)N3CCCC4CCCCC43)cs2)CC1] | CC-032 |
| 43. | 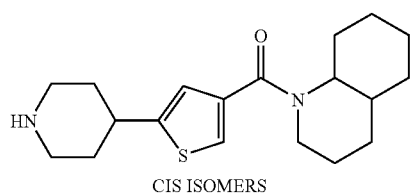 [SMILES: O=C(c1csc(C2CCNCC2)c1)N1CCCC2CCCCC21]  CIS ISOMERS | CC-033 |
| 44. | 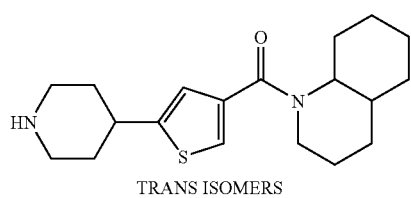 [SMILES: O=C(c1csc(C2CCNCC2)c1)N1CCCC2CCCCC21]  TRANS ISOMERS | CC-034 |
| 45. | 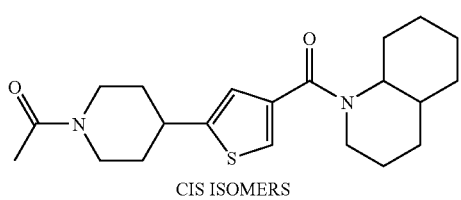 [SMILES: CC(=O)N1CCC(c2cc(C(=O)N3CCCC4CCCCC43)cs2)CC1]  CIS ISOMERS | CC-035 |
| 46. | 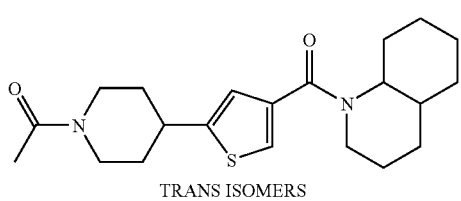 [SMILES: CC(=O)N1CCC(c2cc(C(=O)N3CCCC4CCCCC43)cs2)CC1]  TRANS ISOMERS | CC-036 |
| 47. | 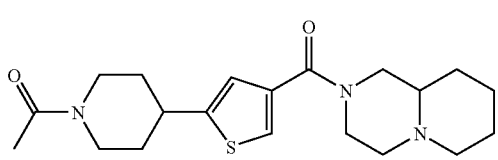 [SMILES: CC(=O)N1CCC(c2cc(C(=O)N3CCN4CCCCC4C3)cs2)CC1] | CC-037 |

| | | |
|---|---|---|
| 48. | 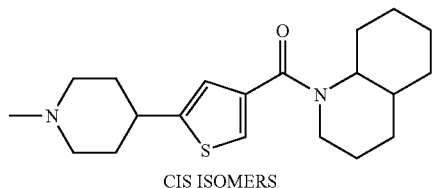 [SMILES: CN1CCC(c2cc(C(=O)N3CCCC4CCCCC43)cs2)CC1]<br>CIS ISOMERS | CC-038 |
| 49. | 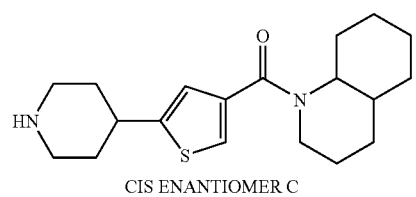 [SMILES: O=C(c1csc(C2CCNCC2)c1)N1CCCC2CCCCC21]<br>CIS ENANTIOMER C | CC-039 |
| 50. | 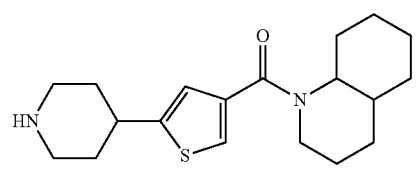 [SMILES: O=C(c1csc(C2CCNCC2)c1)N1CCCC2CCCCC21] | CC-040 |
| 51. | 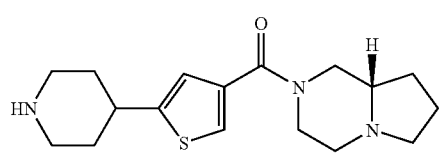 [SMILES: O=C(c1csc(C2CCNCC2)c1)N1CCN2CCC[C@H]2C1] | CC-041 |
| 52. | 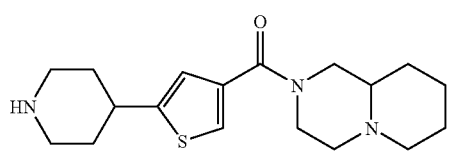 [SMILES: O=C(c1csc(C2CCNCC2)c1)N1CCN2CCCCC2C1] | CC-042 |
| 53. | 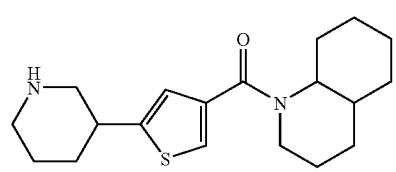 [SMILES: O=C(c1csc(C2CCCNC2)c1)N1CCCC2CCCCC21] | CC-043 |
| 54. | 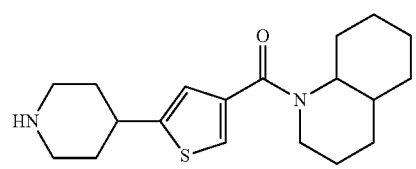 [SMILES: O=C(c1csc(C2CCNCC2)c1)N1CCCC2CCCCC21] | CC-044 |
| 55. | 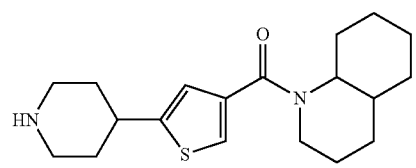 [SMILES: O=C(c1csc(C2CCNCC2)c1)N1CCCC2CCCCC21] | CC-045 |
| 56. | 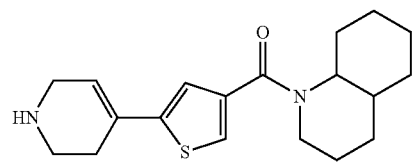 [SMILES: O=C(c1csc(C2=CCNCC2)c1)N1CCCC2CCCCC21] | CC-046 |

| | | |
|---|---|---|
| 57. | 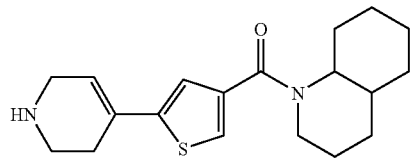<br>TRANS ISOMERS | CC-047 |
| 58. | 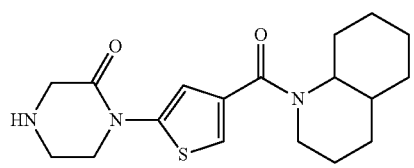 [SMILES: O=C1CNCCN1c1cc(C(=O)N2CCCC3CCCCC32)cs1] | CC-048 |
| 59. | 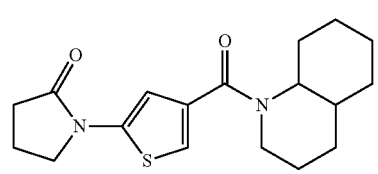 [SMILES: O=C1CCCN1c1cc(C(=O)N2CCCC3CCCCC32)cs1] | CC-049 |
| 60. | 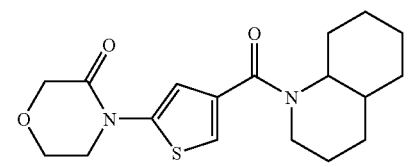<br>CIS ISOMERS | CC-050 |
| 61. | 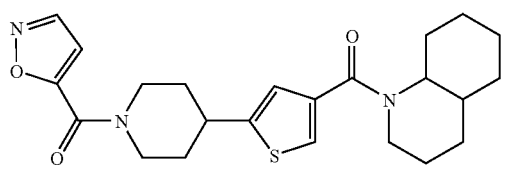<br>CIS ISOMERS | CC-051 |
| 62. | 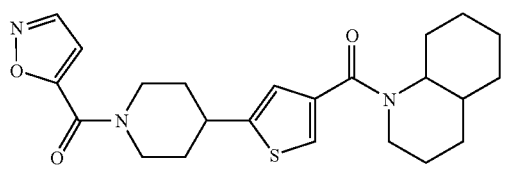<br>TRANS ISOMERS | CC-052 |
| 63. | 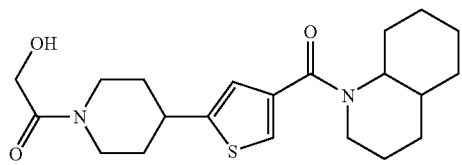<br>CIS ISOMERS | CC-053 |
| 64. | 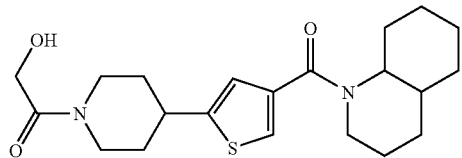<br>TRANS ISOMERS | CC-054 |

| | | |
|---|---|---|
| 65. | 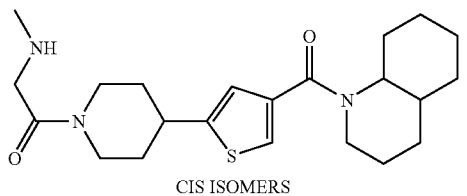 [SMILES: CNCC(=O)N1CCC(c2cc(C(=O)N3CCCC4CCCCC43)cs2)CC1] CIS ISOMERS | CC-055 |
| 66. | 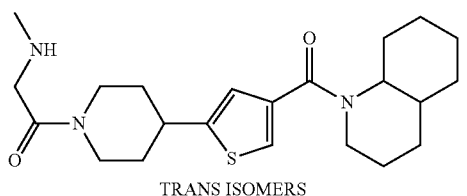 [SMILES: CNCC(=O)N1CCC(c2cc(C(=O)N3CCCC4CCCCC43)cs2)CC1] TRANS ISOMERS | CC-056 |
| 67. | 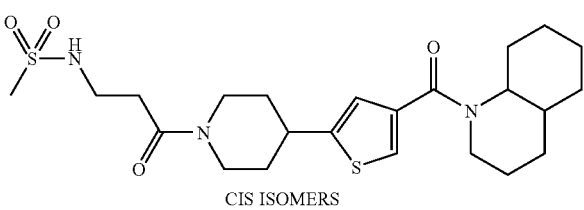 [SMILES: CS(=O)(=O)NCCC(=O)N1CCC(c2cc(C(=O)N3CCCC4CCCCC43)cs2)CC1] CIS ISOMERS | CC-057 |
| 68. | 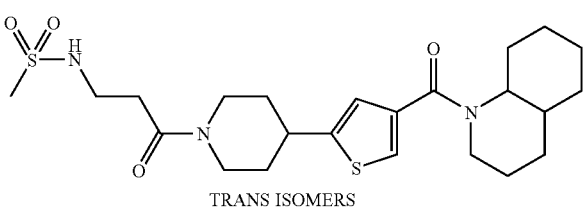 [SMILES: CS(=O)(=O)NCCC(=O)N1CCC(c2cc(C(=O)N3CCCC4CCCCC43)cs2)CC1] TRANS ISOMERS | CC-058 |
| 69. | 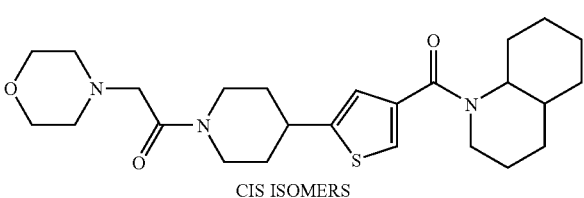 [SMILES: O=C(CN1CCOCC1)N1CCC(c2cc(C(=O)N3CCCC4CCCCC43)cs2)CC1] CIS ISOMERS | CC-059 |
| 70. | 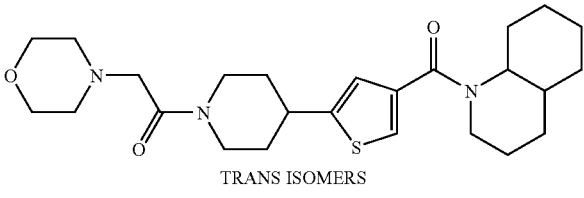 [SMILES: O=C(CN1CCOCC1)N1CCC(c2cc(C(=O)N3CCCC4CCCCC43)cs2)CC1] TRANS ISOMERS | CC-060 |
| 71. | 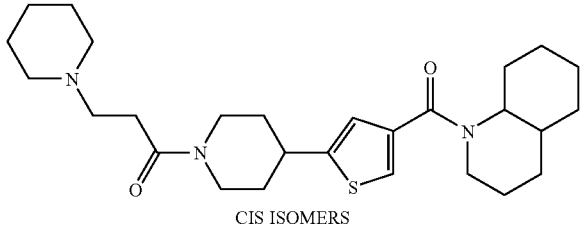 [SMILES: O=C(CCN1CCCCC1)N1CCC(c2cc(C(=O)N3CCCC4CCCCC43)cs2)CC1] CIS ISOMERS | CC-061 |

| | | |
|---|---|---|
| 72. | 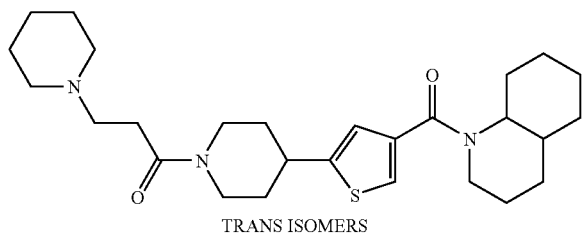 [SMILES: O=C(CCN1CCCCC1)N1CCC(c2cc(C(=O)N3CCCC4CCCCC43)cs2)CC1] TRANS ISOMERS | CC-062 |
| 73. | 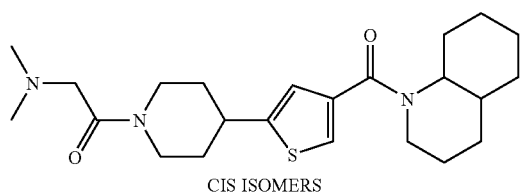 [SMILES: CN(C)CC(=O)N1CCC(c2cc(C(=O)N3CCCC4CCCCC43)cs2)CC1] CIS ISOMERS | CC-063 |
| 74. | 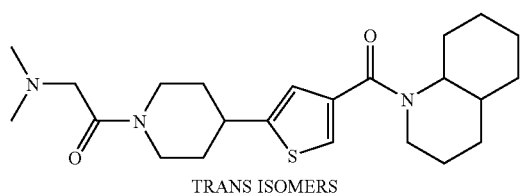 [SMILES: CN(C)CC(=O)N1CCC(c2cc(C(=O)N3CCCC4CCCCC43)cs2)CC1] TRANS ISOMERS | CC-064 |
| 75. | 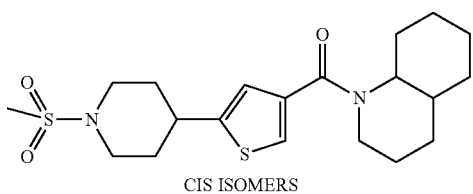 [SMILES: CS(=O)(=O)N1CCC(c2cc(C(=O)N3CCCC4CCCCC43)cs2)CC1] CIS ISOMERS | CC-065 |
| 76. | 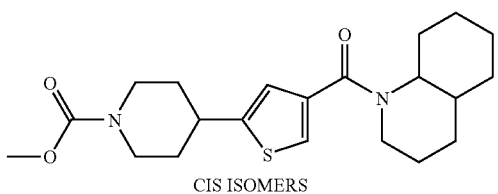 [SMILES: COC(=O)N1CCC(c2cc(C(=O)N3CCCC4CCCCC43)cs2)CC1] CIS ISOMERS | CC-066 |
| 77. | 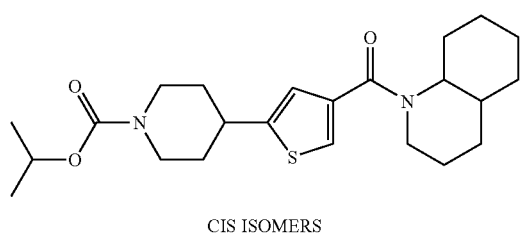 [SMILES: CC(C)OC(=O)N1CCC(c2cc(C(=O)N3CCCC4CCCCC43)cs2)CC1] CIS ISOMERS | CC-067 |
| 78. | 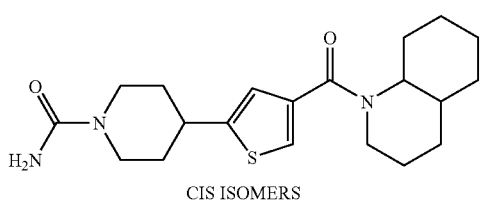 [SMILES: NC(=O)N1CCC(c2cc(C(=O)N3CCCC4CCCCC43)cs2)CC1] CIS ISOMERS | CC-068 |

-continued
| | | |
|---|---|---|
| 79. | 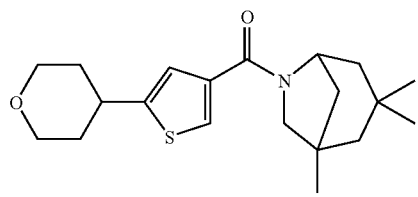 [SMILES: CC1(C)CC2CC(C)(CN2C(=O)c2csc(C3CCOCC3)c2)C1] | CC-069 |
| 80. | 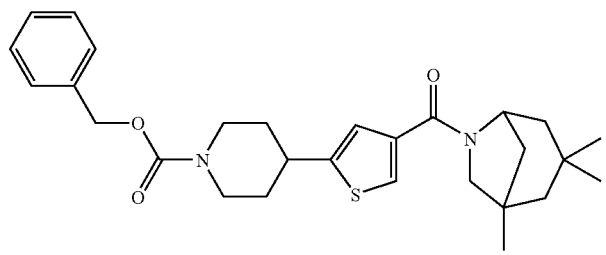 [SMILES: CC1(C)CC2CC(C)(CN2C(=O)c2csc(C3CCN(C(=O)OCc4ccccc4)CC3)c2)C1] | CC-071 |
| 81. | 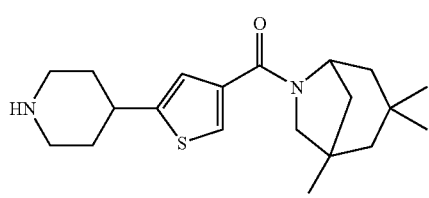 [SMILES: CC1(C)CC2CC(C)(CN2C(=O)c2csc(C3CCNCC3)c2)C1] | CC-072 |
| 82. | 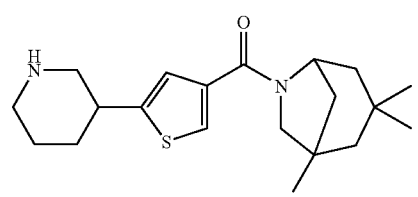 [SMILES: CC1(C)CC2CC(C)(CN2C(=O)c2csc(C3CCCNC3)c2)C1] | CC-073 |
| 83. | 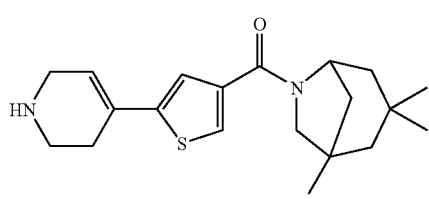 [SMILES: CC1(C)CC2CC(C)(CN2C(=O)c2csc(C3=CCNCC3)c2)C1] | CC-074 |
| 84. | 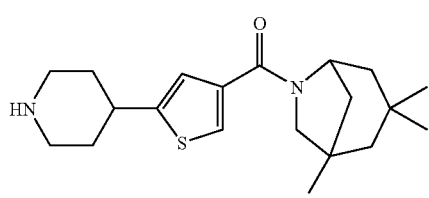<br>ENANTIOMER G | CC-075 |
| 85. | 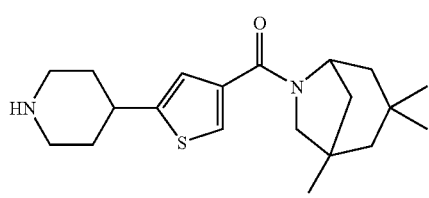<br>ENANTIOMER H | CC-076 |

-continued
| | | |
|---|---|---|
| 86. | 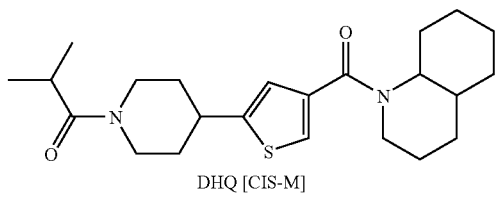 [SMILES: CC(C)C(=O)N1CCC(c2cc(C(=O)N3CCCC4CCCCC43)cs2)CC1] DHQ [CIS-M] | CC-081 |
| 87. | 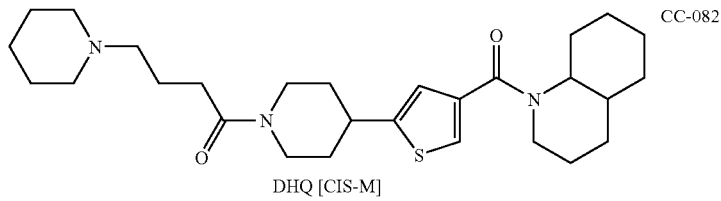 DHQ [CIS-M] | CC-082 |
| 88. | 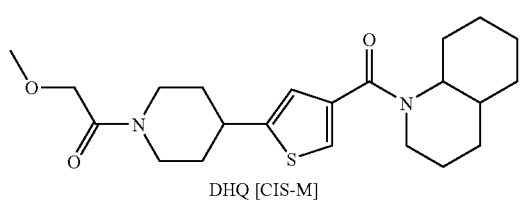 [SMILES: COCC(=O)N1CCC(c2cc(C(=O)N3CCCC4CCCCC43)cs2)CC1] DHQ [CIS-M] | CC-083 |
| 89. | 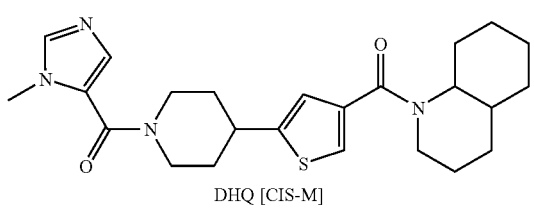 [SMILES: Cn1cncc1C(=O)N1CCC(c2cc(C(=O)N3CCCC4CCCCC43)cs2)CC1] DHQ [CIS-M] | CC-084 |
| 90. | 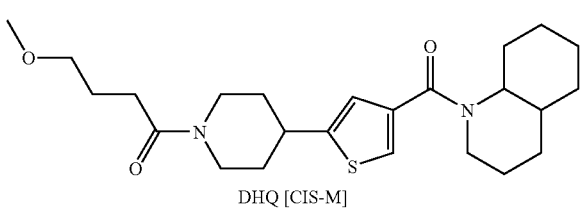 [SMILES: COCCCC(=O)N1CCC(c2cc(C(=O)N3CCCC4CCCCC43)cs2)CC1] DHQ [CIS-M] | CC-085 |
| 91. | 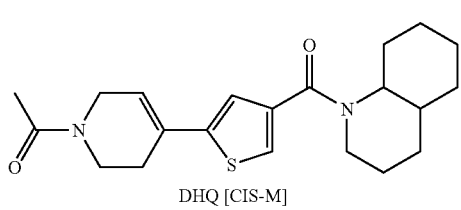 [SMILES: CC(=O)N1CC=C(c2cc(C(=O)N3CCCC4CCCCC43)cs2)CC1] DHQ [CIS-M] | CC-086 |
| 92. | 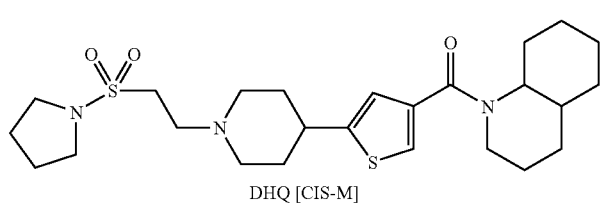 [SMILES: O=C(c1csc(C2CCN(CCS(=O)(=O)N3CCCC3)CC2)c1)N1CCCC2CCCCC21] DHQ [CIS-M] | CC-087 |
| 93. | 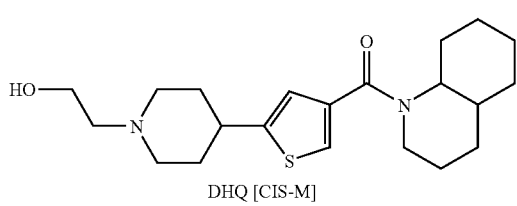 [SMILES: O=C(c1csc(C2CCN(CCO)CC2)c1)N1CCCC2CCCCC21] DHQ [CIS-M] | CC-088 |

| | | |
|---|---|---|
| 94. | 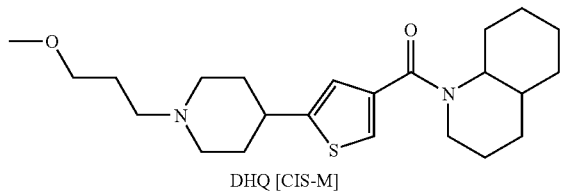 [SMILES: COCCCN1CCC(c2cc(C(=O)N3CCCC4CCCCC43)cs2)CC1] DHQ [CIS-M] | CC-089 |
| 95. | 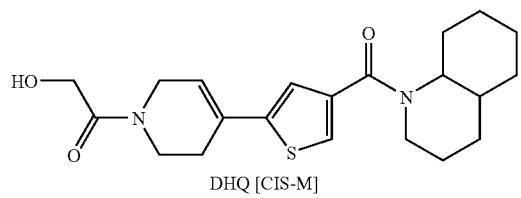 [SMILES: O=C(CO)N1CC=C(c2cc(C(=O)N3CCCC4CCCCC43)cs2)CC1] DHQ [CIS-M] | CC-090 |
| 96. | 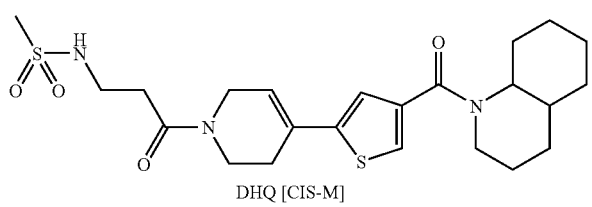 [SMILES: CS(=O)(=O)NCCC(=O)N1CC=C(c2cc(C(=O)N3CCCC4CCCCC43)cs2)CC1] DHQ [CIS-M] | CC-091 |
| 97. | 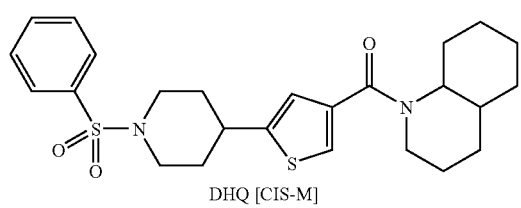 [SMILES: O=C(c1csc(C2CCN(S(=O)(=O)c3ccccc3)CC2)c1)N1CCCC2CCCCC21] DHQ [CIS-M] | CC-092 |
| 98. | 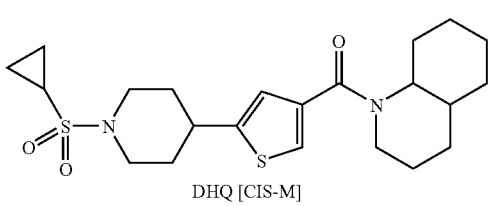 [SMILES: O=C(c1csc(C2CCN(S(=O)(=O)C3CC3)CC2)c1)N1CCCC2CCCCC21] DHQ [CIS-M] | CC-093 |
| 99. | 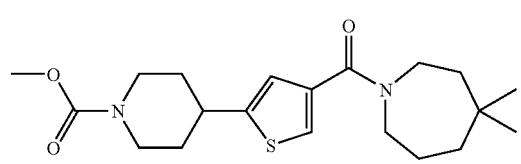 | CC-094 |
| 100. | 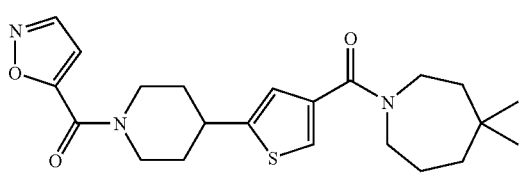 [SMILES: CC1(C)CCCN(C(=O)c2csc(C3CCN(C(=O)c4ccno4)CC3)c2)CC1] | CC-095 |
| 101. | 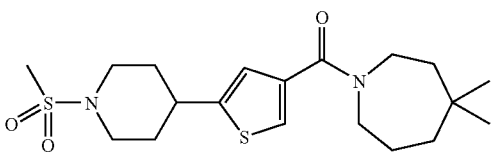 [SMILES: CC1(C)CCCN(C(=O)c2csc(C3CCN(S(C)(=O)=O)CC3)c2)CC1] | CC-096 |

-continued
| | | |
|---|---|---|
| 102. | 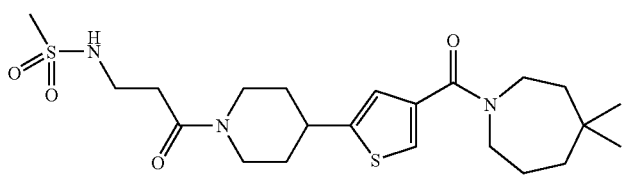 [SMILES: CC1(C)CCCN(C(=O)c2csc(C3CCN(C(=O)CCNS(C)(=O)=O)CC3)c2)CC1] | CC-097 |
| 103. | 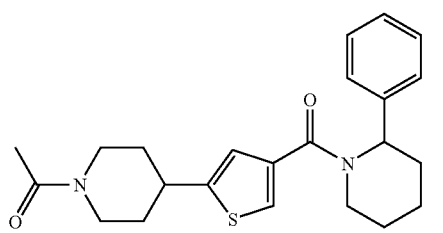 [SMILES: CC(=O)N1CCC(c2cc(C(=O)N3CCCCC3c3ccccc3)cs2)CC1] | CC-098 |
| 104. | 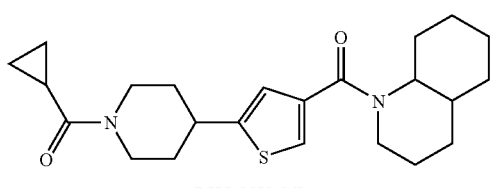
DHQ [CIS-M] | CC-099 |
| 105. | 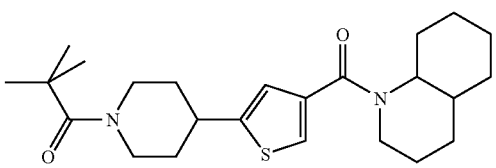
DHQ [CIS-M] | CC-100 |
| 106. | 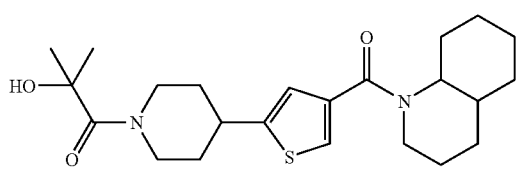
DHQ [CIS-M] | CC-101 |
| 107. | 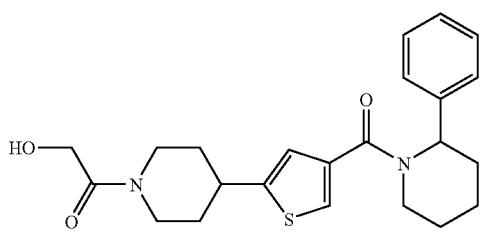 [SMILES: O=C(CO)N1CCC(c2cc(C(=O)N3CCCCC3c3ccccc3)cs2)CC1] | CC-102 |
| 108. | 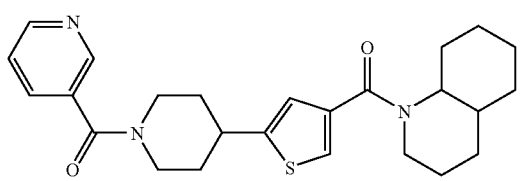
DHQ [CIS-M] | CC-103 |

| | | |
|---|---|---|
| 109. | 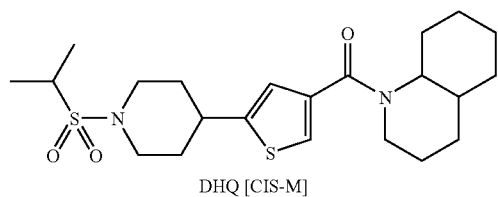 [SMILES: CC(C)S(=O)(=O)N1CCC(c2cc(C(=O)N3CCCC4CCCCC43)cs2)CC1]<br>DHQ [CIS-M] | CC-104 |
| 110. | 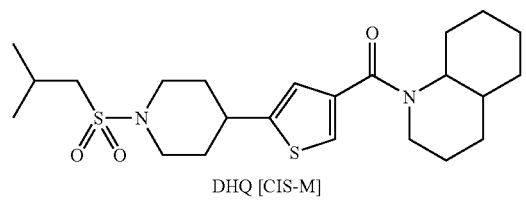 [SMILES: CC(C)CS(=O)(=O)N1CCC(c2cc(C(=O)N3CCCC4CCCCC43)cs2)CC1]<br>DHQ [CIS-M] | CC-105 |
| 111. | 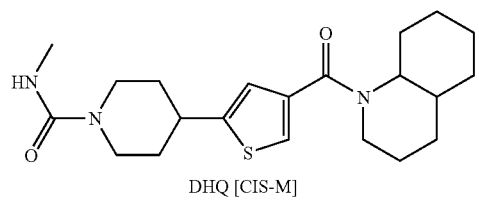 [SMILES: CNC(=O)N1CCC(c2cc(C(=O)N3CCCC4CCCCC43)cs2)CC1]<br>DHQ [CIS-M] | CC-106 |
| 112. | 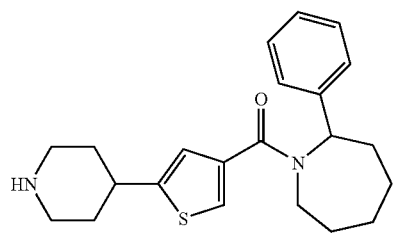 [SMILES: O=C(c1csc(C2CCNCC2)c1)N1CCCCCC1c1ccccc1] | CC-107 |
| 113. | 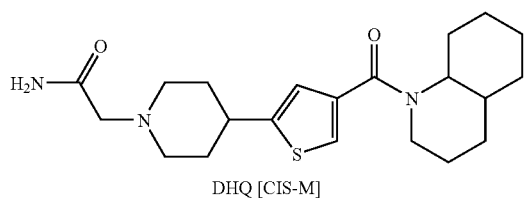 [SMILES: NC(=O)CN1CCC(c2cc(C(=O)N3CCCC4CCCCC43)cs2)CC1]<br>DHQ [CIS-M] | CC-108 |
| 114. | 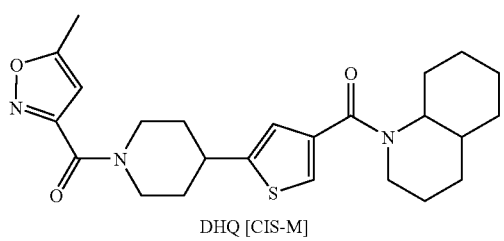 [SMILES: Cc1cc(C(=O)N2CCC(c3cc(C(=O)N4CCCC5CCCCC54)cs3)CC2)no1]<br>DHQ [CIS-M] | CC-109 |
| 115. | 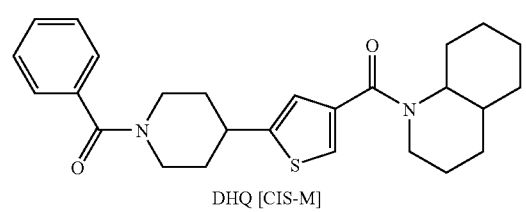 [SMILES: O=C(c1ccccc1)N1CCC(c2cc(C(=O)N3CCCC4CCCCC43)cs2)CC1]<br>DHQ [CIS-M] | CC-110 |

-continued
| | | |
|---|---|---|
| 116. | 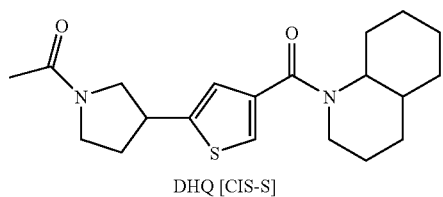 [SMILES: CC(=O)N1CCC(c2cc(C(=O)N3CCCC4CCCCC43)cs2)C1]<br>DHQ [CIS-S] | CC-111 |
| 117. | 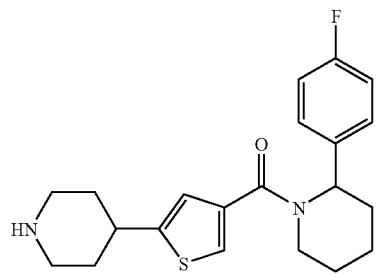 [SMILES: O=C(c1csc(C2CCNCC2)c1)N1CCCCC1c1ccc(F)cc1] | CC-112 |
| 118. | 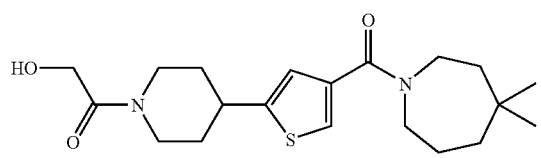 [SMILES: CC1(C)CCCN(C(=O)c2csc(C3CCN(C(=O)CO)CC3)c2)CC1] | CC-113 |
| 119. | 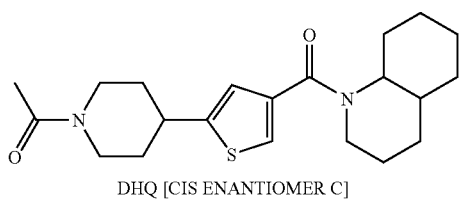 [SMILES: CC(=O)N1CCC(c2cc(C(=O)N3CCCC4CCCCC43)cs2)CC1]<br>DHQ [CIS ENANTIOMER C] | CC-114 |
| 120. | 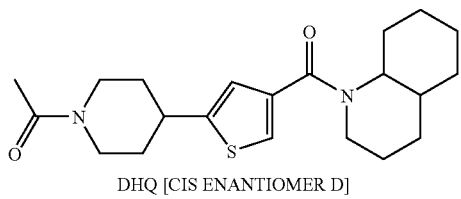 [SMILES: CC(=O)N1CCC(c2cc(C(=O)N3CCCC4CCCCC43)cs2)CC1]<br>DHQ [CIS ENANTIOMER D] | CC-115 |
| 121. | 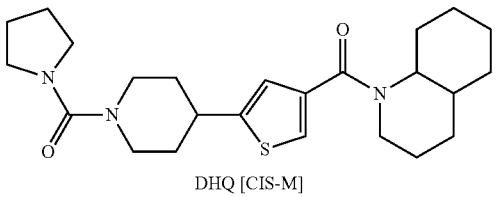 [SMILES: O=C(N1CCCC1)N1CCC(c2cc(C(=O)N3CCCC4CCCCC43)cs2)CC1]<br>DHQ [CIS-M] | CC-116 |
| 122. | 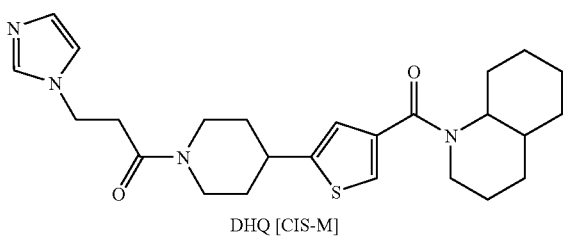 [SMILES: O=C(CCn1ccnc1)N1CCC(c2cc(C(=O)N3CCCC4CCCCC43)cs2)CC1]<br>DHQ [CIS-M] | CC-117 |

-continued
| | | |
|---|---|---|
| 123. | 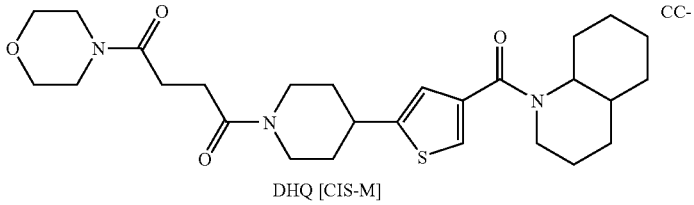 DHQ [CIS-M] | CC-118 |
| 124. | 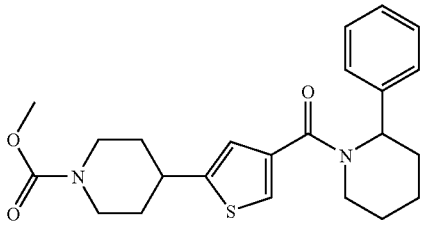 [SMILES: COC(=O)N1CCC(c2cc(C(=O)N3CCCCC3c3ccccc3)cs2)CC1] | CC-119 |
| 125. | 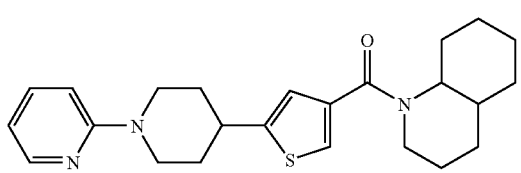 DHQ [CIS-M] | CC-120 |
| 126. | 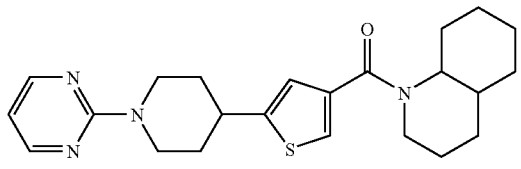 DHQ [CIS-M] | CC-121 |
| 127. | 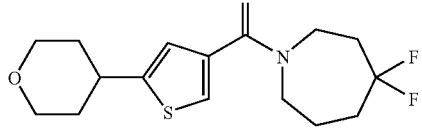 | CC-122 |
| 128. | 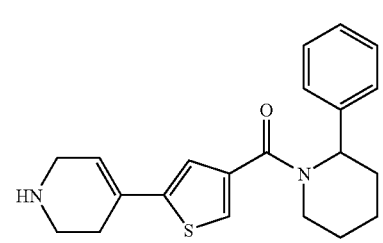 [SMILES: O=C(c1csc(C2=CCNCC2)c1)N1CCCCC1c1ccccc1] | CC-123 |
| 129. | 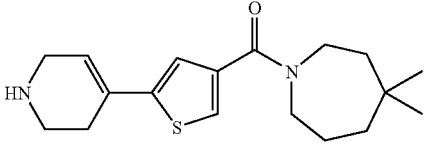 | CC-124 |
| 130. | 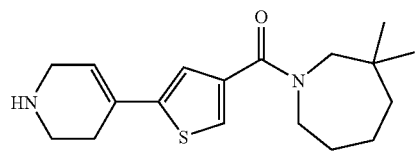 [SMILES: CC1(C)CCCCN(C(=O)c2csc(C3=CCNCC3)c2)C1] | CC-125 |

| | | |
|---|---|---|
| 131. | 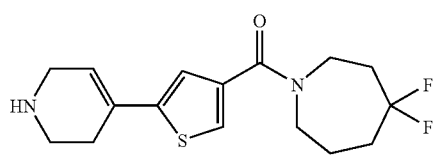 [SMILES: O=C(c1csc(C2=CCNCC2)c1)N1CCCC(F)(F)CC1] | CC-126 |
| 132. | 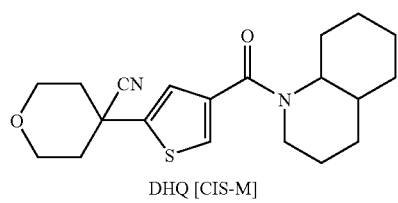 [SMILES: N#CC1(c2cc(C(=O)N3CCCC4CCCCC43)cs2)CCOCC1]  DHQ [CIS-M] | CC-127 |
| 133. | 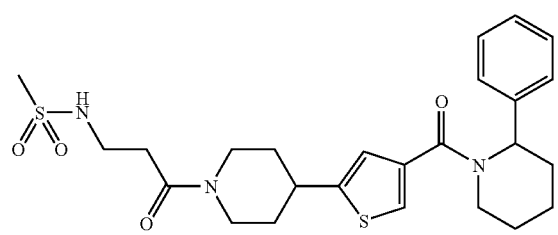 [SMILES: CS(=O)(=O)NCCC(=O)N1CCC(c2cc(C(=O)N3CCCCC3c3ccccc3)cs2)CC1] | CC-128 |
| 134. | 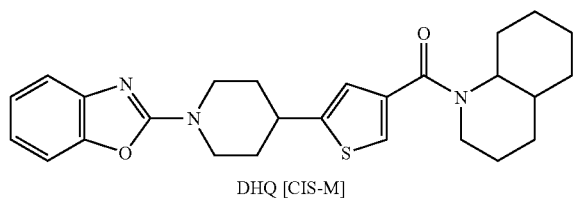 [SMILES: O=C(c1csc(C2CCN(c3nc4ccccc4o3)CC2)c1)N1CCCC2CCCCC21]  DHQ [CIS-M] | CC-129 |
| 135. | 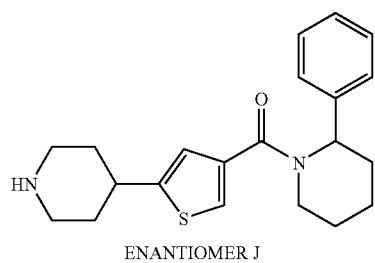 [SMILES: O=C(c1csc(C2CCNCC2)c1)N1CCCCC1c1ccccc1]  ENANTIOMER J | CC-130 |
| 136. | 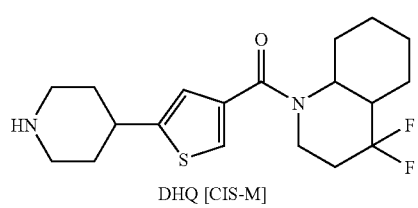 [SMILES: O=C(c1csc(C2CCNCC2)c1)N1CCC(F)(F)C2CCCCC21]  DHQ [CIS-M] | CC-131 |
| 137. | 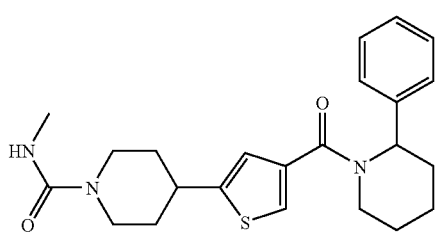 [SMILES: CNC(=O)N1CCC(c2cc(C(=O)N3CCCCC3c3ccccc3)cs2)CC1] | CC-132 |

-continued
| | | |
|---|---|---|
| 138. | 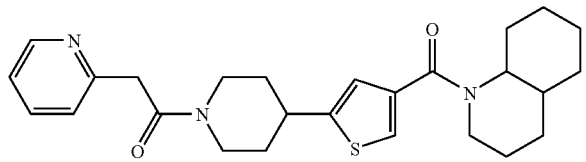 DHQ [CIS-M] | CC-133 |
| 139. | 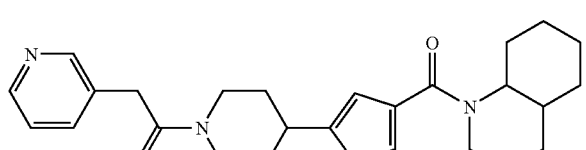 DHQ [CIS-M] | CC-134 |
| 140. | 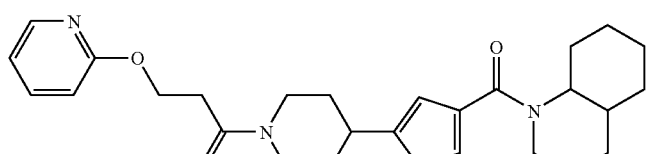 DHQ [CIS-M] | CC-135 |
| 141. | 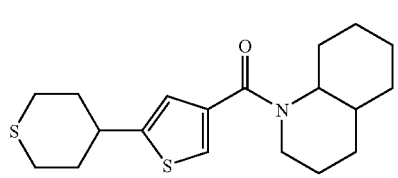 DHQ [CIS-M] | CC-136 |
| 142. | 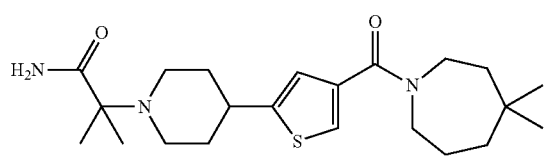 [SMILES: CC1(C)CCCN(C(=O)c2csc(C3CCN(C(C)(C)C(N)=O)CC3)c2)CC1] | CC-137 |
| 143. | 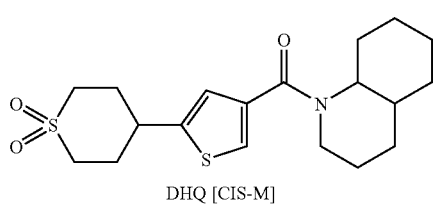 [SMILES: O=C(c1csc(C2CCS(=O)(=O)CC2)c1)N1CCCC2CCCCC21] DHQ [CIS-M] | CC-138 |
| 144. | 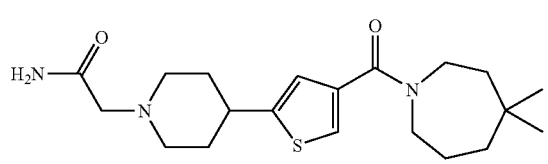 [SMILES: CC1(C)CCCN(C(=O)c2csc(C3CCN(CC(N)=O)CC3)c2)CC1] | CC-139 |
| 145. | 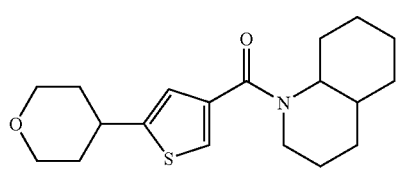 DHQ [CIS ENANTOMER L] | CC-140 |

| | | |
|---|---|---|
| 146. | 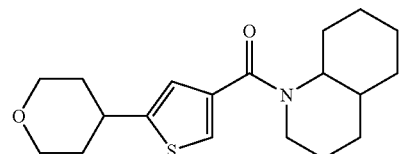<br>DHQ [CIS ENANTIOMER K] | CC-141 |
| 147. | 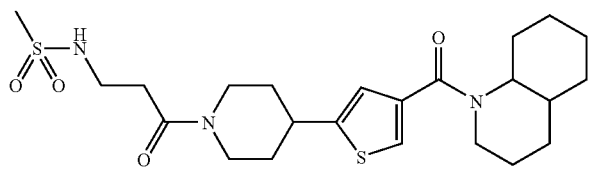<br>DHQ [CIS ENANTIOMER D] | CC-142 |
| 148. | 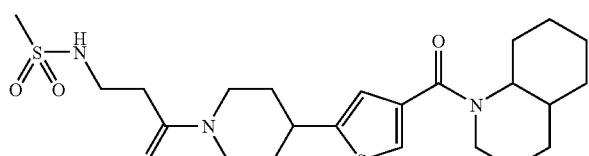<br>DHQ [CIS ENANTIOMER C] | CC-143 |
| 149. | 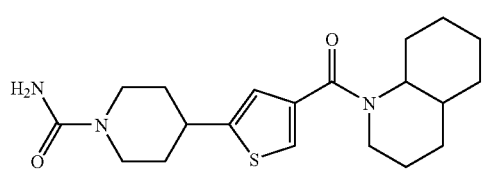<br>DHQ [CIS ENANTIOMER C] | CC-144 |
| 150. | 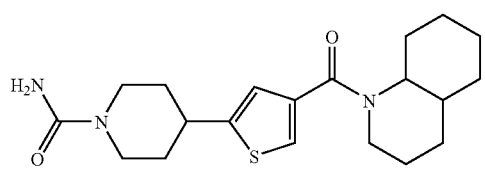<br>DHQ [CIS ENANTIOMER D] | CC-145 |
| 151. | 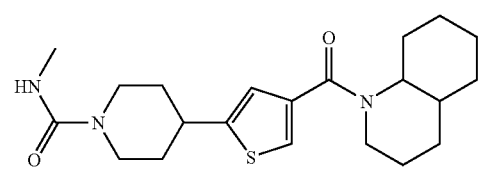<br>DHQ [CIS ENANTIOMER D] | CC-146 |
| 152. | 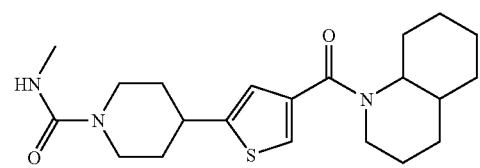<br>DHQ [CIS ENANTIOMER C] | CC-147 |

| | | |
|---|---|---|
| 153. | 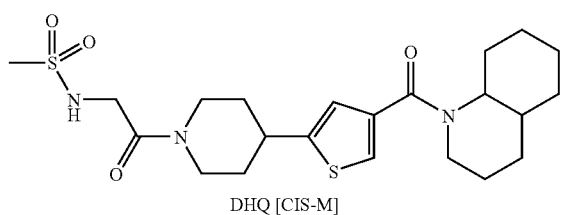 [SMILES: CS(=O)(=O)NCC(=O)N1CCC(c2cc(C(=O)N3CCCC4CCCCC43)cs2)CC1]<br>DHQ [CIS-M] | CC-148 |
| 154. | 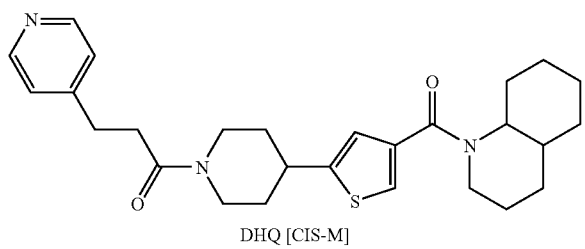 [SMILES: O=C(CCc1ccncc1)N1CCC(c2cc(C(=O)N3CCCC4CCCCC43)cs2)CC1]<br>DHQ [CIS-M] | CC-149 |
| 155. | 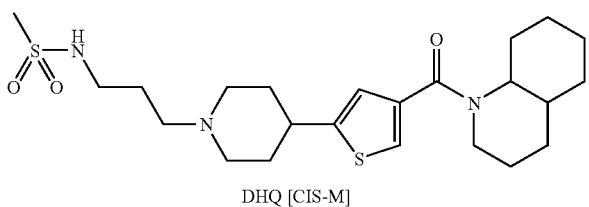 [SMILES: CS(=O)(=O)NCCCN1CCC(c2cc(C(=O)N3CCCC4CCCCC43)cs2)CC1]<br>DHQ [CIS-M] | CC-150 |
| 156. | 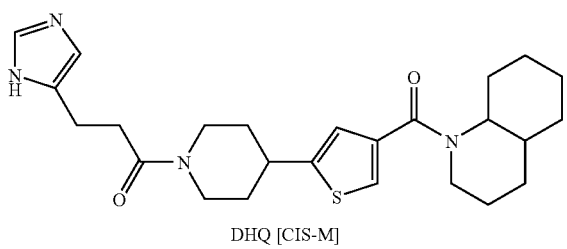 [SMILES: O=C(CCc1cnc[nH]1)N1CCC(c2cc(C(=O)N3CCCC4CCCCC43)cs2)CC1]<br>DHQ [CIS-M] | CC-151 |
| 157. | 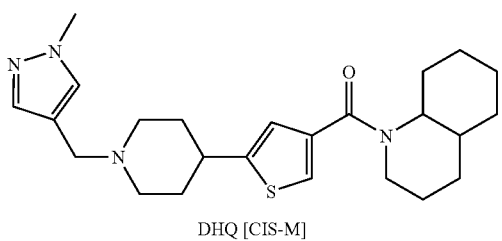 [SMILES: Cn1cc(CN2CCC(c3cc(C(=O)N4CCCC5CCCCC54)cs3)CC2)cn1]<br>DHQ [CIS-M] | CC-152 |
| 158. | 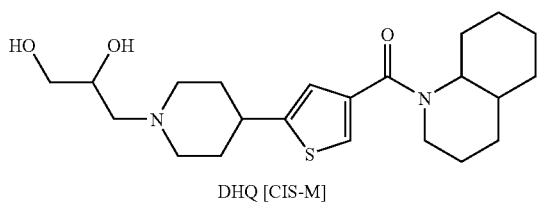 [SMILES: O=C(c1csc(C2CCN(CC(O)CO)CC2)c1)N1CCCC2CCCCC21]<br>DHQ [CIS-M] | CC-153 |
| 159. | 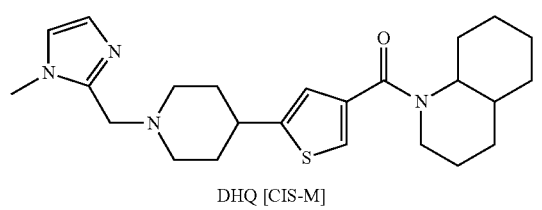 [SMILES: Cn1ccnc1CN1CCC(c2cc(C(=O)N3CCCC4CCCCC43)cs2)CC1]<br>DHQ [CIS-M] | CC-154 |

-continued
160. 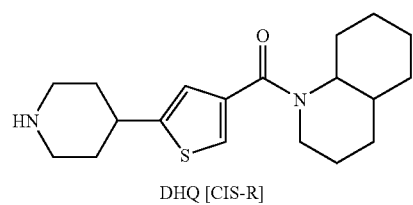 [SMILES: O=C(c1csc(C2CCNCC2)c1)N1CCCC2CCCCC21]
DHQ [CIS-R]
CC-155
161. 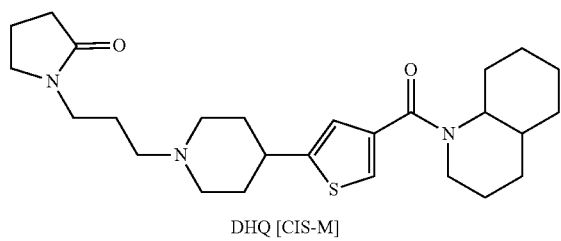 [SMILES: O=C1CCCN1CCCN1CCC(c2cc(C(=O)N3CCCC4CCCCC43)cs2)CC1]
DHQ [CIS-M]
CC-156
162. 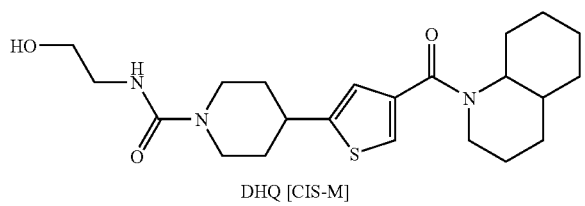 [SMILES: O=C(NCCO)N1CCC(c2cc(C(=O)N3CCCC4CCCCC43)cs2)CC1]
DHQ [CIS-M]
CC-157
163. 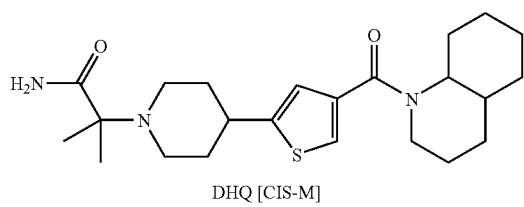 [SMILES: CC(C)(C(N)=O)N1CCC(c2cc(C(=O)N3CCCC4CCCCC43)cs2)CC1]
DHQ [CIS-M]
CC-158
164. 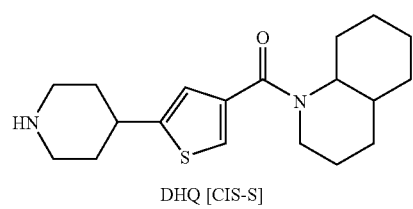
DHQ [CIS-S]
CC-159
165. 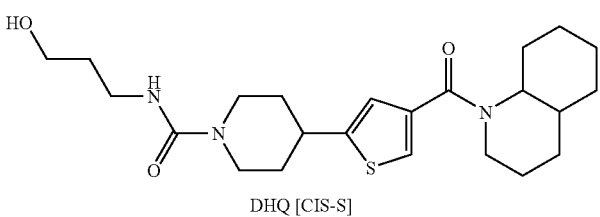 [SMILES: O=C(NCCCO)N1CCC(c2cc(C(=O)N3CCCC4CCCCC43)cs2)CC1]
DHQ [CIS-S]
CC-160
166. 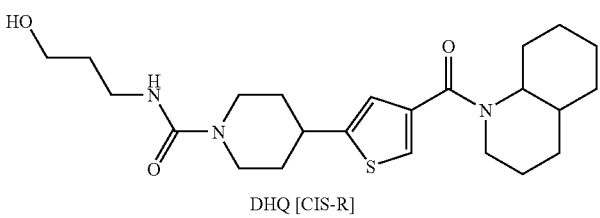 [SMILES: O=C(NCCCO)N1CCC(c2cc(C(=O)N3CCCC4CCCCC43)cs2)CC1]
DHQ [CIS-R]
CC-161

-continued

| | | |
|---|---|---|
| 167. | [structure] DHQ [CIS-S] | CC-162 |
| 168. | [structure] DHQ [CIS-R] | CC-163 |
| 169. | [structure] | CC-164 |
| 170. | [structure] DHQ [CIS-S] | CC-165 |
| 171. | [structure] DHQ [CIS-R] | CC-166 |
| 172. | [structure] DHQ [CIS-S] | CC-167 |
| 173. | [structure] DHQ [CIS-S] | CC-168 |

-continued
| | | |
|---|---|---|
| 174. | 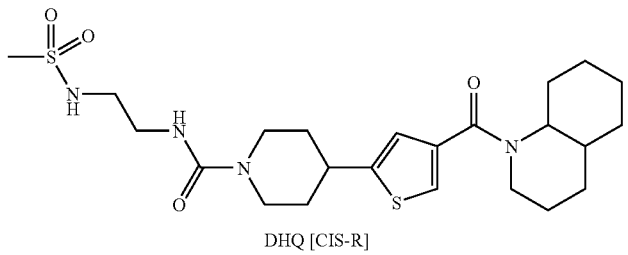 [SMILES: CS(=O)(=O)NCCNC(=O)N1CCC(c2cc(C(=O)N3CCCC4CCCCC43)cs2)CC1] DHQ [CIS-R] | CC-169 |
| 175. | 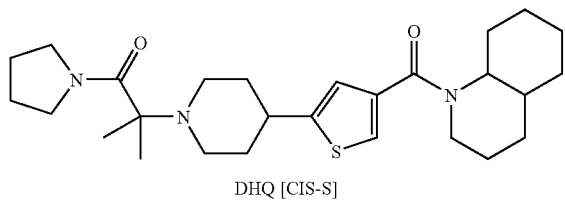 [SMILES: CC(C)(C(=O)N1CCCC1)N1CCC(c2cc(C(=O)N3CCCC4CCCCC43)cs2)CC1] DHQ [CIS-S] | CC-170 |
| 176. | 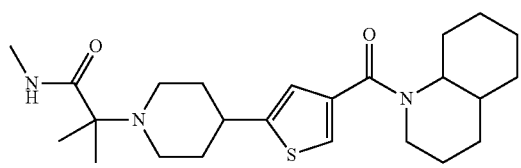 [SMILES: CNC(=O)C(C)(C)N1CCC(c2cc(C(=O)N3CCCC4CCCCC43)cs2)CC1] | CC-171 |
| 177. | 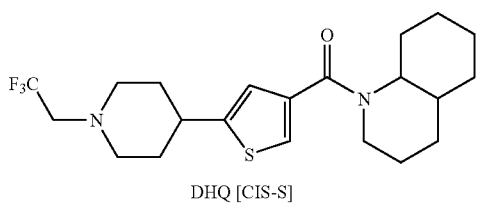 [SMILES: O=C(c1csc(C2CCN(CC(F)(F)F)CC2)c1)N1CCCC2CCCCC21] DHQ [CIS-S] | CC-172 |
| 178. | 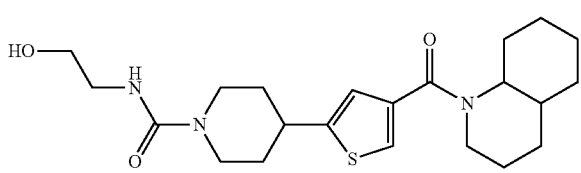 [SMILES: O=C(NCCO)N1CCC(c2cc(C(=O)N3CCCC4CCCCC43)cs2)CC1] | CC-173 |
| 179. | 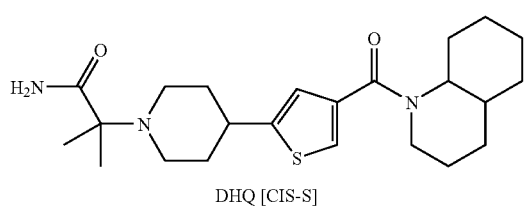 [SMILES: CC(C)(C(N)=O)N1CCC(c2cc(C(=O)N3CCCC4CCCCC43)cs2)CC1] DHQ [CIS-S] | CC-174 |
| 180. | 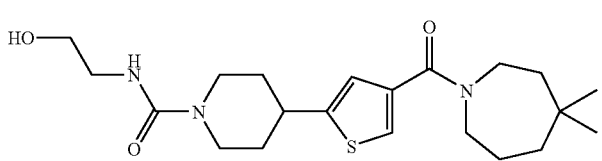 [SMILES: CC1(C)CCCN(C(=O)c2csc(C3CCN(C(=O)NCCO)CC3)c2)CC1] | CC-175 |
| 181. | 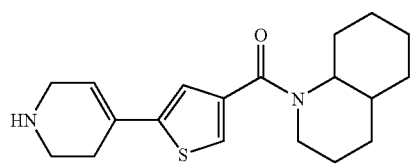 DHQ [CIS-S] | CC-176 |

| | |
|---|---|
| 182. 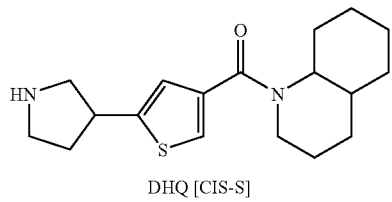 [SMILES: O=C(c1csc(C2CCNC2)c1)N1CCCC2CCCCC21]<br>DHQ [CIS-S] | CC-177. |
43. A pharmaceutical composition comprising a compound according to claim 1, and a pharmaceutically acceptable carrier or diluent.
44. A method of preparing a pharmaceutical composition comprising the step of admixing a compound according to claim 1, and a pharmaceutically acceptable carrier or diluent.
* * * * *